(12) United States Patent
Sydora et al.

(10) Patent No.: US 9,580,453 B2
(45) Date of Patent: Feb. 28, 2017

(54) PREPARATION OF TRANSITION METAL CARBOXYLATES

(71) Applicant: Chevron Phillips Chemical Company LP, The Woodlands, TX (US)

(72) Inventors: Orson L. Sydora, Houston, TX (US); Ronald D. Knudsen, Bartlesville, OK (US); Eduardo J. Baralt, Kingwood, TX (US)

(73) Assignee: Chevron Phillips Chemical Company LP, The Woodlands, TX (US)

( * ) Notice: Subject to any disclaimer, the term of this patent is extended or adjusted under 35 U.S.C. 154(b) by 22 days.

(21) Appl. No.: 14/575,803

(22) Filed: Dec. 18, 2014

(65) Prior Publication Data

US 2015/0105574 A1    Apr. 16, 2015

Related U.S. Application Data

(63) Continuation of application No. 13/323,191, filed on Dec. 12, 2011, now Pat. No. 8,957,235.

(51) Int. Cl.
| | | |
|---|---|---|
| C07F 11/00 | (2006.01) | |
| C07F 13/00 | (2006.01) | |
| C07C 2/32 | (2006.01) | |

(52) U.S. Cl.
CPC ............... *C07F 11/00* (2013.01); *C07C 2/32* (2013.01); *C07F 11/005* (2013.01);
(Continued)

(58) Field of Classification Search
CPC ........ C07F 11/00; C07F 11/005; C07F 13/005
(Continued)

(56) References Cited

U.S. PATENT DOCUMENTS

| | | |
|---|---|---|
| 3,164,620 A | 1/1965 | van der Minne et al. |
| 3,725,305 A | 4/1973 | Wilkinson |

(Continued)

FOREIGN PATENT DOCUMENTS

| | | |
|---|---|---|
| CN | 1422839 A | 6/2003 |
| CN | 101100594 A | 1/2008 |

(Continued)

OTHER PUBLICATIONS

Taylor et al., Journal of Molecular Chemistry, vol. 787, pp. 113-120 (2006).*

(Continued)

*Primary Examiner* — Porfirio Nazario Gonzalez
(74) *Attorney, Agent, or Firm* — Conley Rose, P.C.; Rodney B. Carroll; Lynda Jolly

(57) ABSTRACT

This disclosure provides a process for making transition metal carboxylate compositions by combining in an polar aprotic first solvent a transition metal precursor and a Group 1 or Group 2 metal carboxylate under substantially acid-free and substantially anhydrous conditions, to generate a mixture comprising the transition metal carboxylate composition. Optionally, the transition metal carboxylate composition can be purified, for example, by substantially removing the first solvent provide a residue comprising the transition metal carboxylate composition, and also optionally, further by extracting the transition metal carboxylate composition from the residue with a non-coordinating second solvent to provide an extract comprising the transition metal carboxylate composition.

18 Claims, 20 Drawing Sheets
(1 of 20 Drawing Sheet(s) Filed in Color)

(52) U.S. Cl.
 CPC ......... *C07F 13/005* (2013.01); *B01J 2231/20* (2013.01); *B01J 2531/62* (2013.01); *C07C 2523/26* (2013.01)

(58) Field of Classification Search
 USPC .......................................................... 556/61
 See application file for complete search history.

(56) References Cited

U.S. PATENT DOCUMENTS

| | | | |
|---|---|---|---|
| 4,017,429 | A | 4/1977 | Steele et al. |
| 4,853,356 | A | 8/1989 | Briggs |
| 5,591,878 | A | 1/1997 | Nelson et al. |
| 5,689,028 | A | 11/1997 | Lashier et al. |
| 5,856,257 | A | 1/1999 | Freeman et al. |
| 6,133,495 | A | 10/2000 | Urata et al. |
| 6,455,648 | B1 | 9/2002 | Freeman et al. |
| 6,800,702 | B2 | 10/2004 | Wass |
| 7,384,886 | B2 | 6/2008 | Knudsen et al. |
| 8,049,052 | B2 | 11/2011 | Kreischer et al. |
| 8,957,235 | B2 | 2/2015 | Sydora et al. |
| 2004/0236163 | A1 | 11/2004 | Ewert et al. |
| 2005/0187391 | A1 | 8/2005 | Knudsen et al. |
| 2007/0043181 | A1 | 2/2007 | Knudsen et al. |
| 2013/0150642 | A1 | 6/2013 | Sydora et al. |

FOREIGN PATENT DOCUMENTS

| | | |
|---|---|---|
| GB | 1469986 | 4/1977 |
| JP | 62265237 A | 11/1987 |
| JP | 5059314 B2 | 10/2012 |
| JP | 2015507524 A | 3/2015 |
| WO | 2013089962 A1 | 6/2013 |
| WO | 2013089963 A1 | 6/2013 |

OTHER PUBLICATIONS

Office Action dated Apr. 27, 2015 (30 pages), U.S. Appl. No. 13/323,328, filed Dec. 12, 2011.
Cannon, Roderick D., et al., "Chemical and Physical Properties of Triangular Bridged Metal Complexes," Progress in Inorganic Chemistry, vol. 36, 1988, John Wiley & Sons, Inc., pp. 195-298.
Cayton, Roger H., et al., "Multiple Bonds Between Metal Atoms in Ordered Assemblies: Liquid Crystals Containing Mo-Mo Quadruple Bonds," Angew. Chem. Int. Ed. Engl., 1990, pp. 1481-1483, vol. 29, No. 12, VCH Verlagsgesellschaft mbH, Weinheim.
Deacon, G. B., et al., "Relationships Between the Carbon-Oxygen Stretching Frequencies of Carboxylato Complexes and the Type of Carboxylate Coordination," Coordination Chemistry Reviews, vol. 33, 1980, pp. 227-250, Elsevier Scientific Publishing Company, Amsterdam.
Eshel, Michal, et al., "Polynuclear Chromium(III) Carboxylates. 1. Synthesis, Structure, and Magnetic Properties of an Octanuclear Complex with a Ring Structure," Inorg. Chem., 2000, vol. 39, No. 7, pp. 1376-1380, American Chemical Society.
Eshel, Michal, et al., "Polynuclear chromium(III) carboxylates. 3. Cyclic and cubane type hexachromium acetates," Inorganica Chimica Acta, vol. 329, 2002, pp. 45-50, Elsevier Science B.V.
Fang, Yiqun, et al., "A new chromium-based catalyst coated with paraffin for ethylene oligomerization and the effect of chromium state on oligomerization selectivity," Applied Catalysis A: General, vol. 235, 2002, pp. 33-38, Elsevier Science B.V.
Farrow, C. L., et al., "PDFfit2 and PDFgui: computer programs for studying nanostructure in crystals," Journal of Physics: Condensed Matter, vol. 19, 2007, pp. 1-7, IOP Publishing Ltd.
Figgis, B. N., et al., "Crystal-Molecular Structure and Magnetic Properties of $Cr_3$ $(CH_3 COO)_6$ O $CI.5H_2O$," Nature, vol. 205, No. 4972, pp. 694-695, Feb. 13, 1965.
Foreign communication from a related counterpart application—International Search Report and Written Opinion, PCT/US2012/065289, Feb. 18, 2013, 11 pages.
Foreign communication from a related counterpart application—International Preliminary Report on Patentability, PCT/US2012/065289, Jun. 17, 2014, 8 pages.
Foreign communication from a related counterpart application—International Search Report and Written Opinion, PCT/US2012/065285, Feb. 18, 2013, 12 pages.
Foreign communication from a related counterpart application—International Preliminary Report on Patentability, PCT/US2012/065285, Jun. 17, 2014, 7 pages.
"Group notation revised in periodic table," C&EN, pp. 26-27, Feb. 4, 1985.
Hammersley, A. P., et al., "Two-dimensional detector software: from real detector to idealised image or two-theta scan," High Pressure Research, vol. 14, 1996, pp. 235-248, OPA (Overseas Publishers Association) Amsterdam B.V.
Hart, Rob, et al., "Synthesis and structures of metal carboxylate liquids," National Meeting of the American Chemical Society, Mar. 23, 2009, pp. 1-23, Shepherd.
Machine Translation (provided by WIPO) of CN 101100594, downloaded from Internet on Nov. 12, 2013, 5 pages.
McNaught, Alan D., et al., "Compendium of Chemical Terminology IUPAC Recommendations," Second Edition, 4 pages: cover, title, publishing, and contents information, Blackwell Science, The Royal Society of Chemistry, United Kingdom.
Nakamoto, Kazuo, "Infrared and Raman Spectra of Inorganic and Coordination Compounds," 4th Edition, John Wiley & Sons Inc., 1986, pp. 231-233 plus one page cover and publishing information.
Office Action (Restriction Requirement) dated Sep. 18, 2014 (10 pages), U.S. Appl. No. 13/323,328, filed Dec. 12, 2011.
Palacios, E. G., et al., "Infrared spectroscopy of metal carboxylates II. Analysis of Fe(III), Ni and Zn carboxylate solutions," Hydrometallurgy, 2004, pp. 139-148, vol. 72, Elsevier B.V.
Proffen TH., et al., "PDFFIT, a program for full profile structural refinement of the atomic pair distribution function," Journal of Applied Crystallography, vol. 32, 1999, pp. 572-575, International Union of Crystallography.
Qiu, Xiangyun, et al "PDFgetX2: a GUI-driven program to obtain the pair distribution function from X-ray powder diffraction data," Journal of Applied Crystallography, vol. 37, 2004, p. 678, International Union of Crystallography.
Tomberli, B., et al., "Isotopic quantum effects in water structure measured with high energy photon diffraction," J. Phys.: Condens. Matter, vol. 12, pp. 2597-2612, 2000, IOP Publishing Ltd.
Vlachos, Antonis, et al., "A nearly symmetric trinuclear chromium(III) oxo carboxylate assembly: preparation, molecular and crystal structure, and magnetic properties of $[Cr_3O(O_2CPh)_6(MeOH)_3]NO_3$)•$2MeOH$,"Inorganica Chimica Acta, vol. 357, pp. 3162-3172, 2004, Elsevier B.V.
Specification for patent application entitled "Processes for Preventing Generation of Hydrogen Halides in an Oligmerization Product Recovery System," by Jeffrey W. Freeman, et al., filed Dec. 29, 1999 as U.S. Appl. No. 09/473,688.
Office Action (Final) dated Sep. 4, 2015 (12 pages), U.S. Appl. No. 13/323,328, filed Dec. 12, 2011.
Examiner's Answer dated Jul. 8, 2016 (12 pages), U.S. Appl. No. 13/323,328, filed Dec. 12, 2011.
Foreign communication from a related counterpart application—English translation of Japanese Office Action, Japanese Patent Application No. 2014-547253, May 31, 2016, 4 pages.

* cited by examiner

Example 3
Chromium(III) 2-ethylhexanoate

Example 3
Chromium(III) 2-ethylhexanoate

Example 4
Chromium(III) 2-ethylhexanoate

Example 4
Chromium(III) 2-ethylhexanoate

Example 5
Chromium(III) 2-ethylhexanoate

Example 5
Chromium(III) 2-ethylhexanoate

Example 6
Chromium(III) 2-ethylhexanoate

Example 6
Chromium(III) 2-ethylhexanoate

Example 7
Chromium(III) 2-ethylhexanoate

US 9,580,453 B2

PREPARATION OF TRANSITION METAL CARBOXYLATES

CROSS REFERENCE TO RELATED APPLICATIONS

This application is a continuation of and claims priority to U.S. patent application Ser. No. 13/323,191 filed on Dec. 12, 2011, published as US 2013/0150605 A1 and entitled "Preparation of Transition Metal Carboxylates," which is incorporated by reference herein in its entirety.

TECHNICAL FIELD OF THE INVENTION

This disclosure relates to transition metal carboxylates and methods for making transition metal carboxylates, including chromium-containing carboxylates useful for preparing olefin oligomerization catalysts.

BACKGROUND OF THE INVENTION

The trimerization of ethylene to produce 1-hexene constitutes a commercially significant process for the selective preparation of this alpha olefin, which in turn is useful for preparing a range of polyolefins, usually as a comonomer with ethylene. One widely employed catalyst system utilizes chromium carboxylates as a component. For example, tris (2-ethylhexanoate) chromium(III) compositions are utilized as a component of some effective chromium (III) catalyst system for the selective trimerization of ethylene to 1-hexene.

Batch-to-batch variations in the quality of commercial chromium(III) 2-ethylhexanoate, and the attendant inconsistency in catalytic system performance, have prompted the search for new synthetic approaches to chromium carboxylates. This search for alternative preparative approaches is further motivated by the desire to improve productivity and selectivity of a catalyst system and to attempt to reduce catalyst system cost. Therefore, there remains a need for new synthetic approaches to produce transition metal carboxylates.

SUMMARY OF THE INVENTION

In an aspect, the present application is directed to a process to prepare a transition metal carboxylate compositions comprising contacting under substantially anhydrous and substantially acid-free conditions 1) a transition metal precursor having a formula $[((M^B)_{y1}X_{x1}L_l)^m]_q[C^c]_{m1}[A^a]_{m2}$; 2) a Group 1 or Group 2 metal $C_3$-$C_{25}$ carboxylate; and 3) a first solvent to form a transition metal carboxylate, wherein $M^B$ is a transition metal in the +x oxidation state where x is an integer from +1 to +6, each X independently is an anionic ligand having charge y where y is an integer from −3 to −1, each L independently is a neutral ligand, l is an integer from 0 to 7, m is an integer from −4 to 4, m=(y*x1)+(x*y1), C is a cationic species having a charge c and c is an integer from +1 to +3, A is an anionic species having a charge a and a is an integer from −1 to −3, and when m<0, |m*q|=c*m1 and m2=0, when m=0, m1=0, and m=0 or when m>0, m*q=|a*m2| and m1=0. In an embodiment, the transition metal precursor that can be utilized in the process can have a formula $M^B X_x L_l$ where $M^B$ is a transition metal in the x oxidation state and x is an integer from 1 to 6; each X independently is a monoanionic ligand; each L independently is a neutral ligand; and l is an integer from 0 to 7. In some embodiments, the transition metal, $M^B$, can be, comprise, or consist essentially of, Ti, Zr, V, Nb, Cr, Mn, Fe, Co or Cu. In other embodiments, the transition metal precursor has a formula $CrX_3L_l$ where each X independently is an anionic ligand having charge y where y is an integer from −3 to −1, each L independently is a neutral ligand, l is an integer from 0 to 7.

In an embodiment, the Group 1 or Group 2 metal $C_3$-$C_{25}$ carboxylate utilized in the process can have a formula $(M^A)_q[(O_2C)_rR^{1c}]_s$ where $M^A$ is a Group 1 or Group 2 metal, $(O_2C)_rR^{1c}$ can be a $C_3$-$C_{25}$ carboxylate where r can be an integer from 1 to 4 and $R^{1c}$ can be a hydrocarbon group or a substituted hydrocarbon group, q can be r divided by the greatest common divisor of r and the oxidation state of $M^A$, and s can be the oxidation state of $M^A$ divided by the greatest common divisor of r and the oxidation state of $M^A$. In other embodiments, the Group 1 or Group 2 metal $C_3$-$C_{25}$ carboxylate can be, comprise, or consist essentially of, a Group 1 or Group 2 metal $C_3$-$C_{25}$ monocarboxylate. In yet other embodiments, the Group 1 or Group 2 metal carboxylate can have a formula $M^A O_2 CR^{2c}$ where $M^A$ can be a Group 1 metal, $O_2CR^{2c}$ can be, comprise, or consist essentially of, a $C_3$-$C_{25}$ monocarboxylate, and $R^{2c}$ can be a hydrocarbyl group or a substituted hydrocarbyl group. In further embodiments, the carboxylate of the Group 1 metal carboxylate comprises a propionate, a butyrate, a pentanoate, a hexanoate, a heptanoate, an octanoate, a nonanoate, a decanoate, an undecanoate, a dodecanoate, a tridecanoate, a tetradecanoate, a pentadecanoate, a hexadecanoate, a heptadecanoate, an octadecanoate, or any combination thereof; or alternatively, 2-ethylhexanoate.

In an embodiment, the first solvent utilized in the process can be, comprise, or consist essentially of, a non-polar solvent. In some embodiments, the first solvent can be, comprise, or consist essentially of, a polar solvent. In other embodiments, the first solvent can comprise a $C_2$-$C_{40}$ ether, a $C_2$-$C_{40}$ thioether, a $C_2$-$C_{20}$ nitrile, a $C_1$-$C_{60}$ amine, or a $C_3$-$C_{60}$ phosphine, or any combination thereof.

In an aspect, the present application is directed to a transition metal carboxylate composition prepared by any process described herein. In some embodiments, the present application is directed to a chromium(III) carboxylate composition prepared by any process described herein.

In an aspect, the present application is directed to a chromium carboxylate composition prepared by any process described herein. In another aspect, the present application is directed to a chromium carboxylate composition having a distinctive infrared adsorption peak characteristic(s) and/or distinctive infrared adsorption peak ratio(s). In an embodiment, the chromium carboxylate composition can have a KBr pellet infrared adsorption spectrum with a $\upsilon_{asym}$ ($CO_2$) peak infrared adsorption peak within 110 cm$^{-1}$ of the $\upsilon_{sym}$ ($CO_2$) infrared adsorption peak. In some embodiments, a chromium carboxylate composition can further have a KBr pellet infrared adsorption spectrum having an infrared absorbance peak height ratio of a $\upsilon_{asym}$ ($CO_2$) infrared absorbance peak at 1516±15 cm$^{-1}$ to infrared absorbance peak located at 700±50 cm$^{-1}$ greater than or equal to 3:1, an infrared absorbance peak height ratio of an infrared absorbance peak at 1516±15 cm$^{-1}$ to an infrared absorbance peak at 1429±15 cm$^{-1}$ greater than or equal to 0.5:1, having an infrared absorbance peak height ratio of a $\upsilon_{sym}$ ($CO_2$) infrared absorbance peak located at 1616±20 cm$^{-1}$ to a $\upsilon_{asym}$ ($CO_2$) infrared absorbance peak at 1429±15 cm$^{-1}$ less than or equal to 0.8:1, and/or having an infrared absorbance peak height ratio of a $\upsilon_{sym}$ ($CO_2$) infrared absorbance peak located at 1429±15 cm$^{-1}$ to a $\upsilon_{asym}$ ($CO_2$) infrared absorbance peak at 1685±20 cm$^{-1}$ greater than or equal to 3.5:1. In some embodiments, the chromium(III) carboxylate composition having a distinctive infrared adsorption spectrum feature(s) can comprise a $C_3$ to $C_{25}$ carboxylate; alternatively, comprises propionate, a butyrate, a pentanoate, a hexanoate, a heptanoate, an octanoate, a nonanoate, a decanoate, an undecanoate, a dodecanoate, a tridecanoate, a tetradecanoate, a pentadecanoate, a hexadecanoate, a heptadecanoate, an octadecanoate, or any combination thereof; or alternatively, comprises 2-ethylhexanoate.

In an aspect, the present disclosure is directed to a chromium carboxylate composition having a distinctive high energy X-ray diffraction g(r) versus r spectrum feature(s). In an embodiment, the present invention is directed to a chromium carboxylate composition having a goodness of fit test value, $R^2$, greater than 0.6 when comparing high-energy X-ray diffraction g(r) data points of the chromium(III) carboxylate composition to a calculated high energy X-ray diffraction g(r) data points of a theoretical model of mononuclear chromium(III) acetate over an r range from 1.3 Angstroms to 4 Angstroms. In some embodiments, the chromium(III) carboxylate composition having distinctive high energy X-ray diffraction g(r) versus r spectrum feature(s) can comprise a $C_3$ to $C_{25}$ carboxylate; alternatively, comprises propionate, a butyrate, a pentanoate, a hexanoate, a heptanoate, an octanoate, a nonanoate, a decanoate, an undecanoate, a dodecanoate, a tridecanoate, a tetradecanoate, a pentadecanoate, a hexadecanoate, a heptadecanoate, an octadecanoate, or any combination thereof; or alternatively, comprises 2-ethylhexanoate.

BRIEF DESCRIPTION OF THE FIGURES

The patent or application file contains at least one drawing executed in color. Copies of this patent or patent application publication with color drawing(s) will be provided by the Office upon request and payment of the necessary fee.

DETAILED DESCRIPTION OF THE INVENTION

Figure 1:
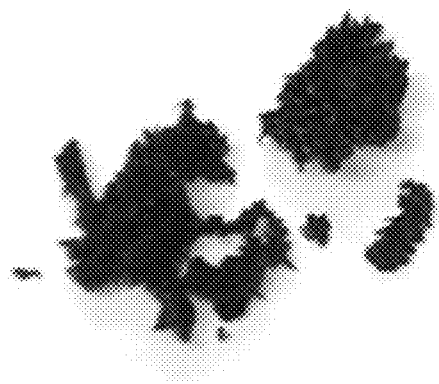
FIG. 1 is a picture of an isolated transition metal carboxylate (chromium(III) 2-ethylhexanoate) of the present disclosure.

In one aspect, this disclosure provides for synthetic approaches to prepare transition metal carboxylate compositions, that is, compositions comprising at least one transition metal carboxylate compound. The term carboxylate is used herein to describe chemical moieties that contain one or more carboxylate functional group. For example, the Group 1 or Group 2 carboxylate starting materials and the transition metal carboxylate compositions of this disclosure can encompass carboxylate-containing moieties of the general formula $(O_2C)_rR^{1c}$, where the carboxylate-containing moiety has r carboxylate groups and r can be an integer from 1 to 4. In this aspect, for example, the methods of this disclosure are applicable to the preparation of compositions comprising simple mono-carboxylates such as $O_2CR^{2c}$.

A common synthetic approach to prepare transition metal carboxylate compositions involves reacting a transition metal acetate precursor with the corresponding carboxylic acid, for example propanoic acid ($CH_3CH_2CO_2H$), butyric acid ($CH_3CH_2CH_2CO_2H$), and the like. For example, commercial preparations of chromium (III) carboxylates such as Cr(2-ethylhexanoate)$_3$ ("Cr(EH)$_3$") typically entail heating chromium (III) acetate in the presence of excess 2-ethylhexanoic acid. The resulting acetic acid, excess 2-ethylhexanoic acid, and water typically are removed to the extent possible by heating the reaction mixture under vacuum. Alternatively, the chromium(III) carboxylate has been produced by the reduction of chromium trioxide in the presence of the carboxylic acid where the reductant is the carboxylic acid. For example, commercial preparations of chromium (III) carboxylates such as Cr(2-ethylhexanoate)$_3$ can entail heating a mixture comprising chromium trioxide and excess of 2-ethylhexanoic acid. However, these methods typically can leave residual carboxylic acid within the chromium(III) carboxylate compositions, introduce difficult to remove water into the chromium(III) carboxylate composition, and/or produce oligomeric chromium carboxylate compounds. Because some of the intended applications of the resulting Cr(EH)$_3$ are water- and/or acid-sensitive, the presence of water and residual carboxylic acid can complicate the use of these compositions in some applications. Additionally, the presence protic carboxylic acids and chromium carboxylate oligomers can introduce problems in the production of olefin oligomerization catalyst systems and their subsequent use in oligomerizing olefins. For example, and not to be limited by theory, the protic carboxylic acids can consume cocatalyst and increase catalyst system costs while chromium carboxylate oligomers can lead to insoluble products which must be filtered and/or increase polymer production during olefin oligomerization. Accordingly, this disclosure provides synthetic methods, which reduce, minimize, or substantially eliminate undesirable protic sources, such as $H_2O$ and/or carboxylic acid such as 2-ethylhexanoic acid, and/or minimize the presence of chromium carboxylate oligomers. Specifically, this disclosure provides for an improved process for producing transition metal carboxylate compositions comprising contacting a transition metal precursor and a Group 1 or Group 2 metal $C_3$-$C_{25}$ carboxylate in a polar aprotic solvent to provide a mixture comprising a transition metal carboxylate.

To define more clearly the terms used herein, the following definitions are provided. Unless otherwise indicated, the following definitions are applicable to this disclosure. If a term is used in this disclosure but is not specifically defined herein, the definition from the IUPAC Compendium of Chemical Terminology, $2^{nd}$ Ed (1997) can be applied, as long as that definition does not conflict with any other disclosure or definition applied herein, or render indefinite or non-enabled any claim to which that definition is applied. To the extent that any definition or usage provided by any document incorporated herein by reference conflicts with the definition or usage provided herein, the definition or usage provided herein controls.

Groups of elements of the table are indicated using the numbering scheme indicated in the version of the periodic table of elements published in *Chemical and Engineering News*, 63(5), 27, 1985. In some instances a group of elements can be indicated using a common name assigned to the group; for example alkali metals for Group 1 elements, alkaline earth metals for Group 2 elements, transition metals for Group 3-12 elements, and halogens for Group 17 elements.

Regarding claim transitional terms or phrases, the transitional term "comprising", which is synonymous with "including," "containing," "having," or "characterized by," is inclusive or open-ended and does not exclude additional, unrecited elements or method steps. The transitional phrase "consisting of" excludes any element, step, or ingredient not specified in the claim. The transitional phrase "consisting essentially of" limits the scope of a claim to the specified materials or steps and those that do not materially affect the basic and novel characteristic(s) of the claimed invention. A "consisting essentially of" claim occupies a middle ground between closed claims that are written in a "consisting of" format and fully open claims that are drafted in a "comprising" format. Absent an indication to the contrary, when describing a compound or composition "consisting essentially of" is not to be construed as "comprising," but is intended to describe the recited component that includes materials which do not significantly alter the composition or method to which the term is applied. For example, a feedstock consisting of a material A can include impurities typically present in a commercially produced or commercially available sample of the recited compound or composition. When a claim includes different features and/or feature classes (for example, a method step, feedstock features, and/or product features, among other possibilities), the transitional terms comprising, consisting essentially of, and consisting of apply only to the feature class which is utilized and it is possible to have different transitional terms or phrases utilized with different features within a claim. For example, a method can comprise several recited steps (and other non-recited steps) but utilize a catalyst system preparation consisting of specific or alternatively consist of specific steps and/or utilize a catalyst system comprising recited components and other non-recited components.

Within this disclosure, use of "comprising" or an equivalent expression contemplates the use of the phrase "consisting essentially of," "consists essentially of," or equivalent expressions as an alternative embodiments to the open-ended expression. Additionally, use of "comprising" or an equivalent expression or use of "consisting essentially of" in the specification contemplates the use of the phrase "consisting of," "consists of," or equivalent expression as an alternative to the open-ended expression or middle ground expression, respectively. For example, "comprising" should be understood to include "consisting essentially of," and "consisting of" as alternative embodiments for the aspect, features, and/or elements presented in the specification unless specifically indicated otherwise.

The terms "a," "an," and "the" are intended, unless specifically indicated otherwise, to include plural alternatives (e.g., at least one). For instance, the disclosure of "a chromium halide hydrate" is meant to encompass one chromium halide hydrate, or mixtures or combinations of more than one chromium halide hydrate unless otherwise specified.

In this disclosure, the terms first, second, and third, among others, can be utilized to differentiate multiple occurrences of a similar element. For example a method can utilize two or more solvents in different steps of a method, or alternatively two different solvent in a mixture. The differentiating term can be applied to any element described herein when necessary to provide a differentiation. It should be understood that the numerical or alphabetical precedence of the differentiating terms do not imply a particular order or preference of the element in a method or compound described herein unless specifically specified otherwise.

In this disclosure, a process can have multiple steps or can include features having a number of different elements (e.g., components in a catalyst system or components in an olefin trimerization oligomerization process, among other features). This steps and/or elements can be designated utilizing the series a), b), c), etc., i), ii), iii), etc., (a), (b), (c), etc., and/or (i), (ii), (iii), etc. (among other designation series) as necessary to provide a designation for each process step and/or element. It should be understood that the numerical or alphabetical precedence of the designations within a designation series does not imply a particular order or preference of the process step in a process described herein, the feature(s) described herein, and/or an element(s) in a feature unless specifically specified otherwise or necessitated by other process steps, elements, and/or element features. Additionally, these designations series are provided to differentiate different process steps and/or elements in a feature and can be utilized as necessary, and without regard to the designation series utilized for a particular step, element, or feature utilized within this description as long as the designation series consistently distinguish different features, different process steps, and/or different elements of a feature.

The term "substantially anhydrous," when referring to a compound, solution, solvent, or general conditions, means that the amount of water is less than or equal to 100 ppm (by weight) based upon the weight of the compound, solution, or solvent. The term "substantially dry," when referring to an atmosphere, means that the atmosphere, regardless of the atmosphere's composition, means that the amount of water in the atmosphere is less than or equal to 100 ppm, by weight.

The term "acid-free" refers to process being carried out without the discrete addition of an acidic or protic compound or substance. For example, "acid-free" means that there has been no addition of a carboxylic acid, mineral or inorganic acid, alcohol, or other protic compounds or substances to the reaction or solution described as "acid-free." The term "acid-free" is not intended to reflect a 0 ppm concentration of $[H_3O]^+$ or 0 ppm concentration of an acidic or protic source, as "acid-free" conditions still can reflect the presence of small amounts of acid that can exist as contaminants in an added component or can arise as a by-product during the course of the reaction or preparation of a reaction solution. For example, the transition metal carboxylate(s) and transition metal carboxylate composition(s) prepared by the disclosed methods can contain measurable amounts of free carboxylic acid, or other protogenic compounds that can arise as contaminants or as by-products during the preparation of such compounds or compositions. The term "substantially acid-free," when referring to a compound, solution, solvent, or general conditions, means that the amount of acid is less than or equal to 1000 ppm (by weight) based upon the weight of the compound, solution, or solvent.

The terms "room temperature" or "ambient temperature" are used herein to describe any temperature from 15° C. to 35° C. wherein no external heat or cooling source is directly applied to the reaction vessel. Accordingly, the terms "room temperature" and "ambient temperature" encompass the individual temperatures and any and all ranges, subranges, and combinations of subranges of temperatures from 15° C. to 35° C. wherein no external heating or cooling source is directly applied to the reaction vessel.

The term "atmospheric pressure" is used herein to describe an earth air pressure wherein no external pressure modifying means is utilized. Generally, unless practiced at extreme earth altitudes, "atmospheric pressure" is about 1 atmosphere (alternatively, about 14.7 psi or about 101 kPa).

The term "aprotic" is used herein to describe a solvent that is non-protogenic under the given conditions. Thus, an "aprotic" compound or solvent is not capable of acting as a proton donor, either strongly or weakly acidic as a Brønsted acid, under the specific conditions. For example, acetonitrile can be an aprotic solvent even though it can be deprotonated in the presence of a strong base such as potassium tert-butoxide.

For any particular compound disclosed herein, the general structure or name presented is also intended to encompass all structural isomers, conformational isomers, and stereoisomers that can arise from a particular set of substituents, unless indicated otherwise. Thus, a general reference to a compound includes all structural isomers unless explicitly indicated otherwise; e.g., a general reference to pentane includes n-pentane, 2-methyl-butane, and 2,2-dimethylpropane while a general reference to a butyl group includes an n-butyl group, a sec-butyl group, an iso-butyl group, and a tert-butyl group. Additionally, the reference to a general structure or name encompasses all enantiomers, diastereomers, and other optical isomers whether in enantiomeric or racemic forms, as well as mixtures of stereoisomers, as the context permits or requires. For any particular formula or name that is presented, any general formula or name presented also encompasses all conformational isomers, regioisomers, and stereoisomers that can arise from a particular set of substituents.

A chemical "group" is described according to how that group is formally derived from a reference or "parent" compound, for example, by the number of hydrogen atoms formally removed from the parent compound to generate the group, even if that group is not literally synthesized in this manner. These groups can be utilized as substituents or coordinated or bonded to metal atoms. By way of example, an "alkyl group" formally can be derived by removing one hydrogen atom from an alkane, while an "alkylene group" formally can be derived by removing two hydrogen atoms from an alkane. Moreover, a more general term can be used to encompass a variety of groups that formally can be derived by removing any number ("one or more") hydrogen atoms from a parent compound, which in this example can be described as an "alkane group," and which encompasses an "alkyl group," an "alkylene group," and materials have three or more hydrogens atoms, as necessary for the situation, removed from the alkane. Throughout, the disclosure that a substituent, ligand, or other chemical moiety can constitute a particular "group" implies that the well-known rules of chemical structure and bonding are followed when that group is employed as described. When describing a group as being "derived by," "derived from," "formed by," or "formed from," such terms are used in a formal sense and are not intended to reflect any specific synthetic methods or procedure, unless specified otherwise or the context requires otherwise. Other identifiers or qualifying terms may be utilized to indicate the presence or absence of a particular substituent, a particular regiochemistry and/or stereochemistry, or the presence or absence of a branched underlying structure or backbone.

The term "substituted" when used to describe a group, for example, when referring to a substituted analog of a particular group, is intended to describe any non-hydrogen moiety that formally replaces a hydrogen in that group, and is intended to be non-limiting. A group or groups can also be referred to herein as "unsubstituted" or by equivalent terms such as "non-substituted," which refers to the original group in which a non-hydrogen moiety does not replace a hydrogen within that group. "Substituted" is intended to be non-limiting and include inorganic substituents or organic substituents.

A "carboxylate" is an anionic organic group having the general formula $[ZC(=O)O]^-$ where Z represents any organyl group.

A "nitrile" is an organic compound having the formula $R^1C\equiv N$, wherein $R^1$ is provided herein. Aliphatic nitriles are nitriles which do not contain aromatic groups. Aromatic nitriles are nitriles which have aromatic groups (e.g. benzonitrile).

An "ether" is an organic compound having the formula $R^2-O-R^3$ wherein $R^2$ and $R^3$ are provided herein. Aliphatic ethers are ethers which do not have aromatic groups. Aromatic ethers are ethers which have aromatic groups (either containing or not containing the ether oxygen atom). Acyclic ethers are ethers in which the ether oxygen atom is not contained in a ring (but can have a ring, aliphatic or aromatic, as or within $R^2$ and/or $R^3$). Cyclic ethers are ethers wherein the ether oxygen atom is incorporated within a ring (either an aliphatic ring or aromatic ring). Aliphatic cyclic ethers are cyclic ethers wherein the ether oxygen atom is incorporated within an aliphatic ring (e.g. tetrahydrofuran, 2,3-dihydrofuran, pyran, among others). Aromatic cyclic ethers are ethers wherein the ether oxygen atom is incorporated within an aromatic ring or aromatic ring system (e.g. furan, benzofuran, isobenzofuran, among others).

A "thioether" is an organic compound having the formula $R^4-S-R^5$ wherein $R^4$ and $R^5$ are provided herein. Aliphatic thioethers are thioethers which do not have aromatic groups. Aromatic thioethers are ethers which have aromatic groups (either containing or not containing the thioether sulfur atom). Acyclic thioethers are thioethers in which the thioether sulfur atom is not contained in a ring (but can have a ring, aliphatic or aromatic, as or within $R^4$ and/or $R^5$). Cyclic thioethers are thioethers wherein the thioether sulfur atom is incorporated within a ring (either an aliphatic ring or aromatic ring). Aliphatic cyclic thioethers are cyclic thioethers wherein the thioether sulfur atom is incorporated within an aliphatic ring (e.g. tetrahydrothiophene, thiane, among others). Aromatic cyclic thioethers are thioethers wherein the thioether sulfur atom is incorporated within an aromatic ring or aromatic ring system (e.g. thiophene, benzothiophene, among others).

An "amine" is an organic compound having the formula $NR^6R^7R^8$, $NHR^6R^7$, $NH_2R^6$, or $NH_3$, wherein $R^6$, $R^7$, and $R^8$ are provided herein. Aliphatic amines are amines which do not have aromatic groups. Aromatic amines are amines which have aromatic groups (either containing or not containing the amine nitrogen atom). Acyclic amines are amines in which the amine nitrogen atom is not contained in a ring (but can have a ring, aliphatic or aromatic, as or within $R^6$, $R^7$, and/or $R^8$). Cyclic amines are amines wherein the amine nitrogen atom is incorporated within a ring (either an aliphatic ring or aromatic ring). Aliphatic cyclic amines are cyclic amines wherein the amine nitrogen atom is incorporated within an aliphatic ring (e.g. pyrrolidine, piperidine, among others). Aromatic cyclic amines are amines wherein the amine nitrogen atom is incorporated within an aromatic ring or aromatic ring system (e.g. pyridine, pyrrole, indole, among others).

A "phosphine" is an organic compound having the formula $PR^9R^{10}R^{11}$, $PHR^9R^{10}$, or $PH_2R^9$, wherein $R^9$, $R^{10}$, and $R^{11}$ are provided herein. Aliphatic phosphines are phosphines which do not have aromatic groups. Aromatic phosphines are phosphines which have aromatic groups (either containing or not containing the phosphine phosphorus atom). Acyclic phosphines are phosphines in which the phosphine phosphorus atom is not contained in a ring (but can have a ring, aliphatic or aromatic, as or within $R^9$, $R^{10}$, and/or $R^{11}$). Cyclic phosphines are phosphines wherein the phosphine phosphorus atom is incorporated within a ring (either an aliphatic ring or aromatic ring). Aliphatic cyclic phosphines are cyclic phosphines wherein the phosphine phosphorus atom is incorporated within an aliphatic ring (e.g. phospholane, phosphinane, among others). Aromatic cyclic phosphines are phosphines wherein the phosphine phosphorus atom is incorporated within an aromatic ring or aromatic ring system (e.g. phosphole, among others).

A "phosphite" is an organic compound having the formula $P(OR^{12})(OR^{13})(OR^{14})$ or $PH(O)(OR^{12})(OR^{13})$, wherein $R^{12}$, $R^{13}$, and $R^{14}$ are provided herein. Aliphatic phosphites are phosphites which do not have aromatic groups. Aromatic phosphites are phosphites which have aromatic groups (either containing or not containing the phosphite phosphorus atom). Acyclic phosphites are phosphites in which the phosphite phosphorus atom is not contained in a ring (but can have a ring, aliphatic or aromatic, as or within $R^{12}$, $R^{13}$, and/or $R^{14}$). Cyclic phosphites are phosphites wherein the phosphite phosphorus atom is incorporated within a ring (either an aliphatic ring or aromatic ring). Aliphatic cyclic phosphites are cyclic phosphites wherein the phosphite phosphorus atom is incorporated within an aliphatic ring. Aromatic cyclic phosphites are phosphites wherein the phosphite phosphorus atom is incorporated within an aromatic ring or aromatic ring system.

The term "cyclic" as compared to an "acyclic" when referring to an ether, thioether, amine, phosphine, or phosphite is used to refer to a compound in which the heteroatom O, S, N, or P, respectively, is encompassed within a cyclic structure, which also encompasses the $R^2$ and $R^3$ groups of the ether $R^2-O-R^3$, the $R^4$ and $R^5$ groups of the thioether $R^4-S-R^5$, any combination of $R^6$, $R^7$, and $R^8$ of the amine $NR^6R^7R^8$ or $NHR^6R^7$, any combination of $R^9$, $R^{10}$, and $R^{11}$ of the phosphine $PR^9R^{10}R^{11}$ or $PHR^9R^{10}$, or any combination of $R^{12}$, $R^{11}$, and $R^{14}$ of the phosphite $P(OR^{12})(OR^{13})(OR^{14})$ or $PH(O)(OR^{12})(OR^{13})$. For example, a "cyclic ether" is an analog of the acyclic ether structure $R^2-O-R^3$, in which $R^2$ and $R^3$ are generally as provided above in describing the (acyclic) ether $R^2-O-R^3$, except that $R^2$ and $R^3$ are linked or bonded to each other by removing a hydrogen atom from each of $R^2$ and $R^3$ and forming a bond between $R^2$ and $R^3$ where the hydrogen atoms were removed so as to form a cyclic structure that includes the ether oxygen. Tetrahydrofuran (THF) is a prototypical cyclic ether that can be formally derived by removing a hydrogen atom from each $CH_3$ groups of diethyl ether ($CH_3CH_2OCH_2CH_3$) or a hydrogen atom from each $CH_3$ groups of methyl n-propyl ether ($CH_3CH_2CH_2OCH_3$), followed by linking or bonding the two carbons from which the hydrogen atoms are removed. Similarly, the cyclic ether 2-methyloxetane can be formally derived by removing a hydrogen atom from the $CH_3$ group of one ethyl group of ethyl ether and a hydrogen atom from the CH$_2$ of the other ethyl group of diethyl ether (CH$_3$CH$_2$OCH$_2$CH$_3$), followed by a formal linking of the two carbons from which the hydrogen atoms are removed.

The term "organyl group" is used herein in accordance with the definition specified by IUPAC: an organic substituent group, regardless of functional type, having one free valence at a carbon atom. Similarly, an "organylene group" refers to an organic group, regardless of functional type, derived by removing two hydrogen atoms from an organic compound, either two hydrogen atoms from one carbon atom or one hydrogen atom from each of two different carbon atoms. An "organic group" refers to a generalized group formed by removing one or more hydrogen atoms from carbon atoms of an organic compound. Thus, an "organyl group," an "organylene group," and an "organic group" can contain organic functional group(s) and/or atom(s) other than carbon and hydrogen, that is, an organic group that can comprise functional groups and/or atoms in addition to carbon and hydrogen. For instance, non-limiting examples of atoms other than carbon and hydrogen can include, but is not limited to, halogens, oxygen, sulfur, nitrogen, and phosphorus, among other elements. Non-limiting examples of functional groups include ethers, aldehydes, ketones, esters, sulfides, amines, and phosphines, and so forth. In one aspect, the hydrogen atom(s) removed to form the "organyl group," "organylene group," or "organic group" can be attached to a carbon atom belonging to a functional group, for example, an acyl group (—C(O)R), a formyl group (—C(O)H), a carboxy group (—C(O)OH), a hydrocarboxycarbonyl group (—C(O)OR), a cyano group (—C≡N), a carbamoyl group (—C(O)NH$_2$), a N-hydrocarbylcarbamoyl group (—C(O)NHR), or N,N'-dihydrocarbylcarbamoyl group (—C(O)NR$_2$), among other possibilities. In another aspect, the hydrogen atom(s) removed to form the "organyl group," "organylene group," or "organic group" can be attached to a carbon atom not belonging to, and remote from, a functional group, for example, —CH$_2$C(O)CH$_3$, and —CH$_2$NR$_2$, among other elements. An "organyl group," "organylene group," or "organic group" can be aliphatic, inclusive of being cyclic or acyclic, or can be aromatic. "Organyl groups," "organylene groups," and "organic groups" also can encompass heteroatom-containing rings, heteroatom-containing ring systems, heteroaromatic rings, and heteroaromatic ring systems. "Organyl groups," "organylene groups," and "organic groups" can be linear or branched unless otherwise specified. Finally, it is noted that the "organyl group," "organylene group," or "organic group" definitions include "hydrocarbyl group," "hydrocarbylene group," "hydrocarbon group," respectively, and "alkyl group," "alkylene group," and "alkane group," respectively, as members.

The term "organyl group consisting of inert functional groups" refers to an organyl group wherein the organic functional group(s) and/or atom(s) other than carbon and hydrogen present in the functional group are restricted to those functional group(s) and/or atom(s) other than carbon and hydrogen which do not complex with a metal compound and/or are inert under the process conditions defined herein. Thus, the term or variation of the term "organyl groups consisting of inert functional groups" further defines the particular organyl groups that can be present within the organyl group consisting of inert functional groups. Additionally, the term "organyl group consisting of inert functional groups" can refer to the presence of one or more inert functional groups within the organyl group. The term or variation of the term "organyl group consisting of inert functional group" includes the hydrocarbyl group as a member. Similarly, an "organylene group consisting of inert functional groups" refers to an organic group formed by removing two hydrogen atoms from one or two carbon atoms of an organic compound consisting of inert functional groups and an "organic group consisting of inert functional group" refers to a generalized organic group consisting of inert functional groups formed by removing one or more hydrogen atoms from one or more carbon atoms of an organic compound consisting of inert functional groups.

For purposes of this application, an "inert functional group" is a group having a free valence on a heteroatom which does not substantially interfere with the process described herein in which the material having an inert functional group takes part and/or does not complex with the metal compound of the metal complex. The term "does not complex with the metal compound" can include groups that could complex with a metal compound but in particular molecules described herein may not complex with a metal compound due to its positional relationship within a ligand. Thus, the inertness of a particular functional group is not only related to the functional group's inherent inability to complex the metal compound but can also be related to the functional group's position within the metal complex. Non-limiting examples of inert functional groups which do not substantially interfere with processes described herein can include a halide (fluoride, chloride, bromide, and iodide), nitro, hydrocarboxy groups (e.g, alkoxy, and/or aroxy, among others), and/or hydrocarbosulfidyl groups (e.g., RS—), among others.

The term "hydrocarbon" whenever used in this specification and claims refers to a compound containing only carbon and hydrogen. Other identifiers can be utilized to indicate the presence of particular groups in the hydrocarbon (e.g. halogenated hydrocarbon indicates that the presence of one or more halogen atoms replacing an equivalent number of hydrogen atoms in the hydrocarbon). The term "hydrocarbyl group" is used herein in accordance with the definition specified by IUPAC: a univalent group formed by removing a hydrogen atom from a hydrocarbon (that is, a group containing only carbon and hydrogen). Non-limiting examples of hydrocarbyl groups include ethyl, phenyl, tolyl, propenyl, and the like. Similarly, a "hydrocarbylene group" refers to a group formed by removing two hydrogen atoms from a hydrocarbon, either two hydrogen atoms from one carbon atom or one hydrogen atom from each of two different carbon atoms. Therefore, in accordance with the terminology used herein, a "hydrocarbon group" refers to a generalized group formed by removing one or more hydrogen atoms (as necessary for the particular group) from a hydrocarbon. A "hydrocarbyl group," "hydrocarbylene group," and "hydrocarbon group" can be acyclic or cyclic groups, and/or can be linear or branched. A "hydrocarbyl group," "hydrocarbylene group," and "hydrocarbon group" can include rings, ring systems, aromatic rings, and aromatic ring systems, which contain only carbon and hydrogen. "Hydrocarbyl groups," "hydrocarbylene groups," and "hydrocarbon groups" include, by way of example, aryl, arylene, arene groups, alkyl, alkylene, alkane group, cycloalkyl, cycloalkylene, cycloalkane groups, aralkyl, aralkylene, and aralkane groups, respectively, among other groups as members.

An aliphatic compound is an acyclic or cyclic, saturated or unsaturated, carbon compound, excluding aromatic compounds. An "aliphatic group" is a generalized group formed by removing one or more hydrogen atoms (as necessary for the particular group) from the carbon atom of an aliphatic compound. Aliphatic compounds and aliphatic groups can contain organic functional group(s) and/or atom(s) other than carbon and hydrogen.

The term "alkane" whenever used in this specification and claims refers to a saturated hydrocarbon compound. Other identifiers can be utilized to indicate the presence of particular groups in the alkane (e.g. halogenated alkane indicates that the presence of one or more halogen atoms replacing an equivalent number of hydrogen atoms in the alkane). The term "alkyl group" is used herein in accordance with the definition specified by IUPAC: a univalent group formed by removing a hydrogen atom from an alkane. Similarly, an "alkylene group" refers to a group formed by removing two hydrogen atoms from an alkane (either two hydrogen atoms from one carbon atom or one hydrogen atom from two different carbon atoms). An "alkane group" is a general term that refers to a group formed by removing one or more hydrogen atoms (as necessary for the particular group) from an alkane. An "alkyl group," "alkylene group," and "alkane group" can be acyclic or cyclic groups, and/or can be linear or branched unless otherwise specified. Primary, secondary, and tertiary alkyl group are derived by removal of a hydrogen atom from a primary, secondary, tertiary carbon atom, respectively, of an alkane. The n-alkyl group derived by removal of a hydrogen atom from a terminal carbon atom of a linear alkane. The groups $RCH_2$ (where R is not H), $R_2CH$ (where R is not H), and $R_3C$ (where R is not H) are primary, secondary, and tertiary alkyl groups, respectively.

A "cycloalkane" is a saturated cyclic hydrocarbon, with or without side chains, for example, cyclobutane. Unsaturated cyclic hydrocarbons having one or more endocyclic double or one triple bond are called cycloalkenes and cycloalkynes, respectively. Cycloalkenes and cycloalkynes having only one, only two, only three, and so forth, endocyclic double or triple bonds can be identified by use of the term "mono," "di," "tri," and so forth, within the name of the cycloalkene or cycloalkyne. Cycloalkenes and cycloalkynes can further identify the position of the endocyclic double or triple bonds. Other identifiers can be utilized to indicate the presence of particular groups in the cycloalkane (e.g. halogenated cycloalkane indicates the presence of one or more halogen atoms replacing an equivalent number of hydrogen atoms in the cycloalkane).

A "cycloalkyl group" is a univalent group derived by removing a hydrogen atom from a ring carbon atom of a cycloalkane. For example, a 1-methylcyclopropyl group and a 2-methylcyclopropyl group are illustrated as follows.

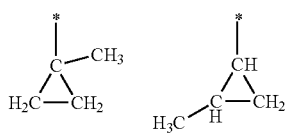

Similarly, a "cycloalkylene group" refers to a group derived by removing two hydrogen atoms from a cycloalkane, at least one of which is a ring carbon. Thus, a "cycloalkylene group" includes both a group derived from a cycloalkane in which two hydrogen atoms are formally removed from the same ring carbon, a group derived from a cycloalkane in which two hydrogen atoms are formally removed from two different ring carbons, and a group derived from a cycloalkane in which a first hydrogen atom is formally removed from a ring carbon and a second hydrogen atom is formally removed from a carbon atom that is not a ring carbon. A "cycloalkane group" refers to a generalized group formed by removing one or more hydrogen atoms (as necessary for the particular group and at least one of which is a ring carbon) from a cycloalkane. It should be noted that according to the definitions provided herein, general cycloalkane groups (including cycloalkyl groups and cycloalkylene groups) include those having zero, one, or more than one hydrocarbyl substituent groups attached to a cycloalkane ring carbon atom (e.g. a methylcyclopropyl group) and is member of the group of hydrocarbon groups. However, when referring to a cycloalkane group having a specified number of cycloalkane ring carbon atoms (e.g. cyclopentane group or cyclohexane group, among others), the base name of the cycloalkane group having a defined number of cycloalkane ring carbon atoms refers to the unsubstituted cycloalkane group (including having no hydrocarbyl groups located on cycloalkane group ring carbon atom). Consequently, a substituted cycloalkane group having a specified number of ring carbon atoms (e.g. substituted cyclopentane or substituted cyclohexane, among others) refers to the respective group having one or more substituent groups (including halogens, hydrocarbyl groups, or hydrocarboxy groups, among other substituent groups) attached to a cycloalkane group ring carbon atom. When the substituted cycloalkane group having a defined number of cycloalkane ring carbon atoms is a member of the group of hydrocarbon groups (or a member of the general group of cycloalkane groups), each substituent of the substituted cycloalkane group having a defined number of cycloalkane ring carbon atoms is limited to hydrocarbyl substituent group. One can readily discern and select general groups, specific groups, and/or individual substituted cycloalkane group(s) having a specific number of ring carbons atoms which can be utilized as member of the hydrocarbon group (or a member of the general group of cycloalkane groups).

The term "olefin" whenever used in this specification and claims refers to compounds that have at least one carbon-carbon double bond that is not part of an aromatic ring or ring system. The term "olefin" includes aliphatic and aromatic, cyclic and cyclic, and/or linear and branched compounds having at least one carbon-carbon double bond that is not part of an aromatic ring or ring system unless specifically stated otherwise. The term "olefin," by itself, does not indicate the presence or absence of heteroatoms and/or the presence or absence of other carbon-carbon double bonds unless explicitly indicated. Olefins having only one, only two, only three, and so forth, carbon-carbon double bonds can be identified by use of the term "mono," "di," "tri," and so forth, within the name of the olefin. The olefins can be further identified by the position of the carbon-carbon double bond(s).

The term "alkene" whenever used in this specification and claims refers to a hydrocarbon olefin that has at least one non-aromatic carbon-carbon double bond. The term "alkene" includes aliphatic or aromatic (an alkene having an aromatic substituent within the compound), cyclic or acyclic, and/or linear and branched compounds having at least one non-aromatic carbon-carbon double bond unless expressly stated otherwise. Alkenes having only one, only two, only three, and so forth, carbon double bonds can be identified by use of the term "mono," "di," "tri," and so forth, within the name. For example, alkamonoenes, alkadienes, and alkatrienes refer to a linear or branched hydrocarbon olefins having only one carbon-carbon double bond (general formula $C_nH_{2n}$), only two carbon-carbon double bonds (general formula $CnH_{2n-2}$), and only three carbon-carbon double bonds (general formula $C_nH_{2n-4}$), respectively. Alkenes can be further identified by the position of the carbon-carbon double bond(s). Other identifiers can be utilized to indicate the presence or absence of particular groups within an alkene. For example, a haloalkene refers to an alkene having one or more hydrogen atoms replace with a halogen atom.

An "alkenyl group" is a univalent group derived from an alkene by removal of a hydrogen atom from any carbon atom of the alkene. Thus, "alkenyl group" includes groups in which the hydrogen atom is formally removed from a sp2 hybridized (olefinic) carbon atom and groups in which the hydrogen atom is formally removed from any other carbon atom. For example and unless otherwise specified, propen-1-yl (—CH=CHCH$_3$), propen-2-yl [(CH$_3$)C=CH$_2$], and propen-3-yl (—CH$_2$CH=CH$_2$) groups are all encompassed with the term "alkenyl group." Similarly, an "alkenylene group" refers to a group formed by formally removing two hydrogen atoms from an alkene, either two hydrogen atoms from one carbon atom or one hydrogen atom from two different carbon atoms. An "alkene group" refers to a generalized group formed by removing one or more hydrogen atoms (as necessary for the particular group) from an alkene. When the hydrogen atom is removed from a carbon atom participating in a carbon-carbon double bond, the regiochemistry of the carbon from which the hydrogen atom is removed, and regiochemistry of the carbon-carbon double bond can both be specified. Alkenyl groups can also have more than one such multiple bond. The alkene group can also be further identified by the position of the carbon-carbon double bond(s). Other identifiers can be utilized to indicate the presence or absence of particular groups within an alkene group. For example, a haloalkene group refers to an alkene group having one or more hydrogen atoms replaced with a halogen atom.

The term "alkyne" is used in this specification and claims to refer to a hydrocarbon compound that has at least one non-aromatic carbon-carbon triple bond. The term "alkyne" includes aliphatic or aromatic (an alkyne having an aromatic substituent within the compound), cyclic or acyclic, and/or linear and branched compounds having at least one non-aromatic carbon-carbon triple bond unless expressly stated otherwise. Alkynes having only one, only two, only three, and so forth, carbon-carbon triple bonds can be identified by use of the term "mono," "di," "tri," and so forth, within the name. For example, alkamonoynes, alkadiynes, and alkatriynes refer to a linear or branched hydrocarbon olefins having only one carbon-carbon triple bond (general formula $C_nH_{2n-2}$), only two carbon-carbon triple bonds (general formula $C_nH_{2n-6}$), and only three carbon-carbon triple bonds (general formula $C_nH_{2n-10}$), respectively. Alkynes can be further identified by the position of the carbon-carbon triple bond(s). Other identifiers can be utilized to indicate the presence or absence of particular groups within an alkyne. For example, a haloalkyne refers to an alkyne having one or more hydrogen atoms replace with a halogen atom.

An "alkynyl group" is a univalent group derived from an alkyne by removal of a hydrogen atom from any carbon atom of the alkyne. Thus, "alkynyl group" includes groups in which the hydrogen atom is formally removed from a sp hybridized (acetylenic) carbon atom and groups in which the hydrogen atom is formally removed from any other carbon atom. For example and unless otherwise specified, propyn-1-yl (—C≡CCH$_3$) and propyn-1-yl (HC≡CCH$_2$—) groups are all encompassed with the term "alkynyl group." Similarly, an "alkynylene group" refers to a group formed by formally removing two hydrogen atoms from an alkyne, either two hydrogen atoms from one carbon atom if possible or one hydrogen atom from two different carbon atoms. An "alkyne group" refers to a generalized group formed by removing one or more hydrogen atoms (as necessary for the particular group) from an alkyne. Alkynyl groups can also have more than one such multiple bond. The alkyne group can also be further identified by the position of the carbon-carbon triple bond(s). Other identifiers can be utilized to indicate the presence or absence of particular groups within an alkyne group. For example, a haloalkyne group refers to an alkyne group having one or more hydrogen atoms replaced with a halogen atom.

A "heterocyclic compound" is a cyclic compound having at least two different elements as ring member atoms. For example, heterocyclic compounds can comprise rings containing carbon and nitrogen (for example, tetrahydropyrrole and pyrrole, among others), carbon and oxygen (for example, tetrahydrofuran and furan, among others), or carbon and sulfur (for example, tetrahydrothiophene and thiophene, among others). Heterocyclic compounds and heterocyclic groups can be either aliphatic or aromatic.

A "heterocyclyl group" is a univalent group formed by removing a hydrogen atom from a heterocyclic ring or ring system carbon atom of a heterocyclic compound. By specifying that the hydrogen atom is removed from a heterocyclic ring or ring system carbon atom, a "heterocyclyl group" is distinguished from a "cycloheteryl group," in which a hydrogen atom is removed from a heterocyclic ring or ring system heteroatom. For example, a pyrrolidin-2-yl group illustrated below is one example of a "heterocyclyl group," and a pyrrolidin-1-yl group illustrated below is one example of a "cycloheteryl" group."

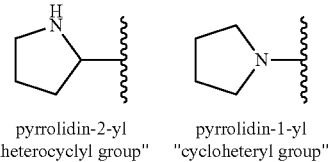

pyrrolidin-2-yl "heterocyclyl group"   pyrrolidin-1-yl "cycloheteryl group"

Similarly, a "heterocyclylene group" or more simply, a "heterocyclene group," refers to a group formed by removing two hydrogen atoms from a heterocyclic compound, at least one of which is from a heterocyclic ring or ring system carbon. Thus, in a "heterocyclylene group," at least one hydrogen is removed from a heterocyclic ring or ring system carbon atom, and the other hydrogen atom can be removed from any other carbon atom, including for example, the same heterocyclic ring or ring system carbon atom, a different heterocyclic ring or ring system ring carbon atom, or a non-ring carbon atom. A "heterocyclic group" refers to a generalized group formed by removing one or more hydrogen atoms (as necessary for the particular group and at least one of which is a heterocyclic ring carbon atom) from a heterocyclic compound.

A "cycloheteryl group" is a univalent group formed by removing a hydrogen atom from a heterocyclic ring or ring system heteroatom of a heterocyclic compound, as illustrated herein. By specifying that the hydrogen atom is removed from a heterocyclic ring or ring system heteroatom and not from a ring carbon atom, a "cycloheteryl group" is distinguished from a "heterocyclyl group" in which a hydrogen atom is removed from a heterocyclic ring or ring system carbon atom. Similarly, a "cycloheterylene group" refers to a group formed by removing two hydrogen atoms from an heterocyclic compound, at least one of which is removed from a heterocyclic ring or ring system heteroatom of the heterocyclic compound; the other hydrogen atom can be removed from any other atom, including for example, a heterocyclic ring or ring system ring carbon atom, another heterocyclic ring or ring system heteroatom, or a non-ring atom (carbon or heteroatom). A "cyclohetero group" refers to a generalized group formed by removing one or more hydrogen atoms (as necessary for the particular group and at least one of which is from a heterocyclic ring or ring system heteroatom) from a heterocyclic compound.

An aromatic compound is a compound containing a cyclically conjugated double bond system that follows the Hückel (4n+2) rule and contains (4n+2) pi-electrons, where n is an integer from 1 to 5. Aromatic compounds include "arenes" (hydrocarbon aromatic compounds) and "heteroarenes," also termed "hetarenes" (heteroaromatic compounds formally derived from arenes by replacement of one or more methine (—C=) carbon atoms of the cyclically conjugated double bond system with a trivalent or divalent heteroatoms, in such a way as to maintain the continuous pi-electron system characteristic of an aromatic system and a number of out-of-plane pi-electrons corresponding to the Hückel rule (4n+2). While arene compounds and heteroarene compounds are mutually exclusive members of the group of aromatic compounds, a compound that has both an arene group and a heteroarene group are generally considered a heteroarene compound. Aromatic compounds, arenes, and heteroarenes can be monocyclic (e.g., benzene, toluene, furan, pyridine, methylpyridine) or polycyclic unless otherwise specified. Polycyclic aromatic compounds, arenes, and heteroarenes, include, unless otherwise specified, compounds wherein the aromatic rings can be fused (e.g., naphthalene, benzofuran, and indole), compounds where the aromatic groups can be separate and joined by a bond (e.g., biphenyl or 4-phenylpyridine), or compounds where the aromatic groups are joined by a group containing linking atoms (e.g., carbon—the methylene group in diphenylmethane; oxygen—diphenyl ether; nitrogen-triphenyl amine; among other linking groups). As disclosed herein, the term "substituted" can be used to describe an aromatic group, an arene, or a heteroarene wherein a non-hydrogen moiety formally replaces a hydrogen in the compound, and is intended to be non-limiting.

An "aromatic group" refers to a generalized group formed by removing one or more hydrogen atoms (as necessary for the particular group and at least one of which is an aromatic ring carbon atom) from an aromatic compound. For a univalent "aromatic group," the removed hydrogen atom must be from an aromatic ring carbon. For an "aromatic group" formed by removing more than one hydrogen atom from an aromatic compound, at least one hydrogen atom must be from an aromatic hydrocarbon ring carbon. Additionally, an "aromatic group" can have hydrogen atoms removed from the same ring of an aromatic ring or ring system (e.g., phen-1,4-ylene, pyridin-2,3-ylene, naphth-1,2-ylene, and benzofuran-2,3-ylene), hydrogen atoms removed from two different rings of a ring system (e.g., naphth-1,8-ylene and benzofuran-2,7-ylene), or hydrogen atoms removed from two isolated aromatic rings or ring systems (e.g., bis(phen-4-ylene)methane).

An arene is an aromatic hydrocarbon, with or without side chains (e.g. benzene, toluene, or xylene, among others). An "aryl group" is a group derived from the formal removal of a hydrogen atom from an aromatic ring carbon of an arene. It should be noted that the arene can contain a single aromatic hydrocarbon ring (e.g., benzene, or toluene), contain fused aromatic rings (e.g., naphthalene or anthracene), and contain one or more isolated aromatic rings covalently linked via a bond (e.g., biphenyl) or non-aromatic hydrocarbon group(s) (e.g., diphenylmethane). One example of an "aryl group" is ortho-tolyl (o-tolyl), the structure of which is shown here.

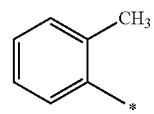

Similarly, an "arylene group" refers to a group formed by removing two hydrogen atoms (at least one of which is from an aromatic ring carbon) from an arene. An "arene group" refers to a generalized group formed by removing one or more hydrogen atoms (as necessary for the particular group and at least one of which is an aromatic ring carbon) from an arene. However, if a group contains separate and distinct arene and heteroarene rings or ring systems (e.g. the phenyl and benzofuran moieties in 7-phenylbenzofuran) its classification depends upon the particular ring or ring system from which the hydrogen atom was removed, that is, an arene group if the removed hydrogen came from the aromatic hydrocarbon ring or ring system carbon atom (e.g. the 2 carbon atom in the phenyl group of 6-phenylbenzofuran) and a heteroarene group if the removed hydrogen carbon came from a heteroaromatic ring or ring system carbon atom (e.g. the 2 or 7 carbon atom of the benzofuran group or 6-phenylbenzofuran). It should be noted that according the definitions provided herein, general arene groups (including an aryl group and an arylene group) include those having zero, one, or more than one hydrocarbyl substituent groups located on an aromatic hydrocarbon ring or ring system carbon atom (e.g. a toluene group or a xylene group, among others) and is a member of the group of hydrocarbon groups. However, a phenyl group (or phenylene group) and/or a naphthyl group (or naphthylene group) refer to the specific unsubstituted arene groups (including no hydrocarbyl group located on an aromatic hydrocarbon ring or ring system carbon atom). Consequently, a substituted phenyl group or substituted naphthyl group refers to the respective arene group having one or more substituent groups (including halogens, hydrocarbyl groups, or hydrocarboxy groups, among others) located on an aromatic hydrocarbon ring or ring system carbon atom. When the substituted phenyl group and/or substituted naphthyl group is a member of the group of hydrocarbon groups (or a member of the general group of arene groups), each substituent is limited to a hydrocarbyl substituent group. One can readily discern and select general substituted phenyl and/or substituted naphthyl groups, specific substituted phenyl and/or substituted naphthyl groups, and/or individual substituted phenyl or substituted naphthyl groups which can be utilized as a member of the group of hydrocarbon groups (or a member of the general group of arene groups).

A heteroarene is aromatic compound, with or without side chains, having a heteroatom within the aromatic ring or aromatic ring system (e.g. pyridine, indole, or benzofuran, among others). A "heteroaryl group" is a class of "heterocyclyl group" and is a univalent group formed by removing a hydrogen atom from a heteroaromatic ring or ring system carbon atom of a heteroarene compound. By specifying that the hydrogen atom is removed from a ring carbon atom, a "heteroaryl group" is distinguished from an "arylheteryl group," in which a hydrogen atom is removed from a heteroaromatic ring or ring system heteroatom. For example, an indol-2-yl group illustrated below is one example of a "heteroaryl group," and an indol-1-yl group illustrated below is one example of an "arylheteryl" group."

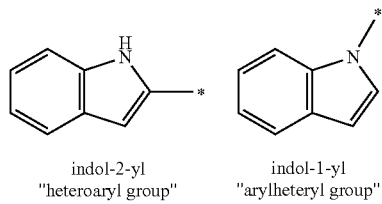

indol-2-yl
"heteroaryl group"

indol-1-yl
"arylheteryl group"

Similarly, a "heteroarylene group" refers to a group formed by removing two hydrogen atoms from a heteroarene compound, at least one of which is from a heteroarene ring or ring system carbon atom. Thus, in a "heteroarylene group," at least one hydrogen is removed from a heteroarene ring or ring system carbon atom, and the other hydrogen atom can be removed from any other carbon atom, including for example, a heteroarene ring or ring system carbon atom, or a non-heteroarene ring or ring system atom. A "heteroarene group" refers to a generalized group formed by removing one or more hydrogen atoms (as necessary for the particular group and at least one of which is a heteroarene ring or ring system carbon atom) from a heteroarene compound. If a hydrogen atom is removed from a heteroaromatic ring or ring system heteroatom and from a heteroaromatic ring or ring system carbon atom or an aromatic hydrocarbon ring or ring system carbon atom, the group is classified as an "arylheterylene group" or an "arylhetero group."

An "arylheteryl group" is a class of "cycloheteryl group" and is a univalent group formed by removing a hydrogen atom from a heteroaromatic ring or ring system heteroatom, as illustrated. By specifying that the hydrogen atom is removed from of a heteroaromatic ring or ring system heteroatom and not from a heteroaromatic ring or ring system carbon atom, an "arylheteryl group" is distinguished from a "heteroaryl group" in which a hydrogen atom is removed from a heteroaromatic ring or a ring system carbon atom. Similarly, an "arylheterylene group" refers to a group formed by removing two hydrogen atoms from a heteroaryl compound, at least one of which is removed from a heteroaromatic ring or ring system heteroatom of the heteroaryl compound; the other hydrogen atom can be removed from any other atom, including for example, a heteroaromatic ring or ring system carbon atom, another heteroaromatic ring or ring system heteroatom, or a non-ring atom (carbon or heteroatom) from a heteroaromatic compound. An "arylhetero group" refers to a generalized group formed by removing one or more hydrogen atoms (as necessary for the particular group and at least one of which is from a heteroaromatic ring or ring system) heteroatom from a heteroarene compound.

An "aralkyl group" is an aryl-substituted alkyl group having a free valance at a non-aromatic carbon atom (e.g. a benzyl group, or a 2-phenyleth-1-yl group, among others). Similarly, an "aralkylene group" is an aryl-substituted alkylene group having two free valencies at a single non-aromatic carbon atom or a free valence at two non-aromatic carbon atoms while an "aralkane group" is a generalized an aryl-substituted alkane group having one or more free valencies at a non-aromatic carbon atom(s). A "heteroaralkyl group" is a heteroaryl-substituted alkyl group having a free valence at a non-heteroaromatic ring or ring system carbon atom. Similarly a "heteroaralkylene group" is a heteroaryl-substituted alkylene group having two free valencies at a single non-heteroaromatic ring or ring system carbon atom or a free valence at two non-heteroaromatic ring or ring system carbon atoms while a "heteroaralkane group" is a generalized aryl-substituted alkane group having one or more free valencies at a non-heteroaromatic ring or ring system carbon atom(s). It should be noted that according the definitions provided herein, general aralkane groups include those having zero, one, or more than one hydrocarbyl substituent groups located on an aralkane aromatic hydrocarbon ring or ring system carbon atom and is a member of the group of hydrocarbon groups. However, specific aralkane groups specifying a particular aryl group (e.g. the phenyl group in a benzyl group or a 2-phenylethyl group, among others) refer to the specific unsubstituted aralkane groups (including no hydrocarbyl group located on the aralkane aromatic hydrocarbon ring or ring system carbon atom). Consequently, a substituted aralkane group specifying a particular aryl group refers to a respective aralkane group having one or more substituent groups (including halogens, hydrocarbyl groups, or hydrocarboxy groups, among others). When the substituted aralkane group specifying a particular aryl group is a member of the group of hydrocarbon groups (or a member of the general group of aralkane groups), each substituent is limited to a hydrocarbyl substituent group. One can readily discern and select substituted aralkane groups specifying a particular aryl group which can be utilized as a member of the group of hydrocarbon groups (or a member of the general group of aralkane groups).

A "halide" has its usual meaning; therefore, examples of halides include fluoride, chloride, bromide, and iodide.

An "organoheteryl group" is a univalent group containing carbon, which are thus organic, but which have their free valence at an atom other than carbon. Thus, organoheteryl and organyl groups are complementary and mutually exclusive. Organoheteryl groups can be cyclic or acyclic, and/or aliphatic or aromatic, and thus encompasses aliphatic "cycloheteryl groups" (e.g. pyrrolidin-1-yl or morpholin-1-yl, among others), aromatic "arylheteryl groups" (e.g. pyrrol-1-yl or indol-1-yl, among others), and acyclic groups (e.g. organylthio, trihydrocarbylsilyl, aryloxy, or alkoxy, among others). Similarly, an "organoheterylene group" is a divalent group containing carbon and at least one heteroatom having two free valencies, at least one of which is at a heteroatom. An "organohetero group" is a generalized group containing carbon and at least one heteroatom having one or more free valencies (as necessary for the particular group and at least one of which is at a heteroatom) from an organohetero compound.

If a compound or group contains more than one moiety it is formally a member of the group having the highest naming priority as stipulated by IUPAC. For example 4-phenylpyridine is a heteroaromatic compound and a 4-(phen-2-ylene)pyridin-2-yl group is heteroaromatic group because the highest naming group is the pyridine group and the pyridin-2-yl group respectively.

In some instances, reference can be made to "cyclic groups." Unless otherwise specified, "cyclic groups" include aromatic and aliphatic groups having a ring structure, including homocyclic and heterocyclic groups, and "cyclo" is a prefix used in names to designate a ring structure.

In an aspect, this disclosure provides synthetic methods for preparing transition metal carboxylate compositions. In an aspect the disclosed synthetic methods eliminate the requirement for reaction of a transition metal acetate or other carboxylate complexes with a carboxylic acid. Specifically, this disclosure encompasses a synthetic route to a desired transition metal carboxylate composition, in which a Group 1 or Group 2 carboxylate and a transition metal precursor are combined in a solvent. In an aspect, but not as a limitation, the method(s) of this disclosure can be utilized to produce chromium(III) carboxylates, according to Equation 1.

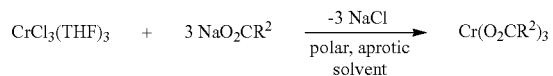

(1)

In an embodiment, this process can produce by-products (e.g. sodium chloride as illustrated in Equation 1) which can be separated from the desired transition metal carboxylate (e.g. a chromium(III) carboxylate as illustrated in Eq.1). The general method for producing the transition metal carboxylate compositions can be extended to encompass the preparation of other transition metal compositions having various transition metals (e.g. Ti, Zr, V, Nb, Cr, Mn, Fe, Co, and Cu, among others) and various carboxylate containing moieties (e.g. naphthanates, benzoates, and oxalates, among others).

In an aspect, this disclosure provides for a transition metal carboxylate composition. In an embodiment, the transition metal carboxylate composition can be, can comprise, or can consist essentially of, the product of any process to produce a transition metal carboxylate composition described herein. In another embodiment, the transition metal carboxylate composition can be described as having particular spectroscopic features. In some embodiments, the transition metal carboxylate composition can have particular infrared spectrum features. In other embodiments, the transition metal carboxylate composition can have particular high energy X-ray diffraction spectral features. In yet other embodiments, the transition metal carboxylate composition can have a high-energy X-ray diffraction spectrum which compares favorably to a calculated high-energy X-ray diffraction spectrum of a theoretical model of a mononuclear transition metal carboxylate.

In an aspect, the present disclosure describes a process for preparing a transition metal carboxylate composition comprising: contacting 1) a transition metal precursor, 2) a Group 1 or Group 2 metal carboxylate, and 3) a solvent to form a transition metal carboxylate. In an embodiment, the transition metal carboxylate can be formed under conditions capable of forming a transition metal carboxylate. In some embodiments, the transition metal, Group 1 or Group 2 metal carboxylate, and solvent can be contacted under particular contact conditions. In some embodiments, a solution comprising the transition metal carboxylate can be formed. Generally, the transition metal precursor, the Group 1 or Group 2 metal carboxylate, the solvent, the step(s) of contacting, the contact conditions, and the condition(s) capable of forming the transition metal carboxylate, among other features of the process to prepare the transition metal carboxylate composition (e.g. isolation and/or purification step or methods, among others) are independent elements of the process to produce a transition metal carboxylate composition. Any herein described aspects and/or embodiments, of the transition metal precursor described herein, the Group 1 or Group 2 metal carboxylate described herein, the solvent described herein, the step(s) of contacting described herein, the contact conditions described herein, the condition(s) capable of forming the transition metal carboxylate described herein, and other features of the process to prepare the transition metal carboxylate composition (e.g. isolation and/or purification step or methods, among others) described herein can be utilized to further describe the process to produce the transition metal carboxylate composition.

In a non-limiting aspect, the transition metal carboxylate (or transition metal carboxylate composition) can have particular properties. These properties are independently described herein and can be utilized to further describe the process for preparing the transition metal carboxylate composition.

In another aspect, the present disclosure describes a process for preparing a chromium carboxylate composition (e.g. a chromium(III) carboxylate composition) comprising: contacting 1) a chromium precursor (e.g. a chromium(III) precursor), 2) a Group 1 or Group 2 metal carboxylate, and 3) a solvent to form a chromium carboxylate (e.g. a chromium(III) carboxylate). In an embodiment, the chromium carboxylate can be formed under conditions capable of forming a chromium carboxylate. In some embodiments, the chromium precursor, Group 1 or Group 2 metal carboxylate, and solvent can be contacted under particular contact conditions. In some embodiments, a solution comprising the chromium carboxylate can be formed. Generally, the chromium precursor, the Group 1 or Group 2 metal carboxylate, the solvent, the step(s) of contacting, the contact conditions, the contact conditions, and the condition(s) capable of forming the chromium carboxylate, among other features of the process to prepare the chromium carboxylate composition (e.g. isolation and/or purification step or methods, among others) are independent elements of the process to produce a chromium carboxylate composition. Any aspects or any embodiments of the chromium precursor described herein, the Group 1 or Group 2 metal carboxylate described herein, the solvent described herein, the step(s) of contacting described herein, the contact conditions described herein, the condition(s) capable of forming the chromium carboxylate described herein, and other features of the process to prepare the chromium carboxylate composition (e.g. isolation and/or purification step or methods, among others) described herein can be utilized to further describe the process to produce the chromium carboxylate composition.

In a non-limiting aspect, the chromium carboxylate (or chromium carboxylate composition) may have particular properties. These properties are independently described herein and can be utilized to further describe the process for preparing the chromium carboxylate composition.

In accordance with an aspect of this disclosure, the method for making a transition metal carboxylate composition utilizes a transition metal precursor. Generally, the transitional metal precursor comprises a transition metal complex which can be neutral, cationic or anionic. When the transition metal complex is neutral the transition metal complex is the transition metal precursor. When the transition metal complex is cationic, the transition metal precursor comprises an appropriate number of transition metal complexes and anionic species to provide a neutral transition metal precursor. When the transition metal complex is anionic, the transition metal precursor comprises an appropriate number of transition metal complexes and cationic species to provide a neutral transition metal precursor.

Minimally, the transition metal precursor and/or transition metal complex comprises a transition metal. In an embodiment, the transition metal precursor and/or the transition metal complex comprises, consists essentially of, or consists of, a transition metal and an anionic ligand. In another embodiment, the transition metal precursor and/or the transition metal complex can comprise, consists essentially of, or consists of, a transition metal and a neutral ligand. In an embodiment, the transition metal precursor can comprise an anionic transition metal complex; or alternatively, a cationic transition metal complex. In other embodiments, the transition metal precursor can comprise, consists essentially of, or consists of, a cationic transition metal complex and at least one anionic specie; alternatively, an anionic transition metal complex and at least one cationic specie. In an embodiment, the transition metal complex (anionic, cationic, or neutral) can comprise, consists essentially of, or consists of, a transition metal, an anionic ligand, and a neutral ligand. In some embodiments, the transition metal complex (anionic, cationic, or neutral) can comprise, consist essentially of, or consist of, at least one transition metal and at least one anionic ligand; alternatively, at least one transition metal and at least one neutral ligand; or alternatively, at least one transition metal, at least one anionic ligand, and at least one neutral ligand.

In an aspect, the transition metal precursor can have the formula $[((M^B)_{y1}X_{x1}L_l)^m]_q[C^c]_{m1}[A^a]_{m2}$. Generally, within the transition metal precursors, $M^B$ represents a transition metal having an oxidation state of x, y1 represents the number of transition meals having an oxidation state of x, X represents an anionic ligand having a charge of y, x1 represents the number of anionic ligands having a charge of y, L represents a neutral ligand, l represents the number of neutral ligands, $(M^B)_{y1}X_{x1}L_l$ represents a transition metal complex having charge m, q represents the number of transition metal complex having charge m, C represents a cationic species having charge c, m1 represents the number of cationic species having charge c, A represents an anionic species having charge a, and m2 represents the number of anionic species having charge a. The transition metal ($M^B$) having an oxidation state of x, the number of transition metals (y1) having an oxidation state of x, the anionic ligand (X) having a charge of y, the number of anionic ligands (x1) having a charge of y, the neutral ligand (L), the number of neutral ligands (l), the charge (m) on the transition metal complex $((M^B)_{y1}X_{x1}L_l)$, the number (q) of transition metal complexes $((M^B)_{y1}X_{x1}L_l)$, the cationic species (C) having charge c, the number of cationic species having charge c (m1), the anionic species (A) having charge a, and the number of anionic species having charge a (m2) are independently described herein. These independent descriptions can be utilized in any compatible manner and/or combination to further describe the transition metal precursor having the formula $[((M^B)_{y1}X_{x1}L_l)^m]_q[C^c]_{m1}[A^a]_{m2}$. Depending upon the particular values of x (the oxidation state of the transition metal, $M^B$), y1 (the number of transition meals having an oxidation state of x), y (the charge on the anionic ligand, X), x1 (the number of anionic ligands having a charge of y), l (the number of neutral ligands, L), m (the charge on the transition metal complex, $(M^B)_{y1}X_{x1}L_l$), q (the number of transition metal complexes, $(M^B)_{y1}X_{x1}L_l$), c (the charge on the cationic species, C), m1 (the number of cationic species, C), a (the charge on the anionic species, A), and m2 (the number of anionic species, A), there can be other viable general formulas for the transition metal precursor. These other transition metal precursor formulas are provided herein and can be utilized as the transition metal precursor in any applicable aspect and/or embodiment described herein.

In an embodiment, the transition metal precursor can have the formula $[((M^B)_{y1}X_{x1}L_l)^m]_q[C^c][A^a]_{m2}$, $[((M^B)_{y1}X_{x1}L_l)^m]_q[C^c]_{m1}$, $[((M^B)_{y1}X_{x1}L_l)^m]_q[A^a]_{m2}$, $[(M^BL_l)^m]_q[A^a]_{m2}$, $(M^B)_{y1}X_{x1}L_l$, $[(M^BX_xL_l)^m]_q[C^c]_{m1}[A^a]_{m2}$, $[(M^BX_xL_l)^m]_q[C^c]_{m1}$, $[(M^BX_xL_l)^m]_q[A^a]_{m2}$, $M^BX_xL_l$, $[((M^B)_{y1}X_{x1})^m]_q[C^c]_{m1}[A^a]_{m2}$, $[((M^B)_{y1}X_{x1})^m]_q[C^c]_{m1}$, $[((M)_{y1}X_{x1})^m]_q[A^a]_{m2}$, $(M^B)_{y1}X_{x1}$, $[(M^BX_x)^m]_q[C^c]_{m1}[A^a]_{m2}$, $[(M^BX_x)^m]_q[C^c]_{m1}$, $[(M^BX_x)^m]_q[A^a]_{m2}$, or $M^BX_x$. In some embodiments, the transition metal precursor can have the formula $[((M^B)_{y1}X_{x1}L_l)^m]_q[C^c]_{m1}[A^a]_{m2}$, $[((M^B)_{y1}X_{x1}L_l)^m]_q[C^c]_{m1}$, $[((M)_{y1}X_{x1}L_l)^m]_q[A^a]_{m2}$, $[(M^BL_l)^m]_q[A^a]_{m2}$, $(M^B)_{y1}X_{x1}L_l$, $[(M^BX_xL_l)^m]_q[C^c]_{m1}[A^a]_{m2}$, $[(M^BX_xL_l)^m]_q[C^c]_{m1}$, $[(M^BX_xL_l)^m]_q[A^a]_{m2}$, or $M^BX_xL_l$, alternatively, $((M^B)_{y1}X_{x1}L_l$, $[(M^BX_xL_l)^m]_q[C^c]_{m1}[A^a]_{m2}$, $[((M^B)_{y1}X_{x1})^m]_q[C^c]_{m1}$, $[((M^B)_{y1}X_{x1})^m]_q[A^a]_{m2}$, $(M^B)_{y1}X_{x1}$, $[(M^BX_x)^m]_q[C^c]_{m1}[A^a]_{m2}$, $[(M^BX_x)^m]_q[C^c]_{m1}$, $[(M^BX_x)^m]_q[A^a]_{m2}$, or $M^BX_x$; alternatively, $[((M^B)_{y1}X_{x1}L_l)^m]_q[C^c]_{m1}[A^a]_{m2}$, $[((M^B)_{y1}X_{x1}L_l)^m]_q[C^c]_{m1}$, $[((M)_{y1}X_{x1}L_l)^m]_q[A^a]_{m2}$, $[(M^BL_l)^m]_q[A^a]_{m2}$, or $(M^B)_{y1}X_{x1}L_l$; alternatively, $[(M^BX_xL_l)^m]_q[C^c]_{m1}[A^a]_{m2}$, $[(M^BX_xL_l)^m]_q[C^c]_{m1}$, $[(M^BX_xL_l)^m]_q[A^a]_{m2}$, or $M^BX_xL_l$, alternatively, $[((M^B)_{y1}X_{x1})^m]_q[C^c]_{m1}[A^a]_{m2}$, $[((M^B)_{y1}X_{x1})^m]_q[C^c]_{m1}$, $[((M^B)_{y1}X_{x1})^m]_q[A^a]_{m2}$, $(M^B)_{y1}X_{x1}$, or alternatively, $[(M^BX_x)^m]_q[C^c]_{m1}[A^a]_{m2}$, $[(M^BX_x)^m]_q[C^c]_{m1}$, $[(M^BX_x)^m]_q[A^a]_{m2}$, or $M^BX_x$. In other embodiments, the transition metal precursor can have the formula $[((M^B)_{y1}X_{x1}L_l)^m]_q[C^c]_{m1}[A^a]_{m2}$, $[((M^B)_{y1}X_{x1}L_l)^m]_q[C^c]_{m1}$, $[((M^B)_{y1}X_{x1}L_l)^m]_q[A^a]_{m2}$, $[(M^BL_l)^m]_q[A^a]_{m2}$, $(M^B)_{y1}X_{x1}L_l$, $[((M^B)_{y1}X_{x1})^m]_q[C^c]_{m1}[A^a]_{m2}$, $[((M^B)_{y1}X_{x1})^m]_q[C^c]_{m1}$, $[(M^BX_xL_l)^m]_q[A^a]_{m2}$, or $(M^B)_{y1}X_{x1}$; or alternatively, $[(M^BX_xL_l)^m]_q[C^c]_{m1}[A^a]_{m2}$, $[(M^BX_xL_l)^m]_q[C^c]_{m1}$, $[(M^BX_xL_l)^m]_q[A^a]_{m2}$, $M^BX_xL_l$, $[(M^BX_x)^m]_q[C^c]_{m1}[A^a]_{m2}$, $[(M^BX_x)^m]_q[C^c]_{m1}$, $[(M^BX_x)^m]_q[A^a]_{m2}$, or $M^BX_x$. In yet other embodiments, the transition metal precursor can have the formula $[((M^B)_{y1}X_{x1}L_l)^m]_q[C^c]_{m1}[A^a]_{m2}$; alternatively, $[((M^B)_{y1}X_{x1}L_l)^m]_q[C^c]_{m1}$; alternatively, $[((M)_{y1}X_{x1}L_l)^m]_q[A^a]_{m2}$; alternatively, $[(M^BL_l)^m]_q[A^a]_{m2}$; alternatively, $(M^B)_{y1}X_{x1}L_l$; alternatively, $[(M^BX_xL_l)^m]_q[C^c]_{m1}[A^a]_{m2}$; alternatively, $[(M^BX_xL_l)^m]_q[C^c]_{m1}$; alternatively, $[(M^BX_xL_l)^m]_q[A^a]_{m2}$; alternatively, $M^BX_xL_l$; alternatively, $[((M)_{y1}X_{x1})^m]_q[C^c]_{m1}[A^a]_{m2}$; alternatively, $[((M^B)_{y1}X_{x1})^m]_q[C^c]_{m1}$; alternatively, $[((M^B)_{y1}X_{x1})^m]_q[A^a]_{m2}$; alternatively, $(M^B)_{y1}X_{x1}$; alternatively, $[(M^BX_x)^m]_q[C^c]_{m1}[A^a]_{m2}$; alternatively, $[(M^BX_x)^m]_q[C^c]_{m1}$; alternatively, $[(M^BX_x)^m]_q[A^a]_{m2}$; or alternatively, $M^BX_x$.

In an embodiment, the transition metal of the transition metal precursor can comprise, consist essentially of, or consist of, a Group 4-11 metal. In some embodiments, the transition metal of the transition metal precursor can comprise, consist essentially of, or consist of, a Group 5-9 metal; alternatively, a group 4 metal; alternatively, a group 5 metal; alternatively, a group 6 metal; alternatively, a group 7 metal; alternatively, a group 8 metal; alternatively, a group 9 metal; alternatively, a group 10 metal; or alternatively, a group 11 metal. In other embodiments, the transition metal of the transition metal precursor can comprise, consist essentially of, or consist of, Ti, Zr, V, Nb, Cr, Mn, Fe, Co, or Cu; alternatively, Ti, Zr, Cr, Fe, or Co; alternatively, Cr, Fe, or Co; alternatively, Ti; alternatively, Zr; alternatively, Cr; alternatively, Fe; or alternatively, Co. In a particular embodiment, the transition metal can comprise, consist essentially of, or consist of, chromium. In some embodiments, the transition metal precursor can comprise, consist essentially of, or consist of, a chromium precursor. Generally, the transition metal of the transition metal carboxylate can be, comprise, or consist essentially of, the same transition metal as the transition metal of the transition metal precursor.

Generally, the transition metal oxidation state, n, of the transition metal precursor can have any positive oxidation state that the transition metal can take. In an aspect, the transition metal of the transition metal precursor can have an oxidation state from 1 to 6. In some embodiments the transition metal of the transition metal precursor can have an oxidation state of 2, 3, or 4; alternatively, 2 or 3; alternatively, 2; or alternatively, 3. In should be noted that the transition metal oxidation state can be designated as a Roman numeral within parenthesis following the transition metal name (e.g. chromium having an oxidation state of 3 can be designated by chromium(III)). In some non-limiting embodiments, the transition metal of the transition metal precursor can comprise, consist essentially of, or consist of a chromium(II) or a chromium(III); alternatively, a chromium(II); or alternatively, a chromium(III).

The number of transition metal atoms, y1, in the transition metal precursor (or transition metal complex) is a function of the oxidation state of the transition metal atom(s), the charge of the anionic ligand the number of anionic ligands, the charge of the anionic ligand(s), and the charge on the transition metal complex. Generally, the number of transition metal atoms, y1, in the transition metal precursor (or transition metal complex) can be an integer ranging from 1 to 3; alternatively, 1; alternatively, 2; or alternatively, 3.

When the transition metal complex of the transition metal precursor is anionic or cationic (e.g. having the formula $[((M^B)_{y1}X_{x1}L_l)^m]_q[C^c]_{m1}[A^a]_{m2}$, $[((M)_{y1}X_{x1}L_l)^m]_q[C^c]_{m1}$, $[((M)_{y1}X_{x1}L_l)^m]_q[A^a]_{m2}$, $[(M^BL_l)^m]_q[A^a]_{m2}$, $[(M^BX_xL_l)^m]_q[C^c]_{m1}[A^a]_{m2}$, $[(M^BX_xL_l)^m]_q[C^c]_{m1}$, $[(M^BX_xL_l)^m]_q[A^a]_{m2}$, $[(M^B)_{y1}X_{x1})^m]_q[C^c]_{m1}[A^a]_{m2}$, $[((M^B)_{y1}X_{x1})^m]_q[C^c]_{m1}$, $[((M^B)_{y1}X_{x1})^m]_q[A^a]_{m2}$, $[(M^BX_x)^m]_q[C^c]_{m1}[A^a]_{m2}$, $[(M^BX_x)_m]_q[C^c]_{m1}$, and/or $[(M^BX_x)^m]_q[A^a]_{m2}$, among others described herein where m≠0), the number of transition metal atoms (y1) having the oxidation state x, the number of anionic ligands (A) having charge y, and the charge on the anionic or cationic transition metal complex can be related by the equation m=(y*x1)+(x*y1). When the transition metal complex of the transition metal precursor is neutral (e.g. having the formula $(M^B)_{y1}X_{x1}L_l$, $M^BX_xL_l$, $(M^B)_{y1}X_{x1}$, and/or $M^BX_x$, among others where m=0), the number of transition metal atoms (y1) having the oxidation state x and the number of anionic ligands (A) having charge y can be related by the equation x*y1=|y*x1|. In some embodiments when the transition metal complex of the transition metal precursor is neutral (e.g. having the formula $(M^B)_{y1}X_{x1}L_l$, $M^BX_xL_l$, $(M^B)_{y1}X_{x1}$, and/or $M^BX_x$, among others where m=0), the number of transition metal atoms, y1, can be related to the transition metal oxidation state (x) and the anionic ligand (A) charge (y) by the relationship that y1=|y| divided by the greatest common divisor of x and |y|.

In an aspect, each anionic ligand, X, can independently be a halide, nitrate, nitrite, sulfate, sulfite, bisulfate, phosphate, chlorate, cyano, cyanate, thiocyanate, or isothiocyanate. In an embodiment, the each anionic ligand can independently be a halide, nitrate, sulfate, phosphate; or alternatively, halide or nitrate. In some embodiments, the anionic ligand, X, can be a halide; alternatively, nitrate; alternatively, nitrite; alternatively, sulfate; alternatively, sulfite; alternatively, bisulfate; alternatively, phosphate; alternatively, chlorate; alternatively, cyano; alternatively, cyanate; alternatively, thiocyanate; or alternatively, isothiocyanate. In an embodiment each halide independently can be fluoride, chloride, bromide, or iodide; alternatively, fluoride; alternatively, chloride; alternatively, bromide; or alternatively, iodide. In an embodiment, each halate independently can be fluorate, chlorate, bromate, or iodate; alternatively, fluorate; alternatively, chlorate; alternatively, bromate; or alternatively, iodate. In a further embodiment, the transition metal precursor can comprise any combination of these ligands. In some embodiments, each anionic ligand can independently be a monoanionic ligand.

Generally, when the transition metal precursor (general or specific) comprises at least one anionic ligand, the charge, y, of each anionic ligand, X, independently can be an integer ranging from −1 to −3. In an embodiment, the charge, y, on each anionic ligand independently can be −1 or −2; alternatively, −1; alternatively, −2; or alternatively, −3. In an embodiment, each anionic ligand, X, can be a monoanionic ligand having a charge, y, of −1. Generally, the charge, y of the anionic ligand, X, is apparent by the identity of the anionic ligand. For example, halides, nitrate, nitrite, bisulfate, halates, cyano, cyanate, thiocyanate, and isothiocyanate have charge, y, of −1, sulfate and sulfite have charge, y, of −2, and phosphate has a charge, y, of −3.

The number of anionic ligands, x1, in the transition metal precursor (or transition metal complex) is a function of the number of transition metal atoms, the oxidation state of the transition metal atom(s), the charge, y, of the anionic ligand(s), and the charge on the transition metal complex. Generally, the number of anionic ligands, x1, in the transition metal precursor (or transition metal complex) can be an integer from 0 to 7; alternatively, from 0 to 6; alternatively, from 0 to 5; alternatively, from 0 to 4; alternatively, from 0 to 3; alternatively, 1 to 7; alternatively, from 1 to 6; alternatively, from 1 to 5; alternatively, from 1 to 4; alternatively, from 1 to 3; alternatively, from 2 to 5; alternatively, from 2 to 4; alternatively, from 2 to 3; or alternatively, from 3 to 7. In some embodiments, the number of anionic ligands, x1, in the transition metal precursor (or transition metal complex) can be 0; alternatively, 1; alternatively, 2; alternatively, 3; alternatively, 4; or alternatively, 5, alternatively, 6; or alternatively, 7.

When the transition metal complex of the transition metal precursor is anionic or cationic (e.g. having the formula $[((M^B)_{y1}X_{x1}L_l)^m]_q[C^c]_{m1}[A^a]_{m2}$, $[((M)_{y1}X_{x1}L_l)^m]_q[C^c]_{m1}$, $[((M)_{y1}X_{x1}L_l)^m]_q[A^a]_{m2}$, $[(M^BL_l)^m]_q[A^a]_{m2}$, $[(M^BX_xL_l)^m]_q[C^c]_{m1}[A^a]_{m2}$, $[(M^BX_xL_l)^m]_q[C^c]_{m1}$, $[(M^BX_xL_l)^m]_q[A^a]_{m2}$, $[((M^B)_{y1}X_{x1})^m]_q[C^c]_{m1}[A^a]_{m2}$, $[((M^B)_{y1}X_{x1})^m]_q[C^c]_{m1}$, $[((M^B)_{y1}X_{x1})^m]_q[A^a]_{m2}$, $[(M^BX_x)_m]_q[C^c]_{m1}[A^a]_{m2}$, $[(M^BX_x)_m]_q[C^c]_{m1}$, and/or $[(M^BX_x)^m]_q[A^a]_{m2}$, among others where m≠0), the number of transition metal atoms (y1) having the oxidation state x, the number of anionic ligands (A) having charge y, and the charge on the anionic or cationic transition metal complex can be related by the equation m=(y*x1)+(x*y1). When the transition metal complex of the transition metal precursor is neutral (e.g. having the formula $(M^B)_{y1}X_{x1}L_l$, $M^BX_xL_l$, $(M^B)_{y1}X_{x1}$, and/or $M^BX_x$, among others where m=0), the number of transition metal atoms (y1) having the oxidation state x and the number of anionic ligands (X) having charge y can be related by the equation x*y1=|*y*x1|. In some embodiments when the transition metal complex of the transition metal precursor is neutral (e.g. having the formula $(M^B)_{y1}X_{x1}L_l$, $M^BX_xL_l$, $(M^B)_{y1}X_{x1}$, and/or $M^BX_x$, among others where m=0), the number of anionic ligands, x1, can be related to the transition metal oxidation state (x) and the anionic ligand (X) charge (y) by the relationship that x1=x divided by the greatest common divisor of x and |y|.

In an aspect, each neutral ligand(s) for a transition metal precursor (general or specific) independently can be any neutral ligand that can form a stable or isolatable transition metal complex; or alternatively, any combination of neutral ligands that can from a stable or isolatable transition metal complex. Suitable neutral ligands include sigma-donor compounds that contain at least one coordinating atom that can coordinate to the transition metal atom. In an embodiment, the coordinating atom of the neutral ligand(s) can include, but are not limited to, oxygen, nitrogen, sulfur, phosphorus, or any combination thereof; alternatively, oxygen, nitrogen, sulfur, or any combination thereof; alternatively, oxygen, nitrogen, or any combination thereof; alternatively, oxygen, sulfur, or any combination thereof; alternatively, oxygen; alternatively, nitrogen; alternatively, sulfur; or alternatively, phosphorus. Unless otherwise specified, the coordinating compound can be unsubstituted or can be substituted. Substituent groups are independently described herein and can be utilized, without limitation, to describe a substituted neutral ligand which can be utilized in any transition metal precursor and/or transition metal complex described herein.

In an aspect, each neutral ligand independently can be, comprise, or consist essentially of, an acyclic heteroatomic compound, or heterocyclic compound; alternatively, an acyclic heteroatomic compound; or alternatively, a heterocyclic compound. In an embodiment, each neutral ligand (cyclic or acyclic) independently can be, comprise, or consist essentially of, an aliphatic heteroatomic compound or a heteroarene; alternatively, an aliphatic heteroatomic compound; or alternatively, a heteroarene. Suitable heteroatoms for each neutral ligand (cyclic or acyclic, and/or aliphatic or aromatic) are described herein and can be utilized without limitation to further describe heteroatomic compound which can be utilized as the neutral ligand.

In an embodiment, each neutral ligand independently can be, comprise, or consist essentially of, an aliphatic acyclic heterocyclic compound, a substituted aliphatic acyclic heterocyclic compound, an aliphatic heterocyclic compound, a substituted aliphatic heterocyclic compound, a heteroarene, or a substituted heteroarene. In some embodiments, each neutral ligand independently can be, comprise, or consist essentially of, an aliphatic acyclic heterocyclic compound or a substituted aliphatic acyclic heterocyclic compound; alternatively, an aliphatic heterocyclic compound or a substituted aliphatic heterocyclic compound; or alternatively, a heteroarene or a substituted heteroarene. In other embodiments, each neutral ligand independently can be, comprise, or consist essentially of, an aliphatic acyclic heterocyclic compound, an aliphatic heterocyclic compound, or a heteroarene; alternatively, an aliphatic acyclic heterocyclic compound; alternatively, an aliphatic heterocyclic compound; or alternatively, a heteroarene. In an embodiment, any aliphatic acyclic heterocyclic compound (substituted or unsubstituted) which can be utilized as the neutral ligand can be, comprise, or consist essentially of, a $C_2$-$C_{60}$ aliphatic acyclic heterocyclic compound; alternatively, a $C_2$-$C_{45}$ aliphatic acyclic heterocyclic compound; alternatively, a $C_2$-$C_{30}$ aliphatic acyclic heterocyclic compound; or alternatively, a $C_2$-$C_{20}$ aliphatic acyclic heterocyclic compound; alternatively, a $C_2$-$C_{10}$ aliphatic acyclic heterocyclic compound; or alternatively, a $C_2$-$C_5$ aliphatic acyclic heterocyclic compound. In an embodiment, any aliphatic heterocyclic compound (substituted or unsubstituted) which can be utilized as the neutral ligand can be, comprise, or consist essentially of, a $C_3$-$C_{60}$ aliphatic heterocyclic compound; alternatively, a $C_3$-$C_{45}$ aliphatic heterocyclic compound; alternatively, a $C_3$-$C_{30}$ aliphatic heterocyclic compound; alternatively, a $C_3$-$C_{20}$ aliphatic heterocyclic compound; alternatively, a $C_3$-$C_{15}$ aliphatic heterocyclic compound; or alternatively, a $C_3$-$C_{10}$ aliphatic heterocyclic compound. In an embodiment, any heteroarene compound (substituted or unsubstituted) which can be utilized as the neutral ligand can be, comprise, or consist essentially of, a $C_4$-$C_{60}$ heteroarene; alternatively, a $C_4$-$C_{45}$ heteroarene; alternatively, a $C_4$-$C_{30}$ heteroarene; alternatively, a $C_4$-$C_{20}$ heteroarene; alternatively, a $C_4$-$C_{15}$ heteroarene; or alternatively, a $C_4$-$C_{10}$ heteroarene. Substituents for a substituted coordinating compound are disclosed herein and can be utilized without limitation to describe a substituted aliphatic acyclic heterocyclic compound, a substituted aliphatic heterocyclic compound, and/or a substituted heteroarene which can be utilized as a neutral ligand.

In an embodiment, each neutral ligand independently can be, but is not limited to, an ether, a thioether, a nitrile, an amine, a phosphine, a phosphite or any combination thereof; alternatively, an ether; alternatively, a thioether; alternatively, a nitrile; alternatively, an amine; alternatively, a phosphine; or alternatively, a phosphite. In some embodiments, each neutral ligand independently can be, but is not limited to, an acyclic ether, a substituted acyclic ether, a cyclic ether, a substituted cyclic ether, an acyclic thioether, a substituted acyclic thioether, a cyclic thioether, a substituted cyclic thioether, an aliphatic nitrile, a substituted aliphatic nitrile, an aromatic nitrile, a substituted aromatic nitrile, an acyclic amine, a substituted acyclic amine, a cyclic amine, a substituted cyclic amine, an acyclic phosphine, a substituted acyclic phosphine, a cyclic phosphine, a substituted cyclic phosphine, an acyclic phosphite, a substituted acyclic phosphite, a cyclic phosphite, a substituted cyclic phosphite, or any combination thereof; alternatively, an acyclic ether, a substituted acyclic ether, an acyclic thioether, a substituted acyclic thioether, an aliphatic nitrile, a substituted aliphatic nitrile, an acyclic amine, a substituted acyclic amine, an acyclic phosphine, a substituted acyclic phosphine, an acyclic phosphite, a substituted acyclic phosphite, or any combination thereof; alternatively, a cyclic ether, a substituted cyclic ether, a cyclic thioether, a substituted cyclic thioether, a cyclic amine, a substituted cyclic amine, a cyclic phosphine, a substituted cyclic phosphine, a cyclic phosphite, a substituted cyclic phosphite, or any combination thereof; alternatively, an acyclic ether, a substituted acyclic ether, a cyclic ether, or a substituted cyclic ether; alternatively, an acyclic thioether, a substituted acyclic thioether, a cyclic thioether, or a substituted cyclic thioether; alternatively, an aliphatic nitrile, a substituted aliphatic nitrile, an aromatic nitrile, or a substituted aromatic nitrile; alternatively, an acyclic amine, a substituted acyclic amine, a cyclic amine, or a substituted cyclic amine; alternatively, an acyclic phosphine, a substituted acyclic phosphine, a cyclic phosphine, or a substituted cyclic phosphine; or alternatively, an acyclic phosphite, a substituted acyclic phosphite, a cyclic phosphite, or a substituted cyclic phosphite. In other embodiments, each neutral ligand independently can be, but is not limited to, an acyclic ether, a cyclic ether, an acyclic thioether, a cyclic thioether, an aliphatic nitrile, an aromatic nitrile, an acyclic amine, a cyclic amine, or any combination thereof; alternatively, an acyclic ether or a substituted acyclic ether; alternatively, a cyclic ether or a substituted cyclic ether; alternatively, an acyclic thioether or a substituted acyclic thioether; alternatively, a cyclic thioether or a substituted cyclic thioether; alternatively, an aliphatic nitrile or a substituted aliphatic nitrile; alternatively, an aromatic nitrile or a substituted aromatic nitrile; alternatively, an acyclic amine or a substituted acyclic amine; alternatively, a cyclic amine or a substituted cyclic amine; alternatively, an acyclic phosphine or a substituted acyclic phosphine; alternatively, a cyclic phosphine or a substituted cyclic phosphine; alternatively, an acyclic phosphite or a substituted acyclic phosphite; alternatively, a cyclic phosphite or a substituted cyclic phosphite; alternatively, an acyclic ether; alternatively, a cyclic ether; alternatively, an acyclic thioether; alternatively, a cyclic thioether; alternatively, an aliphatic nitrile; alternatively, an aromatic nitrile; alternatively, an acyclic amine; alternatively, a cyclic amine; alternatively, an acyclic phosphine; alternatively, a cyclic phosphine; alternatively, an acyclic phosphite; or alternatively, a cyclic phosphite. In an embodiment, the cyclic ether (substituted or unsubstituted), cyclic thioether (substituted or unsubstituted), cyclic amine (substituted or unsubstituted), cyclic phosphine (substituted or unsubstituted), and/or cyclic phosphite (substituted or unsubstituted) can be aliphatic or aromatic; alternatively, aliphatic; or alternatively, aromatic. Substituents (also referred to as non-hydrogen substituents or non-hydrogen substituent groups) are independently disclosed herein and can be utilized without limitation to further describe a substituted ether (acyclic, cyclic, aliphatic or aromatic), a substituted thioether (acyclic, cyclic, aliphatic or aromatic), a substituted nitrile (aliphatic or aromatic), a substituted amine (acyclic, cyclic, aliphatic or aromatic), a substituted phosphine (acyclic, cyclic, aliphatic or aromatic), and/or a substituted phosphite (acyclic, cyclic, aliphatic or aromatic) which can be utilized as a neutral ligand.

In an embodiment, a nitrile utilized as the neutral ligand can have the formula $R^1C\equiv N$. In an embodiment, an ether utilized as the neutral ligand can have the formula $R^2—O—R^3$. In an embodiment, a thioether utilized as the neutral ligand can have the formula $R^4—S—R^5$. In an embodiment, an amine utilized as the neutral ligand can have the formula $NR^6R^7R^8$, $NHR^6R^7$, or $NH_2R^6$; alternatively, $NR^6R^7R^8$; alternatively, $NHR^6R^7$; or alternatively, $NH_2R^6$. In an embodiment, a phosphine utilized as the neutral ligand can have the formula $PR^9R^{10}R^{11}$, $PHR^9R^{10}$, or $PH_2R^9$; alternatively, $PR^9R^{10}R^{11}$; alternatively, $PHR^9R^{10}$; or alternatively, $PH_2R^9$. In an embodiment, an phosphite utilized as the coordinating compound can have the formula $P(OR^{12})(OR^{13})(OR^{14})$ or $PH(O)(OR^{12})(OR^{13})$; alternatively, $P(OR^{12})(OR^{13})(OR^{14})$; or alternatively, $PH(O)(OR^{12})(OR^{13})$. In an embodiment, each $R^1$, $R^2$, $R^3$, $R^4$, $R^5$, $R^6$, $R^7$, $R^8$, $R^9$, $R^{10}$, $R^{11}$, $R^{12}$, $R^{13}$, or $R^{14}$ independently can be a $C_1$-$C_{20}$ organyl group; alternatively, a $C_1$-$C_{10}$ organyl group; or alternatively, a $C_1$-$C_{20}$ organyl group. In some embodiments, each $R^1$, $R^2$, $R^3$, $R^4$, $R^5$, $R^6$, $R^7$, $R^8$, $R^9$, $R^{10}$, $R^{11}$, $R^{12}$, $R^{13}$, or $R^{14}$ independently can be an $C_1$-$C_{20}$ hydrocarbyl group or a $C_1$-$C_{20}$ substituted hydrocarbyl group; alternatively, $C_1$-$C_{20}$ hydrocarbyl group; or alternatively, a $C_1$-$C_{20}$ substituted hydrocarbyl group. In other embodiments, each $R^1$, $R^2$, $R^3$, $R^4$, $R^5$, $R^6$, $R^7$, $R^8$, $R^9$, $R^{10}$, $R^{11}$, $R^{12}$, $R^{13}$, or $R^{14}$ independently can be an $C_1$-$C_{10}$ hydrocarbyl group or a $C_1$-$C_{10}$ substituted hydrocarbyl group; alternatively, $C_1$-$C_{10}$ hydrocarbyl group; or alternatively, a $C_1$-$C_{10}$ substituted hydrocarbyl group. In yet other embodiments, each $R^1$, $R^2$, $R^3$, $R^4$, $R^5$, $R^6$, $R^7$, $R^8$, $R^9$, $R^{10}$, $R^{11}$, $R^{12}$, $R^{13}$, or $R^{14}$ independently can be an $C_1$-$C_5$ hydrocarbyl group or a $C_1$-$C_5$ substituted hydrocarbyl group; alternatively, $C_1$-$C_5$ hydrocarbyl group; or alternatively, a $C_1$-$C_5$ substituted hydrocarbyl group.

It should be noted that $R^2$ and $R^3$ of the ether having formula $R^2—O—R^3$, $R^4$ and $R^5$ having the formula $R^4—S—R^5$, any two of $R^6$, $R^7$, and $R^8$ of the amine having the formula $NR^6R^7R^8$ or $NHR^6R^7$, any two of $R^9$, $R^{10}$, and $R^{11}$ of the phosphine having the formula $PR^9R^{10}R^{11}$, or $PHR^9R^{10}$, and/or any two of $R^{12}$, $R^{13}$, and $R^{14}$ of the phosphite having the formula $P(OR^{12})(OR^{13})(OR^{14})$ or $PH(O)(OR^{12})(OR^{13})$ can be joined to form a ring containing the ether oxygen atom, the thioether sulfur atom, the amine nitrogen atom, the phosphine phosphorus atom, or the phosphite phosphorus atom to form a cyclic ether, thioether, amine, phosphine, or phosphite, respectively, as described herein in regards to cyclic ethers, thioethers, amines, phosphines, and phosphites.

In an embodiment, each $R^1$, $R^2$, $R^3$, $R^4$, $R^5$, $R^6$, $R^7$, $R^8$, $R^9$, $R^{10}$, $R^{11}$, $R^{12}$, $R^{13}$, or $R^{14}$ independently can be an alkyl group, a substituted alkyl group, a cycloalkyl group, a substituted cycloalkyl group, an aryl group, a substituted aryl group, an aralkyl group, or a substituted aralkyl group; alternatively, an alkyl group or a substituted alkyl group; alternatively, a cycloalkyl group or a substituted cycloalkyl group; alternatively, an aryl group or a substituted aryl group; alternatively, an aralkyl group, or a substituted aralkyl group; alternatively, an alkyl group, a cycloalkyl group, an aryl group, or an aralkyl group; alternatively, an alkyl group; alternatively, a substituted alkyl group, alternatively, a cycloalkyl group; alternatively, a substituted cycloalkyl group; alternatively, an aryl group; alternatively, a substituted aryl group; alternatively, an aralkyl group; or alternatively, a substituted aralkyl group. Generally, the alkyl groups, substituted alkyl groups, cycloalkyl groups, substituted cycloalkyl groups, aryl groups, a substituted aryl groups, aralkyl groups, and substituted aralkyl groups which can be utilized as $R^1$, $R^2$, $R^3$, $R^4$, $R^5$, $R^6$, $R^7$, $R^8$, $R^9$, $R^{10}$, $R^{11}$, $R^{12}$, $R^{13}$, or $R^{14}$ can have the same number of carbon atoms as organyl group or hydrocarbyl group of which they are a member.

In an embodiment, the alkyl group (substituted or unsubstituted) which can be utilized as $R^1$, $R^2$, $R^3$, $R^4$, $R^5$, $R^6$, $R^7$, $R^8$, $R^9$, $R^{10}$, $R^{11}$, $R^{12}$, $R^{13}$, and/or $R^{14}$ can be a $C_1$-$C_{20}$ alkyl group (substituted or unsubstituted); alternatively, a $C_1$-$C_{10}$ alkyl group (substituted or unsubstituted); or alternatively, a $C_1$-$C_5$ alkyl group (substituted or unsubstituted). In some embodiments, each alkyl group which can be utilized as $R^1$, $R^2$, $R^3$, $R^4$, $R^5$, $R^6$, $R^7$, $R^8$, $R^9$, $R^{10}$, $R^{11}$, $R^{12}$, $R^{13}$, and/or $R^{14}$ independently can be a methyl group, an ethyl group, a propyl group, a butyl group, a pentyl group, a hexyl group, a heptyl group, an octyl group, a nonyl group, a decyl group, a undecyl group, a dodecyl group, a tridecyl group, a tetradecyl group, a pentadecyl group, a hexadecyl group, a heptadecyl group, an octadecyl group, or a nonadecyl group; or alternatively, a methyl group, an ethyl group, a propyl group, a butyl group, a pentyl group, a hexyl group, a heptyl group, an octyl group, a nonyl group, or a decyl group. In other embodiments, each alkyl group which can be utilized as $R^1$, $R^2$, $R^3$, $R^4$, $R^5$, $R^6$, $R^7$, $R^8$, $R^9$, $R^{10}$, $R^{11}$, $R^{12}$, $R^{13}$, and/or $R^{14}$ independently can be a methyl group, an ethyl group, a n-propyl group, an iso-propyl group, a n-butyl group, an iso-butyl group, a sec-butyl group, a tert-butyl group, an n-pentyl group, an iso-pentyl group, a sec-pentyl group, or a neopentyl group; alternatively, a methyl group, an ethyl group, an iso-propyl group, a tert-butyl group, or a neopentyl group; alternatively, a methyl group; alternatively, an ethyl group; alternatively, a n-propyl group; alternatively, an iso-propyl group; alternatively, a tert-butyl group; or alternatively, a neopentyl group. In an embodiment, each substituent of a substituted alkyl group independently can be a halide or hydrocarboxy group; alternatively, a halide; or alternatively a hydrocarboxy group.

In an embodiment, the cycloalkyl group (substituted or unsubstituted) which can be utilized as $R^1$, $R^2$, $R^3$, $R^4$, $R^5$, $R^6$, $R^7$, $R^8$, $R^9$, $R^{10}$, $R^{11}$, $R^{12}$, $R^{13}$, and/or $R^{14}$ can be a $C_4$-$C_{20}$ cycloalkyl group (substituted or unsubstituted); alternatively, a $C_4$-$C_{15}$ cycloalkyl group (substituted or unsubstituted); or alternatively, a $C_4$-$C_{10}$ cycloalkyl group (substituted or unsubstituted). In some embodiments, each group which can be utilized as $R^1$, $R^2$, $R^3$, $R^4$, $R^5$, $R^6$, $R^7$, $R^8$, $R^9$, $R^{10}$, $R^{11}$, $R^{12}$, $R^{13}$, and/or $R^{14}$ independently can be a cyclobutyl group, a substituted cyclobutyl group, a cyclopentyl group, a substituted cyclopentyl group, a cyclohexyl group, a substituted cyclohexyl group, a cycloheptyl group, a substituted cycloheptyl group, a cyclooctyl group, or a substituted cyclooctyl group; alternatively, a cyclopentyl group, a substituted cyclopentyl group, a cyclohexyl group, or a substituted cyclohexyl group. In other embodiments, each group which can be utilized as $R^1$, $R^2$, $R^3$, $R^4$, $R^5$, $R^6$, $R^7$, $R^8$, $R^9$, $R^{10}$, $R^{11}$, $R^{12}$, $R^{13}$, and/or $R^{14}$ independently can be a cyclobutyl group or a substituted cyclobutyl group; alternatively, a cyclopentyl group or a substituted cyclopentyl group; alternatively, a cyclohexyl group or a substituted cyclohexyl group; alternatively, a cycloheptyl group or a substituted cycloheptyl group; or alternatively, a cyclooctyl group, or a substituted cyclooctyl group; alternatively, a cyclopentyl group; alternatively, a substituted cyclopentyl group; a cyclohexyl group; or alternatively, a substituted cyclohexyl group. In an embodiment, each substituent of a substituted cycloalkyl group independently can be a halide, a hydrocarbyl group, or a hydrocarboxy group; alternatively, a halide or a hydrocarbyl group; alternatively, a halide or a hydrocarboxy group; alternatively, a hydrocarbyl group or a hydrocarboxy group; alternatively, a halide; alternatively, a hydrocarbyl group; or alternatively, a hydrocarboxy group.

In an embodiment, the aryl group (substituted or unsubstituted) which can be utilized as $R^1$, $R^2$, $R^3$, $R^4$, $R^5$, $R^6$, $R^7$, $R^8$, $R^9$, $R^{10}$, $R^{11}$, $R^{12}$, $R^{13}$, and/or $R^{14}$ can be a $C_6$-$C_{20}$ aryl group (substituted or unsubstituted); alternatively, a $C_6$-$C_{15}$ aryl group (substituted or unsubstituted); or alternatively, a $C_6$-$C_{10}$ aryl group (substituted or unsubstituted). In some embodiments, each group which can be utilized as $R^1$, $R^2$, $R^3$, $R^4$, $R^5$, $R^6$, $R^7$, $R^8$, $R^9$, $R^{10}$, $R^{11}$, $R^{12}$, $R^{13}$, and/or $R^{14}$ independently can be a phenyl group, a substituted phenyl group, a naphthyl group, or a substituted naphthyl group; alternatively, a phenyl group or a substituted phenyl group; alternatively, a naphthyl group or a substituted naphthyl group; alternatively, a phenyl group or a naphthyl group; or alternatively, a substituted phenyl group or a substituted naphthyl group. In an embodiment, each substituted phenyl group which can be utilized as $R^1$, $R^2$, $R^3$, $R^4$, $R^5$, $R^6$, $R^7$, $R^8$, $R^9$, $R^{10}$, $R^{11}$, $R^{12}$, $R^{13}$, and/or $R^{14}$ independently can be a 2-substituted phenyl group, a 3-substituted phenyl group, a 4-substituted phenyl group, a 2,4-disubstituted phenyl group, a 2,6-disubstituted phenyl group, 3,5-disubstituted phenyl group, or a 2,4,6-trisubstituted phenyl group. In other embodiments, each substituted phenyl group which can be utilized as $R^1$, $R^2$, $R^3$, $R^4$, $R^5$, $R^6$, $R^7$, $R^8$, $R^9$, $R^{10}$, $R^{11}$, $R^{12}$, $R^{13}$, and/or $R^{14}$ independently can be a 2-substituted phenyl group, a 4-substituted phenyl group, a 2,4-disubstituted phenyl group, or a 2,6-disubstituted phenyl group; alternatively, a 3-substituted phenyl group or a 3,5-disubstituted phenyl group; alternatively, a 2-substituted phenyl group or a 4-substituted phenyl group; alternatively, a 2,4-disubstituted phenyl group or a 2,6-disubstituted phenyl group; alternatively, a 2-substituted phenyl group; alternatively, a 3-substituted phenyl group; alternatively, a 4-substituted phenyl group; alternatively, a 2,4-disubstituted phenyl group; alternatively, a 2,6-disubstituted phenyl group; alternatively, 3,5-disubstituted phenyl group; or alternatively, a 2,4,6-trisubstituted phenyl group. In an embodiment, each substituent of a substituted aryl group independently can be a halide, a hydrocarbyl group, or a hydrocarboxy group; alternatively, a halide or a hydrocarbyl group; alternatively, a halide or a hydrocarboxy group; alternatively, a hydrocarbyl group or a hydrocarboxy group; alternatively, a halide; alternatively, a hydrocarbyl group; or alternatively, a hydrocarboxy group.

In some embodiments, the aralkyl group (substituted or unsubstituted) which can be utilized as $R^1$, $R^2$, $R^3$, $R^4$, $R^5$, $R^6$, $R^7$, $R^8$, $R^9$, $R^{10}$, $R^{11}$, $R^{12}$, $R^{13}$, and/or $R^{14}$ can be a $C_7$-$C_{20}$ aralkyl group (substituted or unsubstituted); alternatively, a $C_7$-$C_{15}$ aralkyl group (substituted or unsubstituted); or alternatively, a $C_7$-$C_{10}$ aralkyl group (substituted or unsubstituted). In some embodiments, each group which can be utilized as $R^1$, $R^2$, $R^3$, $R^4$, $R^5$, $R^6$, $R^7$, $R^8$, $R^9$, $R^{10}$, $R^{11}$, $R^{12}$, $R^{13}$, and/or $R^{14}$ independently can be a benzyl group or a substituted benzyl group; alternatively, a benzyl group, or alternatively, a substituted benzyl group. In an embodiment, each substituent of a substituted aralkyl group independently can be a halide, a hydrocarbyl group, or a hydrocarboxy group; alternatively, a halide or a hydrocarbyl group; alternatively, a halide or a hydrocarboxy group; alternatively, a hydrocarbyl group or a hydrocarboxy group; alternatively, a halide; alternatively, a hydrocarbyl group; or alternatively, a hydrocarboxy group.

Halide, hydrocarbyl group, and hydrocarboxy group substituents (also referred to as non-hydrogen substituents or non-hydrogen substituent groups) are independently disclosed herein. These substituent groups can be utilized without limitation to further describe any substituted $R^1$, $R^2$, $R^3$, $R^4$, $R^5$, $R^6$, $R^7$, $R^8$, $R^9$, $R^{10}$, $R^{11}$, $R^{12}$, $R^{13}$, and/or $R^{14}$ group described herein.

In an embodiment, each ether and/or acyclic ether (substituted or unsubstituted), which can be utilized as the neutral ligand(s) of any transition metal complex (general or specific) or transition metal precursor (general or specific) described herein, independently can be a $C_2$-$C_{40}$ ether and/or acyclic ether; alternatively, a $C_2$-$C_{30}$ ether and/or acyclic ether; alternatively, a $C_2$-$C_{20}$ ether and/or acyclic ether; alternatively, a $C_2$-$C_{15}$ ether and/or acyclic ether; or alternatively, a $C_2$-$C_{10}$ ether and/or acyclic ether. In an embodiment, each cyclic ether (substituted or unsubstituted, and/or aliphatic or aromatic), which can be utilized as the neutral ligand(s) of any transition metal complex (general or specific) or transition metal precursor (general or specific) described herein, independently can be a $C_3$-$C_{40}$ cyclic ether; alternatively, a $C_4$-$C_{30}$ cyclic ether; alternatively, a $C_4$-$C_{20}$ cyclic ether; alternatively, a $C_4$-$C_{15}$ cyclic ether; or alternatively, a $C_4$-$C_{10}$ cyclic ether.

In an aspect of this disclosure, each neutral ligand(s) of any transition metal complex (general or specific) or transition metal precursor (general or specific) described herein, independently can be, comprise, or consist essentially of, a dihydrocarbyl ether or a substituted dihydrocarbyl ether; or alternatively, a dihydrocarbyl ether. Hydrocarbyl groups (substituted or substituted) are generally disclosed within the present disclosure (e.g. as a selection for $R^{2c}$, for the monocarboxylate having the formula $^-O_2CR^{2c}$ and/or as a selection for $R^1$, $R^2$, $R^3$, $R^4$, $R^5$, $R^6$, $R^7$, $R^8$, $R^9$, $R^{10}$, $R^{11}$, $R^{12}$, $R^{13}$, or $R^{14}$, among other places). The aspects and embodiments of these hydrocarbyl groups described herein (either explicitly specified or implicitly recognized by those skilled in the art), can be utilized without limitation as hydrocarbyl groups of the dihydrocarbyl ethers (substituted or unsubstituted) which can be utilized as the neutral ligand.

In a non-limiting embodiment, each neutral ligand(s) of any transition metal complex (general or specific) or transition metal precursor (general or specific) described herein, independently can be, comprise, or consist essentially of, dimethyl ether, diethyl ether, dipropyl ether, dibutyl ether, methyl ethyl ether, methyl propyl ether, methyl butyl ether, or any combination thereof; alternatively, dimethyl ether; alternatively, diethyl ether; alternatively, dipropyl ether; alternatively, dibutyl ether; alternatively, methyl ethyl ether;

alternatively, methyl propyl ether; or alternatively, methyl butyl ether. In another non-limiting embodiment, each neutral ligand(s) of any transition metal complex (general or specific) or transition metal precursor (general or specific) described herein, independently can be, comprise, or consist essentially of, diphenyl ether, a substituted diphenyl ether, ditolyl ether, a substituted ditolyl ether, or any combination thereof; alternatively, diphenyl ether, ditolyl ether, or any combination thereof. In an embodiment, each neutral ligand(s) of any transition metal complex (general or specific) or transition metal precursor (general or specific) described herein, independently can be, comprise, or consist essentially of, diphenyl ether; alternatively, a substituted diphenyl ether; alternatively, ditolyl ether; or alternatively, a substituted ditolyl ether.

In a non-limiting embodiment, each neutral ligand(s) of any transition metal complex (general or specific) or transition metal precursor (general or specific) described herein, independently can be, comprise, or consist essentially of, tetrahydrofuran, a substituted tetrahydrofuran, 2,3-dihydrofuran, a substituted 2,3-dihydrofuran, 2,5-dihydrofuran, a substituted 2,5-dihydrofuran, or a combination thereof; alternatively, tetrahydrofuran, 2,3-dihydrofuran, 2,5-dihydrofuran, or a combination thereof; alternatively tetrahydrofuran; alternatively, a substituted tetrahydrofuran; 2,3-dihydrofuran; alternatively, a substituted 2,3-dihydrofuran; alternatively, 2,5-dihydrofuran; or alternatively, a substituted 2,5-dihydrofuran. In another non-limiting embodiment, each neutral ligand(s) of any transition metal complex (general or specific) or transition metal precursor (general or specific) described herein, independently can be, comprise, or consist essentially of, tetrahydrofuran, a 2-substituted tetrahydrofuran, a 3-substituted tetrahydrofuran, or any combination thereof; alternatively, tetrahydrofuran; alternatively, a 2-substituted tetrahydrofuran; or alternatively, a 3-substituted tetrahydrofuran. In further non-limiting embodiments, each neutral ligand(s) of any transition metal complex (general or specific) or transition metal precursor (general or specific) described herein, independently can be tetrahydrofuran, a 2-alkyl substituted tetrahydrofuran, a 3-alkyl substituted tetrahydrofuran, or any combination thereof; alternatively, tetrahydrofuran; alternatively, a 2-alkyl substituted tetrahydrofuran; or alternatively, a 3-alkyl substituted tetrahydrofuran.

In a non-limiting embodiment, each neutral ligand(s) of any transition metal complex (general or specific) or transition metal precursor (general or specific) described herein, independently can be, comprise, or consist essentially of, furan, a substituted furan, benzofuran, a substituted benzofuran, isobenzofuran, a substituted isobenzofuran, dibenzofuran, a substituted dibenzofuran, or any combination thereof. In another non-limiting embodiment, each neutral ligand(s) of any transition metal complex (general or specific) or transition metal precursor (general or specific) described herein, independently can be, comprise, or consist essentially of, furan, benzofuran, isobenzofuran, dibenzofuran, or any combination thereof; alternatively, furan; alternatively, a substituted furan; alternatively, benzofuran; alternatively, a substituted benzofuran; alternatively, isobenzofuran; alternatively, a substituted isobenzofuran; alternatively, dibenzofuran; alternatively, a substituted dibenzofuran.

In a non-limiting embodiment, each neutral ligand(s) of any transition metal complex (general or specific) or transition metal precursor (general or specific) described herein, independently can be, comprise, or consist essentially of, tetrahydrofuran, a substituted tetrahydrofuran, tetrahydropyran, a substituted tetrahydropyran, 3,4-dihydro-2H-pyran, a substituted 3,4-dihydro-2H-pyran, 3,6-dihydro-2H-pyran, a substituted 3,6-dihydro-2H-pyran, 2H-pyran, a substituted 2H-pyran, 4H-pyran, a substituted 4H-pyran, 1,3-dioxane, a substituted 1,3-dioxane, 1,4-dioxane, a substituted 1,4-dioxane, morpholine, a substituted morpholine, an N-substituted morpholine, a substituted N-substituted morpholine, or any combination thereof; alternatively, tetrahydrofuran, tetrahydropyran, 3,4-dihydro-2H-pyran, 3,6-dihydro-2H-pyran, 2H-pyran, 4H-pyran, 1,3-dioxane, 1,4-dioxane, morpholine, an N-substituted morpholine, or any combination thereof. In another non-limiting embodiment, each neutral ligand(s) of any transition metal complex (general or specific) or transition metal precursor (general or specific) described herein, independently can be, comprise, or consist essentially of, tetrahydrofuran, tetrahydropyran, 1,3-dioxane, 1,4-dioxane, or any combination thereof. In further non-limiting embodiments, each neutral ligand(s) of any transition metal complex (general or specific) or transition metal precursor (general or specific) described herein, independently can be, comprise, or consist essentially of, tetrahydropyran; alternatively, a substituted tetrahydropyran; alternatively, 3,4-dihydro-2H-pyran; alternatively, a substituted 3,4-dihydro-2H-pyran; alternatively, 3,6-dihydro-2H-pyran; alternatively, a substituted 3,6-dihydro-2H-pyran; alternatively, 2H-pyran; alternatively, a substituted 2H-pyran; alternatively, 4H-pyran; alternatively, a substituted 4H-pyran; alternatively, 1,3-dioxane; alternatively, a substituted 1,3-dioxane; alternatively, 1,4-dioxane; alternatively, a substituted 1,4-dioxane; alternatively, morpholine; alternatively, a substituted morpholine; alternatively, an N-substituted morpholine; or alternatively, a substituted N-substituted morpholine.

General substituents (also referred to as non-hydrogen substituents or non-hydrogen substituent groups) are independently disclosed herein. These substituent groups can be utilized without limitation to further describe any substituted ether, substituted acyclic ether, substituted cyclic ether (aliphatic or aromatic), substituted diphenyl ethers, substituted ditolyl ethers, substituted tetrahydrofurans, alkyl substituted tetrahydrofurans, substituted furans, benzofurans, isobenzofurans, dibenzofurans, substituted tetrahydropyrans, substituted 3,4-dihydro-2H-pyrans, substituted 3,6-dihydro-2H-pyrans, substituted 4H-pyrans, substituted 1,3-dioxanes, substituted 1,4-dioxanes, substituted morpholines, N-hydrocarbyl morpholines, and/or substituted N-hydrocarbyl morpholines which can be utilized as the neutral ligand.

In an embodiment, any thioether and/or acyclic thioether (substituted or unsubstituted), which can be utilized as the neutral ligand, can be, comprise, or consist essentially of, a $C_2$-$C_{40}$ thioether and/or acyclic thioether; alternatively, a $C_2$-$C_{30}$ thioether and/or acyclic thioether; alternatively, a $C_2$-$C_{20}$ thioether and/or acyclic thioether; alternatively, a $C_2$-$C_{15}$ thioether and/or acyclic thioether; or alternatively, a $C_2$-$C_{10}$ thioether and/or acyclic thioether. In an embodiment, any cyclic thioether (substituted or unsubstituted, and/or aliphatic or aromatic), which can be utilized as the neutral ligand, can be, comprise, or consist essentially of a $C_3$-$C_{40}$ cyclic thioether; alternatively, a $C_4$-$C_{30}$ cyclic thioether; alternatively, a $C_4$-$C_{20}$ cyclic thioether; alternatively, a $C_4$-$C_{15}$ cyclic thioether; or alternatively, a $C_4$-$C_{10}$ cyclic thioether.

In an aspect of this disclosure, each neutral ligand(s) of any transition metal complex (general or specific) or transition metal precursor (general or specific) described herein, independently can be, comprise, or consist essentially of, a dihydrocarbyl thioether or a substituted dihydrocarbyl thioether; or alternatively, a dihydrocarbyl thioether. Hydrocarbyl groups (substituted or substituted) are generally disclosed within the present disclosure (e.g. as a selection for $R^{2c}$, for the monocarboxylate having the formula $^-O_2CR^{2c}$ and/or as a selection for $R^1$, $R^2$, $R^3$, $R^4$, $R^5$, $R^6$, $R^7$, $R^8$, $R^9$, $R^{10}$, $R^{11}$, $R^{12}$, $R^{13}$, or $R^{14}$, among other places). The aspects and embodiments of these hydrocarbyl groups described herein (either explicitly specified or implicitly recognized by those skilled in the art), can be utilized without limitation as hydrocarbyl groups of the dihydrocarbyl thioethers (substituted or unsubstituted) which can be utilized as the neutral ligand.

In a non-limiting embodiment, each neutral ligand(s) of any transition metal complex (general or specific) or transition metal precursor (general or specific) described herein, independently can be, comprise, or consist essentially of, dimethyl thioether, diethyl thioether, dipropyl thioether, dibutyl thioether, methyl ethyl thioether, methyl propyl thioether, methyl butyl thioether, or any combination thereof. In another non-limiting embodiment, each neutral ligand(s) of any transition metal complex (general or specific) or transition metal precursor (general or specific) described herein, independently can be, comprise, or consist essentially of, dimethyl thioether; alternatively, diethyl thioether; alternatively, dipropyl thioether; alternatively, dibutyl thioether; alternatively, methyl ethyl thioether; alternatively, methyl propyl thioether; alternatively, or methyl butyl thioether. In a non-limiting embodiment, each neutral ligand(s) of any transition metal complex (general or specific) or transition metal precursor (general or specific) described herein, independently can be, comprise, or consist essentially of, diphenyl thioether, a substituted diphenyl thioether, ditolyl thioether, a substituted ditolyl thioether, or any combination thereof; alternatively, diphenyl thioether, ditolyl thioether, or any combination thereof. In an embodiment, each neutral ligand(s) of any transition metal complex (general or specific) or transition metal precursor (general or specific) described herein, independently can be, comprise, or consist essentially of, diphenyl thioether; alternatively, a substituted diphenyl thioether; alternatively, ditolyl thioether; or alternatively, a substituted ditolyl thioether.

In a non-limiting embodiment, each neutral ligand(s) of any transition metal complex (general or specific) or transition metal precursor (general or specific) described herein, independently can be, comprise, or consist essentially of, thiophene, a substituted thiophene, benzothiophene, a substituted benzothiophene, or any combination thereof. In another non-limiting embodiment, each neutral ligand(s) of any transition metal complex (general or specific) or transition metal precursor (general or specific) described herein, independently can be, comprise, or consist essentially of, thiophene, benzothiophene, or any combination thereof; alternatively, thiophene; alternatively, a substituted thiophene; alternatively, benzothiophene; or alternatively, a substituted benzothiophene.

In a non-limiting embodiment, each neutral ligand(s) of any transition metal complex (general or specific) or transition metal precursor (general or specific) described herein, independently can be, comprise, or consist essentially of, tetrahydrothiophene, a substituted tetrahydrothiophene, thiane, a substituted thiane, or any combination thereof. In another non-limiting embodiment, each neutral ligand(s) of any transition metal complex (general or specific) or transition metal precursor (general or specific) described herein, independently can be, comprise, or consist essentially of, tetrahydrothiophene, thiane, or a combination thereof; alternatively, tetrahydrothiophene; alternatively, a substituted tetrahydrothiophene; alternatively, thiane; or alternatively, a substituted thiane.

General substituents (also referred to as non-hydrogen substituents or non-hydrogen substituent groups) are independently disclosed herein. These substituent groups can be utilized without limitation to further describe any substituted thioether, substituted acyclic thioether, substituted cyclic thioether, substituted diphenyl thiol ethers, substituted ditolyl thioethers, substituted thiophenes, and/or substituted benzothiophenes which can be utilized as the neutral ligand.

In an embodiment, any nitrile (substituted or unsubstituted), which can be utilized as the neutral ligand, can be, comprise, or consist essentially of, a $C_2$-$C_{20}$ aliphatic nitrile; alternatively, a $C_2$-$C_{15}$ aliphatic nitrile; alternatively, a $C_2$-$C_{10}$ aliphatic nitrile; or alternatively, a $C_2$-$C_5$ aliphatic nitrile. In an embodiment, any nitrile (substituted or unsubstituted), which can be utilized as the neutral ligand, can be, comprise, or consist essentially of, a $C_6$-$C_{20}$ aromatic nitrile; alternatively, a $C_6$-$C_{15}$ aromatic nitrile; or alternatively, a $C_6$-$C_{10}$ aromatic nitrile.

In an aspect of this disclosure, each neutral ligand(s) of any transition metal complex (general or specific) or transition metal precursor (general or specific) described herein, independently can be, comprise, or consist essentially of, a hydrocarbyl nitrile or a substituted hydrocarbyl nitrile; or alternatively, a hydrocarbyl nitrile. Hydrocarbyl groups (substituted or substituted) are generally disclosed within the present disclosure (e.g. as a selection for $R^{2c}$, for the monocarboxylate having the formula $^-O_2CR^{2c}$ and/or as a selection for $R^1$, $R^2$, $R^3$, $R^4$, $R^5$, $R^6$, $R^7$, $R^8$, $R^9$, $R^{10}$, $R^{11}$, $R^{12}$, $R^{13}$, or $R^{14}$, among other places). The aspects and embodiments of these hydrocarbyl groups described herein (either explicitly specified or implicitly recognized by those skilled in the art), can be utilized without limitation as hydrocarbyl groups of the hydrocarbyl nitrile (substituted or unsubstituted) which can be utilized as the neutral ligand.

In a non-limiting embodiment, each neutral ligand(s) of any transition metal complex (general or specific) or transition metal precursor (general or specific) described herein, independently can be, comprise, or consist essentially of, acetonitrile, propionitrile, butyronitrile, or any combination thereof. In another non-limiting embodiment, each neutral ligand(s) of any transition metal complex (general or specific) or transition metal precursor (general or specific) described herein, independently can be, comprise, or consist essentially of, acetonitrile; alternatively, propionitrile; or alternatively, butyronitrile.

In a non-limiting embodiment, each neutral ligand(s) of any transition metal complex (general or specific) or transition metal precursor (general or specific) described herein, independently can be, comprise, or consist essentially of, benzonitrile, a substituted benzonitrile, or any combination thereof; alternatively, benzonitrile; or alternatively, a substituted benzonitrile. In another non-limiting embodiment, each neutral ligand(s) of any transition metal complex (general or specific) or transition metal precursor (general or specific) described herein, independently can be, comprise, or consist essentially of, benzonitrile, a 2-substituted benzonitrile, a 3-substituted benzonitrile, a 4-substituted benzonitrile, a 2,4-substituted benzonitrile, a 3,5-disubstituted, a 2,4,6-trisubstituted benzonitrile, or any combination thereof alternatively, a 2-substituted benzonitrile, a 4-substituted benzonitrile, a 2,4-substituted benzonitrile, a 2,4,6-trisubstituted benzonitrile, or any combination thereof alternatively, a 2-substituted benzonitrile; alternatively, a 3-substituted benzonitrile; alternatively, a 4-substituted benzonitrile; alternatively, a 2,4-substituted benzonitrile; alternatively, a 3,5-disubstituted; or alternatively, a 2,4,6-trisubstituted benzonitrile. In yet other embodiments, each neutral ligand(s) of any transition metal complex (general or specific) or transition metal precursor (general or specific) described herein, independently can be, comprise, or consist essentially of, benzonitrile, a 2-alkyl benzonitrile, a 3-alkyl benzonitrile, a 4-methylbenzonitrile, a 2,4-alkyl benzonitrile, a 3,5-dialkyl, a 2,4,6-trialkyl benzonitrile, or any combination thereof; alternatively, a 2-alkyl benzonitrile, a 4-alkyl benzonitrile, a 2,4-alkyl benzonitrile, a 2,4,6-trialkyl benzonitrile, or any combination thereof alternatively, a 2-alkyl benzonitrile; alternatively, a 3-alkyl benzonitrile; alternatively, a 4-alkyl benzonitrile; alternatively, a 2,4-alkyl benzonitrile; alternatively, a 3,5-dialkyl; or alternatively, a 2,4,6-trialkyl benzonitrile.

General substituents (also referred to as non-hydrogen substituents or non-hydrogen substituent groups) are independently disclosed herein. These substituent groups can be utilized without limitation to further describe any substituted aliphatic nitrile, substituted aromatic nitrile, substituted benzonitriles, and/or alkyl substituted benzonitriles which can be utilized as the neutral ligand.

In an embodiment, any amine and/or acyclic amine (substituted or unsubstituted), which can be utilized as the neutral ligand, can be, comprise, or consist essentially of, a $C_1$-$C_{60}$ amine and/or acyclic amine; alternatively, a $C_1$-$C_{45}$ amine and/or acyclic amine; alternatively, a $C_1$-$C_{30}$ amine and/or acyclic amine; alternatively, a $C_1$-$C_{20}$ amine and/or acyclic amine; alternatively, a $C_1$-$C_{15}$ amine and/or acyclic amine; or alternatively, a $C_1$-$C_{10}$ amine and/or acyclic amine. In an embodiment, any cyclic amine (substituted or unsubstituted, and/or aliphatic or aromatic), which can be utilized as the neutral ligand, can be a $C_3$-$C_{60}$ cyclic amine; alternatively, a $C_3$-$C_{45}$ cyclic amine; alternatively, a $C_3$-$C_{30}$ cyclic amine; alternatively, a $C_4$-$C_{20}$ cyclic amine; or alternatively, a $C_4$-$C_{15}$ cyclic amine.

In an aspect of this disclosure, each neutral ligand(s) of any transition metal complex (general or specific) or transition metal precursor (general or specific) described herein, independently can be, comprise, or consist essentially of, a hydrocarbylamine, a substituted hydrocarbyl amine, a dihydrocarbylamine, a substituted dihydrocarbylamine, a trihydrocarbylamine, a substituted trihydrocarbylamine, any combination thereof; a hydrocarbylamine, a dihydrocarbylamine, a trihydrocarbylamine, or any combination thereof; alternatively, a hydrocarbylamine or a substituted hydrocarbylamine; alternatively, a dihydrocarbylamine or a substituted dihydrocarbylamine; alternatively, a trihydrocarbylamine or a substituted trihydrocarbylamine; alternatively, a hydrocarbylamine; alternatively, a substituted hydrocarbylamine; alternatively, a dihydrocarbylamine; alternatively, a substituted dihydrocarbylamine; alternatively, a trihydrocarbylamine; or alternatively, a substituted trihydrocarbylamine Hydrocarbyl groups (substituted or substituted) are generally disclosed within the present disclosure (e.g. as a selection for $R^{2c}$, for the monocarboxylate having the formula $^-O_2CR^{2c}$ and/or as a selection for $R^1$, $R^2$, $R^3$, $R^4$, $R^5$, $R^6$, $R^7$, $R^8$, $R^9$, $R^{10}$, $R^{11}$, $R^{12}$, $R^{13}$, or $R^{14}$, among other places). The aspects and embodiments of these hydrocarbyl groups described herein (either explicitly specified or implicitly recognized by those skilled in the art), can be utilized without limitation as the hydrocarbyl groups of the hydrocarbylamine (substituted or unsubstituted), a dihydrocarbylamine (substituted or unsubstituted), a trihydrocarbylamine (substituted or unsubstituted) which can be utilized as the neutral ligand.

In a non-limiting embodiment, each neutral ligand(s) of any transition metal complex (general or specific) or transition metal precursor (general or specific) described herein, independently can be, comprise, or consist essentially of, methyl amine, ethyl amine, propyl amine, butyl amine, dimethyl amine, diethyl amine, dipropyl amine, dibutylamine, trimethyl amine, triethyl amine, tripropyl amine, tributyl amine, or any combination thereof. In another non-limiting embodiment, each neutral ligand(s) of any transition metal complex (general or specific) or transition metal precursor (general or specific) described herein, independently can be, comprise, or consist essentially of, methyl amine, ethyl amine, propyl amine, butyl amine, or any combination thereof; alternatively, dimethyl amine, diethyl amine, dipropyl amine, dibutylamine, or any combination thereof; or alternatively, trimethyl amine, triethyl amine, tripropyl amine, tributyl amine, or any combination thereof. In yet another non-limiting embodiment, each neutral ligand(s) of any transition metal complex (general or specific) or transition metal precursor (general or specific) described herein, independently can be, comprise, or consist essentially of, methyl amine; alternatively, ethyl amine; alternatively, propyl amine; alternatively, butyl amine; alternatively, dimethyl amine; alternatively, diethyl amine; alternatively, dipropyl amine; alternatively, dibutylamine; alternatively, trimethyl amine; alternatively, triethyl amine; alternatively, tripropyl amine; or alternatively, tributyl amine.

In a non-limiting embodiment, each neutral ligand(s) of any transition metal complex (general or specific) or transition metal precursor (general or specific) described herein, independently can be, comprise, or consist essentially of, aniline, a substituted aniline, a N-hydrocarbyl aniline, a substituted N-hydrocarbyl aniline, a N,N-dihydrocarbyl aniline, a substituted N,N-dihydrocarbylaniline, diphenylamine, a di(substituted phenyl)amine, a N-hydrocarbyl diphenylamine, a N-hydrocarbyl di(substituted phenyl)amine, triphenylamine, a substituted triphenylamine, or any combination thereof. In another non-limiting embodiment, each neutral ligand(s) of any transition metal complex (general or specific) or transition metal precursor (general or specific) described herein, independently can be, comprise, or consist essentially of, aniline, a substituted aniline, a N-hydrocarbyl aniline, a substituted N-hydrocarbyl aniline, a N,N-dihydrocarbyl aniline, a substituted N,N-dihydrocarbyl aniline, or any combination thereof alternatively, diphenylamine, a di(substituted phenyl)amine, a N-hydrocarbyl diphenylamine, a N-hydrocarbyl di(substitute phenyl)amine, or any combination thereof or alternatively, triphenylamine, a substituted triphenylamine, or any combination thereof. In yet another non-limiting embodiment, each neutral ligand(s) of any transition metal complex (general or specific) or transition metal precursor (general or specific) described herein, independently can be, comprise, or consist essentially of, aniline; alternatively, a substituted aniline; alternatively, a N-hydrocarbyl aniline; alternatively, a substituted N-hydrocarbyl aniline; alternatively, a N,N-dihydrocarbyl aniline; alternatively, a substituted N,N-dihydrocarbyl aniline; alternatively, diphenylamine; alternatively, a di(substituted phenyl)amine; alternatively, a N-hydrocarbyl diphenylamine; alternatively, a N-hydrocarbyl di(substitute phenyl)amine; alternatively, triphenylamine; or alternatively, a substituted triphenylamine. In some non-limiting embodiments, each neutral ligand(s) of any transition metal complex (general or specific) or transition metal precursor (general or specific) described herein, independently can be, comprise, or consist essentially of, aniline, tolylamine, xylylamine, diphenylamine, ditolylamine, triphenylamine, or any combination thereof. In other non-limiting embodiments, each coordinating compound can aniline; alternatively, tolylamine; alternatively, xylylamine; alternatively, diphenylamine; alternatively, ditolylamine; or alternatively, triphenylamine.

In a non-limiting embodiment, each neutral ligand(s) of any transition metal complex (general or specific) or transition metal precursor (general or specific) described herein, independently can be, comprise, or consist essentially of, pyrrole, a substituted pyrrole, indole, a substituted indole, pyridine, a substituted pyridine, quinoline, a substituted quinoline, or any combination thereof. In another non-limiting embodiment, each neutral ligand(s) of any transition metal complex (general or specific) or transition metal precursor (general or specific) described herein, independently can be, comprise, or consist essentially of, pyrrole, a substituted pyrrole, or any combination thereof; alternatively, indole, a substituted indole, or any combination thereof; alternatively, pyridine, a substituted pyridine, or any combination thereof; or alternatively, quinoline, a substituted quinoline, or any combination thereof; alternatively, pyrrole, indole, pyridine, quinoline, or any combination thereof. In yet another non-limiting embodiment, each neutral ligand(s) of any transition metal complex (general or specific) or transition metal precursor (general or specific) described herein, independently can be, comprise, or consist essentially of, pyrrole; alternatively, a substituted pyrrole; alternatively, indole; alternatively, a substituted indole; alternatively, pyridine; alternatively, a substituted pyridine; alternatively, quinoline; or alternatively, an substituted quinoline.

General substituents (also referred to as non-hydrogen substituents or non-hydrogen substituent groups) are independently disclosed herein. These substituent groups can be utilized without limitation to further describe any substituted amine, substituted acyclic amine, substituted cyclic amine, N-hydrocarbyl aniline (substituted or unsubstituted), N,N-dihydrocarbyl aniline (substituted or unsubstituted), substituted diphenylamines, substituted triphenylamines, substituted pyrroles, substituted indoles, substituted pyridines, and/or substituted quinolines which can be utilized as the neutral ligand.

In an aspect, the neutral ligand(s) of any transition metal complex (general or specific) or transition metal precursor (general or specific) described herein, independently can be a pyrrole compound. In an embodiment, the pyrrole compound which can be utilized as a neutral ligand can have Structure P1.

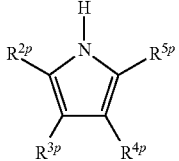

Structure P1

In Structure P1, $R^{2p}$, $R^{3p}$, $R^{4p}$, and $R^{5p}$ independently can be a hydrogen atom or a substituent group. In an embodiment where the pyrrole has Structure P1, $R^{3p}$, $R^{4p}$, and $R^{5p}$ can be hydrogen and $R^{2p}$ can be any non-hydrogen pyrrole substituent described herein; or alternatively, $R^{2p}$, $R^{4p}$, and $R^{5p}$ can be hydrogen and $R^{3p}$ can be any non-hydrogen pyrrole substituent described herein. In an embodiment where the pyrrole has Structure P1, $R^{3p}$ and $R^{4p}$ can be hydrogen and $R^{2p}$ and $R^{5p}$ independently can be any non-hydrogen pyrrole substituent described herein; alternatively, $R^{2p}$ and $R^{5p}$ can be hydrogen and $R^{3p}$ and $R^{4p}$ independently can be any non-hydrogen pyrrole substituent described herein; or alternatively, $R^{2p}$ and $R^{4p}$ can be hydrogen and $R^{3p}$ and $R^{5p}$ independently can be any non-hydrogen pyrrole substituent described herein. In an embodiment where the pyrrole has Structure P1, $R^{5p}$ can be hydrogen and $R^{2p}$, $R^{3p}$, and $R^{4p}$ independently can be any non-hydrogen pyrrole substituent described herein; or alternatively, $R^{4p}$ can be hydrogen and $R^{2p}$, $R^{3p}$, and $R^{5p}$ can be any non-hydrogen pyrrole substituent described herein. In other embodiments, $R^{2p}$, $R^{3p}$, $R^{4p}$, and $R^{5p}$ independently can be any non-hydrogen pyrrole substituent described herein.

In an embodiment, the pyrrole compound which can be utilized as a neutral ligand can have Structure P2, Structure P3, Structure P4, Structure P5, or a combination thereof; alternatively, Structure P2, Structure P3, Structure P4, or any combination thereof; alternatively, Structure P2; alternatively, Structure P3; alternatively, Structure P4; or alternatively, Structure P5.

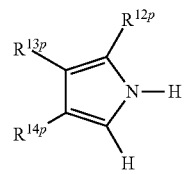

Structure P2

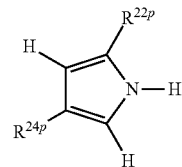

Structure P3

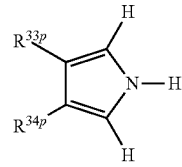

Structure P4

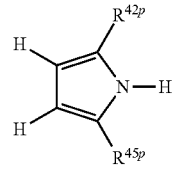

Structure P5

In pyrrole Structures P2, P3, P4, and P5, $R^{12p}$, $R^{13p}$, $R^{14p}$, $R^{22p}$, $R^{24p}$, $R^{33p}$, $R^{34p}$, $R^{42p}$, and $R^{45p}$ independently can be any non-hydrogen pyrrole substituent described herein.

In an embodiment, each non-hydrogen substituent groups which can be utilized as $R^{2p}$, $R^{3p}$, $R^{4p}$, and $R^{5p}$ of the pyrrole compound having Structure P1 or utilized as $R^{12p}$, $R^{13p}$, $R^{14p}$, $R^{22p}$, $R^{24p}$, $R^{33p}$, $R^{34p}$, $R^{42p}$, and $R^{45p}$ of the pyrrole compounds having Structures P2, P3, P4, and/or P5 independently can be a halide, a organoxy group, or an organyl group; alternatively, a halide or an organoxy group; alternatively, a halide or an organyl group; alternatively, a organoxy group or an organyl group; alternatively, a halide; alternatively, a organoxy group; or alternatively, an organyl group. In an embodiment, each non-hydrogen substituent groups which can be utilized as $R^{2p}$, $R^{3p}$, $R^{4p}$, and $R^{5p}$ of the pyrrole compound having Structure P1 or utilized as $R^{12p}$, $R^{13p}$, $R^{14p}$, $R^{22p}$, $R^{24p}$, $R^{33p}$, $R^{34p}$, $R^{42p}$, and $R^{45p}$ of the pyrrole compounds having Structures P2, P3, P4, and/or P5 independently can be a halide, a organoxy group consisting of inert functional groups, or an organyl group consisting of inert functional groups; alternatively, a halide or an organoxy group consisting of inert functional groups; alternatively, a halide or an organyl group consisting of inert functional groups; alternatively, a organoxy group consisting of inert functional groups or an organyl group consisting of inert functional groups; alternatively, a halide; alternatively, a organoxy group consisting of inert functional groups; or alternatively, an organyl group consisting of inert functional groups. In an embodiment, each non-hydrogen substituent groups which can be utilized as $R^{2p}$, $R^{3p}$, $R^{4p}$, and $R^{5p}$ of the pyrrole compound having Structure P1 or utilized as $R^{12p}$, $R^{13p}$, $R^{14p}$, $R^{22p}$, $R^{24p}$, $R^{33p}$, $R^{34p}$, $R^{42p}$, and $R^{45p}$ of the pyrrole compounds having Structures P2, P3, P4, and/or P5 independently can be a halide, a hydrocarboxy group, or a hydrocarbyl group; alternatively, a halide or a hydrocarboxy group; alternatively, a halide or a hydrocarbyl group; alternatively, a hydrocarboxy group or a hydrocarbyl group; alternatively, a halide; alternatively, a hydrocarboxy group; or alternatively, a hydrocarbyl group.

In an aspect or any embodiment described herein, each organyl group which can be utilized as a non-hydrogen substituent group of the pyrrole compound having Structure P1, P2, P3, P4, and/or P5 independently can be a $C_1$-$C_{30}$ organyl group; alternatively, a $C_1$-$C_{18}$ organyl group; alternatively, a $C_1$-$C_{10}$ organyl group; or alternatively, a $C_1$-$C_5$ organyl group. In an aspect or any embodiment described herein, each organoxy group which can be utilized as a non-hydrogen substituent group of the pyrrole compound having Structure P1, P2, P3, P4, and/or P5 independently can be a $C_1$-$C_{30}$ organoxy group; alternatively, a $C_1$-$C_{18}$ organoxy group; alternatively, a $C_1$-$C_{10}$ organoxy group; or alternatively, a $C_1$-$C_5$ organoxy group. In an aspect or any embodiment described herein, each organyl group consisting of inert functional groups which can be utilized as a non-hydrogen substituent group of the pyrrole compound having Structure P1, P2, P3, P4, and/or P5 independently can be a $C_1$-$C_{30}$ organyl group consisting of inert functional groups; alternatively, a $C_1$-$C_{18}$ organyl group consisting of inert functional groups; alternatively, a $C_1$-$C_{10}$ organyl group consisting of inert functional groups; or alternatively, a $C_1$-$C_5$ organyl group consisting of inert functional groups. In an aspect or any embodiment described herein, each organoxy group consisting of inert functional groups which can be utilized as a non-hydrogen substituent group of the pyrrole compound having Structure P1, P2, P3, P4, and/or P5 independently can be a $C_1$-$C_{30}$ organoxy group consisting of inert functional groups; alternatively, a $C_1$-$C_{18}$ organoxy group consisting of inert functional groups; alternatively, a $C_1$-$C_{10}$ organoxy group consisting of inert functional groups; or alternatively, a $C_1$-$C_5$ organoxy group consisting of inert functional groups. In an aspect or any embodiment described herein, each hydrocarbyl group which can be utilized as a non-hydrogen substituent group of the pyrrole compound having Structure P1, P2, P3, P4, and/or P5 independently can be a $C_1$-$C_{30}$ hydrocarbyl group; alternatively, a $C_1$-$C_{18}$ hydrocarbyl group; alternatively, a $C_1$-$C_{10}$ hydrocarbyl group; or alternatively, a $C_1$-$C_5$ hydrocarbyl group. In an aspect or any embodiment described herein, each hydrocarboxy group which can be utilized as a non-hydrogen substituent group of the pyrrole compound having Structure P1, P2, P3, P4, and/or P5 independently can be a $C_1$-$C_{30}$ hydrocarboxy group; alternatively, a $C_1$-$C_{18}$ hydrocarboxy group; alternatively, a $C_1$-$C_{10}$ hydrocarboxy group; or alternatively, a $C_1$-$C_5$ hydrocarboxy group.

In an aspect or any embodiment described herein, each halide which can be utilized as a non-hydrogen substituent group of the pyrrole compound having Structure P1, P2, P3, P4, and/or P5 independently can be fluoride, chloride, bromide, or iodide. In an aspect or any embodiment described herein, each halide which can be utilized as a non-hydrogen substituent group of the pyrrole compound having Structure P1, P2, P3, P4, and/or P5 independently can be fluoride; alternatively, chloride; alternatively, bromide; or alternatively, iodide.

In an embodiment, each non-hydrogen substituent group which can be utilized as a non-hydrogen substituent group of the pyrrole compound having Structure P1, P2, P3, P4, and/or P5 independently can be an alkyl group, a substituted alkyl group, a cycloalkyl group, a substituted cycloalkyl group, an aryl group, a substituted aryl group, an aralkyl group, or a substituted aralkyl group; alternatively, an alkyl group, a cycloalkyl group, an aryl group, or an aralkyl group; alternatively, an alkyl group or a substituted alkyl group; alternatively, a cycloalkyl group or a substituted cycloalkyl group; alternatively, an aryl group or a substituted aryl group; or alternatively, an aralkyl group or a substituted aralkyl group. In other embodiments, each non-hydrogen substituent group which can be utilized as a non-hydrogen substituent group of the pyrrole compound having Structure P1, P2, P3, P4, and/or P5 independently can be alkyl group; alternatively, a substituted alkyl group; alternatively, a cycloalkyl group; alternatively, a substituted cycloalkyl group; alternatively, an aryl group; alternatively, a substituted aryl group; alternatively, an aralkyl group; or alternatively, a substituted aralkyl group. Generally, the alkyl group, substituted alkyl group, cycloalkyl group, substituted cycloalkyl group, aromatic group, substituted aromatic group, aryl group, substituted aryl group, aralkyl group, substituted aralkyl group, and/or silyl group which can be utilized as a non-hydrogen substituent group of the pyrrole compound having Structure P1, P2, P3, P4, and/or P5 can have the same number of carbons as its respective organyl group or hydrocarbyl group which can be utilized as a non-hydrogen substituent group of the pyrrole compound having Structure P1, P2, P3, P4, and/or P5 disclosed herein.

In an embodiment, each alkyl group (substituted or unsubstituted) which can be utilized as a non-hydrogen substituent group of the pyrrole compound having Structure P1, P2, P3, P4, and/or P5 independently can be a $C_1$-$C_{20}$ alkyl group (substituted or unsubstituted); alternatively, a $C_1$-$C_{10}$ alkyl group (substituted or unsubstituted); or alternatively, a $C_1$-$C_5$ alkyl group (substituted or unsubstituted). In some embodiments, each non-hydrogen substituent group which can be utilized as a non-hydrogen substituent group of the pyrrole compound having Structure P1, P2, P3, P4, and/or P5 independently can be a methyl group, an ethyl group, a propyl group, a butyl group, a pentyl group, a hexyl group, a heptyl group, an octyl group, a nonyl group, or a decyl group. In some embodiments, each alkyl group which can be utilized as a non-hydrogen substituent group of the pyrrole compound having Structure P1, P2, P3, P4, and/or P5 independently can be a methyl group, an ethyl group, a n-propyl group, an iso-propyl group, a n-butyl group, an iso-butyl group, a sec-butyl group, a tert-butyl group, a n-pentyl group, an iso-pentyl group, a sec-pentyl group, or a neopentyl group; alternatively, a methyl group, an ethyl group, an iso-propyl group, a tert-butyl group, or a neopentyl group; alternatively, a methyl group; alternatively, an ethyl group; alternatively, a n-propyl group; alternatively, an iso-propyl group; alternatively, a tert-butyl group; or alternatively, a neopentyl group. In an embodiment, any of these alkyl groups can be substituted to form a substituted alkyl group. In an embodiment, each substituent of a substituted alkyl group independently can be a halide or hydrocarboxy group; alternatively, a halide; or alternatively a hydrocarboxy group. Substituent halides and hydrocarboxy groups are independently disclosed herein and can be utilized without limitation to further describe the substituted alkyl group which can be utilized as a non-hydrogen substituent group of the pyrrole compound having Structure P1, P2, P3, P4, and/or P5.

In an embodiment, the cycloalkyl group (substituted or unsubstituted) which can be utilized as a non-hydrogen substituent group of the pyrrole compound having Structure P1, P2, P3, P4, and/or P5 independently can be a $C_4$-$C_{20}$ cycloalkyl group (substituted or unsubstituted); alternatively, a $C_4$-$C_{15}$ cycloalkyl group (substituted or unsubstituted); or alternatively, a $C_4$-$C_{10}$ cycloalkyl group (substituted or unsubstituted). In some embodiments, each non-hydrogen substituent group which can be utilized as a non-hydrogen substituent group of the pyrrole compound having Structure P1, P2, P3, P4, and/or P5 independently can be a cyclopentyl group, a substituted cyclopentyl group, a cyclohexyl group, or a substituted cyclohexyl group. In other embodiments, each non-hydrogen substituent group which can be utilized as a non-hydrogen substituent group of the pyrrole compound having Structure P1, P2, P3, P4, and/or P5 independently can be a cyclopentyl group or a substituted cyclopentyl group; or alternatively, a cyclohexyl group or a substituted cyclohexyl group. In further embodiments, each non-hydrogen substituent group which can be utilized as a non-hydrogen substituent group of the pyrrole compound having Structure P1, P2, P3, P4, and/or P5 independently can be a cyclopentyl group; alternatively, a substituted cyclopentyl group; alternatively, a cyclohexyl group; or alternatively, a substituted cyclohexyl group. Substituents which can be utilized for the substituted cycloalkyl groups are independently disclosed herein and can be utilized without limitation to further describe the substituted cycloalkyl group which can be utilized as a non-hydrogen substituent group of the pyrrole compound having Structure P1, P2, P3, P4, and/or P5.

In some embodiments, the aryl group (substituted or unsubstituted) which can be utilized as a non-hydrogen substituent group of the pyrrole compound having Structure P1, P2, P3, P4, and/or P5 independently can be a $C_6$-$C_{20}$ aryl group (substituted or unsubstituted); alternatively, a $C_6$-$C_{15}$ aryl group (substituted or unsubstituted); or alternatively, a $C_6$-$C_{10}$ aryl group (substituted or unsubstituted). In some embodiments, each non-hydrogen substituent group which can be utilized as a non-hydrogen substituent group of the pyrrole compound having Structure P1, P2, P3, P4, and/or P5 independently can be a phenyl group, a substituted phenyl group, a naphthyl group, or a substituted naphthyl group. In an embodiment, each non-hydrogen substituent group which can be utilized as a non-hydrogen substituent group of the pyrrole compound having Structure P1, P2, P3, P4, and/or P5 independently can be a phenyl group or a substituted phenyl group; alternatively, a naphthyl group or a substituted naphthyl group; alternatively, a phenyl group or a naphthyl group; or alternatively, a substituted phenyl group or a substituted naphthyl group. Substituents which can be utilized for the substituted phenyl groups or substituted naphthyl groups are independently disclosed herein and can be utilized without limitation to further describe the substituted phenyl groups or substituted naphthyl groups which can be utilized as a non-hydrogen substituent group of the pyrrole compound having Structure P1, P2, P3, P4, and/or P5.

In an embodiment, each substituted phenyl group which can be utilized as a non-hydrogen substituent group of the pyrrole compound having Structure P1, P2, P3, P4, and/or P5 independently can be a 2-substituted phenyl group, a 3-substituted phenyl group, a 4-substituted phenyl group, a 2,4-disubstituted phenyl group, a 2,6-disubstituted phenyl group, 3,5-disubstituted phenyl group, or a 2,4,6-trisubstituted phenyl group. In other embodiments, each substituted phenyl group which can be utilized as a non-hydrogen substituent group of the pyrrole compound having Structure P1, P2, P3, P4, and/or P5 independently can be a 2-substituted phenyl group, a 4-substituted phenyl group, a 2,4-disubstituted phenyl group, or a 2,6-disubstituted phenyl group; alternatively, a 3-substituted phenyl group or a 3,5-disubstituted phenyl group; alternatively, a 2-substituted phenyl group or a 4-substituted phenyl group; alternatively, a 2,4-disubstituted phenyl group or a 2,6-disubstituted phenyl group; alternatively, a 2-substituted phenyl group; alternatively, a 3-substituted phenyl group; alternatively, a 4-substituted phenyl group; alternatively, a 2,4-disubstituted phenyl group; alternatively, a 2,6-disubstituted phenyl group; alternatively, 3,5-disubstituted phenyl group; or alternatively, a 2,4,6-trisubstituted phenyl group. Substituents which can be utilized for these specific substituted phenyl groups are independently disclosed herein and can be utilized without limitation to further describe these substituted phenyl groups which can be utilized as a non-hydrogen substituent group of the pyrrole compound having Structure P1, P2, P3, P4, and/or P5.

In an embodiment, the aralkyl group (substituted or unsubstituted) which can be utilized as a non-hydrogen substituent group of the pyrrole compound having Structure P1, P2, P3, P4, and/or P5 independently can be a $C_7$-$C_{20}$ aralkyl group (substituted or unsubstituted); alternatively, a $C_7$-$C_{15}$ aralkyl group (substituted or unsubstituted); or alternatively, a $C_7$-$C_{10}$ aralkyl group (substituted or unsubstituted). In some embodiments, each non-hydrogen substituent group which can be utilized as a non-hydrogen substituent group of the pyrrole compound having Structure P1, P2, P3, P4, and/or P5 independently can be a benzyl group or a substituted benzyl group. In an embodiment, each non-hydrogen substituent group which can be utilized as a non-hydrogen substituent group of the pyrrole compound having Structure P1, P2, P3, P4, and/or P5 independently can be a benzyl group, or alternatively, a substituted benzyl group. Substituents which can be utilized for the substituted aralkyl groups are independently disclosed herein and can be utilized without limitation to further describe the substituted aralkyl groups which can be utilized as a non-hydrogen substituent group of the pyrrole compound having Structure P1, P2, P3, P4, and/or P5.

In an embodiment, each non-hydrogen substituent group which can be utilized as a non-hydrogen substituent group of the pyrrole compound having Structure P1, P2, P3, P4, and/or P5 independently can be an alkoxy group, a substituted alkoxy group, a cycloalkoxy group, a substituted cycloalkoxy group, an aroxy group, a substituted aroxy group, an aralkoxy group, or a substituted aralkoxy group; alternatively, an alkoxy group, a cycloalkoxy group, an aroxy group, or an aralkoxy group; alternatively, an alkoxy group or a substituted alkoxy group; alternatively, a cycloalkoxy group or a substituted cycloalkoxy group; alternatively, an aroxy group or a substituted aroxy group; or alternatively, an aralkoxy group or a substituted aralkoxy group. In other embodiments, each non-hydrogen substituent group which can be utilized as a non-hydrogen substituent group of the pyrrole compound having Structure P1, P2, P3, P4, and/or P5 independently can be alkoxy group; alternatively, a substituted alkoxy group; alternatively, a cycloalkoxy group; alternatively, a substituted cycloalkoxy group; alternatively, an aroxy group; alternatively, a substituted aroxy group; alternatively, an aralkoxy group; or alternatively, a substituted aralkoxy group. Generally, the alkoxy group, substituted alkoxy group, cycloalkoxy group, substituted cycloalkoxy group, aromatic group, substituted aromatic group, aroxy group, substituted aroxy group, aralkoxy group, and/or substituted aralkoxy group which can be utilized as a non-hydrogen substituent group of the pyrrole compound having Structure P1, P2, P3, P4, and/or P5 can have the same number of carbons as the hydrocarboxy group which can be utilized as a non-hydrogen substituent group of the pyrrole compound having Structure P1, P2, P3, P4, and/or P5 disclosed herein. Substituent group are independently described herein and can be utilized without limitation to further describe the substituted alkoxy group, cycloalkoxy group, substituted cycloalkoxy group, aromatic group, substituted aromatic group, aroxy group, substituted aroxy group, aralkoxy group, and/or substituted aralkoxy group which can be utilized as a non-hydrogen substituent group of the pyrrole compound having Structure P1, P2, P3, P4, and/or P5.

In an embodiment, each non-hydrogen substituent group which can be utilized as a non-hydrogen substituent group of the pyrrole compound having Structure P1, P2, P3, P4, and/or P5 independently can be a methoxy group, an ethoxy group, a propoxy group, a butoxy group, a pentoxy group, a hexoxy group, a heptoxy group, or an octoxy group; or alternatively, a methoxy group, an ethoxy group, a propoxy group, a butoxy group, or a pentoxy group. In an embodiment, each non-hydrogen substituent group which can be utilized as a non-hydrogen substituent group of the pyrrole compound having Structure P1, P2, P3, P4, and/or P5 independently can be a methoxy group, an ethoxy group, a n-propoxy group, an iso-propoxy group, an n-butoxy group, an iso-butoxy group, a tert-butoxy group, an n-pentoxy group, an neo-pentoxy group, an n-hexoxy group, an n-heptoxy group, an n-octoxy group; or alternatively, a methoxy group, an ethoxy group, a n-propoxy group, an iso-propoxy group, an n-butoxy group, an iso-butoxy group, a tert-butoxy group, an n-pentoxy group, or an neo-pentoxy group. In an embodiment, each non-hydrogen substituent group which can be utilized as a non-hydrogen substituent group of the pyrrole compound having Structure P1, P2, P3, P4, and/or P5 independently can be a methoxy group; alternatively, an ethoxy group; alternatively, a n-propoxy group; alternatively, an iso-propoxy group; alternatively, an n-butoxy group; alternatively, an iso-butoxy group; alternatively, a tert-butoxy group; alternatively, an n-pentoxy group; alternatively, an neo-pentoxy group; alternatively, an n-hexoxy group; alternatively, an n-heptoxy group; or alternatively, an n-octoxy group.

In an embodiment, each non-hydrogen substituent group which can be utilized as a non-hydrogen substituent group of the pyrrole compound having Structure P1, P2, P3, P4, and/or P5 independently can be an cyclobutoxy group, a substituted cyclobutoxy group, a cyclopentoxy group, a substituted cyclopentoxy group, a cyclohexoxy group, a substituted cyclohexoxy group, a cycloheptoxy group, a substituted cycloheptoxy group, a cyclooctoxy group, or a substituted cyclooctoxy group. In some embodiments, each non-hydrogen substituent group which can be utilized as a non-hydrogen substituent group of the pyrrole compound having Structure P1, P2, P3, P4, and/or P5 independently can be a cyclopentoxy group, a substituted cyclopentoxy group, a cyclohexoxy group, or a substituted cyclohexoxy group. In other embodiments, each non-hydrogen substituent group which can be utilized as a non-hydrogen substituent group of the pyrrole compound having Structure P1, P2, P3, P4, and/or P5 independently can be a cyclobutoxy group or a substituted cyclobutoxy group; alternatively, a cyclopentoxy group or a substituted cyclopentoxy group; alternatively, a cyclohexoxy group or a substituted cyclohexoxy group; alternatively, a cycloheptoxy group or a substituted cycloheptoxy group; or alternatively, a cyclooctoxy group or a substituted cyclooctoxy group. In further embodiments, each non-hydrogen substituent group which can be utilized as a non-hydrogen substituent group of the pyrrole compound having Structure P1, P2, P3, P4, and/or P5 independently can be a cyclopentoxy group; alternatively, a substituted cyclopentoxy group; alternatively, a cyclohexoxy group; or alternatively, a substituted cyclohexoxy group. Substituents which can be utilized for the substituted cycloalkoxy groups are independently disclosed herein and can be utilized without limitation to further describe the substituted cycloalkoxy group which can be utilized as a non-hydrogen substituent group of the pyrrole compound having Structure P1, P2, P3, P4, and/or P5.

In an aspect, each non-hydrogen substituent group which can be utilized as a non-hydrogen substituent group of the pyrrole compound having Structure P1, P2, P3, P4, and/or P5 independently can be a phenoxy group or a substituted phenoxy group; or alternatively, a phenoxy group. In an embodiment, the substituted phenoxy group which can be utilized as a non-hydrogen substituent group of the pyrrole compound having Structure P1, P2, P3, P4, and/or P5 independently can be a 2-substituted phenoxy group, a 4-substituted phenoxy group, a 2,4-substituted phenoxy group, a 2,6-disubstituted phenoxy group, or a 2,4,6-trisubstituted phenoxy group; alternatively, a 2-substituted phenoxy group or a 4-substituted phenoxy group; alternatively, a 2,4-substituted phenoxy group or a 2,6-disubstituted phenoxy group; a 2-substituted phenoxy group; alternatively, a 4-substituted phenoxy group; alternatively, a 2,4-substituted phenoxy group; alternatively, a 2,6-disubstituted phenoxy group; or alternatively, a 2,4,6-trisubstituted phenoxy group. Substituents which can be utilized for the substituted cycloalkoxy groups are independently disclosed herein and can be utilized without limitation to further describe the substituted phenoxy group which can be utilized as a non-hydrogen substituent group of the pyrrole compound having Structure P1, P2, P3, P4, and/or P5.

In an aspect, each non-hydrogen substituent group which can be utilized as a non-hydrogen substituent group of the pyrrole compound having Structure P1, P2, P3, P4, and/or P5 independently can be a benzoxy group or a substituted benzoxy group; alternatively a substituted benzoxy group. In an embodiment, the substituted benzoxy group which can be utilized as a non-hydrogen substituent group of the pyrrole compound having Structure P1, P2, P3, P4, and/or P5 independently can be a 2-substituted benzoxy group, a 4-substituted benzoxy group, a 2,4-substituted benzoxy group, a 2,6-disubstituted benzoxy group, or a 2,4,6-trisubstituted benzoxy group; alternatively, a 2-substituted benzoxy group or a 4-substituted benzoxy group; alternatively, a 2,4-substituted benzoxy group or a 2,6-disubstituted benzoxy group; a 2-substituted benzoxy group; alternatively, a 4-substituted benzoxy group; alternatively, a 2,4-substituted benzoxy group; alternatively, a 2,6-disubstituted benzoxy group; or alternatively, a 2,4,6-trisubstituted benzoxy group. Substituents which can be utilized for the substituted cycloalkoxy groups are independently disclosed herein and can be utilized without limitation to further describe the substituted benzoxy group which can be utilized as a non-hydrogen substituent group of the pyrrole compound having Structure P1, P2, P3, P4, and/or P5.

In a non-limiting embodiment, each neutral ligand(s) of any transition metal complex (general or specific) or transition metal precursor (general or specific) described herein, independently can be, comprise, or consist essentially of, pyrrole, 2,5-dimethylpyrrole, 2-methyl-5-ethylpyrrole, 2,5-diethylpyrrrole, 2-ethyl-5-n-propylpyrrole, 2,5-di-n-propylpyrrole, 2,5-diisopropylpyrrole, 2,5-di-n-butylpyrrole, 2,5-di-n-pentylpyrrole, 2,5-di-n-hexylpyrrole, 2,5-di-n-heptylpyrrole, 2,5-di-n-octylpyrrole, 2-methyl-4-isopropylpyrrole, 2-ethyl-4-isopropylpyrrole, 2-methyl-4-sec-butylpyrrole, 2-ethyl-4-sec-butylpyrrole, 2-methyl-4-isobutylpyrrole, 2-ethyl-4-isobutylpyrrole, 2-methyl-4-t-butylpyrrole, 2-ethyl-4-t-butylpyrrole, 2-methyl-4-neopentylpyrrole, 2-ethyl-4-neopentylpyrrole, 3,4-diisopropylpyrrole, 3,4-di-sec-butylpyrrole, 3,4-diisobutylpyrrole, 3,4-di-t-butylpyrrole, 3,4-di-neopentylpropylpyrrole, 2,3,5-triethylpyrrrole, 2,3,5-tri-n-butylpyrrole, 2,3,5-tri-n-pentylpyrrole, 2,3,5-tri-n-hexylpyrrole, 2,3,5-tri-n-heptylpyrrole, 2,3,5-tri-n-octylpyrrole, 2,3,4,5-tetraethylpyrrole, 2,3,4,5-tetra-n-butylpyrrole, 2,3,4,5-tetra-n-hexylpyrrole, 2,5-dibenzylpyrrole, 2,4-dimethylpyrrole, 2-methyl-4-isopropylpyrrole, 2,4-dimethyl-3-ethylpyrrole, 2,4-diethylpyrrole, 2-ethyl-4-isopropylpyrrole, 2-methyl-4-sec-butylpyrrole, 2-ethyl-4-sec-butylpyrrole, 2-methyl-4-isobutylpyrrole, 2-ethyl-4-isobutylpyrrole, 2-methyl-4-t-butylpyrrole, 2-ethyl-4-t-butylpyrrole, 2-methyl-4-neopentylpyrrole, 2-ethyl-4-neopentylpyrrole, 3,4-dimethylpyrrole, 3,4-diethylpyrrole, 3,4-diisopropylpyrrole, 3,4-di-sec-butylpyrrole, 3,4-diisobutylpyrrole, 3,4-di-t-butylpyrrole, 3,4-di-neopentylpyrrole, or any combination thereof. In other non-limiting embodiments, each neutral ligand(s) of any transition metal complex (general or specific) or transition metal precursor (general or specific) described herein, independently can be, comprise, or consist essentially of, pyrrole, 2,5-dimethylpyrrole, 2-methyl-5-ethylpyrrole, 2,5-diethylpyrrrole, 2,5-di-n-propylpyrrole, 2,5-di-n-butylpyrrole, 2,5-di-n-pentylpyrrole, 2,5-di-n-hexylpyrrole, 2,5-di-n-heptylpyrrole, 2,5-di-n-octylpyrrole, or any combination thereof; alternatively, pyrrole; alternatively, 2,5-dimethylpyrrole, alternatively, 2-methyl-5-ethylpyrrole; alternatively, 2,5-diethylpyrrrole; alternatively, 2,5-di-n-propylpyrrole; alternatively, 2,5-di-n-butylpyrrole; alternatively, 2,5-di-n-pentylpyrrole; alternatively, 2,5-n-hexylpyrrole; alternatively, 2,5-di-n-heptylpyrrole; or alternatively, 2,5-di-n-octylpyrrole.

In a non-limiting embodiment each neutral ligand(s) of any transition metal complex (general or specific) or transition metal precursor (general or specific) described herein, independently can be, comprise, or consist essentially of, pyrrole, 2,5-bis(2',2',2'-trifluoroethyl)pyrrole, 2,5-bis(2'-methoxymethyl)pyrrole, pyrrole-2-carboxylic acid, 2-acetylpyrrole, pyrrole-2-carboxaldehyde, 3-acetyl-2,4-dimethylpyrrole, ethyl-2,4-dimethyl-5-(ethoxycarbonyl)-3-pyrrole-proprionate, or ethyl-3,5-dimethyl-2-pyrrolecarboxylate, or any combination thereof; alternatively, 3,4-dichloropyrrole, 2,3,4,5-tetrachloropyrrole, or any combination thereof. In yet other non-limiting embodiments, each neutral ligand(s) of any transition metal complex (general or specific) or transition metal precursor (general or specific) described herein, independently can be 2,5-bis(2',2',2'-trifluoroethyl)pyrrole; alternatively, 2,5-bis(2'-methoxymethyl)pyrrole; alternatively, pyrrole-2-carboxylic acid; alternatively, 2-acetylpyrrole; alternatively, pyrrole-2-carboxaldehyde; alternatively, 3-acetyl-2,4-dimethylpyrrole; alternatively, ethyl-2,4-dimethyl-5-(ethoxycarbonyl)-3-pyrrole-proprionate; alternatively, ethyl-3,5-dimethyl-2-pyrrolecarboxylate; alternatively, 3,4-dichloropyrrole; or alternatively, 2,3,4,5-tetrachloropyrrole.

In an embodiment, any phosphine and/or acyclic phosphine (substituted or unsubstituted), which can be utilized as the neutral ligand, can be, comprise, or consist essentially of, a $C_3$-$C_{60}$ phosphine and/or acyclic phosphine; alternatively, a $C_3$-$C_{45}$ phosphine and/or acyclic phosphine; alternatively, a $C_3$-$C_{30}$ phosphine and/or acyclic phosphine; alternatively, a $C_3$-$C_{20}$ phosphine and/or acyclic phosphine; or alternatively, a $C_3$-$C_{10}$ phosphine and/or acyclic phosphine. In an embodiment, any cyclic phosphine (substituted or unsubstituted, and/or aliphatic or aromatic), which can be utilized as the neutral ligand, can be, comprise, or consist essentially of, a $C_4$-$C_{60}$ cyclic phosphine; alternatively, a $C_4$-$C_{45}$ cyclic phosphine; alternatively, a $C_4$-$C_{30}$ cyclic phosphine; alternatively, a $C_4$-$C_{20}$ cyclic phosphine; or alternatively, a $C_4$-$C_{15}$ cyclic phosphine.

In an aspect of this disclosure, each neutral ligand(s) of any transition metal complex (general or specific) or transition metal precursor (general or specific) described herein, independently can be, comprise, or consist essentially of, a hydrocarbylphosphine, a substituted hydrocarbyl phosphine, a dihydrocarbylphosphine, a substituted dihydrocarbylphosphine, a trihydrocarbylphosphine, a substituted trihydrocarbylphosphine, any combination thereof; a hydrocarbylphosphine, a dihydrocarbylphosphine, a trihydrocarbylphosphine, or any combination thereof; alternatively, a hydrocarbylphosphine or a substituted hydrocarbylphosphine; alternatively, a dihydrocarbylphosphine or a substituted dihydrocarbylphosphine; alternatively, a trihydrocarbylphosphine or a substituted trihydrocarbylphosphine; alternatively, a hydrocarbylphosphine; alternatively, a substituted hydrocarbylphosphine; alternatively, a dihydrocarbylphosphine; alternatively, a substituted dihydrocarbylphosphine; alternatively, a trihydrocarbylphosphine; or alternatively, a substituted trihydrocarbylphosphine. Hydrocarbyl groups (substituted or substituted) are generally disclosed within the present disclosure (e.g. as a selection for $R^{2c}$, for the monocarboxylate having the formula $^-O_2CR^{2c}$ and/or as a selection for $R^1$, $R^2$, $R^3$, $R^4$, $R^5$, $R^6$, $R^7$, $R^8$, $R^9$, $R^{10}$, $R^{11}$, $R^{12}$, $R^{13}$, or $R^{14}$, among other places). The aspects and embodiments of these hydrocarbyl groups described herein (either explicitly specified or implicitly recognized by those skilled in the art), can be utilized without limitation as the hydrocarbyl groups of the hydrocarbylphosphines (substituted or unsubstituted), dihydrocarbylphosphines (substituted or unsubstituted), and/or trihydrocarbylphosphines (substituted or unsubstituted) which can be utilized as the neutral ligand.

In a non-limiting embodiment, each neutral ligand(s) of any transition metal complex (general or specific) or transition metal precursor (general or specific) described herein, independently can be, comprise, or consist essentially of, trimethylphosphine, triethylphosphine, tripropylphosphine, tributylphosphine, or any combination thereof. In another non-limiting embodiment, each neutral ligand(s) of any transition metal complex (general or specific) or transition metal precursor (general or specific) described herein, independently can be, comprise, or consist essentially of, trimethylphosphine, triethylphosphine, tripropylphosphine, tributylphosphine, or any combination thereof; alternatively, trimethylphosphine; alternatively, triethylphosphine; alternatively, tripropylphosphine; or alternatively, tributylphosphine.

In a non-limiting embodiment, each neutral ligand(s) of any transition metal complex (general or specific) or transition metal precursor (general or specific) described herein, independently can be, comprise, or consist essentially of, phenylphosphine, a substituted phenylphosphine, diphenylphosphine, a di(substituted phenyl)phosphine, triphenylphosphine, a tri(trisubstituted phenyl)phosphine, or any combination thereof; alternatively, phenylphosphine, a substituted phenylphosphine, or any combination thereof; alternatively, diphenylphosphine, a di(substituted phenyl)phosphine, or any combination thereof, or alternatively, triphenylphosphine, a tri(trisubstituted phenyl)phosphine, or any combination thereof. In a non-limiting embodiment, each neutral ligand(s) of any transition metal complex (general or specific) or transition metal precursor (general or specific) described herein, independently can be, comprise, or consist essentially of, phenylphosphine; alternatively, a substituted phenylphosphine; alternatively, diphenylphosphine; alternatively, a di(substituted phenyl)phosphine; alternatively, triphenylphosphine; or alternatively, a tri(substituted phenyl)phosphine.

General substituents (also referred to as non-hydrogen substituents or non-hydrogen substituent groups) are independently disclosed herein. These substituent groups can be utilized without limitation to further describe any substituted phosphine, substituted acyclic phosphine, substituted cyclic phosphine (acyclic or cyclic), substituted phenylphosphine, di(substituted phenyl)phosphine, and/or tri(substituted phenyl)phosphine which can be utilized as the neutral ligand.

In some non-limiting embodiments, each neutral ligand(s) of any transition metal complex (general or specific) or transition metal precursor (general or specific) described herein, independently can be, comprise, or consist essentially of, phenylphosphine, tolylphosphine, diphenylphosphine, ditolylphosphine, triphenylphosphine, tritolylphosphine, methyldiphenylphosphine, dimethylphenylphosphine, ethyldiphenylphosphine, diethylphenyl phosphine, or any combination thereof. In other non-limiting embodiments each neutral ligand(s) of any transition metal complex (general or specific) or transition metal precursor (general or specific) described herein, independently can be, comprise, or consist essentially of, phenylphosphine; alternatively, diphenylphosphine; alternatively, triphenylphosphine; alternatively, tolylphosphine; alternatively, ditolylphosphine; alternatively, tritolylphosphine; alternatively, methyldiphenylphosphine; alternatively, dimethylphenylphosphine; alternatively, ethyldiphenylphosphine; or alternatively, diethylphenylphosphine.

In an embodiment, any phosphite and/or acyclic phosphite (substituted or unsubstituted), which can be utilized as the neutral ligand, can be, comprise, or consist essentially of, a $C_3$-$C_{60}$ phosphite and/or acyclic phosphite; alternatively, a $C_3$-$C_{45}$ phosphite and/or acyclic phosphite; alternatively, a $C_3$-$C_{30}$ phosphite and/or acyclic phosphite; alternatively, a $C_3$-$C_{20}$ phosphite and/or acyclic phosphite; or alternatively, a $C_3$-$C_{10}$ phosphite and/or acyclic phosphite. In an embodiment, any cyclic phosphite (substituted or unsubstituted, and/or aliphatic or aromatic), which can be utilized as the neutral ligand, can be, comprise, or consist essentially of, a $C_3$-$C_{60}$ cyclic phosphite; alternatively, a $C_4$-$C_{45}$ cyclic phosphite; alternatively, a $C_4$-$C_{30}$ cyclic phosphite; alternatively, a $C_4$-$C_{20}$ cyclic phosphite; or alternatively, a $C_4$-$C_{15}$ cyclic phosphite.

According to an aspect of this disclosure, each neutral ligand(s) of any transition metal complex (general or specific) or transition metal precursor (general or specific) described herein, independently can be, comprise, or consist essentially of, a dihydrocarbylphosphite, a substituted dihydrocarbylphosphite, a trihydrocarbylphosphite, a substituted trihydrocarbylphosphite, or any combination thereof; alternatively, a dihydrocarbylphosphite, a trihydrocarbylphosphite, or any combination thereof; a dihydrocarbylphosphite or a substituted dihydrocarbylphosphite; alternatively, a trihydrocarbylphosphite or a substituted trihydrocarbylphosphite; alternatively, a dihydrocarbylphosphite; alternatively, a substituted dihydrocarbylphosphite; alternatively, a trihydrocarbylphosphite; or alternatively, a substituted trihydrocarbylphosphite. Hydrocarbyl groups (substituted or substituted) are generally disclosed within the present disclosure (e.g. as a selection for $R^{2c}$, for the monocarboxylate having the formula $^-O_2CR^{2c}$ and/or as a selection for $R^1$, $R^2$, $R^3$, $R^4$, $R^5$, $R^6$, $R^7$, $R^8$, $R^9$, $R^{10}$, $R^{11}$, $R^{12}$, $R^{13}$, or $R^{14}$, among other places). These hydrocarbyl groups described herein (either explicitly specified or implicitly recognized by those skilled in the art), can be utilized without limitation as the hydrocarbyl groups of the dihydrocarbylphosphite (substituted or unsubstituted) and/or trihydrocarbylphosphites (substituted or unsubstituted) which can be utilized as the neutral ligand.

In a non-limiting embodiment, each neutral ligand(s) of any transition metal complex (general or specific) or transition metal precursor (general or specific) described herein, independently can be, comprise, or consist essentially of, trimethylphosphite, triethylphosphite, tripropylphosphite, tributylphosphite, methyldiphenylphosphite, dimethylphenylphosphite, ethyldiphenylphosphite, diethylphenylphosphite, diphenylphosphite, triphenylphosphite, ditolylphosphite, tritolylphosphite, or any combination thereof. In another non-limiting embodiment, each neutral ligand(s) of any transition metal complex (general or specific) or transition metal precursor (general or specific) described herein, independently can be, comprise, or consist essentially of, trimethylphosphite, triethylphosphite, tripropylphosphite, tributylphosphite, or any combination thereof.

In a non-limiting embodiment, each neutral ligand(s) of any transition metal complex (general or specific) or transition metal precursor (general or specific) described herein, independently can be, comprise, or consist essentially of, diphenylphosphite, a di(substituted phenyl)phosphite, triphenylphosphite, a tri(substituted phenyl)phosphite, or any combination thereof; alternatively, diphenylphosphite, triphenylphosphite, or any combination thereof. In other non-limiting embodiments, each neutral ligand(s) of any transition metal complex (general or specific) or transition metal precursor (general or specific) described herein, independently can be, comprise, or consist essentially of, diphenylphosphite; alternatively, a di(substituted phenyl)phosphite; alternatively, a triphenylphosphite; or alternatively, a tri(substituted phenyl)phosphite.

General substituents (also referred to as non-hydrogen substituents or non-hydrogen substituent groups) are independently disclosed herein. These substituent groups can be utilized without limitation to further describe any substituted phosphite, substituted acyclic phosphite, and/or substituted cyclic phosphite, di(substituted phenyl)phosphites, and/or tri(substituted phenyl)phosphites which can be utilized as the neutral ligand.

In another non-limiting embodiment, each neutral ligand(s) of any transition metal complex (general or specific) or transition metal precursor (general or specific) described herein, independently can be, comprise, or consist essentially of, methyldiphenylphosphite, dimethylphenylphosphite, ethyldiphenylphosphite, diethylphenylphosphite, or any combination thereof alternatively, diphenylphosphite, triphenylphosphite, ditolylphosphite, tritolylphosphite, or any combination thereof alternatively, triphenylphosphite, tritolylphosphite, or any combination thereof. In yet another non-limiting embodiment, each neutral ligand(s) of any transition metal complex (general or specific) or transition metal precursor (general or specific) described herein, independently can be, comprise, or consist essentially of, dimethylphenylphosphite; alternatively, ethyldiphenylphosphite; alternatively, diethylphenylphosphite; alternatively, diphenylphosphite; alternatively, triphenylphosphite; alternatively, ditolylphosphite; or alternatively, tritolylphosphite.

According to an aspect of this disclosure, each neutral ligand(s) of any transition metal complex (general or specific) or transition metal precursor (general or specific) described herein, independently can be, comprise, or consist essentially of, a substituted or unsubstituted azetidine, oxetane, thietane, dioxetane, dithietane, tetrahydropyrrole, dihydropyrrole, pyrrole, indole, isoindole, tetrahydrofuran, dihydrofuran, furan, benzofuran, isobenzofuran, tetrahydrothiophene, dihydrothiophene, thiophene, benzothiophene, isobenzothiophene, imidazolidine, pyrazole, imidazole, oxazolidine, oxazole, isoxazole, thiazolidine, thiazole, isothiazole, benzothiazole, dioxolane, dithiolane, triazole, dithiazole, piperidine, pyridine, tetrahydropyran, dihydropyran, pyran, thiane, piperazine, diazine, oxazine, thiazine, dithiane, dioxane, dioxin, triazine, triazinane, trioxane, oxepin, azepine, thiepin, diazepine, morpholine, quinoline, tetrahydroquinone, bicyclo[3.3.1]tetrasiloxane, or any combination thereof alternatively, a substituted or unsubstituted azetidine, oxetane, thietane, dioxetane, dithietane, tetrahydropyrrole, tetrahydrofuran, tetrahydrothiophene, imidazolidine, oxazolidine, oxazole, thiazolidine, thiazole, dioxolane, dithiolane, piperidine, tetrahydropyran, pyran, thiane, piperazine, oxazine, thiazine, dithiane, dioxane, dioxin, triazinane, trioxane, azepine, thiepin, diazepine, morpholine, 1,2-thiazole, bicyclo[3.3.1]tetrasiloxane, or any combination thereof; alternatively, a substituted or unsubstituted tetrahydropyrrole, tetrahydrofuran, tetrahydrothiophene, oxazolidine, thiazolidine, dioxolane, dithiolane, dithiazole, piperidine, tetrahydropyran, pyran, thiane, piperazine, dithiane, dioxane, dioxin, trioxane, morpholine, or any combination thereof alternatively, a substituted or unsubstituted tetrahydrofuran, tetrahydrothiophene, dioxolane, dithiolane, tetrahydropyran, pyran, thiane, dithiane, dioxane, dioxin, trioxane, or any combination thereof alternatively, tetrahydrofuran, dioxolane, tetrahydropyran, dioxane, trioxane; or any combination thereof alternatively, a substituted or unsubstituted pyrrole, furan, pyrazole, imidazole, oxazole, isoxazole, thiazole, isothiazole, triazole, pyridine, diazine, triazine, quinoline, or combinations thereof alternatively, a substituted or unsubstituted pyrrole, furan, imidazole, oxazole, thiazole, triazole, pyridine, diazine, triazine, or combinations thereof alternatively, furan, oxazole, thiazole, triazole, pyridine, diazine, triazine, or combinations thereof.

According to an aspect of this disclosure, each neutral ligand(s) of any transition metal complex (general or specific) or transition metal precursor (general or specific) described herein, independently can be, comprise, or consist essentially of, azetidine, oxetane, thietane, dioxetane, dithietane, tetrahydropyrrole, dihydropyrrole, pyrrole, indole, isoindole, tetrahydrofuran, dihydrofuran, furan, benzofuran, isobenzofuran, tetrahydrothiophene, dihydrothiophene, thiophene, benzothiophene, isobenzothiophene, imidazolidine, pyrazole, imidazole, oxazolidine, oxazole, isoxazole, thiazolidine, thiazole, isothiazole, benzothiazole, dioxolane, dithiolane, triazole, dithiazole, piperidine, pyridine, tetrahydropyran, dihydropyran, pyran, thiane, piperazine, diazine, oxazine, thiazine, dithiane, dioxane, dioxin, triazine, triazinane, trioxane, oxepin, azepine, thiepin, diazepine, morpholine, quinoline, tetrahydroquinone, bicyclo[3.3.1]tetrasiloxane, or any combination thereof; alternatively, azetidine, oxetane, thietane, dioxetane, dithietane, tetrahydropyrrole, tetrahydrofuran, tetrahydrothiophene, imidazolidine, oxazolidine, oxazole, thiazolidine, thiazole, dioxolane, dithiolane, piperidine, tetrahydropyran, pyran, thiane, piperazine, oxazine, thiazine, dithiane, dioxane, dioxin, triazinane, trioxane, azepine, thiepin, diazepine, morpholine, 1,2-thiazole, bicyclo[3.3.1]tetrasiloxane, or any combination thereof; alternatively, tetrahydropyrrole, tetrahydrofuran, tetrahydrothiophene, oxazolidine, thiazolidine, dioxolane, dithiolane, dithiazole, piperidine, tetrahydropyran, pyran, thiane, piperazine, dithiane, dioxane, dioxin, trioxane, morpholine, or any combination thereof; alternatively, tetrahydrothiophene, dioxolane, dithiolane, tetrahydropyran, pyran, thiane, dithiane, dioxane, dioxin, trioxane, or any combination thereof; alternatively, tetrahydrofuran, dioxolane, tetrahydropyran, dioxane, trioxane; or any combination thereof; alternatively, pyrrole, furan, pyrazole, imidazole, oxazole, isoxazole, thiazole, isothiazole, triazole, pyridine, diazine, triazine, quinoline, or combinations thereof; alternatively, pyrrole, furan, imidazole, oxazole, thiazole, triazole, pyridine, diazine, triazine, or combinations thereof; alternatively, furan, oxazole, thiazole, triazole, pyridine, diazine, triazine, or combinations thereof.

According to an aspect of this disclosure, each neutral ligand(s) of any transition metal complex (general or specific) or transition metal precursor (general or specific) described herein, independently can be, comprise, or consist essentially of, a substituted or unsubstituted azetidine, tetrahydropyrrole, dihydropyrrole, pyrrole, indole, isoindole, imidazolidine, pyrazole, imidazole, oxazolidine, oxazole, isoxazole, thiazolidine, thiazole, isothiazole, triazole, benzotriazole, dithiazole, piperidine, pyridine, piperazine, diazine, oxazine, thiazine, triazine, azepine, diazepine, morpholine, quinoline, tetrahydroisoquinoline, or any combination thereof; alternatively, a substituted or unsubstituted tetrahydropyrrole, pyrrole, indole, isoindole, imidazolidine, imidazole, oxazolidine, oxazole, thiazolidine, thiazole, piperidine, pyridine, piperazine, diazine, triazine, morpholine, quinoline, tetrahydroisoquinoline, or any combination thereof; alternatively, a substituted or unsubstituted tetrahydropyrrole, pyrrole, isoindole, imidazole, oxazolidine, oxazole, thiazolidine, thiazole, piperidine, pyridine, piperazine, diazine, triazine, morpholine, quinoline, or any combination thereof; alternatively, a substituted or unsubstituted tetrahydropyrrole, pyrrole, imidazole, oxazole, thiazole, piperidine, pyridine, piperazine, diazine, triazine, morpholine, quinoline, or any combination thereof; alternatively, a substituted or unsubstituted tetrahydropyrrole, pyrrole, piperidine, piperazine, morpholine, quinoline, or any combination thereof; or alternatively, a substituted or unsubstituted imidazole, oxazole, thiazole, pyridine, diazine, triazine, or any combination thereof. In some embodiments, each neutral ligand(s) of any transition metal complex (general or specific) or transition metal precursor (general or specific) described herein, independently can be, comprise, or consist essentially of, azetidine, tetrahydropyrrole, dihydropyrrole, pyrrole, indole, isoindole, imidazolidine, pyrazole, imidazole, oxazolidine, oxazole, isoxazole, thiazolidine, thiazole, isothiazole, triazole, benzotriazole, dithiazole, piperidine, pyridine, piperazine, diazine, oxazine, thiazine, triazine, azepine, diazepine, morpholine, quinoline, tetrahydroisoquinoline, or any combination thereof; alternatively, tetrahydropyrrole, pyrrole, indole, isoindole, imidazolidine, imidazole, oxazolidine, oxazole, thiazolidine, thiazole, piperidine, pyridine, piperazine, diazine, triazine, morpholine, quinoline, tetrahydroisoquinoline, or any combination thereof; alternatively, tetrahydropyrrole, pyrrole, isoindole, imidazole, oxazolidine, oxazole, thiazolidine, thiazole, piperidine, pyridine, piperazine, diazine, triazine, morpholine, quinoline, or any combination thereof; alternatively, tetrahydropyrrole, pyrrole, imidazole, oxazole, thiazole, piperidine, pyridine, piperazine, diazine, triazine, morpholine, quinoline, or any combination thereof; alternatively, tetrahydropyrrole, pyrrole, piperidine, piperazine, morpholine, quinoline, or any combination thereof; or alternatively, imidazole, oxazole, thiazole, pyridine, diazine, triazine, or any combination thereof.

According to an aspect of this disclosure, each neutral ligand(s) of any transition metal complex (general or specific) or transition metal precursor (general or specific) described herein, independently can be, comprise, or consist essentially of, a substituted or unsubstituted oxetane, dioxetane, tetrahydrofuran, dihydrofuran, furan, benzofuran, isobenzofuran, oxazolidine, oxazole, isoxazole, dioxolane, tetrahydropyran, dihydropyran, pyran, oxazine, dioxane, dioxin, trioxane, oxepin, morpholine, or bicyclo[3.3.1]tetrasiloxane, or any combination thereof; alternatively, a substituted or unsubstituted oxetane, dioxetane, tetrahydrofuran, furan, isobenzofuran, oxazolidine, oxazole, dioxolane, tetrahydropyran, pyran, dioxane, dioxin, trioxane, morpholine, or any combination thereof; alternatively, a substituted or unsubstituted tetrahydrofuran, oxazole, dioxolane, tetrahydropyran, dioxane, dioxin, trioxane, or any combination thereof; or alternatively, a substituted or unsubstituted tetrahydrofuran, dioxolane, tetrahydropyran, dioxane, trioxane, or any combination thereof. In some embodiments, each neutral ligand(s) of any transition metal complex (general or specific) or transition metal precursor (general or specific) described herein, independently can be, comprise, or consist essentially of, oxetane, dioxetane, tetrahydrofuran, dihydrofuran, furan, benzofuran, isobenzofuran, oxazolidine, oxazole, isoxazole, dioxolane, tetrahydropyran, dihydropyran, pyran, oxazine, dioxane, dioxin, trioxane, oxepin, morpholine, or bicyclo[3.3.1]tetrasiloxane, or any combination thereof; alternatively, oxetane, dioxetane, tetrahydrofuran, furan, isobenzofuran, oxazolidine, oxazole, dioxolane, tetrahydropyran, pyran, dioxane, dioxin, trioxane, morpholine, or any combination thereof; alternatively, tetrahydrofuran, oxazole, dioxolane, tetrahydropyran, dioxane, dioxin, trioxane, or any combination thereof; or alternatively, tetrahydrofuran, dioxolane, tetrahydropyran, dioxane, trioxane, or any combination thereof.

According to an aspect of this disclosure, each neutral ligand(s) of any transition metal complex (general or specific) or transition metal precursor (general or specific) described herein, independently can be, comprise, or consist essentially of, a substituted or unsubstituted thietane, dithietane, tetrahydrothiophene, dihydrothiophene, thiophene, benzothiophene, isobenzothiophene, thiazolidine, thiazole, isothiazole, dithiolane, dithiazole, thiane, thiazine, dithiane, thiepin, or any combination thereof; alternatively, a substituted or unsubstituted thietane, dithietane, tetrahydrothiophene, thiophene, isobenzothiophene, thiazolidine, thiazole, dithiolane, thiane, dithiane, or any combination thereof; or alternatively, a substituted or unsubstituted tetrahydrothiophene, dithiolane, thiane, dithiane, or any combination thereof. In some embodiments, each coordinating compound independently can be, comprise, or consist essentially of, a substituted or unsubstituted substituted or unsubstituted, thietane, dithietane, tetrahydrothiophene, dihydrothiophene, thiophene, benzothiophene, isobenzothiophene, thiazolidine, thiazole, isothiazole, dithiolane, dithiazole, thiane, thiazine, dithiane, thiepin, or any combination thereof; alternatively, thietane, dithietane, tetrahydrothiophene, thiophene, isobenzothiophene, thiazolidine, thiazole, dithiolane, thiane, dithiane, or any combination thereof; or alternatively, tetrahydrothiophene, dithiolane, thiane, dithiane, or any combination thereof.

In some embodiments, each neutral ligand(s) of any transition metal complex (general or specific) or transition metal precursor (general or specific) described herein, independently can be, comprise, or consist essentially of, azetidine; alternatively, oxetane; alternatively, thietane; alternatively, dioxetane; alternatively, dithietane; alternatively, tetrahydropyrrole; alternatively, dihydropyrrole, alternatively, pyrrole; alternatively, indole; alternatively, isoindole; alternatively, tetrahydrofuran; alternatively, dihydropyrrole; alternatively, furan; alternatively, benzofuran; alternatively, isobenzofuran; alternatively, tetrahydrothiophene; alternatively, dihydrothiophene; alternatively, thiophene; alternatively, benzothiophene; alternatively, isobenzothiophene; alternatively, imidazolidine; alternatively, pyrazole; alternatively, imidazole; alternatively, oxazolidine; alternatively, oxazole; alternatively, isoxazole; alternatively, thiazolidine; alternatively, thiazole; alternatively, benzothiazole; alternatively, isothiazole; alternatively, dioxolane; alternatively, dithiolane; alternatively, triazole; alternatively, dithiazole; alternatively, piperidine; alternatively, pyridine; alternatively, tetrahydropyran; alternatively, dihydropyran; alternatively, pyran; alternatively, thiane; alternatively, piperazine; alternatively, diazine; alternatively, oxazine; alternatively, thiazine; alternatively, dithiane; alternatively, dioxane; alternatively, dioxin; alternatively, triazine; alternatively, triazinane; alternatively, trioxane; alternatively, oxepin; alternatively, azepine; alternatively, thiepin; alternatively, diazepine; alternatively, morpholine; alternatively, quinoline; alternatively, tetrahydroquinone; or alternatively, bicyclo[3.3.1]tetrasiloxane.

According to an aspect of this disclosure, each neutral ligand(s) of any transition metal complex (general or specific) or transition metal precursor (general or specific) described herein, independently can be, comprise, or consist essentially of, tetrahydrofuran (THF), furan, methyltetrahydrofuran, dihydrofuran, tetrahydropyran, 2,3-dihydropyran, 1,3-dioxane, 1,4-dioxane, morpholine, N-methylmorpholine, acetonitrile, propionitrile, butyronitrile, benzonitrile, pyridine, ammonia ($NH_3$), methyl amine ($NH_2Me$), ethylamine ($NH_2Et$), dimethylamine ($NHMe_2$), diethylamine ($NHEt_2$), trimethylamine ($NMe_3$), triethylamine ($NEt_3$), trimethylphosphine ($PMe_3$), triethylphosphine ($PEt_3$), triphenylphosphine ($PPh_3$), tri-n-butylphosphine ($P(n-Bu)_3$), trimethylphosphite ($P(OMe)_3$), triethylphosphite ($P(OEt)_3$), tri-n-butylphosphite ($P(O-n-Bu)_3$), methyl isocyanide, n-butyl isocyanide, phenyl isocyanide, $SMe_2$, thiophene, or tetrahydrothiophene (THT). In some embodiments, each neutral ligand(s) of any transition metal complex (general or specific) or transition metal precursor (general or specific) described herein, independently can be, comprise, or consist essentially of, tetrahydrofuran (THF), methyltetrahydrofuran, tetrahydropyran, 1,4-dioxane, acetonitrile, pyridine, ammonia ($NH_3$), trimethylamine ($NMe_3$), triethylamine ($NEt_3$), trimethylphosphine ($PMe_3$), triethylphosphine ($PEt_3$), triphenylphosphine ($PPh_3$), $SMe_2$, or tetrahydrothiophene (THT); alternatively, tetrahydrofuran (THF), methyltetrahydrofuran, tetrahydropyran, or 1,4-dioxane; alternatively, ammonia ($NH_3$), trimethylamine ($NMe_3$), or triethylamine ($NEt_3$); or alternatively, trimethylphosphine ($PMe_3$), triethylphosphine ($PEt_3$), triphenylphosphine ($PPh_3$). In other embodiments, each neutral ligand(s) of any transition metal complex (general or specific) or transition metal precursor (general or specific) described herein, independently can be, comprise, or consist essentially of, tetrahydrofuran, acetonitrile, pyridine, ammonia, trimethylamine, trimethylphosphine, or triphenylphosphine; alternatively, tetrahydrofuran, acetonitrile, pyridine, trimethylamine, trimethylphosphine, or triphenylphosphine; or alternatively, tetrahydrofuran or acetonitrile. In still other embodiments, each coordinating compound independently can be tetrahydrofuran (THF); alternatively, tetrahydropyran; alternatively, 1,4-dioxane; alternatively, acetonitrile; alternatively, pyridine; alternatively, ammonia ($NH_3$); alternatively, trimethylamine ($NMe_3$); alternatively, triethylamine ($NEt_3$); alternatively, trimethylphosphine ($PMe_3$); alternatively, triethylphosphine ($PEt_3$); alternatively, triphenylphosphine ($PPh_3$); alternatively, $SMe_2$; or alternatively, tetrahydrothiophene (THT). In yet another embodiment, each neutral ligand(s) of any transition metal complex (general or specific) or transition metal precursor (general or specific) described herein, independently can be, comprise, or consist essentially of, tetrahydrofuran, acetonitrile, pyridine, ammonia, trimethylamine, trimethylphosphine, or triphenylphosphine; alternatively, tetrahydrofuran, acetonitrile, pyridine, trimethylamine, trimethylphosphine, or triphenylphosphine; or alternatively, tetrahydrofuran or acetonitrile.

General substituents (also referred to as non-hydrogen substituents or non-hydrogen substituent groups) are independently disclosed herein. These substituent groups can be utilized without limitation to further describe any azetidine, oxetane, thietane, dioxetane, dithietane, tetrahydropyrrole, dihydropyrrole, pyrrole, indole, isoindole, tetrahydrofuran, dihydrofuran, furan, benzofuran, isobenzofuran, tetrahydrothiophene, dihydrothiophene, thiophene, benzothiophene, isobenzothiophene, imidazolidine, pyrazole, imidazole, oxazolidine, oxazole, isoxazole, thiazolidine, thiazole, isothiazole, benzothiazole, dioxolane, dithiolane, triazole, dithiazole, piperidine, pyridine, tetrahydropyran, dihydropyran, pyran, thiane, piperazine, diazine, oxazine, thiazine, dithiane, dioxane, dioxin, triazine, triazinane, trioxane, oxepin, azepine, thiepin, diazepine, morpholine, quinoline, tetrahydroquinone, bicyclo[3.3.1]tetrasiloxane, oxetane, and/or dioxetane which can be utilized as the neutral ligand.

In an aspect, the transition metal complex can be a neutral transition metal complex (m equals 0 and in which case the transition metal complex is the transition metal precursor), a cationic transition metal complex (m is a positive number), or an anionic transition metal complex (m is a negative number); alternatively, a neutral transition metal complex; alternatively, a cationic transition metal complex; or alternatively, an anionic transition metal complex. In an embodiment, the charge, m, of a cationic transition metal complex can be from 1 to 4; alternatively, 1; alternatively, 2, alternatively, 3, or alternatively 4. In an embodiment, the charge, m, of an anionic transition metal complex can be from −1 to −4; alternatively, −1; alternatively, −2, alternatively, −3, or alternatively −4.

The transition metal complex has been described herein as a component of transition metal precursor (or alternatively, as the transition metal precursor). Within these descriptions, the transition metal complex can have the formula $((M^B)_{y1}X_{x1}L_l)^m$, $(M^BX_{x1}L_l)^m$, $(M^BL_l)^m$, $(M^B)_{y1}X_{x1}L_l$, $M^BX_xL_l$, $((M^B)_{y1}X_{x1})^m$, or $(M^BX_{x1})^m$; alternatively, $((M^B)_{y1}X_{x1}L_l)^m$, $(M^BX_{x1}L_l)^m$, or $(M^BL_l)^m$; alternatively, $((M^B)_{y1}X_{x1}L_l)^m$ or $(M^BX_{x1}L_l)^m$; alternatively, $((M^B)_{y1}X_{x1})^m$ or $(M^BX_{x1})^m$; alternatively, $(M^B)_{y1}X_{x1}L_l$, $((M^B)_{y1}X_{x1}L_l)^m$ or $M^BX_x$; alternatively, $(M^B)_{y1}X_{x1}L_l$ or $M^BX_xL_l$; alternatively $(M^B)_{y1}X_{x1}$ or $M^BX_x$; alternatively, $((M^B)_{y1}X_{x1}L_l)^m$; alternatively, $(M^BX_{x1}L_l)^m$; alternatively, $(M^BL_l)^m$; alternatively, $(M^B)_{y1}X_{x1}L_l$; alternatively, $M^BX_xL_l$; alternatively, $((M^B)_{y1}X_{x1})^m$; alternatively, $(M^BX_{x1})^m$; alternatively, $(M^B)_{y1}X_{x1}$; or alternatively, $M^BX_x$. Generally, the transition metal ($M^B$), the oxidation state of the transition metal (x), the number of transition metals (y1) the anionic ligand (X), the charge of the anionic ligand(s) (y), the number of anionic ligands (x1), the neutral ligand (L), the number of neutral ligands (l), and the charge of the transition metal complex have been previously described herein and the transition metal complex can be described utilizing any compatible combination of these independently described elements which fit the transition metal complex features described herein.

In an aspect, the number of number of transition metal complex(es) (q) which can be present in the transition metal precursor can range from 1 to 3; or alternatively, from 2 to 3. In some embodiments, the number of transition metal complex(es) (q) which can be present in the transition metal precursor can be 1; alternatively, 2; or alternatively, 3.

In a non-limiting embodiment, the transition metal complex can be, comprise, or consist essentially of, a neutral transition metal(II) complex, a cationic transition metal(II) complex, or an anionic transition metal(II) complex; alternatively, a neutral transition metal(III) complex, a cationic transition metal(III) complex, or an anionic transition metal (III) complex; alternatively, a neutral transition metal(IV) complex, a cationic transition metal(IV) complex, or an anionic transition metal(IV) complex. In some non-limiting embodiments, the transition metal complex can be, comprise, or consist essentially of, a neutral transition metal(II) complex; alternatively, a cationic transition metal(II) complex; alternatively, an anionic transition metal(II) complex; alternatively, a neutral transition metal(III) complex; alternatively, a cationic transition metal(III) complex; alternatively, an anionic transition metal(III) complex; alternatively, a neutral transition metal(IV) complex; alternatively, a cationic transition metal(IV) complex; or alternatively, an anionic transition metal(IV) complex.

In a non-limiting embodiment, the transition metal complex can be, comprise, or consist essentially of, chromium complex. In an embodiment, the chromium complex can be, comprise, or consist essentially of, a neutral chromium complex, a cationic chromium complex, or an anionic chromium complex; alternatively, a neutral chromium complex; alternatively, a cationic chromium complex; or alternatively, an anionic chromium complex. In some non-limiting embodiments wherein the transition metal is chromium, the transition metal complex can be, comprise, or consist essentially of, a neutral chromium(II) complex, a cationic chromium(II) complex, an anionic chromium(II)

complex, a neutral chromium(III) complex, a cationic chromium(III) complex, or an anionic chromium(III) complex; a neutral chromium(II) complex, a cationic chromium(II) complex, or an anionic chromium(II) complex; or alternatively, a neutral chromium(III) complex, a cationic chromium(III) complex, or an anionic chromium(III) complex. In other non-limiting embodiments wherein the transition metal is chromium, the transition metal complex can be, comprise, or consist essentially of, a neutral chromium(II) complex; alternatively, a cationic chromium(II) complex; alternatively, an anionic chromium (II) complex; alternatively, a neutral chromium (III) complex; alternatively, a cationic chromium (III) complex; or alternatively, an anionic chromium (III) complex.

In an aspect and in any embodiment, the neutral transition metal complex (in which case the transition metal complex would be the transition metal precursor) can have the formula $(M^B)_{y1}X_{x1}L_l$, $M^BX_xL_l$, $(M^B)_{y1}X_{x1}$, or $M^BX_x$; alternatively, $(M^B)_{y1}X_{x1}L_l$ or $M^BX_xL_l$; alternatively, $(M^B)_{y1}X_{x1}$ or $M^BX_x$; alternatively, $(M^B)_{y1}X_{x1}L_l$; alternatively, $M^BX_xL_l$; alternatively, $(M^B)_{y1}X_{x1}$; or alternatively, $M^BX_x$. Generally, the neutral transition metal complex can be described using any compatible combination of transition metal $(M^B)$ described herein, oxidation state of the transition metal (x) described herein, number of transition metals (y1) described herein, anionic ligand (X) described herein, charge of the anionic ligand(s) (y) described herein, number of anionic ligands (x1) described herein, neutral ligand (L) described herein, and number of neutral ligands (l) described herein.

In a non-limiting embodiment, the neutral transition metal complex can be, comprise, or consist essentially of, a neutral transition metal halide, a neutral transition metal halide hydrocarbylnitrile complex, a neutral transition metal halide trihydrocarbylamine complex, a neutral transition metal halide dihydrocarbylether complex, a neutral transition metal halide dihydrocarbylsulfide complex, or a neutral transition metal halide trihydrocarbylphosphine complex. In some non-limiting embodiments, the neutral transition metal complex can be, comprise, or consist essentially of, a neutral transition metal halide trihydrocarbylamine complex, a neutral transition metal halide dihydrocarbylether complex, or a neutral transition metal halide dihydrocarbylsulfide complex. In some non-limiting embodiments, the neutral transition metal complex can be, comprise, or consist essentially of, a neutral transition metal halide ammonia complex, a neutral transition metal halide tetrahydrofuran complex, or a neutral transition metal halide tetrahydrothiophene complex. In yet other non-limiting embodiments, the neutral transition metal complex can be, comprise, or consist essentially of, a neutral transition metal halide; alternatively, a neutral transition metal halide ammonia complex; alternatively, a neutral transition metal halide hydrocarbylnitrile complex; alternatively, a neutral transition metal halide trihydrocarbylamine complex; alternatively, a neutral transition metal halide dihydrocarbylether complex; alternatively, a neutral transition metal halide dihydrocarbylsulfide complex; alternatively, a neutral transition metal halide tetrahydrofuran complex; alternatively, a neutral transition metal halide tetrahydrothiophene complex; or alternatively, a neutral transition metal halide trihydrocarbylphosphine complex. Generally, the individual elements of these non-limiting embodiments of the neutral transition metal complex are independently described herein and can be utilized in any compatible combination to further describe the neutral transition metal complex.

Transition metals and transition metal oxidation states which can be utilized to describe the neutral transition metal complexes are independently described herein and can be utilized in any combination to further describe the neutral transition metal complexes which can be utilized in any aspect or any embodiment disclosed herein. In a non-limiting embodiment, the neutral transition metal complexes which can be utilized in any aspect or any embodiment disclosed herein can be, comprise, or consist essentially of, a neutral titanium(III) complex, a neutral vanadium(III) complex, a neutral niobium(III) complex, a neutral chromium(III) complex, a neutral manganese(III) complex, or a neutral iron(III) complex having any anionic ligand described herein and any neutral ligand described herein. In some embodiments, any anionic ligand described herein and any neutral ligand described herein can be utilized to further describe a non-limiting neutral titanium(III) complex; alternatively, a neutral vanadium(III) complex; alternatively, a neutral niobium(III) complex; alternatively, a neutral chromium(III) complex; alternatively, a neutral manganese(III) complex; or alternatively, a neutral iron(III) complex. In a non-limiting embodiment, the neutral transition metal complex can be, comprise, or consist essentially of, a neutral titanium(III) halide complex, a neutral vanadium(III) halide complex, a neutral niobium(III) halide complex, a neutral chromium(III) complex, a neutral manganese(III) halide complex, or a neutral iron(III) halide complex; alternatively, a neutral titanium(III) halide complex; alternatively, a neutral vanadium(III) halide complex; alternatively, a neutral niobium(III) halide complex; alternatively, a neutral chromium(III) complex; alternatively, a neutral manganese(III) halide complex; or alternatively, a neutral iron(III) halide complex.

In a non-limiting embodiment, the transition metal complex which can be utilized in any aspect or any embodiment described herein can be, comprise, or consist essentially of, a neutral titanium(III) halide, a neutral titanium(III) halide hydrocarbylnitrile complex, a neutral titanium(III) halide trihydrocarbylamine complex, a neutral titanium(III) halide dihydrocarbyl ether complex, a neutral titanium(III) halide dihydrocarbylsulfide complex, a neutral titanium(III) halide trihydrocarbylphosphine complex, a neutral vanadium(III) halide, a neutral vanadium(III) halide hydrocarbylnitrile complex, a neutral vanadium(III) halide trihydrocarbylamine complex, a neutral vanadium(III) halide dihydrocarbyl ether complex, a neutral vanadium(III) halide dihydrocarbylsulfide complex, a neutral vanadium(III) halide trihydrocarbylphosphine complex, a neutral niobium(III) halide, a neutral niobium(III) halide hydrocarbylnitrile complex, a neutral niobium(III) halide trihydrocarbylamine complex, a neutral niobium(III) halide dihydrocarbyl ether complex, a neutral niobium(III) halide dihydrocarbylsulfide complex, a neutral niobium(III) halide trihydrocarbylphosphine complex, a neutral chromium(III) halide, a neutral chromium (III) halide hydrocarbylnitrile complex, a neutral chromium (III) halide trihydrocarbylamine complex, a neutral chromium(III) halide dihydrocarbyl ether complex, a neutral chromium(III) halide dihydrocarbylsulfide complex, a neutral chromium(III) halide trihydrocarbylphosphine complex, a neutral manganese(III), a neutral manganese(III) halide hydrocarbylnitrile complex, a neutral manganese(III) halide trihydrocarbylamine complex, a neutral manganese(III) halide dihydrocarbyl ether complex, a neutral manganese (III) halide dihydrocarbylsulfide complex, a neutral manganese(III) halide trihydrocarbylphosphine complex, a neutral iron (III) halide, a neutral iron(III) halide hydrocarbylnitrile complex, a neutral iron(III) halide trihydrocarbylamine complex, a neutral iron(III) halide dihydrocarbyl ether complex, a neutral iron(III) halide dihydrocarbylsulfide complex, or a neutral iron(III) halide trihydrocarbylphosphine complex. In some non-limiting embodiments, the neutral transition metal complexes which can be utilized in any aspect or any embodiment disclosed herein can be, comprise, or consist essentially of, a neutral titanium(III) halide, a neutral titanium(III) halide hydrocarbylnitrile complex, a neutral titanium(III) halide trihydrocarbylamine complex, a neutral titanium(III) halide dihydrocarbyl ether complex, a neutral titanium(III) halide dihydrocarbylsulfide complex, or a neutral titanium(III) halide trihydrocarbylphosphine complex; alternatively, a neutral vanadium(III) halide, a neutral vanadium(III) halide hydrocarbylnitrile complex, a neutral vanadium(III) halide trihydrocarbylamine complex, a neutral vanadium(III) halide dihydrocarbyl ether complex, a neutral vanadium(III) halide dihydrocarbylsulfide complex, or a neutral vanadium(III) halide trihydrocarbylphosphine complex; alternatively, a neutral niobium(III) halide, a neutral niobium(III) halide hydrocarbylnitrile complex, a neutral niobium(III) halide trihydrocarbylamine complex, a neutral niobium(III) halide dihydrocarbyl ether complex, a neutral niobium(III) halide dihydrocarbylsulfide complex, or a neutral niobium(III) halide trihydrocarbylphosphine complex; alternatively, a neutral chromium(III) halide, a neutral chromium(III) halide hydrocarbylnitrile complex, a neutral chromium(III) halide trihydrocarbylamine complex, a neutral chromium(III) halide dihydrocarbyl ether complex, a neutral chromium(III) halide dihydrocarbylsulfide complex, or a neutral chromium(III) halide trihydrocarbylphosphine complex; alternatively, a neutral manganese(III) halide, a neutral manganese(III) halide hydrocarbylnitrile complex, a neutral manganese(III) halide trihydrocarbylamine complex, a neutral manganese(III) halide dihydrocarbyl ether complex, a neutral manganese(III) halide dihydrocarbylsulfide complex, or a neutral manganese(III) halide trihydrocarbylphosphine complex; or alternatively, a neutral iron(III) halide, a neutral iron(III) halide hydrocarbylnitrile complex, a neutral iron(III) halide trihydrocarbylamine complex, a neutral iron(III) halide dihydrocarbyl ether complex, a neutral iron(III) halide dihydrocarbylsulfide complex, a neutral iron(III) halide trihydrocarbylphosphine complex. In yet other non-limiting embodiments, the neutral transition metal complexes which can be utilized in any aspect or any embodiment disclosed herein can be, comprise, or consist essentially of, a neutral titanium(III) halide tetrahydrofuran complex, a neutral vanadium(III) halide tetrahydrofuran complex, a neutral niobium(III) halide tetrahydrofuran complex, a neutral chromium(III) halide tetrahydrofuran complex, a neutral manganese(III) halide tetrahydrofuran complex, or a neutral iron(III) halide tetrahydrofuran complex. In further non-limiting embodiments, the neutral transition metal complexes which can be utilized in any aspect or any embodiment disclosed herein can be, comprise, or consist essentially of, a neutral titanium (III) halide; alternatively, a neutral titanium(III) halide tetrahydrofuran complex; alternatively, neutral titanium(III) halide hydrocarbylnitrile complex; alternatively, a neutral titanium(III) halide trihydrocarbylamine complex; alternatively, a neutral titanium(III) halide dihydrocarbyl ether complex; alternatively, a neutral titanium(III) halide dihydrocarbylsulfide complex; alternatively, a neutral titanium (III) halide trihydrocarbylphosphine complex; alternatively, a neutral chromium(III) halide; alternatively, a neutral chromium(III) halide tetrahydrofuran complex; alternatively, a neutral chromium(III) halide hydrocarbylnitrile complex; alternatively, a neutral chromium(III) halide trihydrocarbylamine complex; alternatively, a neutral chromium(III) halide dihydrocarbyl ether complex; alternatively, a neutral chromium(III) halide dihydrocarbylsulfide complex; alternatively, a neutral chromium(III) halide trihydrocarbylphosphine complex; alternatively, a neutral iron(III) halide; alternatively, a neutral iron(III) halide tetrahydrofuran complex; alternatively, a neutral iron(III) halide hydrocarbylnitrile complex; alternatively, a neutral iron(III) halide trihydrocarbylamine complex; alternatively, a neutral iron(III) halide dihydrocarbyl ether complex; alternatively, a neutral iron (III) halide dihydrocarbylsulfide complex; or alternatively, a neutral iron(III) halide trihydrocarbylphosphine complex. Other general or specific neutral transition metal complexes having the formula $M^B L_l$ can be described using aspects and embodiments of the present disclosure. These general and specific neutral chromium complexes are readily apparent and contemplated.

In an aspect, the cationic transition metal complex (a transition metal complex where m is a positive integer) can have the formula $((M^B)_{y1} X_{x1} L_l)^m$, $(M^B X_{x1} L_l)^m$, $(M^B L_l)^m$, $(M^B)_{y1} X_{x1})^m$, or $(M^B X_{x1})^m$; alternatively, $((M^B)_{y1} X_{x1} L_l)^m$, $(M^B X_{x1} L_l)^m$, $(M^B L_l)^m$, $((M^B)_{y1} X_{x1})^m$, or $(M^B X_{x1})^m$; alternatively, $((M^B)_{y1} X_{x1} L_l)^m$, $(M^B X_{x1} L_l)^m$, or $(M^B L_l)^m$; alternatively, $((M^B)_{y1} X_{x1} L_l)^m$ or $(M^B X_{x1} L_l)^m$; alternatively, $((M^B)_{y1} X_{x1})^m$ or $(M^B X_{x1})^m$; alternatively, $((M^B)_{y1} X_{x1} L_l)^m$; alternatively, $(M^B X_{x1} L_l)^m$; alternatively, $(M^B L_l)^m$; alternatively, $((M^B)_{y1} X_{x1})^m$; or alternatively, $(M^B X_{x1})^m$. Generally, the cationic transition metal complex can be described using any compatible combination of transition metal ($M^B$) described herein, oxidation state of the transition metal (x) described herein, number of transition metals (y1) described herein, anionic ligand (X) described herein, charge of the anionic ligand(s) (y) described herein, number of anionic ligands (x1) described herein, neutral ligand (L) described herein, and number of neutral ligands (l) described herein, and positive charge of the cationic transition metal complex (m) described herein.

In a non-limiting embodiment, the cationic transition metal complex can be, comprise, or consist essentially of, a cationic transition metal halide, a cationic transition metal halide trihydrocarbylamine complex, a cationic transition metal halide dihydrocarbylether complex, or a cationic transition metal halide dihydrocarbylsulfide complex. In some non-limiting embodiments, the cationic transition metal complex can be, comprise, or consist essentially of, a cationic transition metal halide trihydrocarbylamine complex, a cationic transition metal halide dihydrocarbylether complex, or a cationic transition metal halide dihydrocarbylsulfide complex. In other non-limiting embodiments, the cationic transition metal complex can be, comprise, or consist essentially of, a cationic transition metal halide ammonia complex, a cationic transition metal halide tetrahydrofuran complex, or a cationic transition metal halide tetrahydrothiophene complex. In yet other non-limiting embodiments, the cationic transition metal complex can be, comprise, or consist essentially of, a cationic transition metal halide complex; alternatively, a cationic transition metal halide ammonia complex; alternatively, a cationic transition metal halide trihydrocarbylamine complex; alternatively, a cationic transition metal halide dihydrocarbylether complex; alternatively, a cationic transition metal halide dihydrocarbylsulfide complex; alternatively, a cationic transition metal halide tetrahydrofuran complex; or alternatively, a cationic transition metal halide tetrahydrothiophene complex. Generally, the individual elements of these non-limiting embodiments of the cationic transition metal complex are independently described herein and can be utilized in any compatible combination to further describe the cationic transition metal complex.

Transition metals and transition metal oxidation states which can be utilized to describe the cationic transition metal complexes are described herein and can be utilized in any combination to further describe the cationic transition metal complexes which can be utilized in any aspect or any embodiment disclosed herein. In a non-limiting embodiment, the cationic transition metal complex can be, comprise, or consist essentially of, a cationic titanium(III) complex, a cationic vanadium(III) complex, a cationic niobium (III) complex, a cationic chromium(III) complex, a cationic iron(III) complex, or a cationic cobalt(III) complex having any anionic ligand described herein and any neutral ligand described herein. In some embodiments, any anionic ligand described herein and any neutral ligand described herein can be utilized to further describe a non-limiting cationic titanium(III) complex; alternatively, a cationic vanadium(III) complex; alternatively, a cationic niobium(III) complex; alternatively, a cationic chromium(III) complex; alternatively, a cationic iron(III) complex; or alternatively, a cationic cobalt(III) complex. In a non-limiting embodiment, the cationic transition metal complex can be, comprise, or consist essentially of, a cationic titanium(III) halide complex, a cationic vanadium(III) halide complex, a cationic niobium(III) halide complex, a cationic chromium(III) complex, a cationic iron(III) halide complex, or a cationic cobalt(III) halide complex; alternatively, a cationic titanium(III) halide complex; alternatively, a cationic vanadium(III) halide complex; alternatively, a cationic niobium(III) halide complex; alternatively, a cationic chromium(III) halide complex; alternatively, a cationic iron(III) halide complex; or alternatively, a cationic cobalt(III) halide complex.

In a non-limiting embodiment, the transition metal complex which can be utilized in any aspect or any embodiment described herein can be, comprise, or consist essentially of, a cationic titanium(III) trihydrocarbylamine complex, a cationic titanium(III) dihydrocarbylether complex, a cationic titanium(III) dihydrocarbylsulfide complex, a cationic vanadium(III) ammonia complex, a cationic vanadium(III) trihydrocarbylamine complex, a cationic vanadium(III) dihydrocarbylether complex, a cationic vanadium(III) dihydrocarbylsulfide complex, a cationic vanadium(III) trihydrocarbylamine complex, a cationic vanadium(III) dihydrocarbylether complex, a cationic vanadium(III) dihydrocarbylsulfide complex, a cationic niobium(III) trihydrocarbylamine complex, a cationic niobium(III) dihydrocarbylether complex, a cationic niobium(III) dihydrocarbylsulfide complex, a cationic chromium(III) trihydrocarbylamine complex, a cationic chromium(III) dihydrocarbylether complex, a cationic chromium(III) dihydrocarbylsulfide complex, a cationic iron(III) trihydrocarbylamine complex, a cationic iron(III) dihydrocarbylether complex, a cationic iron(III) dihydrocarbylsulfide complex, a cationic cobalt(III) trihydrocarbylamine complex, a cationic cobalt(III) dihydrocarbylether complex, a cationic cobalt(III) dihydrocarbylsulfide complex. In some non-limiting embodiments, the transition metal complex which can be utilized in any aspect or any embodiment described herein can be, comprise, or consist essentially of, a cationic titanium(III) trihydrocarbylamine complex, a cationic vanadium(III) trihydrocarbylamine complex, a cationic niobium (III) trihydrocarbylamine complex, a cationic chromium(III) trihydrocarbylamine complex, or a cationic iron(III) trihydrocarbylamine complex, a cationic cobalt(III) trihydrocarbylamine complex; alternatively, a cationic titanium(III) dihydrocarbylether complex, a cationic vanadium(III) dihydrocarbylether complex, a cationic niobium(III) dihydrocarbylether complex, a cationic chromium(III) dihydrocarbylether complex, a cationic iron(III) dihydrocarbylether complex, or a cationic cobalt(III) dihydrocarbylether complex; or alternatively, a cationic titanium(III) dihydrocarbylsulfide complex, a cationic vanadium(III) dihydrocarbylsulfide complex, a cationic niobium(III) dihydrocarbylsulfide complex, a cationic chromium(III) dihydrocarbylsulfide complex, a cationic iron(III) dihydrocarbylsulfide complex, or a cationic cobalt(III) dihydrocarbylsulfide complex. In other non-limiting embodiments, the transition metal complex which can be utilized in any aspect or any embodiment described herein can be, comprise, or consist essentially of, a cationic titanium(III) trihydrocarbylamine complex, a cationic titanium(III) dihydrocarbylether complex, a cationic titanium(III) dihydrocarbylsulfide complex; alternatively, a cationic vanadium(III) trihydrocarbylamine complex, a cationic vanadium(III) dihydrocarbylether complex, a cationic vanadium(III) dihydrocarbylsulfide complex; alternatively, a cationic niobium(III) trihydrocarbylamine complex, a cationic niobium(III) dihydrocarbylether complex, a cationic niobium(III) dihydrocarbylsulfide complex; alternatively, a cationic chromium(III) trihydrocarbylamine complex, a cationic chromium(III) dihydrocarbylether complex, a cationic chromium(III) dihydrocarbylsulfide complex; alternatively, a cationic iron(III) trihydrocarbylamine complex, a cationic iron(III) dihydrocarbylether complex, a cationic iron(III) dihydrocarbylsulfide complex; or alternatively, a cationic cobalt(III) trihydrocarbylamine complex, a cationic cobalt(III) dihydrocarbylether complex, or a cationic cobalt(III) dihydrocarbylsulfide complex. In yet other non-limiting embodiments, the transition metal complex which can be utilized in any aspect or any embodiment described herein can be, comprise, or consist essentially of, a cationic titanium(III) trihydrocarbylamine complex; alternatively, a cationic vanadium(III) trihydrocarbylamine complex; alternatively, a cationic niobium(III) trihydrocarbylamine complex; alternatively, a cationic chromium(III) trihydrocarbylamine complex; alternatively, a cationic iron(III) trihydrocarbylamine complex; alternatively, a cationic cobalt(III) trihydrocarbylamine complex; alternatively, a cationic titanium (III) dihydrocarbylether complex; alternatively, a cationic vanadium(III) dihydrocarbylether complex; alternatively, a cationic niobium(III) dihydrocarbylether complex; alternatively, a cationic chromium(III) dihydrocarbylether complex; alternatively, a cationic iron(III) dihydrocarbylether complex; alternatively, a cationic cobalt(III) dihydrocarbylether complex; alternatively, a cationic titanium(III) dihydrocarbylsulfide complex; alternatively, a cationic vanadium (III) dihydrocarbylsulfide complex; alternatively, a cationic niobium(III) dihydrocarbylsulfide complex; alternatively, a cationic chromium(III) dihydrocarbylsulfide complex; alternatively, a cationic iron(III) dihydrocarbylsulfide complex; or alternatively, a cationic cobalt(III) dihydrocarbylsulfide complex.

In a non-limiting embodiment, the transition metal complex which can be utilized in any aspect or any embodiment described herein can be, comprise, or consist essentially of, a cationic titanium(III) ammonia complex, a cationic vanadium(III) ammonia complex, a cationic niobium(III) ammonia complex, a cationic chromium(III) ammonia complex, a cationic iron(III) ammonia complex, a cationic cobalt(III) ammonia complex, a cationic titanium(III) tetrahydrofuran complex, a cationic vanadium(III) tetrahydrofuran complex, a cationic niobium(III) tetrahydrofuran complex, a cationic chromium(III) tetrahydrofuran complex, a cationic iron(III) tetrahydrofuran complex, a cationic cobalt(III) tetrahydrofuran complex, a cationic titanium(III) tetrahydrothiophene complex, a cationic vanadium(III) tetrahydrothiophene complex, a cationic niobium(III) tetrahydrothiophene complex, a cationic chromium(III) tetrahydrothiophene complex, a cationic iron(III) tetrahydrothiophene complex, or a cationic cobalt(III) tetrahydrothiophene complex. In some non-limiting embodiments, the transition metal complex which can be utilized in any aspect or any embodiment described herein can be, comprise, or consist essentially of, a cationic titanium(III) ammonia complex, a cationic vanadium(III) ammonia complex, a cationic niobium(III) ammonia complex, a cationic chromium(III) ammonia complex, a cationic iron(III) ammonia complex, or a cationic cobalt(III) ammonia complex; alternatively, a cationic titanium(III) tetrahydrofuran complex, a cationic vanadium(III) tetrahydrofuran complex, a cationic niobium(III) tetrahydrofuran complex, a cationic chromium(III) tetrahydrofuran complex, a cationic iron(III) tetrahydrofuran complex, or a cationic cobalt(III) tetrahydrofuran complex; or alternatively, a cationic titanium(III) tetrahydrothiophene complex, a cationic vanadium(III) tetrahydrothiophene complex, a cationic niobium(III) tetrahydrothiophene complex, a cationic chromium(III) tetrahydrothiophene complex, a cationic iron(III) tetrahydrothiophene complex, or a cationic cobalt(III) tetrahydrothiophene complex. In other non-limiting embodiments, the transition metal complex which can be utilized in any aspect or any embodiment described herein can be, comprise, or consist essentially of, a cationic titanium(III) ammonia complex, a cationic titanium(III) tetrahydrofuran complex, a cationic titanium(III) tetrahydrothiophene complex; alternatively, a cationic vanadium(III) ammonia complex, a cationic vanadium(III) tetrahydrofuran complex, a cationic vanadium(III) tetrahydrothiophene complex; alternatively, a cationic niobium(III) ammonia complex, a cationic niobium(III) tetrahydrofuran complex, a cationic niobium(III) tetrahydrothiophene complex; alternatively, a cationic chromium(III) ammonia complex, a cationic chromium(III) tetrahydrofuran complex, a cationic chromium(III) tetrahydrothiophene complex; alternatively, a cationic iron(III) ammonia complex, a cationic iron(III) tetrahydrofuran complex, a cationic iron(III) tetrahydrothiophene complex; or alternatively, a cationic cobalt(III) ammonia complex, a cationic cobalt(III) tetrahydrofuran complex, or a cationic cobalt(III) tetrahydrothiophene complex. In yet other non-limiting embodiments, the transition metal complex which can be utilized in any aspect or any embodiment described herein can be, comprise, or consist essentially of, a cationic titanium(III) ammonia complex; alternatively, a cationic vanadium(III) ammonia complex; alternatively, a cationic niobium(III) ammonia complex; alternatively, a cationic chromium(III) ammonia complex; alternatively, a cationic iron(III) ammonia complex; alternatively, a cationic cobalt(III) ammonia complex; alternatively, a cationic titanium(III) tetrahydrofuran complex; alternatively, a cationic vanadium(III) tetrahydrofuran complex; alternatively, a cationic niobium(III) tetrahydrofuran complex; alternatively, a cationic chromium(III) tetrahydrofuran complex; alternatively, a cationic iron(III) tetrahydrofuran complex; alternatively, a cationic cobalt(III) tetrahydrofuran complex; alternatively, a cationic titanium(III) tetrahydrothiophene complex; alternatively, a cationic vanadium(III) tetrahydrothiophene complex; alternatively, a cationic niobium(III) tetrahydrothiophene complex; alternatively, a cationic chromium(III) tetrahydrothiophene complex; alternatively, a cationic iron(III) tetrahydrothiophene complex; or alternatively, a cationic cobalt(III) tetrahydrothiophene complex.

In a non-limiting embodiment, the transition metal complex which can be utilized in any aspect or any embodiment described herein can be, comprise, or consist essentially of, a cationic titanium(III) halide, a cationic titanium(III) halide trihydrocarbylamine complex, a cationic titanium(III) halide dihydrocarbylether complex, a cationic titanium(III) halide dihydrocarbylsulfide complex, a cationic vanadium(III) halide, a cationic vanadium(III) halide trihydrocarbylamine complex, a cationic vanadium(III) halide dihydrocarbylether complex, a cationic vanadium(III) halide dihydrocarbylsulfide complex, a cationic niobium(III) halide, a cationic niobium(III) halide trihydrocarbylamine complex, a cationic niobium(III) halide dihydrocarbylether complex, a cationic niobium(III) halide dihydrocarbylsulfide complex, a cationic chromium(III) halide, a cationic chromium(III) halide trihydrocarbylamine complex, a cationic chromium(III) halide dihydrocarbylether complex, a cationic chromium(III) halide dihydrocarbylsulfide complex, a cationic iron(III) halide, a cationic iron(III) halide trihydrocarbylamine complex, a cationic iron(III) halide dihydrocarbylether complex, a cationic iron(III) halide dihydrocarbylsulfide complex, a cationic cobalt(III) halide, a cationic cobalt(III) halide trihydrocarbylamine complex, a cationic cobalt(III) halide dihydrocarbylether complex, or a cationic cobalt(III) halide dihydrocarbylsulfide complex. In some non-limiting embodiments, the transition metal complex which can be utilized in any aspect or any embodiment described herein can be, comprise, or consist essentially of, a cationic titanium(III) halide, a cationic vanadium(III) halide, a cationic niobium(III) halide, a cationic chromium(III) halide, a cationic iron(III) halide, or a cationic cobalt(III) halide; alternatively, a cationic titanium(III) halide trihydrocarbylamine complex, a cationic vanadium(III) halide trihydrocarbylamine complex, a cationic niobium(III) halide trihydrocarbylamine complex, a cationic chromium(III) halide trihydrocarbylamine complex, a cationic iron(III) halide trihydrocarbylamine complex, or a cationic cobalt(III) halide trihydrocarbylamine complex; alternatively, a cationic titanium(III) halide dihydrocarbylether complex, a cationic vanadium(III) halide dihydrocarbylether complex, a cationic niobium(III) halide dihydrocarbylether complex, a cationic chromium(III) halide dihydrocarbylether complex, a cationic iron(III) halide dihydrocarbylether complex, or a cationic cobalt(III) halide dihydrocarbylether complex; or alternatively, a cationic titanium(III) halide dihydrocarbylsulfide complex, a cationic vanadium(III) halide dihydrocarbylsulfide complex, a cationic niobium(III) halide dihydrocarbylsulfide complex, a cationic chromium(III) halide dihydrocarbylsulfide complex, a cationic iron(III) halide dihydrocarbylsulfide complex, or a cationic cobalt(III) halide dihydrocarbylsulfide complex. In other non-limiting embodiments, the transition metal complex which can be utilized in any aspect or any embodiment described herein can be, comprise, or consist essentially of, a cationic titanium(III) halide, a cationic titanium(III) halide trihydrocarbylamine complex, a cationic titanium(III) halide dihydrocarbylether complex, a cationic titanium(III) halide dihydrocarbylsulfide complex; alternatively, a cationic vanadium(III) halide, a cationic vanadium(III) halide trihydrocarbylamine complex, a cationic vanadium(III) halide dihydrocarbylether complex, a cationic vanadium(III) halide dihydrocarbylsulfide complex; alternatively, a cationic niobium(III) halide, a cationic niobium(III) halide trihydrocarbylamine complex, a cationic niobium(III) halide dihydrocarbylether complex, a cationic niobium(III) halide dihydrocarbylsulfide complex; alternatively, a cationic chromium(III) halide, a cationic chromium(III) halide trihydrocarbylamine complex, a cationic chromium(III) halide dihydrocarbylether complex, a cationic chromium(III) halide dihydrocarbylsulfide complex; alternatively, a cationic iron(III) halide, a cationic iron(III) halide trihydrocarbylamine complex, a cationic iron(III) halide dihydrocarbylether complex, a cationic iron(III) halide dihydrocarbylsulfide complex; or alternatively, a cationic cobalt(III) halide, a cationic cobalt(III) halide trihydrocarbylamine complex, a cationic cobalt(III) halide dihydrocarbylether complex, or a cationic cobalt(III) halide dihydrocarbylsulfide complex. In yet other non-limiting embodiments, the transition metal complex which can be utilized in any aspect or any embodiment described herein can be, comprise, or consist essentially of, a cationic titanium(III) halide; alternatively, a cationic vanadium(III) halide; alternatively, a cationic niobium(III) halide; alternatively, a cationic chromium(III) halide; alternatively, a cationic iron(III) halide; alternatively, a cationic cobalt(III) halide; alternatively, a cationic titanium(III) halide trihydrocarbylamine complex; alternatively, a cationic vanadium(III) halide trihydrocarbylamine complex; alternatively, a cationic niobium(III) halide trihydrocarbylamine complex; alternatively, a cationic chromium(III) halide trihydrocarbylamine complex; alternatively, a cationic iron(III) halide trihydrocarbylamine complex; alternatively, a cationic cobalt(III) halide trihydrocarbylamine complex; alternatively, a cationic titanium(III) halide dihydrocarbylether complex; alternatively, a cationic vanadium(III) halide dihydrocarbylether complex; alternatively, a cationic niobium(III) halide dihydrocarbylether complex; alternatively, a cationic chromium(III) halide dihydrocarbylether complex; alternatively, a cationic iron(III) halide dihydrocarbylether complex; alternatively, a cationic cobalt(III) halide dihydrocarbylether complex; alternatively, a cationic titanium(III) halide dihydrocarbylsulfide complex; alternatively, a cationic vanadium(III) halide dihydrocarbylsulfide complex; alternatively, a cationic niobium(III) halide dihydrocarbylsulfide complex; alternatively, a cationic chromium(III) halide dihydrocarbylsulfide complex; alternatively, a cationic iron(III) halide dihydrocarbylsulfide complex; or alternatively, a cationic cobalt(III) halide dihydrocarbylsulfide complex.

In a non-limiting embodiment, the transition metal complex which can be utilized in any aspect or any embodiment described herein can be, comprise, or consist essentially of, a cationic titanium(III) halide ammonia complex, a cationic vanadium(III) halide ammonia complex, a cationic niobium(III) halide ammonia complex, a cationic chromium(III) halide ammonia complex, a cationic iron(III) halide ammonia complex, a cationic cobalt(III) halide ammonia complex, a cationic titanium(III) halide tetrahydrofuran complex, a cationic vanadium(III) halide tetrahydrofuran complex, a cationic niobium(III) halide tetrahydrofuran complex, a cationic chromium(III) halide tetrahydrofuran complex, a cationic iron(III) halide tetrahydrofuran complex, a cationic cobalt(III) halide tetrahydrofuran complex, a cationic titanium(III) halide tetrahydrothiophene complex, a cationic vanadium(III) halide tetrahydrothiophene complex, a cationic niobium(III) halide tetrahydrothiophene complex, a cationic chromium(III) halide tetrahydrothiophene complex, a cationic iron(III) halide tetrahydrothiophene complex, or a cationic cobalt(III) halide tetrahydrothiophene complex. In some non-limiting embodiments, the transition metal complex which can be utilized in any aspect or any embodiment described herein can be, comprise, or consist essentially of, a cationic titanium(III) halide ammonia complex, a cationic vanadium(III) halide ammonia complex, a cationic niobium(III) halide ammonia complex, a cationic chromium(III) halide ammonia complex, a cationic iron(III) halide ammonia complex, or a cationic cobalt(III) halide ammonia complex; alternatively, a cationic titanium(III) halide tetrahydrofuran complex, a cationic vanadium(III) halide tetrahydrofuran complex, a cationic niobium(III) halide tetrahydrofuran complex, a cationic chromium(III) halide tetrahydrofuran complex, a cationic iron(III) halide tetrahydrofuran complex, or a cationic cobalt(III) halide tetrahydrofuran complex; or alternatively, a cationic titanium(III) halide tetrahydrothiophene complex, a cationic vanadium(III) halide tetrahydrothiophene complex, a cationic niobium(III) halide tetrahydrothiophene complex, a cationic chromium(III) halide tetrahydrothiophene complex, a cationic iron(III) halide tetrahydrothiophene complex, or a cationic cobalt(III) halide tetrahydrothiophene complex. In other non-limiting embodiments, the transition metal complex which can be utilized in any aspect or any embodiment described herein can be, comprise, or consist essentially of, a cationic titanium(III) halide ammonia complex, a cationic titanium(III) halide tetrahydrofuran complex, a cationic titanium(III) halide tetrahydrothiophene complex; alternatively, a cationic vanadium(III) halide ammonia complex, a cationic vanadium(III) halide tetrahydrofuran complex, a cationic vanadium(III) halide tetrahydrothiophene complex; alternatively, a cationic niobium(III) halide ammonia complex, a cationic niobium(III) halide tetrahydrofuran complex, a cationic niobium(III) halide tetrahydrothiophene complex; alternatively, a cationic chromium(III) halide ammonia complex, a cationic chromium(III) halide tetrahydrofuran complex, a cationic chromium(III) halide tetrahydrothiophene complex; alternatively, a cationic iron(III) halide ammonia complex, a cationic iron(III) halide tetrahydrofuran complex, a cationic iron(III) halide tetrahydrothiophene complex; or alternatively, a cationic cobalt(III) halide ammonia complex, a cationic cobalt(III) halide tetrahydrofuran complex, or a cationic cobalt(III) halide tetrahydrothiophene complex. In yet other non-limiting embodiments, the transition metal complex which can be utilized in any aspect or any embodiment described herein can be, comprise, or consist essentially of, a cationic titanium(III) halide ammonia complex; alternatively, a cationic vanadium(III) halide ammonia complex; alternatively, a cationic niobium(III) halide ammonia complex; alternatively, a cationic chromium(III) halide ammonia complex; alternatively, a cationic iron(III) halide ammonia complex; alternatively, a cationic cobalt(III) halide ammonia complex; alternatively, a cationic titanium(III) halide tetrahydrofuran complex; alternatively, a cationic vanadium(III) halide tetrahydrofuran complex; alternatively, a cationic niobium(III) halide tetrahydrofuran complex; alternatively, a cationic chromium(III) halide tetrahydrofuran complex; alternatively, a cationic iron(III) halide tetrahydrofuran complex; alternatively, a cationic cobalt(III) halide tetrahydrofuran complex; alternatively, a cationic titanium(III) halide tetrahydrothiophene complex; alternatively, a cationic vanadium(III) halide tetrahydrothiophene complex; alternatively, a cationic niobium(III) halide tetrahydrothiophene complex; alternatively, a cationic chromium(III) halide tetrahydrothiophene complex; alternatively, a cationic iron(III) halide tetrahydrothiophene complex; or alternatively, a cationic cobalt(III) halide tetrahydrothiophene complex.

In a non-limiting embodiment, the cationic transition metal complex can be, comprise, or consist essentially of, $TiCl_2(THF)_4^{1+}$, $V(NH_3)_6^{3+}$, $V(NH_3)_6^{2+}$, $Co(NH_3)_6^{2+}$, or $Co(NH_3)_6^{3+}$. In other non-limiting embodiments, the cationic transition metal complex can be, comprise, or consist essentially of, $TiCl_2(THF)_4^{1+}$; alternatively, $V(NH_3)_6^{3+}$ or $V(NH_3)_6^{2+}$; alternatively, $V(NH_3)_6^{3+}$; alternatively, $V(NH_3)_6^{2+}$; alternatively, $Co(NH_3)_6^{2+}$; or alternatively, Co(NH$_3$)$_6$$^{3+}$. Other general or specific cationic transition metal complexes having the formula M$^B$L$_l$, can be described using aspects and embodiments of the present disclosure. These general and specific cationic transition metal complexes are readily apparent and contemplated.

In an aspect, the anionic transition metal complex (a transition metal complex where m is a negative integer) can have the formula ((M$^B$)$_{y1}$X$_{x1}$L$_l$)$^m$, (M$^B$X$_{x1}$L$_l$)$^m$, (M$^B$L$_l$)$^m$, ((M$^B$)$_{y1}$X$_{x1}$)$^m$, or (M$^B$X$_{x1}$)$^m$; alternatively, ((M$^B$)$_{y1}$X$_{x1}$L$_l$)$^m$, (M$^B$X$_{x1}$L$_l$)$^m$, (M$^B$L$_l$)$^m$, ((M$^B$)$_{y1}$X$_{x1}$)$^m$, or (M$^B$X$_{x1}$)$^m$; alternatively, ((M$^B$)$_{y1}$X$_{x1}$L$_l$)$^m$, (M$^B$X$_{x1}$L$_l$)$^m$, or (M$^B$L$_l$)$^m$; alternatively, ((M$^B$)$_{y1}$X$_{x1}$L$_l$)$^m$ or (M$^B$X$_{x1}$L$_l$)$^m$; alternatively, ((M$^B$)$_{y1}$X$_{x1}$)$^m$ or (M$^B$X$_{x1}$)$^m$; alternatively, ((M$^B$)$_{y1}$X$_{x1}$L$_l$)$_m$; alternatively, (M$^B$X$_{x1}$L$_l$)$^m$; alternatively, (M$^B$L$_l$)$^m$; alternatively, ((M$^B$)$_{y1}$X$_{x1}$)$_m$; or alternatively, (M$^B$X$_{x1}$)$^m$. Generally, the anionic transition metal complex can be described using any compatible combination of transition metal (M$^B$) described herein, oxidation state of the transition metal (x) described herein, number of transition metals (y1) described herein, anionic ligand (X) described herein, charge of the anionic ligand(s) (y) described herein, number of anionic ligands (x1) described herein, neutral ligand (L) described herein, and number of neutral ligands (l) described herein, and negative charge of the anionic transition metal complex (m) described herein.

In a non-limiting embodiment, the anionic transition metal complex can be, comprise, or consist essentially of, an anionic transition metal halide or an anionic transition metal cyanide complex. In some non-limiting embodiments, the anionic transition metal complex can be, comprise, or consist essentially of, an anionic transition metal halide; or alternatively, an anionic transition metal cyanide complex. Generally, the individual elements of these non-limiting embodiments of the anionic transition metal complex are independently described herein and can be utilized in any compatible combination to further describe the anionic transition metal complex.

Transition metals and transition metal oxidation states which can utilized to describe the anionic transition metal complexes are described herein and can be utilized in any combination to further describe the anionic transition metal complexes which can be utilized in any aspect or any embodiment disclosed herein. In a non-limiting embodiment, the anionic transition metal complexes which can be utilized in any aspect or any embodiment disclosed herein can be, comprise, or consist essentially of, an anionic titanium (III) complex, an anionic vanadium(III) complex, an anionic niobium(III) complex, an anionic chromium(III) complex, an anionic manganese(III) complex, an anionic iron(III) complex, or an anionic cobalt(III) complex having any anionic ligand described herein. In some embodiments, any anionic ligand described herein can be utilized to further describe a non-limiting anionic titanium (III) complex; alternatively, an anionic vanadium(III) complex; alternatively, an anionic niobium(III) complex; alternatively, an anionic chromium(III) complex; alternatively, an anionic manganese(III) complex; alternatively, an anionic iron(III) complex; or alternatively, an anionic cobalt(III) complex.

In a non-limiting embodiment, the anionic transition metal complexes which can be utilized in any aspect or any embodiment disclosed herein can be, comprise, or consist essentially of, an anionic titanium (III) halide complex, an anionic vanadium(III) halide complex, an anionic niobium (III) halide complex, an anionic chromium(III) halide complex, an anionic manganese(III) halide complex, an anionic iron(III) halide complex, an anionic cobalt(III) halide complex, an anionic titanium (III) cyanide complex, an anionic vanadium(III) cyanide complex, an anionic niobium(III) cyanide complex, an anionic chromium(III) cyanide complex, an anionic manganese(III) cyanide complex, an anionic iron(III) cyanide complex, or an anionic cobalt(III) cyanide complex. In some non-limiting embodiments, the anionic transition metal complexes which can be utilized in any aspect or any embodiment disclosed herein can be, comprise, or consist essentially of, an anionic titanium (III) halide complex, an anionic vanadium(III) halide complex, an anionic niobium(III) halide complex, an anionic chromium(III) halide complex, an anionic manganese(III) halide complex, an anionic iron(III) halide complex, or an anionic cobalt(III) halide complex; or alternatively, an anionic titanium (III) cyanide complex, an anionic vanadium(III) cyanide complex, an anionic niobium(III) cyanide complex, an anionic chromium(III) cyanide complex, an anionic manganese(III) cyanide complex, an anionic iron(III) cyanide complex, or an anionic cobalt(III) cyanide complex. In yet other embodiments, the anionic transition metal complexes which can be utilized in any aspect or any embodiment disclosed herein can be, comprise, or consist essentially of, an anionic titanium (III) halide complex or an anionic titanium (III) cyanide complex; alternatively, an anionic vanadium(III) halide complex or an anionic vanadium(III) cyanide complex; alternatively, an anionic niobium(III) halide complex or an anionic niobium(III) cyanide complex; alternatively, an anionic chromium(III) halide complex or an anionic chromium(III) cyanide complex; alternatively, an anionic manganese(III) halide complex or an anionic manganese(III) cyanide complex; alternatively, an anionic iron (III) halide complex or an anionic iron(III) cyanide complex; or alternatively, an anionic cobalt(III) halide complex or an anionic cobalt(III) cyanide complex. In yet other embodiments, the anionic transition metal complexes which can be utilized in any aspect or any embodiment disclosed herein can be, comprise, or consist essentially of, an anionic titanium (III) halide complex; alternatively, an anionic vanadium(III) halide complex; alternatively, an anionic niobium (III) halide complex; alternatively, an anionic chromium(III) halide complex; alternatively, an anionic manganese(III) halide complex; alternatively, an anionic iron(III) halide complex; alternatively, an anionic cobalt(III) halide complex; alternatively, an anionic titanium (III) cyanide complex; alternatively, an anionic vanadium(III) cyanide complex; alternatively, an anionic niobium(III) cyanide complex; alternatively, an anionic chromium(III) cyanide complex; alternatively, an anionic manganese(III) cyanide complex; alternatively, an anionic iron(III) cyanide complex; or alternatively, an anionic cobalt(III) cyanide complex.

In a non-limiting embodiment, the anionic transition metal complex can be, comprise, or consist essentially of, (Ti(CN)$_6$)$^{3-}$, (VCl$_4$)$^{1-}$, (CrCl$_4$)$^{1-}$, (Cr(CN)$_6$)$^{3-}$, (MnCl$_5$)$^{2-}$, (MnF$_4$)$^{1-}$, (MnF$_5$)$^{2-}$, (MnF$_6$)$^{3-}$, (FeF$_6$)$^{3-}$, (FeCl$_4$)$^{1-}$, (FeCl$_5$)$^{2-}$, (FeI$_4$)$^{1-}$, (Co(CN)$_6$)$^{3-}$, or (CoF$_6$)$^{3-}$. In other non-limiting embodiments, the anionic transition metal complex can be, comprise, or consist essentially of, (Ti(CN)$_6$)$^{3-}$; alternatively, (VCl$_4$)$^{1-}$; alternatively, (CrCl$_4$)$^{1-}$ or (Cr(CN)$_6$)$^{3-}$; alternatively, (CrCl$_4$)$^{1-}$; alternatively, (Cr(CN)$_6$)$^{3-}$; alternatively, (MnCl$_5$)$^{2-}$; alternatively, (MnF$_4$)$^{1-}$, (MnF$_5$)$^{2-}$, or (MnF$_6$)$^{3-}$; alternatively, (MnF$_4$)$^{1-}$; alternatively, (MnF$_5$)$^{2-}$; alternatively, (MnF$_6$)$^{3-}$; alternatively, (FeF$_6$)$^{3-}$, (FeCl$_4$)$^{1-}$, (FeCl$_5$)$^{2-}$, or (FeI$_4$)$^{1-}$; alternatively, (FeF$_6$)$^{3-}$; alternatively, (FeCl$_4$)$^{1-}$; alternatively, (FeCl$_5$)$^{2-}$; alternatively, (FeI$_4$)$^{1-}$; alternatively, (Co(CN)$_6$)$^{3-}$ or (CoF$_6$)$^{3-}$; alternatively, (Co(CN)$_6$)$^{3-}$; or alternatively, (CoF$_6$)$^{3-}$. Other general or specific cationic transition metal complexes having the formula $[(M^B)_{y1}X_x]^m$ and or the formula $[M^BX_x]^m$ can be, comprise, or consist essentially of, described using aspects and embodiments of the present disclosure. These general and specific anionic transition metal complexes are readily apparent and contemplated.

Generally, when the transition metal complex has a negative charge (e.g. having the formula $[((M^B)_{y1}X_{x1}L_l)^m]_q[C^c]_{m1}[A^a]_{m2}$, $[((M)_{y1}X_{x1}L_l)^m]_q[C^c]_{m1}$, $[(M^BX_xL_l)^m]_q[C^c]_{m1}[A^a]_{m2}$, $[(M^BX_xL_l)^m]_q[C^c]_{m1}$, $[((M^B)_{y1}X_{x1})^m]_q[C^c]_{m1}[A^a]_{m2}$, $[((M^B)_{y1}X_{x1})^m]_q[C^c]_{m1}$, $[(M^BX_x)^m]_q[C^c]_{m1}[A^a]_{m2}$, and/or $[(M^BX_x)^m]_q[C^c]_{m1}$, among others where m can be negative), the negative charge on the transition metal complex can be balanced by a cationic specie(s) to provide a neutral transition metal precursor. Generally, the transition metal precursor can be described using any compatible combination of transition metal(s) ($M^B$) described herein, oxidation state of the transition metal (s) (x) described herein, number of transition metals (y1) described herein, anionic ligand(s) (X) described herein, charge of the anionic ligand(s) (y) described herein, number of anionic ligands (x1) described herein, neutral ligand(s) (L) described herein, number of neutral ligands (l) described herein, charge of the transition metal complex(es) (m) described herein, number of anionic metal complexes (q) described herein, cationic species (C) described herein, charge on the cationic specie(s) (c) described herein, and number of cationic specie(s) (m1) described herein.

Generally, when the transition metal precursor (general or specific) comprises at least one cationic species, the charge, c, of each cationic species, C, independently can be an integer ranging from 1 to 3 or alternatively, an integer ranging from 1 to 2. In an embodiment, the charge, c, of each cationic species, C, independently can be 1; alternatively, 2; or alternatively, 3. Generally, the charge, c, of the cationic specie, C, is apparent by the identity of the cationic specie.

Generally, the number of cationic species, m1, in the transition metal precursor can be an integer ranging from 0 to 5. In an embodiment, m1, in the transition metal precursor can be an integer ranging from 0 to 4; alternatively, 0 to 3; alternatively, 0 to 2; alternatively, 1 to 5; alternatively, 1 to 4; alternatively, 1 to 3; or alternatively, 1 to 2. In an embodiment, m1, in the transition metal precursor can be 0; alternatively, 1; alternatively, 2; alternatively, 3; alternatively, 4; or alternatively, 5.

The number of cationic species, m1, in the transition metal precursor is a function of the charge on the transition metal complex(es) (m), the number of transition metal complexes (q), the cationic specie(s), and the charge (c) on the cationic specie(s). When the transition metal complex is anionic, the number of anionic transition metal complex(es) (q) having charge m and the number of cationic specie(s) (C) having charge c can be related by the equation $|m*q|=c*m1$. In some embodiments when the transition metal complex is anionic, the number of anionic transition metal complex(es), q, can be related to the charge on the anionic transition metal complex(es) (m), the cationic specie(s) (C), and the cationic specie charge (c) by the relationship that q=c divided by the greatest common divisor of c and |m|. In some embodiments when the transition metal complex is anionic, the number of cationic specie(s) (m1) can be related to charge on the anionic transition metal complex(es) (m), the cationic specie(s), and the cationic specie charge (c) by the relationship that m1=|m| divided by the greatest common divisor of c and |m|.

In an aspect, each cationic species, C, which can be utilized in a transition metal precursor independently can be, comprise, or consist essentially of, a Group 1 metal cation, a Group 2 metal cation, a tetraorganylammonium cation, or a tetraorganylphosphonium cation. In an embodiment, each cationic species, C, independently can be, comprise, or consist essentially of, a Group 1 metal cation or Group 2 metal cation; alternatively, a tetraorganylammonium cation or a tetraorganylphosphonium cation; alternatively, a Group 1 metal cation; alternatively, a Group 2 metal cation; alternatively, a tetraorganylammonium cation; or alternatively, tetraorganylphosphonium cation. In an aspect, each organyl group of the tetraorganylammonium cation or tetraorganylphosphonium cation independently can be a hydrocarbyl group or a substituted hydrocarbyl group; alternatively, a hydrocarbyl group; or alternatively, a substituted hydrocarbyl group. In some embodiments, the cationic species, C, which can be utilized in a transition metal precursor can be, comprise, or consist essentially of, a tetrahydrocarbylammonium cation, or a tetrahydrocarbylphosphonium cation; tetrahydrocarbylammonium cation; or alternatively, a tetrahydrocarbylphosphonium cation. In other embodiments, the cationic species, C, which can be utilized in a transition metal precursor can be, comprise, or consist essentially of, a tetraalkylammonium cation, or a tetraalkylphosphonium cation; tetraalkylammonium cation; or alternatively, a tetraalkylphosphonium cation. When the cationic species is a Group 1 metal cation, tetraorganylammonium cation, or a tetraorganylphosphonium cation, the charge, c, on the cationic specie is 1. When the cationic species is a Group 2 metal cation, the charge, c, on the cationic specie is 2.

In an aspect, each Group 1 metal cation which can be utilized as the cationic species independently can be, comprise, or consist essentially of, $Li^+$, $Na^+$, $K^+$, $Rb^+$, or $Cs^+$. In an embodiment, each Group 1 cation which can be utilized as the cationic species independently can be, comprise, or consist essentially of, $Li^+$; alternatively, $Na^+$; alternatively, $K^+$; alternatively, $Rb^+$; or alternatively, $Cs^+$. In an aspect, each Group 2 metal cation which can be utilized as the cationic species independently can be, comprise, or consist essentially of $Be^{2+}$, $Mg^{2+}$, $Ca^{2+}$, $Sr^{2+}$, or $Ba^{2+}$. In an embodiment, each Group 2 metal cation which can be utilized as the cationic species independently can be, comprise, or consist essentially of, $Be^{2+}$; alternatively, $Mg^{2+}$; alternatively, $Ca^{2+}$; alternatively, $Sr^{2+}$; or alternatively, $Ba^{2+}$.

In an aspect, each tetraorganylammonium cation which can be utilized as the cationic species independently can have the formula $NR^{1b}R^{2b}R^{3b}R^{4b}$. In another aspect, the tetraorganylammonium cation can have the formula $N(R^{5b})_4$. In an aspect, each tetraorganylphosphonium cation which can be utilized as the cationic species independently can have the formula $PR^{1d}R^{2d}R^{3d}R^{4d}$. In another aspect, the tetrahydrocarbylphosphonium cation can have the formula $P(R^{5d})_4$. Within the tetraorganylammonium cation having the formula $NR^{1b}R^{2b}R^{3b}R^{4b}$, the tetraorganylammonium cation having the formula $N(R^{5b})_4$, the tetraorganylphosphonium cation having the formula $PR^{1d}R^{2d}R^{3d}R^{4d}$, and the tetrahydrocarbylphosphonium cation having the formula $P(R^{5d})_4$, $R^{1b}$, $R^{2b}$, $R^{3b}$, $R^{4b}$, $R^{5b}$, $R^{1d}$, $R^{2d}$, $R^{3d}$, $R^{4d}$ and/or $R^{5d}$ independently can be a $C^1$ to $C^{20}$ organyl group; alternatively, $C^1$ to $C^{15}$ organyl group; $C^1$ to $C^{10}$ organyl group; or alternatively, $C^1$ to $C^5$ organyl group. In an embodiment, each organyl group which can be utilized as $R^{1b}$, $R^{2b}$, $R^{3b}$, $R^{4b}$, $R^{5b}$, $R^{1d}$, $R^{2d}$, $R^{3d}$, $R^{4d}$, and/or $R^{5d}$ independently can be a hydrocarbyl group or a substituted hydrocarbyl group; alternatively, a hydrocarbyl group; or alternatively, a substituted hydrocarbyl group. Generally, the hydrocarbyl group and/or substituted hydrocarbyl group which can be utilized as $R^{1b}$, $R^{2b}$, $R^{3b}$, $R^{4b}$, $R^{5b}$, $R^{1d}$, $R^{2d}$, $R^{3d}$, $R^{4d}$, and/or $R^{5d}$ independently can have the same number of carbon atoms as the organyl groups which can be utilized as $R^{1b}$, $R^{2b}$, $R^{3b}$, $R^{4b}$, $R^{5b}$, $R^{1d}$, $R^{2d}$, $R^{3d}$, $R^{4d}$, and/or $R^{5d}$. Hydrocarbyl groups (substituted or substituted) are generally disclosed within the present disclosure (e.g. as a selection for $R^{2c}$, for the monocarboxylate having the formula $^-O_2CR^{2c}$ and/or as a selection for $R^1$, $R^2$, $R^3$, $R^4$, $R^5$, $R^6$, $R^7$, $R^8$, $R^9$, $R^{10}$, $R^{11}$, $R^{12}$, $R^{13}$, or $R^{14}$, among other places). The aspects and embodiments of these hydrocarbyl groups described herein (either explicitly specified or implicitly recognized by those skilled in the art), can be utilized without limitation as hydrocarbyl groups which can be utilized as $R^{1b}$, $R^{2b}$, $R^{3b}$, and $R^{4b}$ (of the tetrahydrocarbylammonium cation having the formula $NR^{1b}R^{2b}R^{3b}R^{4b}$), $R^{1d}$, $R^{2d}$, $R^{3d}$, and $R^{4d}$ (of the tetrahydrocarbylphosphonium cation having the formula $PR^{1d}R^{2d}R^{3d}R^{4d}$), $R^{5b}$ (of the tetrahydrocarbylammonium cation having formula $N(R^{5b})_4$), and $R^{5d}$ (of the tetrahydrocarbylammonium cation having formula $P(R^{5d})_4$).

In a non-limiting embodiment, each cationic species independently can be, comprise, or consist essentially of, tetramethylammonium ($NMe_4^+$), tetraethylammonium ($NEt_4^+$), tetrabutylammonium ($NBu_4^+$), or tetraphenylammonium ($NPh_4^+$). In some non-limiting embodiments, each cationic species can be, comprise, or consist essentially of, tetramethylammonium ($NMe_4^+$), tetraethylammonium ($NEt_4^+$), or tetrabutylammonium ($NBu_4^+$); alternatively, tetramethylammonium ($NMe_4^+$); alternatively, tetraethylammonium ($NEt_4^+$); alternatively, tetrabutylammonium ($NBu_4^+$); or alternatively, tetraphenylammonium ($NPh_4^+$). In other non-limiting embodiments, each cationic species can be, comprise, or consist essentially of, tetramethylphosphonium ($PMe_4^+$), tetraethylphosphonium ($PEt_4^+$), tetrabutylphosphonium ($PBu_4^+$), or tetraphenylphosphonium ($PPh_4^+$). In yet other non-limiting embodiments, each cationic species can be, comprise, or consist essentially of, tetramethylphosphonium ($PMe_4^+$), tetraethylphosphonium ($PEt_4^+$), or tetrabutylphosphonium ($PBu_4^+$); alternatively, tetramethylphosphonium ($PMe_4^+$); alternatively, tetraethylphosphonium ($PEt_4^+$); alternatively, tetrabutylphosphonium ($PBu_4^+$); or alternatively, tetraphenylphosphonium ($PPh_4^+$).

Generally, when the transition metal complex has a positive charge (e.g. having the formula $[((M^B)_{y1}X_{x1}L_l)^m]_q$ $[C^c]_{m1}[A^a]_{m2}$, $[((M^B) X_x L_l)^m]_q[A^a]_{m2}$, $[(M^BL_l)^m]_q[A^a]_{m2}$, $[(M^B X_x L_l)^m]_q[C^c]_{m1}[A^a]_{m2}$, $[(M^B X_x)^m]_q[A^a]_{m2}$, $[((M^B)_{y1} X_{x1})^m]_q[C^c]_{m1}[A^a]_{m2}$, $[((M^B)_{y1}X_{x1})^m]_q[A^a]_{m2}$, $[(M^B X_x)^m]_q[C^c]_{m1}[A^a]_{m2}$, and/or $[(M^B X_x)^m]^q[A^a]_{m2}$, among others described herein where m can be positive), the positive charge of the transition metal complex can be balanced by an anionic specie(s) to provide a neutral transition metal precursor. Generally, the transition metal precursor can be described using any compatible combination of transition metal(s) ($M^B$) described herein, oxidation state of the transition metal(s) (x) described herein, number of transition metals (y1) described herein, anionic ligand(s) (X) described herein, charge of the anionic ligand(s) (y) described herein, number of anionic ligands (x1) described herein, neutral ligand(s) (L) described herein, number of neutral ligands (l) described herein, charge of the transition metal complex(es) (m) described herein, number of anionic metal complexes (q) described herein, cationic specie(s) (C) described herein, change on the anionic specie(s) (a) described herein, and number of anionic specie(s) (m2) described herein.

Generally, when the transition metal precursor (general or specific) comprises at least one anionic species, the charge, a, of each cationic species, A, independently can be an integer ranging from −1 to −3 or alternatively, an integer ranging from −1 to −2. In an embodiment, the charge, a, of each cationic species, A, independently can be −1; alternatively, −2; or alternatively, −3. Generally, the charge, a, of the cationic specie, A, is apparent by the identity of the cationic specie.

Generally, the number of anionic species, m2, in the transition metal precursor can be an integer ranging from 0 to 5. In an embodiment, m2, in the transition metal precursor can be an integer ranging from 0 to 4; alternatively, 0 to 3; alternatively, 0 to 2; alternatively, 1 to 5; alternatively, 1 to 4; alternatively, 1 to 3; or alternatively, 1 to 2. In an embodiment, m2, in the transition metal precursor can be 0; alternatively, 1; alternatively, 2; alternatively, 3; alternatively, 4; or alternatively, 5.

The number of anionic specie(s), m2, in the transition metal precursor can be a function of the charge on the transition metal complex(es) (m), the number of transition metal complexes (q), the anionic specie(s), and the charge (a) on the anionic specie(s). When the transition metal complex is cationic, the number of cationic transition metal complex(es) (q) having charge m and the number of anionic specie(s) (A) having charge a can be related by the equation $m*q=|a*m2|$. In some embodiments when the transition metal complex is cationic, the number of cationic transition metal complex(es), q, can be related to the charge on the cationic transition metal complex(es) (m), the anionic specie(s) (A), and the anionic specie(s) charge (c) by the relationship that q=|a| divided by the greatest common divisor of |a| and m. In some embodiments when the transition metal complex is cationic, the number of anionic specie(s), m2, can be related to the charge on the cationic transition metal complex(es) (m), the anionic specie(s) (A), and the anionic specie(s) charge (c) by the relationship that m2=|m| divided by the greatest common divisor of |a| and m.

In an aspect, each anionic species, A, which can be utilized in a transition metal precursor independently can be, but is not limited to, halide, hypohalite, halite, halate, perhalate, nitrate, nitrite, sulfate, sulfite, bisulfate, phosphate, cyanide, cyanate, thiocyanate, a hexahalophosphate, a tetrahaloaluminate, a hexahaloaluminate, hexahalosilicate, metaborate, tetraborate, a tetrahaloborate, or a tetraorganylborate. In an embodiment, each anionic species, A, independently can be a halide, nitrate, sulfate, phosphate, cyano, a hexahalophosphate, a tetrahaloborate, or a tetraorganylborate; alternatively, a halide, nitrate, sulfate, or phosphate; alternatively, a halide; alternatively, a hypohalite; alternatively, a halite; alternatively, a halate; alternatively, a perhalate; alternatively, a nitrate; alternatively, a nitrite; alternatively, a sulfate; alternatively, a sulfite; alternatively, a bisulfate; alternatively, a phosphate; alternatively, a phosphite; alternatively, a cyanide; alternatively, a cyanate; alternatively, a thiocyanate; alternatively, a hexahalophosphate; alternatively, a hexahaloaluminate; alternatively, hexahalosilicate; alternatively, a metaborate; alternatively, a tetraborate; alternatively, a tetrahaloborate; or alternatively, a tetraorganylborate. When the anionic species is a halide, a hypohalite, a halite, a halate, perhalate, nitrate, nitrate, bisulfite, cyanide, cyanate, thiocyanate, a tetrahaloaluminate, a hexahalophosphate, metaborate, tetraborate, or a tetraorganylborate, the charge, a, on the anionic specie is −1. When the anionic species is a sulfate, sulfite, hexahalosilicate, or tetraborate, the charge, a, on the anionic specie is −2. When the anionic species is a phosphate, or hexahaloaluminate, the charge, a, on the anionic specie is −3.

In an embodiment, the halide anionic species can be, comprise, or consist essentially of, fluoride, chloride, bromide, or iodide; alternatively, fluoride; alternatively, chloride: alternatively, bromide; or alternatively, iodide. In an embodiment, the hypohalite anionic species can be hypofluorite, hypochlorite, hypobromite, or hypoiodite; alternatively, hypofluorite; alternatively, hypochlorite; alternatively, hypobromite; or alternatively, hypoiodite. In an embodiment, the halite anionic species can be, comprise, or consist essentially of, fluorite, chlorite, bromite, or iodite; alternatively, fluorite; alternatively, chlorite; alternatively, bromite; or alternatively, iodite. In an embodiment, the halate anionic species can be, comprise, or consist essentially of, fluorate, chlorate, bromate, or iodate; alternatively, fluorate; alternatively, chlorate; alternatively, bromate; or alternatively, iodate. In an embodiment, the perhalate anionic species can be, comprise, or consist essentially of, perfluorate, perchlorate, perbromate, or periodate; alternatively, perfluorate; alternatively, perchlorate; alternatively, perbromate; or alternatively, periodate. In an embodiment, the hexahalophosphate anionic species can be, comprise, or consist essentially of, hexafluorphosphate, hexachlorophosphate, hexabromophosphate, or hexaiodophosphate; alternatively, hexafluorphosphate; alternatively, hexachlorophosphate; alternatively, hexabromophosphate; or alternatively, hexaiodophosphate. In an embodiment, the hexahaloaluminate anionic species can be, comprise, or consist essentially of, hexafluoroaluminate, hexachloroaluminate, hexabromoaluminate, or hexaiodoaluminate; alternatively, hexafluoroaluminate; alternatively, hexachloroaluminate; alternatively, hexabromoaluminate; or alternatively, hexaiodoaluminate. In an embodiment, the hexahalosilicate anionic species can be, comprise, or consist essentially of, hexafluorosilicate, hexachlorosilicate, hexabromosilicate, or hexaiodosilicate; alternatively, hexafluorosilicate; alternatively, hexachlorosilicate; alternatively, hexabromosilicate; or alternatively, hexaiodosilicate. In an embodiment, the tetrahaloborate anionic species can be, comprise, or consist essentially of, tetrafluoroborate, tetrachloroborate, tetrabromoborate, or tetraiodoborate; alternatively, tetrafluoroborate; alternatively, tetrachloroborate; alternatively, tetrabromoborate; or alternatively, or tetraiodoborate.

In an aspect, the tetraorganylborate anion can have the formula $BR^{1g}R^{2g}R^{3g}R^{4g}$. In another aspect, the tetraorganylammonium cation can have the formula $B(R^{5g})_4$. Within the tetraorganylborate anion having the formula $BR^{1g}R^{2g}R^{3g}R^{4g}$ and the tetraorganylborate anion having the formula $B(R^{5g})_4$, $R^{1g}$, $R^{2g}$, $R^{3g}$, $R^{4g}$, and/or $R^{5g}$ independently can be a $C_1$-$C_{20}$ organyl group; alternatively, $C_1$-$C_{15}$ organyl group; $C_1$-$C_{10}$ organyl group; or alternatively, $C_1$-$C_5$ organyl group. In an embodiment, each organyl group which can be utilized as $R^{1g}$, $R^{2g}$, $R^{3g}$, $R^{4g}$, and/or $R^{5g}$ independently can be a hydrocarbyl group or a substituted hydrocarbyl group; alternatively, a hydrocarbyl group; or alternatively, a substituted hydrocarbyl group. Generally, the hydrocarbyl group and/or substituted hydrocarbyl group which can be utilized as $R^{1g}$, $R^{2g}$, $R^{3g}$, $R^{4g}$, and/or $R^{5g}$ independently can have the same number of carbon atoms as the organyl groups which can be utilized as $R^{1g}$, $R^{2g}$, $R^{3g}$, $R^{4g}$, and/or $R^{5g}$. Hydrocarbyl groups (substituted or substituted) are generally disclosed within the present disclosure (e.g. as a selection for $R^{2c}$, for the monocarboxylate having the formula $^-O_2CR^{2c}$ and/or as a selection for $R^1$, $R^2$, $R^3$, $R^4$, $R^5$, $R^6$, $R^7$, $R^8$, $R^9$, $R^{10}$, $R^{11}$, $R^{12}$, $R^{13}$, or $R^{14}$, among other places). The aspects and embodiments of these hydrocarbyl groups described herein (either explicitly specified or implicitly recognized by those skilled in the art), can be utilized without limitation as hydrocarbyl groups which can be utilized as $R^{1g}$, $R^{2g}$, $R^{3g}$, and $R^{4g}$ (of the tetraorganylborate anion having the formula $BR^{1g}R^{2g}R^{3g}R^{4g}$) and $R^{5b}$ (of the tetrahydrocarbylammonium cation having formula $N(R^{5b})_4$), and $R^{5d}$ (of the tetraorganylammonium cation having the formula $B(R^{5g})_4$).

In a non-limiting embodiment, each tetraorganylborate anion which can be utilized as the anionic species independently can be, comprise, or consist essentially of, tetraphenylborate, tetrakis(para-tolyl)borate, tetrakis[3,5-bis(trifluoromethyl)phenyl]borate, or tetrakis(pentafluorophenyl)borate. In some other non-limiting embodiments, each tetraorganylborate anion which can be utilized as the anionic species independently can be a tetraphenylborate; alternatively, tetrakis(para-tolyl)borate; alternatively, tetrakis[3,5-bis(trifluoromethyl)phenyl]borate; or alternatively, tetrakis(pentafluorophenyl)borate.

In an aspect, the transition metal precursor can have the formula $[((M^B)_{y1}X_{x1}L_l)^m]_q[C^c]_{m1}[A^a]_{m2}$. The transition metal ($M^B$) having an oxidation state of x, the number of transition metals having an oxidation state of x (y1), the anionic ligand (X) having a charge of y, the number of anionic ligands having a charge of y (x1), the neutral ligand (L), the number of neutral ligands (l), the charge (m) on the transition metal complex $((M^B)_{y1}X_{x1}L_l)^m$, the number (q) of transition metal complexes $((M^B)_{y1}X_{x1}L_l)^m$, the cationic species (C) having charge c, the number of cationic species having charge c (m1), the anionic species (A) having charge a, and the number of anionic species having charge a (m2) are independently described herein. These independent descriptions can be utilized in any compatible manner and/or combination to further describe the transition metal precursor having the formula $[((M^B)_{y1}X_{x1}L_l)^m]_q[C^c]$ in $[A^a]_{m2}$. In the aspect where the transition metal precursor can have the formula $[((M^B)_{y1}X_{x1}L_l)^m]_q[C^c]_{m1}[A^a]_{m2}$, the formula $[((M^B)_{y1}X_{x1}L_l)^m]_q[C^c]_{m1}[A^a]_{m2}$ can encompass general transition metal precursors having an anionic transition metal complex (i.e. m having any value, or any value range, disclosed wherein where m<0, m1 having a value, or range value, disclosed herein where m1>0, and m2=0), having a cationic transition metal complex (i.e. m having any value, or any value range, disclosed wherein where m>0, m1=0, and m2 having any value, or any value range, disclosed herein where m2>0), and/or having a neutral transition metal precursor (i.e. m=0, m1=0, and m2=0). General and specific transition metal precursors having the formula $[((M^B)_{y1}X_{x1}L_l)^m]_q[C^c]_{m1}[A^a]_{m2}$ can be described using aspects and embodiments of the present disclosure. These general and specific transition metal precursors are readily apparent and contemplated.

When each X of the transition metal precursor having the formula $[((M^B)_{y1}X_{x1}L_l)^m]_q[C^c]_{m1}[A^a]_{m2}$ is a monoanionic ligand, the transition metal precursor can have the formula $[(M^BX_{x1}L_l)^m]_q[C^c]_{m1}[A^a]_{m2}$. In the aspect where the transition metal precursor can have the formula $[(M^BX_{x1}L_l)^m]_q[C^c]_{m1}[A^a]_{m2}$, the formula $[(M^BX_{x1}L_l)^m]_q[C^c]_{m1}[A^a]_{m2}$ can encompass general transition metal precursors having an anionic transition metal complex (i.e. m having any value, or any value range, disclosed wherein where m<0, m1 having any value, or any value range, disclosed herein where m1>0, and m2=0), having a cationic transition metal complex (i.e. m having any value, or any value range, disclosed wherein where m>0, m1=0, and m2 having any value, or any value range, disclosed herein where m2>0), and/or having a neutral transition metal precursor (i.e. m=0, m1=0, and m2=0). General and specific transition metal precursors having the formula $[(M^BX_{x1}L_l)^m]_q[C^c]_{m1}[A^a]_{m2}$ can be described using aspects and embodiments of the present disclosure. These general and specific transition metal precursors are readily apparent and contemplated.

In a non-limiting embodiment, the transition metal precursor having the formula $[((M^B)_{y1}X_{x1}L_l)^m]_q[C^c]_{m1}[A^a]_{m2}$ or the formula $[(M^B X_{x1}L_l)^m]_q[C^c]_{m1}[A^a]_{m2}$ can be, comprise, or consist essentially of, an anionic transition metal complex which has a relationship between the anionic transition metal complex, the cationic specie(s), and the anionic specie wherein m can have any value (or value range) disclosed herein where m<0, q and c independently can have any value (or value range) disclosed herein where q=c divided by the greatest common divisor of c and |m|, m1 can have any value (or value range) disclosed herein where m1=|m| divided by the greatest common divisor of c and |m|, and m2=0. In another non-limiting embodiment, the transition metal precursor having the formula $[((M^B)_{y1}X_{x1}L_l)^m]_q[C^c]_{m1}[A^a]_{m2}$ or the formula $[(M^B X_{x1}L_l)^m]_q[C^c]_{m1}[A^a]_{m2}$ can be, comprise, or consist essentially of, a neutral transition metal complex which has a relationship between the anionic transition metal complex, the cationic specie, and the anionic specie wherein m=0, m1=0 and m2=0. In yet another non-limiting embodiment, the transition metal precursor having the formula $[((M^B)_{y1}X_{x1}L_l)^m]_q[C^c]_{m1}[A^a]_{m2}$ or the formula $[(M^B X_{x1}L_l)^m]_q[C^c]_{m1}[A^a]_{m2}$ can be, comprise, or consist essentially of, a cationic transition metal complex which has a relationship between the cationic transition metal complex, the cationic specie, and the anionic specie(s) wherein m can have any value (or value range) disclosed herein where m>0, q and a independently can have any value (or value range) disclosed herein where q=|a| divided by the greatest common divisor of m and |a|, m1=0, and m2 can have any value (or value range) disclosed herein where m2=m divided by the greatest common divisor of m and |a|.

In an aspect, the transition metal precursor can have the formula $[((M^B)_{y1}X_{x1}L_l)^m]_q[C^c]_{m1}$. The transition metal ($M^B$) having an oxidation state of x, the number of transition metals having an oxidation state of x (y1), the anionic ligand (X) having a charge of y, the number of anionic ligands having a charge of y (x1), the neutral ligand (L), the number of neutral ligands (l), the charge (m) on the transition metal complex $((M^B)_{y1}X_{x1}L_l)^m$, the number (q) of transition metal complexes $((M^B)_{y1}X_{x1}L_l)^m$, the cationic species (C) having charge c, and the number of cationic species having charge c (m1) are independently described herein. These independent descriptions can be utilized in any compatible manner and/or combination to further describe the transition metal precursor having the formula $[((M^B)_{y1}X_{x1}L_l)^m]_q[C^c]_{m1}$. In the aspect where the transition metal precursor can have the formula $[((M^B)_{y1}X_{x1}L_l)^m]_q[C^c]_{m1}$, the formula $[((M^B)_{y1}X_{x1}L_l)^m]_q[C^c]_{m1}$ can encompass general transition metal precursors having an anionic transition metal complex (i.e. m having any value, or any value range, disclosed wherein where m<0, m1 having any value, or any value range, disclosed herein where m1>0). In an embodiment, the transition metal precursor having the formula $[((M^B)_{y1}X_{x1}L_l)^m]_q[C^c]_{m1}$ can encompass general transition metal precursors having an anionic transition metal complex which has a relationship between the anionic transition metal complex and the cationic specie(s) wherein m can have any value (or value range) disclosed herein where m<0, q and c independently can have any value (or value range) disclosed herein, where q=c divided by the greatest common divisor of c and |m|, and m1 can have any value (or value range) disclosed herein where m1=|m| divided by the greatest common divisor of c and |m|. In an embodiment, the transition metal precursor having the formula $[((M^B)_{y1}X_{x1}L_l)^m]_q[C^c]_{m1}$ can encompass general transition metal precursors having an anionic transition metal complex wherein m can any value, or any value range, disclosed wherein where m<0 and m=(x*y1)+(y*x1). As a consequence of the conditions that m<0 and m=(x*y1)+(y*x1), x1 can be any positive integer disclosed herein that satisfies the equation x1>(x*y1)/|y| (using any value of x, y1 and y disclosed herein) and/or y1 can be a positive integer and satisfies the equation y1≤(|y|*x1)/x (using any value of x, x1 and y disclosed herein). In some embodiments, x1 can range from the minimum positive integer that satisfies the equation x1>(x*y1)/|y| (using any value of x, y1 and y disclosed herein) to any value of x1 provided herein that is greater than the minimum positive integer that satisfies the equation x1>(x*y1)/|y| (using any value of x, y1 and y disclosed herein). In some embodiments, y1 can range from any value of y1 disclosed herein to any positive integer that satisfies the equation y1≤(|y|*x1)/x (using any value of x, x1 and y disclosed herein). Regardless of the values of x1, y1, and m, the number of neutral ligands (l) in the transition metal precursor having the formula the $[((M^B)_{y1}X_{x1}L_l)^m]_q[C^c]_{m1}$ can be any value, or any value range, disclosed herein. General and specific transition metal precursors having the formula $[((M^B)_{y1}X_{x1}L_l)^m]_q[C^c]_{m1}$ can be described using aspects and embodiments of the present disclosure. These general and specific transition metal precursors are readily apparent and contemplated.

When each X of the transition metal precursor having the formula $[((M^B)_{y1}X_{x1}L_l)^m]_q[C^c]_{m1}$ is a monoanionic ligand the transition metal precursor can have the formula $[(M^B X_{x1}L_l)^m]_q[C^c]_{m1}$. In the aspect where the transition metal precursor can have the formula $[(M^B X_{x1}L_l)^m]_q[C^c]_{m1}$ (where each X is a monoanionic ligand), the formula $[(M^B X_{x1}L_l)^m]_q[C^c]_{m1}$ can encompass general transition metal precursors having an anionic transition metal complex (i.e. m having any value, or any value range, disclosed wherein where m<0, m1 having any value, or any value range, disclosed herein where m1>0). In the aspect where the transition metal precursor can have the formula $[(M^B X_{x1}L_l)^m]_q[C^c]_{m1}$ (where each X is a monoanionic ligand), the formula $[(M^B X_{x1}L_l)^m]_q[C^c]_{m1}$ can encompass general transition metal precursors having an anionic transition metal complex which has a relationship between the anionic transition metal complex and the cationic specie(s) wherein m can have any value (or value range) disclosed herein where m<0, q and c independently can have any value (or value range) disclosed herein, where q=c divided by the greatest common divisor of c and |m|, and m1 can have any value (or value range) disclosed herein where m1=|m| divided by the greatest common divisor of c and |m|. In an embodiment, the transition metal precursor having the formula $[(M^B X_{x1}L_l)^m]_q[C^c]_{m1}$ (where each X is a monoanionic ligand) can encompass general transition metal precursors having an anionic transition metal complex wherein m can any value, or any value range, disclosed wherein where m<0 and m=x−x1. As a consequence of the conditions that m<0 and m=x−x1, x1 can be any positive integer disclosed herein that satisfies the equation x1>x (using any value of x disclosed herein). In some embodiments, x1 can range from the minimum positive integer that satisfies the equation x1>x (using any value of x disclosed herein) to any value of x1 provided herein that is greater than the minimum positive integer that satisfies the equation x1>x (using any value of x disclosed herein). Regardless of the values of m or x1, the number of neutral ligands (l) in the transition metal precursor having the formula the $[(M^B X_{x1}L_l)^m]_q[C^c]_{m1}$ (where each X is a monoanionic ligand) can be any value, or any value range, disclosed herein. General and specific transition metal precursors having the formula $[(M^B X_{x1}L_l)^m]_q[C^c]_{m1}$ (where each X is a monoanionic ligand) can be described using aspects and embodiments of the present disclosure. These general and specific transition metal precursors are readily apparent and contemplated.

In a non-limiting embodiment, the transition metal precursor can be, comprise, or consist essentially of, $[C^c][(TiCl_4(THF)_2)^{1-}]_q$. In this non-limiting embodiment, C can be any cationic species having charge c described herein, and q=c. In some embodiments, the transition metal precursor having the formula $[C^c][(TiCl_4(THF)_2)^{1-}]_q$ can be, comprise, or consist essentially of, $Na_3CrCl_6$ or $LiCrCl_4$; alternatively, $Na_3CrCl_6$; or alternatively, $LiCrCl_4$. Other general and specific transition metal precursors having the formula $[((M^B)_{x1}X_{n1}L_l)^m]_{q1}[C^c]_{m1}$ and/or $[(M^BX_{n1}L_l)^m]_{q1}[C^c]_{m1}$ can be described using aspects and embodiments of the present disclosure. These general and specific transition metal precursors are readily apparent and contemplated.

In an aspect, the transition metal precursor can have the formula $[((M^B)_{y1}X_{x1}L_l)^m]q[A^a]_{m2}$ The transition metal ($M^B$) having an oxidation state of x, the number of transition metals having an oxidation state of x (y1), the anionic ligand (X) having a charge of y, the number of anionic ligands having a charge of y (x1), the neutral ligand (L), the number of neutral ligands (l), the charge (m) on the transition metal complex $((M^B)_{y1}X_{x1}L_l)^m$, the number (q) of transition metal complexes $((M^B)_{y1}X_{x1}L_l)^m$, the anionic species (A) having charge a, and the number of anionic species having charge a (m2) are independently described herein. These independent descriptions can be utilized in any compatible manner and/or combination to further describe the transition metal precursor having the formula $[((M^B)_{y1}X_{x1}L_l)^m]_q[A^a]_{m2}$. In the aspect where the transition metal precursor can have the formula $[((M^B)_{y1}X_{x1}L_l)^m]_q[A^a]_{m2}$, the formula $[((M^B)_{y1}X_{x1}L_l)^m]_q[A^a]_{m2}$ can encompass general transition metal precursors having a cationic transition metal complex (i.e. m having any value, or any value range, disclosed wherein where m>0, and m2 having any value, or any value range, disclosed herein where m2>0). In an embodiment, the transition metal precursor having the formula $[((M^B)_{y1}X_{x1}L_l)^m]_q[A^a]_{m2}$ can encompass general transition metal precursors having a cationic transition metal complex which has a relationship between the cationic transition metal complex and the anionic specie(s) wherein m can have any value (or value range) disclosed herein where m>0, q and a independently can have any value (or value range) disclosed herein where q=|a| divided by the greatest common divisor of m and |a|, and m2 can have any value (or value range) disclosed herein where m2=m divided by the greatest common divisor of m and |a|. In an embodiment, the transition metal precursor having the formula $[((M^B)_{y1}X_{x1}L_l)^m]_q[A^a]_{m2}$ can encompass general transition metal precursors having a cationic transition metal complex wherein m can any value, or any value range, disclosed wherein where m>0 and m=(x*y1)+(y*x1). As a consequence of the conditions that m>0 and m=(x*y1)+(y*x1), x1 can be any positive integer disclosed herein that satisfies the equation x1<(x*y1)/|y| (using any value of x, y1 and y disclosed herein) and/or y1 can be a positive integer and satisfies the equation y1≥(|y|*x1)/x (using any value of x, x1 and y disclosed herein). In some embodiments, x1 can range from 0, or any x1 value disclosed herein less than that which satisfies the equation x1<(x*y1)/|y| (using any value of x, y1 and y disclosed herein) to any value of x1 provided herein that satisfies the equation x1<(x*y1)/|y| (using any value of x, y1 and y disclosed herein). In some embodiments, y1 can range from any value of y1 disclosed herein that satisfies the equation y1≥(|y|*x1)/x (using any value of x, x1 and y disclosed herein) to any value disclosed herein that is greater than a value that satisfies the equation y1≥(|y|*x1)/x (using any value of x, x1 and y disclosed herein). Regardless of the values of x1, y1, and m, the number of neutral ligands (l) in the transition metal precursor having the formula the $[((M^B)_{y1}X_{x1}L_l)^m]_q[A^a]_{m2}$ can be any value, or any value range, disclosed herein. General and specific transition metal precursors having the formula $[((M)_{y1}X_{x1}L_l)^m]_q[A^a]_{m2}$ can be described using aspects and embodiments of the present disclosure. These general and specific transition metal precursors are readily apparent and contemplated.

When each X of the transition metal precursor having the formula $[((M^B)_{y1}X_{x1}L_l)^m]_q[A^a]_{m2}$ is a monoanionic ligand the transition metal precursor can have the formula $[(M^BX_{x1}L_l)^m]_q[A^a]_{m2}$. In the aspect where the transition metal precursor can have the formula $[(M^BX_{x1}L_l)^m]_q[A^a]_{m2}$ (where each X is a monoanionic ligand), the formula $[(M^BX_{x1}L_l)^m]_q[A^a]_{m2}$ can encompass general transition metal precursors having a cationic transition metal complex (i.e. m having any value, or any value range, disclosed wherein where m>0, m2 having any value, or any value range, disclosed herein where m2>0). In the aspect where the transition metal precursor can have the formula $[(M^BX_{x1}L_l)^m]_q[A^a]_{m2}$ (where each X is a monoanionic ligand), the formula $[(M^BX_{x1}L_l)^m]_q[A^a]_{m2}$ can encompass general transition metal precursors having a cationic transition metal complex which has a relationship between the cationic transition metal complex and the anionic specie(s) wherein m can have any value (or value range) disclosed herein where m>0, q and a independently can have any value (or value range) disclosed herein, where q=a (the charge of the anionic species) divided by the greatest common divisor of m and |a|, and m2 can have any value (or value range) disclosed herein where m2=m divided by the greatest common divisor of m and |a|. As a consequence of the conditions that m>0 and m=x−x1, x1 can be any positive integer disclosed herein that satisfies the equation x1<x (using any value of x disclosed herein). In some embodiments, x1 can range from 0, or any x1 value disclosed herein less than that which satisfies the equation x1<x (using any value of x disclosed herein) to any value of x1 provided herein that satisfies the equation x1<x (using any value of x, y1 and y disclosed herein). Regardless of the values of x1 and m, the number of neutral ligands (l) in the transition metal precursor having the formula the $[(M^BX_{x1}L_l)^m]_q[A^a]_{m2}$ (where each X is a monoanionic ligand) can be any value, or any value range, disclosed herein. General and specific transition metal precursors having the formula $[(M^BX_{x1}L_l)^m]_q[A^a]_{m2}$ (where each X is a monoanionic ligand) can be described using aspects and embodiments of the present disclosure. These general and specific transition metal precursors are readily apparent and contemplated.

In a non-limiting embodiment, the transition metal precursor can be, comprise, or consist essentially of, $[(TiCl_2(THF)_4)^{1+}]_q[A^a]$. In this non-limiting embodiment, A can be any anionic species having charge a described herein and wherein q=Other general and specific transition metal precursors having the formula $[((M^B)_{x1}X_{n1}L_l)^m]_{q2}[A^a]_{m2}$ and/or $[(M^BX_{n1}L_l)^m]_q[A^a]_{m2}$ can be described using aspects and embodiments of the present disclosure. These general and specific transition metal precursors are readily apparent and contemplated.

In an aspect, the transition metal precursor can have the formula $[(M^BL_l)^m]_q[A^a]_{m2}$. The transition metal ($M^B$) having an oxidation state of x, the neutral ligand (L), the number of neutral ligands (l), the charge (m) on the transition metal complex $(M^BL_l)^m$, the number (q) of transition metal complexes $(M^B L_l)^m$, the anionic species (A) having charge a, and the number of anionic species having charge a (m2) are independently described herein. These independent descriptions can be utilized in any compatible manner and/or combination to further describe the transition metal precursor having the formula $[(M^B L_l)^m]_q[A^a]_{m2}$. In the aspect where the transition metal precursor can have the formula $[(M^B L_l)^m]_q[A^a]_{m2}$, the formula $[(M^B L_l)^m]_q[A^a]_{m2}$ can encompass general transition metal precursors having a cationic transition metal complex (i.e. m having any value, or any value range, disclosed wherein where m>0, and m2 having any value, or any value range, disclosed herein where m2>0). Generally, the transition metal precursor having the formula $[(M^B L_l)^m]_q[A^a]_{m2}$ can encompass general transition metal precursors having a cationic transition metal complex where m=x and the number of cationic transition metal complex(es) (q) having charge m (or x) and the number of anionic specie(s) (A) having charge a can be related by the equation m*q=|a*m2| (or x*q=|a*m2|. In some embodiments when the transition metal precursor has the formula $[(M^B L_l)^m]_q[A^a]_{m2}$, the number of cationic transition metal complex(es), q, can be related to the charge on the cationic transition metal complex(es) (m or x), and the anionic specie(s) charge (c) by the relationship q=|a| divided by the greatest common divisor of m (or x) and |a|. In some embodiments when the transition metal precursor has the formula $[(M^B L_l)^m]_q[A^a]_{m2}$j the number of anionic specie(s), m2, can be related to the charge on the cationic transition metal complex(es) (m or x), and the anionic specie(s) charge, c, by the relationship m2=m divided by the greatest common divisor of m and |a|. In an embodiment, the transition metal precursor having the formula $[(M^B L_l)^m]_q[A^a]_{m2}$ can encompass general transition metal precursors having a cationic transition metal complex wherein m can any value, or any value range, disclosed wherein where m>0 and m=x. Regardless of the values of m, the number of neutral ligands (l) in the transition metal precursor having the formula the $[(M^B L_l)^m]_q[A^a]_{m2}$ can be any value, or any value range, disclosed herein. General and specific transition metal precursors having the formula $[(M^B L_l)^m]_q[A^a]_{m2}$ can be described using aspects and embodiments of the present disclosure. These general and specific transition metal precursors are readily apparent and contemplated.

In a non-limiting embodiment, the transition metal precursor can be, comprise, or consist essentially of, $[(V(NH_3)_6)^{3+}]_q[A^a]_{m2}$, $[(V(NH_3)_6)^{2+}]_q[A^a]_{m2}$, $[(Cr(NH_3)_6)^{3+}]_q[A^a]_{m2}$, $[(Cr(NH_3)_6)^{2+}]_q[A^a]_{m2}$, $[(Co(NH_3)_6)^{2+}]_q[A^a]_{m2}$, or $[(Co(NH_3)_6)^{3+}]_q[A^a]_{m2}$. In some non-limiting embodiments, the transition metal precursor can be, comprise, or consist essentially of, $[(V(NH_3)_6)^{3+}]_q[A^a]_{m2}$ or $[(V(NH_3)_6)^{2+}][A^a]_{m2}$; alternatively, $[(Cr(NH_3)_6)^{3+}]_q[A^a]_{m2}$ or $[(Cr(NH_3)_6)^{2+}]_q[A^a]_{m2}$; alternatively, $[(Co(NH_3)_6)^{2+}]_q[A^a]_{m2}$ or $[(Co(NH_3)_6)^{3+}]_q[A^a]_{m2}$; alternatively, $[(V(NH_3)_6)^{3+}]_q[A^a]_{m2}$; alternatively, $[(V(NH_3)_6)^{2+}]_q[A^a]_{m2}$; alternatively, $[(Cr(NH_3)_6)^{3+}]_q[A^a]_{m2}$; alternatively, $[(Cr(NH_3)_6)^{2+}]_q[A^a]_{m2}$; alternatively, $[(Co(NH_3)_6)^{2+}][A^a]_{m2}$; or alternatively, $[(Co(NH_3)_6)^{3+}]_q[A^a]_m 2$. In these non-limiting embodiments, A can be any anionic species having charge a described herein, q=a (the charge of the anionic species) divided by the largest common divisor of |a| and the charge, m, on the transition metal complex $(M^B L_l)^m$, and m2 is the charge, m, on the transition metal complex $(M^B L_l)^m$ divided by the largest common divisor of |a| and the charge, m, on the transition metal complex $(M^B L_l)^m$. Other general and specific transition metal precursors having the formula $[(M^B L_l)^n]_{q2}[A^a]_{m2}$ can be described using aspects and embodiments of the present disclosure. These general and specific transition metal precursors are readily apparent and contemplated.

In an aspect, the transition metal precursor can have the formula $(M^B)_{y1}X_{x1}L_l$. The transition metal $(M^B)$ having an oxidation state of x, the number of transition metals having an oxidation state of x (y1), the anionic ligand (X) having a charge of y, the number of anionic ligands having a charge of y (x1), the neutral ligand (L), and the number of neutral ligands (l) are independently described herein. These independent descriptions can be utilized in any compatible manner and/or combination to further described the transition metal precursor having the formula $(M^B)_{y1}X_{x1}L_l$. In the aspect where the transition metal precursor can have the formula $(M^B)_{y1}X_{x1}L_l$, the formula $(M^B)_{y1}X_{x1}L_l$ can encompass general transition metal precursors which is neutral transition metal complexes (i.e. m=0, m1=0, and m2=0). When the transition metal precursor has the formula $(M^B)_{y1}X_{x1}L_l$ the number of transition metal atoms (y1) having the oxidation state x and the number of anionic ligands (A) having charge y can be related by the equation x*y1=|y*x1|. In some embodiments when the transition metal complex of the transition metal precursor has the formula $(M^B)_{y1}X_{x1}L_l$, the number of transition metal(s), y1, can be related to the transition metal oxidation state (x) and the anionic ligand (X) charge (y) by the relationship that y1=|y| divided by the largest common divisor of x and |y|. In some embodiments when the transition metal complex of the transition metal precursor has the formula $(M^B)_{y1}X_{x1}L_l$, the number of anionic ligands, x1, can be related to the transition metal oxidation state (x) and the anionic ligand (X) charge (y) by the relationship that x1=x divided by the largest common divisor of x and Regardless of the values of x1 and y1, the number of neutral ligands (l) in the transition metal precursor having the formula the $(M^B)_{y1}X_{x1}L_l$ can be any value, or any value range, disclosed herein. General and specific transition metal precursors having formula $(M^B)_{y1}X_{x1}L_l$ can be described using aspects and embodiments of the present disclosure. These general and specific transition metal precursors are readily apparent and contemplated.

When each X is a monoanionic ligand, the transition metal precursor having the formula the $(M^B)_{y1}X_{x1}L_l$ is a monoanionic ligand, the transition metal precursor can have the formula $M^B X_x L_l$. Regardless of the value of x, the number of neutral ligands (l) in the transition metal precursor having the formula the $M^B X_x L_l$ can have any value, or any value range, disclosed herein. General and specific transition metal precursors having formula $M^B X_x L_l$ can be described using aspects and embodiments of the present disclosure. These general and specific transition metal precursors are readily apparent and contemplated.

In a non-limiting embodiment, the transition metal precursor (or transition metal complex) which can be utilized in any aspect or any embodiment disclosed herein can be, comprise, or consist essentially of, $TiCl_3(THF)_3$, $TiCl_3(NCMe)_3$, $TiCl_3(NMe_3)_3$, $VCl_3(THF)_3$, $VCl_3(SMe_2)_2$, $NbCl_3(tetrahydrothiophene)_3$, $CrCl_3(NMe_3)_2$, $CrCl_3(pyridine)_3$, $CrCl_3(THF)_3$, $MnI_3(PMe_3)_2$, or $FeCl_3(PEt_3)_2$. In some embodiments, the transition metal precursor (or transition metal complex) which can be utilized in any aspect or any embodiment disclosed herein can be, comprise, or consist essentially of, $TiCl_3(THF)_3$, $TiCl_3(NCMe)_3$, or $TiCl_3(NMe_3)_3$; alternatively, $VCl_3(THF)_3$ or $VCl_3(SMe_2)_2$; alternatively, $CrCl_3(NMe_3)_2$, $CrCl_3(pyridine)_3$, or $CrCl_3(THF)_3$; alternatively, $TiCl_3(THF)_3$, $VCl_3(THF)_3$, $CrCl_3(NMe_3)_2$, $CrCl_3(pyridine)_3$, or $CrCl_3(THF)_3$. In other non-limiting embodiments, the transition metal precursor (or transition metal complex) which can be utilized in any aspect or any embodiment disclosed herein can be, comprise, or consist essentially of, $TiCl_3(THF)_3$; alternatively, $TiCl_3(NCMe)_3$; alternatively, $TiCl_3(NMe_3)_3$; alternatively, $VCl_3(THF)_3$; alternatively, $VCl_3(SMe_2)_2$; alternatively, $NbCl_3$(tetrahydrothiophene)$_3$; alternatively, $CrCl_3(NMe_3)_3$; alternatively, $CrCl_3$(pyridine)$_3$; alternatively, $CrCl_3(THF)_3$; alternatively, $MnI_3(PMe_3)_2$; or alternatively, $FeCl_3(PEt_3)_2$. In another embodiment, the transition metal precursor (or transition metal complex) which can be utilized in any aspect or any embodiment disclosed herein can be, comprise, or consist essentially of, neutral chromium(III) halide tetrahydrofuran complex, a neutral chromium(III) halide trihydrocarbylamine complex, or a neutral chromium(III) halide pyridine complex; alternatively, a neutral chromium(III) halide tetrahydrofuran complex; alternatively, a neutral chromium (III) halide trihydrocarbylamine complex; or alternatively, a neutral chromium(III) halide pyridine complex. Other general and specific transition metal precursors having the formula $(M^B)_{y1}X_{x1}L_f$ and/or the formula $M^B X_x L_l$ can be described using aspects and embodiments of the present disclosure. These general and specific transition metal precursors are readily apparent and contemplated.

In an aspect, the transition metal precursors can have the formula $[((M^B)_{y1}X_{x1})^m]_q[C^c]_{m1}[A^a]_{m2}$. The transition metal ($M^B$) having an oxidation state of x, the number of transition metals having an oxidation state of x (y1), the anionic ligand (X) having a charge of y, the number of anionic ligands having a charge of y (x1), the charge (m) on the transition metal complex $((M^B)_{y1}X_{x1})^m$, the number (q) of transition metal complexes $((M^B)_{y1}X_{x1})^m$, the cationic species (C) having charge c, the number of cationic species having charge c (m1), the anionic species (A) having charge a, and the number of anionic species having charge a (m2) are independently described herein. These independent descriptions can be utilized in any compatible manner and/or combination to further describe the transition metal precursor having the formula $[((M^B)_{y1}X_{x1})^m]_q[C^c]_{m1}[A^a]_{m2}$. In the aspect where the transition metal precursor can have the formula $[((M^B)_{y1}X_{x1})^m]_q[C^c]_{m1}[A^a]_{m2}$, the formula $[((M^B)_{y1}X_{x1})^m]_q[C^c]_{m1}[A^a]_{m2}$ can encompass general transition metal precursors having an anionic transition metal complex (i.e. m having any value, or any value range, disclosed wherein where m<0, m1 having any value, or any value range, disclosed herein where m1>0, and m2=0), having a cationic transition metal complex (i.e. m having any value, or any value range, disclosed wherein where m>0, m1=0, and m2 having any value, or any value range, disclosed herein where m2>0), and/or having a neutral transition metal precursor (i.e. m=0, m1=0, and m2=0). General and specific transition metal precursors having the formula $[((M^B)_{y1}X_{x1})^m]_q[C^c]_{m1}[A^a]_{m2}$ can be described using aspects and embodiments of the present disclosure. These general and specific transition metal precursors are readily apparent and contemplated.

When each X of the transition metal precursor having the formula $[((M^B)_{y1}X_{x1})^m]_q[C^c]_{m1}[A^a]_{m2}$ is a monoanionic ligand the transition metal precursor can have the formula $[(M^B X_{x1})^m]_q[C^c]_{m1}[A^a]_{m2}$. In the aspect where the transition metal precursor can have the formula $[(M^B X_{x1})^m]_q[C^c]_{m1}[A^a]_{m2}$, the formula $[(M^B X_{x1})^m]_q[C^c]_{m1}[A^a]_{m2}$ can encompass general transition metal precursors having an anionic transition metal complex (i.e. m having any value, or any value range, disclosed wherein where m<0, m1 having any value, or any value range, disclosed herein where m1>0, and m2=0), having a cationic transition metal complex (i.e. m having any value, or any value range, disclosed wherein where m>0, m1=0, and m2 having any value, or any value range, disclosed herein where m2>0), and/or having a neutral transition metal precursor (i.e. m=0, m1=0, and m2=0). General and specific transition metal precursors having the formula $[(M^B X_{x1})^m]_q[C^c]_{m1}[A^a]_{m2}$ can be described using aspects and embodiments of the present disclosure. These general and specific transition metal precursors are readily apparent and contemplated. In a non-limiting embodiment, the transition metal precursor having the formula $[((M^B)_{y1}X_{x1})^m]_q[C^c]_{m1}[A^a]_{m2}$ or the formula $[(M^B X_{x1})^m]_q[C^c]_{m1}[A^a]_{m2}$ can be, comprise, or consist essentially of, an anionic transition metal complex which has a relationship between the anionic transition metal complex, the cationic specie(s), and the anionic specie wherein m can have any value (or value range) disclosed herein where m<0, q and c independently can have any value (or value range) disclosed herein where q=c divided by the greatest common divisor of c and |m|, m1 can have any value (or value range) disclosed herein where m1=|m| divided by the greatest common divisor of c and |m|, and m2=0. In another non-limiting embodiment, the transition metal precursor having the formula $[((M^B)_{y1}X_{x1})_m]_q[C^c]_{m1}[A^a]_{m2}$ or the formula $[(M^B X_{x1})^m]_q[C^c]_{m1}[A^a]_{m2}$ can be, comprise, or consist essentially of, a neutral transition metal complex which has a relationship between the anionic transition metal complex, the cationic specie, and the anionic specie wherein m=0, m1=0 and m2=0. In yet another non-limiting embodiment, the transition metal precursor having the formula $[((M^B)_{y1}X_{x1})^m]_q[C^c]_{m1}[A^a]_{m2}$ or the formula $[(M^B X_{x1})^m]_q[C^c]_{m1}[A^a]_{m2}$ can be, comprise, or consist essentially of, a cationic transition metal complex which has a relationship between the cationic transition metal complex, the cationic specie, and the anionic specie(s) wherein m can have any value (or value range) disclosed herein where m>0, q and a independently can have any value (or value range) disclosed herein where q=|a| divided by the greatest common divisor of m and |a|, m1=0, and m2 can have any value (or value range) disclosed herein where m2=m divided by the greatest common divisor of m and |a|.

In an aspect, the transition metal precursor can have the formula $[((M^B)_{y1}X_{x1})^m]_q[C^c]_{m1}$. The transition metal ($M^B$) having an oxidation state of x, the number of transition metals having an oxidation state of x (y1), the anionic ligand (X) having a charge of y, the number of anionic ligands having a charge of y (x1), the charge (m) on the transition metal complex $((M^B)_{y1}X_{x1})^m$, the number (q) of transition metal complexes $((M^B)_{y1}X_{x1})^m$, the cationic species (C) having charge c, and the number of cationic species having charge c (m1) are independently described herein. These independent descriptions can be utilized in any compatible manner and/or combination to further describe the transition metal precursor having the formula $[((M^B)_{y1}X_{x1})_m]_q[C^c]_{m1}$. In this aspect, the formula $[((M^B)_{y1}X_{x1})^m]_q[C^c]_{m1}$ can encompass general transition metal precursors having an anionic transition metal complex (i.e. m having any value, or any value range, disclosed wherein where m<0, m1 having any value, or any value range, disclosed herein where m1>0). In an embodiment, the transition metal precursor having the formula $[((M^B)_{y1}X_{x1})^m]_q[C^c]_{m1}$ can encompass general transition metal precursors having an anionic transition metal complex which has a relationship between the anionic transition metal complex and the cationic specie(s) wherein m can have any value (or value range) disclosed herein where m<0, q and c independently can have any value (or value range) disclosed herein, where q=c divided by the greatest common divisor of c and |m|, and m1 can have any value (or value range) disclosed herein where m1=|m| divided by the greatest common divisor of c and |m|. In an embodiment, the transition metal precursor having the formula $[((M^B)_{y1}X_{x1})^m]_q[C^c]_{m1}$ can encompass general transition metal precursors having an anionic transition metal complex wherein m can any value, or any value range, disclosed wherein where m<0 and m=(x*y1)+(y*x1). As a consequence of the conditions that m<0 and m=(x*y1)+(y*x1), x1 can be any positive integer disclosed herein that satisfies the equation x1>(x*y1)/|y| (using any value of x, y1 and y disclosed herein) and/or y1 can be a positive integer and satisfies the equation y1≤(|y|*x1)/x (using any value of x, x1 and y disclosed herein). In some embodiments, x1 can range from the minimum positive integer that satisfies the equation x1>(x*y1)/|y| (using any value of x, y1 and y disclosed herein) to any value of x1 provided herein that is greater than the minimum positive integer that satisfies the equation x1≤(x*y1)/|y| (using any value of x, y1 and y disclosed herein). In some embodiments, y1 can range from any value of y1 disclosed herein to any positive integer that satisfies the equation y1≤(|y|*x1)/x (using any value of x, x1 and y disclosed herein). General and specific transition metal precursors having the formula $[((M^B)_{y1}X_{x1})^m]_q[C]_{m1}$ can be described using aspects and embodiments of the present disclosure. These general and specific transition metal precursors are readily apparent and contemplated.

When each X of the transition metal precursor having the formula $[((M^B)_{y1}X_{x1})^m]_q[C]_{m1}$ is a monoanionic ligand the transition metal precursor can have the formula $[(M^B X_{x1})^m]_q[C^c]_{m1}$. In the aspect where the transition metal precursor can have the formula $[(M^B X_{x1})^m]_q[C^c]_{m1}$ (where each X is a monoanionic ligand), the formula $[(M^B X_{x1})^m]_q[C^c]_{m1}$ can encompass general transition metal precursors having an anionic transition metal complex (i.e. m having any value, or any value range, disclosed wherein where m<0, m1 having any value, or any value range, disclosed herein where m1>0). In the aspect where the transition metal precursor can have the formula $[(M^B X_{x1})^m]_q[C^c]_{m1}$ (where each X is a monoanionic ligand), the formula $[(M^B X_{x1})^m]_q[C^c]_{m1}$ can encompass general transition metal precursors having an anionic transition metal complex which has a relationship between the anionic transition metal complex and the cationic specie(s) wherein m can have any value (or value range) disclosed herein where m<0, q and c independently can have any value (or value range) disclosed herein, where q=c divided by the greatest common divisor of c and |m|, and m1 can have any value (or value range) disclosed herein where m1=|m| divided by the greatest common divisor of c and |m|. In an embodiment, the transition metal precursor having the formula $[(M^B X_{x1})^m]_q[C^c]_{m1}$ (where each X is a monoanionic ligand) can encompass a general transition metal precursors having an anionic transition metal complex wherein m can be any value, or any value range, disclosed wherein where m<0 and m=x−x1. As a consequence of the conditions that m<0 and m=x−x1, x1 can be any positive integer disclosed herein that satisfies the equation x1>x (using any value of x disclosed herein). In some embodiments, x1 can range from the minimum positive integer that satisfies the equation x1>x (using any value of x disclosed herein) to any value of x1 provided herein that is greater than the minimum positive integer that satisfies the equation x1>x (using any value of x disclosed herein). General and specific transition metal precursors having the formula $[((M^B)_{y1}X_{x1})^m]_q[C]_{m1}$ (where each X is a monoanionic ligand) can be described using aspects and embodiments of the present disclosure. These general and specific transition metal precursors are readily apparent and contemplated.

In a non-limiting embodiment, the transition metal precursor which can be utilized in any aspect or any embodiment disclosed herein can be, comprise, or consist essentially of, $[C^c]_{m1}[(Ti(CN)_6)^{3-}]_{q1}$, $[C^c]_{m1}[(VCl_4)^{1-}]_{q1}$, $[C^c]_{m1}[(CrCl_4)^{1-}]_{q1}$, $[C^c]_{m1}[(Cr(CN)_6)^{3-}]_{q1}$, $[C^c]_{m1}[(MnCl_5)^{2-}]_{q1}$, $[C^c]_{m1}[MnF_4)^{1-}]_{q1}$, $[C^c]_{m1}[(MnF_5)^{2-}]_{q1}$, $[C^c]_{m1}[(MnF_6)^{3-}]_{q1}$, $[C^c]_{m1}[(FeF_6)^{3-}]_{q1}$, $[C^c]_{m1}[(FeCl_4)^{1-}]_{q1}$, $[C^c]_{m1}[(FeCl_5)^{2-}]_{q1}$, $[C^c]_{m1}[(FeI_4)^{1-}]_{q1}$, $[C^c]_{m1}[(Co(CN)_6)^{3-}]_{q1}$, or $[C^c]_{m1}[C^c]_{m1}[(CoF_6)^{3-}]_{q1}$; alternatively, $[C^c]_{m1}[(CrCl_4)^{1-}]_{q1}$ or $[C^c]_{m1}[(Cr(CN)_6)^{3-}]_{q1}$; alternatively, $[C^c]_{m1}[(MnCl_5)^{2-}]_{q1}$, $[C^c]_{m1}[MnF_4)^{1-}]_{q1}$, $[C^c]_{m1}[(MnF_5)^{2-}]_{q1}$, or $[C^c]_{m1}[(MnF_6)^{3-}]_{q1}$; alternatively, $[C^c]_{m1}[(FeF_6)^{3-}]_{q1}$, $[C^c]_{m1}[(FeCl_4)^{1-}]_{q1}$, $[C^c]_{m1}[(FeCl_5)^{2-}]_{q1}$, or $[C^c]_{m1}[(FeI_4)^{1-}]_{q1}$; or alternatively, $[C^c]_{m1}[(Co(CN)_6)^{3-}]_{q1}$ or $[C^c]_{m1}[(CoF_6)^{3-}]^q$. In other non-limiting embodiments, the transition metal precursor which can be utilized in any aspect or any embodiment disclosed herein can be, comprise, or consist essentially of, $[C^c]_{m1}[(Ti(CN)_6)^{3-}]_{q1}$; alternatively $[C^c]_{m1}[(VCl_4)^{1-}]_{q1}$; alternatively, $[C^c]_{m1}[(CrCl_4)^{1-}]_{q1}$; alternatively, $[C^c]_{m1}[(Cr(CN)_6)^{3-}]_{q1}$; alternatively, $[C^c]_{m1}[(MnCl_5)^{2-}]_{q1}$; alternatively, $[C^c]_{m1}[(MnF_4)^{1-}]_{q1}$; alternatively, $[C^c]_{m1}[(MnF_5)^{2-}]_{q1}$; alternatively, $[C^c]_{m1}[(MnF_6)^{3-}]_{q1}$; alternatively, $[C^c]_{m1}[(FeF_6)^{3-}]_{q1}$; alternatively, $[C^c]_{m1}[(FeCl_4)^{1-}]_{q1}$; alternatively, $[C^c]_{m1}[(FeCl_5)^{2-}]_{q1}$; alternatively, $[C^c]_{m1}[(FeI_4)^{1-}]_{q1}$; alternatively, $[C^c]_{m1}[(Co(CN)_6)^{3-}]_{q1}$; or alternatively, $[C^c]_{m1}[(CoF_6)^{3-}]_{q1}$. In these non-limiting embodiments, C can be any cationic species having charge c described herein, q=c divided by the largest common divisor of c and |m| (the absolute value of the charge on the anionic transition metal complex), and m1=|m| divided by the largest common divisor of c and |m|. Other useful transition metal precursors having formula $[((M^B)_{x1}X_{n1})^m]_{q1}[C^c]_{m1}$ or $[(M^B X_{n1})^m]_{q1}[C^c]_{m1}$ can be described using aspects and embodiments of the present disclosure. These general and specific transition metal precursors are readily apparent and contemplated.

In an aspect, the transition metal precursor can have the formula $[((M^B)_{y1}X_{x1})^m]_q[A^a]_{m2}$. The transition metal ($M^B$) having an oxidation state of x, the number of transition metals having an oxidation state of x (y1), the anionic ligand (X) having a charge of y, the number of anionic ligands having a charge of y (x1), the charge (m) on the transition metal complex $((M^B)_{y1}X_{x1})^m$, the number (q) of transition metal complexes $((M^B)_{y1}X_{x1})^m$, the anionic species (A) having charge a, and the number of anionic species having charge a (m2) are independently described herein. These independent descriptions can be utilized in any compatible manner and/or combination to further describe the transition metal precursor having the formula $[((M^B)_{y1}X_{x1})^m]_q[A^a]_{m2}$. In the aspect where the transition metal precursor can have the formula $[((M^B)_{y1}X_{x1})_m]_q[A^a]_{m2}$, the formula $[((M^B)_{y1}X_{x1})^m]_q[A^a]_{m2}$ can encompass a general transition metal precursors having a cationic transition metal complex (i.e. m having any value, or any value range, disclosed wherein where m>0, and m2 having any value, or any value range, disclosed herein where m2>0). In an embodiment, the transition metal precursor having the formula $[((M^B)_{y1}X_{x1})^m]_q[A^a]_{m2}$ can encompass general transition metal precursors having a cationic transition metal complex which has a relationship between the cationic transition metal complex and the anionic specie(s) wherein m can have any value (or value range) disclosed herein where m>0, q and a independently can have any value (or value range) disclosed herein where q=|a| divided by the greatest common divisor of m and |a|, and m2 can have any value (or value range) disclosed herein where m2=m divided by the greatest common divisor of m and |a|. In an embodiment, the transition metal precursor having the formula $[((M^B)_{y1}X_{x1})^m]_q[A^a]_{m2}$ can encompass general transition metal precursors having a cationic transition metal complex wherein m can any value, or any value range, disclosed wherein where m>0 and $m=(x*y1)+(y*x1)$. As a consequence of the conditions that $m>0$ and $m=(x*y1)+(y*x1)$, $x1$ can be any positive integer disclosed herein that satisfies the equation $x1<(x*y1)/|y|$ (using any value of x, y1 and y disclosed herein) and/or y1 can be a positive integer and satisfies the equation $y1\geq (|y|*x1)/x$ (using any value of x, x1 and y disclosed herein). In some embodiments, x1 can range from 0, or any x1 value disclosed herein less than that which satisfies the equation $x1<(x*y1)/|y|$ (using any value of x, y1 and y disclosed herein) to any value of x1 provided herein that satisfies the equation $x1<(x*y1)/|y|$ (using any value of x, y1 and y disclosed herein). In some embodiments, y1 can range from any value of y1 disclosed herein that satisfies the equation $y1\geq(|y|*x1)/x$ (using any value of x, x1 and y disclosed herein) to any value disclosed herein that is greater than a value that satisfies the equation $y1\geq(|y|*x1)/x$ (using any value of x, x1 and y disclosed herein). General and specific transition metal precursors having the formula $[((M^B)_{y1}X_{x1})^m]_q[A^a]_{m2}$ can be described using aspects and embodiments of the present disclosure. These general and specific transition metal precursors are readily apparent and contemplated.

When each X of the transition metal precursors having the formula $[((M^B)_{y1}X_{x1})^m]_q[A^a]_{m2}$ is a monoanionic ligand, the transition metal precursor can have the formula $[(M^B X_{x1})^m]_q[A^a]_{m2}$. In the aspect where the transition metal precursor can have the formula $[(M^B X_{x1})^m]_q[A^a]_{m2}$ (where each X is a monoanionic ligand), the formula $[(M^B X_{x1})^m]_q[A^a]_{m2}$ can encompass general transition metal precursors having a cationic transition metal complex (i.e. m having any value, or any value range, disclosed wherein where $m>0$, m2 having any value, or any value range, disclosed herein where $m2>0$). In the aspect where the transition metal precursor can have the formula $[(M^B X_{x1})^m]_q[A^a]_{m2}$ (where each X is a monoanionic ligand), the formula $[(M^B X_{x1})^m]_q[A^a]_{m2}$ can encompass general transition metal precursors having a cationic transition metal complex which has a relationship between the cationic transition metal complex and the anionic specie(s) wherein m can have any value (or value range) disclosed herein where $m>0$, q and a independently can have any value (or value range) disclosed herein, where $q=|a|$ divided by the greatest common divisor of m and $|a|$, and m2 can have any value (or value range) disclosed herein where $m2=m$ divided by the greatest common divisor of m and $|a|$. In an embodiment, the transition metal precursor having the formula $[(M^B X_{x1})^m]_q[A^a]_{m2}$ (where each X is a monoanionic ligand) can encompass a general transition metal precursors having a cationic transition metal complex wherein m can be any value, or any value range, disclosed wherein where $m>0$ and $m=x-x1$. As a consequence of the conditions that $m>0$ and $m=x-x1$, x1 can be any positive integer disclosed herein that satisfies the equation $x1<x$ (using any value of x disclosed herein). In some embodiments, x1 can range from 0, or any x1 value disclosed herein less than that which satisfies the equation $x1<x$ (using any value of x disclosed herein) to any value of x1 provided herein that satisfies the equation $x1<x$ (using any value of x, y1 and y disclosed herein). General and specific transition metal precursors having the formula $[(M^B X_{x1})^m]_q[A^a]_{m2}$ (where each X is a monoanionic ligand) can be described using aspects and embodiments of the present disclosure. These general and specific transition metal precursors are readily apparent and contemplated.

In an aspect, the transition metal precursor can have the formula $(M^B)_{y1}X_{x1}$. The transition metal ($M^B$) having an oxidation state of x, the number of transition metals having an oxidation state of x (y1), the anionic ligand (X) having a charge of y, and the number of anionic ligands having a charge of y (x1) are generally and independently described herein. These independent descriptions can be utilized in any compatible manner and/or combination to further described the transition metal precursor having the formula $(M^B)_{y1}X_{x1}$. In the aspect where the transition metal precursor has the formula $(M^B)_{y1}X_{x1}$, the formula $(M^B)_{y1}X_{x1}$ can encompass a general transition metal precursor which is a neutral transition metal complex (i.e. $m=0$, $m1=0$, and $m2=0$). When the transition metal precursor has the formula $(M^B)_{y1}X_{x1}$ the number of transition metal atoms (y1) having the oxidation state x and the number of anionic ligands (A) having charge y can be related by the equation $x*y1=|y*x1|$. In some embodiments when the transition metal complex of the transition metal precursor has the formula $(M^B)_{y1}X_{x1}$, the number of transition metal(s), y1, can be related to the transition metal oxidation state (x) and the anionic ligand (X) charge (y) by the relationship that $y1=|y|$ divided by the largest common divisor of x and $|y|$. In some embodiments when the transition metal complex of the transition metal precursor has the formula $(M^B)_{y1}X_{x1}$, the number of anionic ligands, x1, can be related to the transition metal oxidation state (x) and the anionic ligand (X) charge (y) by the relationship that $x1=x$ divided by the largest common divisor of x and $|y|$. General and specific transition metal precursors having the formula $(M^B)_{y1}X_{x1}$ can be described using aspects and embodiments of the present disclosure. These general and specific transition metal precursors are readily apparent and contemplated.

When each X of the transition metal precursor having the formula $(M^B)_{y1}X_{x1}$ is a monoanionic ligand, the transition metal precursor can have the formula $M^B X_x$. General and specific transition metal precursors having the formula $M^B X_x$ can be described using aspects and embodiments of the present disclosure. These general and specific transition metal precursors are readily apparent and contemplated.

In a non-limiting embodiment, the transition metal precursor (or transition metal complex) which can be utilized in any aspect or any embodiment disclosed herein can be, comprise, or consist essentially of, $TiCl_3$, $TiBr_3$, $TiI_3$, $VCl_3$, $CrF_3$, $CrCl_3$, $CrBr_3$, $CrI_3$, $MnCl_3$, $FeCl_3$, $FeBr_3$, $FeI_3$, $CoF_3$, or $CoCl_3$. In some non-limiting embodiments, the transition metal precursor (or transition metal complex) which can be utilized in any aspect or any embodiment disclosed herein can be, comprise, or consist essentially of, $TiCl_3$, $TiBr_3$, $ZrCl_3$, $ZrBr_3$, $VCl_3$, $CrF_3$, $CrCl_3$, $CrBr_3$, or $CrI_3$; alternatively, $TiCl_3$, $TiBr_3$, $CrF_3$, $CrCl_3$, $CrBr_3$, or $CrI_3$; alternatively, $CrCl_3$ or $CrBr_3$; or alternatively, $CrCl_3$. In other non-limiting embodiments, the transition metal precursor (or transition metal complex) which can be utilized in any aspect or any embodiment disclosed herein can be, comprise, or consist essentially of, $TiCl_3$, $TiBr_3$, or $TiI_3$; alternatively, $VCl_3$; alternatively, $CrF_3$, $CrCl_3$, $CrBr_3$, or $CrI_3$; alternatively, $MnCl_3$; alternatively, $FeCl_3$, $FeBr_3$, or $FeI_3$; or alternatively, $CoF_3$ or $CoCl_3$. In an embodiment, the transition metal precursor (or transition metal complex) which can be utilized in any aspect or any embodiment disclosed herein can be, comprise, or consist essentially of, $TiCl_3$; alternatively, $TiBr_3$; alternatively, $TiI_3$; alternatively, $CrF_3$; alternatively, $CrCl_3$; alternatively, $CrBr_3$; alternatively, $CrI_3$; alternatively, $FeCl_3$; alternatively, $FeBr_3$; alternatively, $FeI_3$; alternatively, $CoF_3$; or alternatively, $CoCl_3$. According to a further aspect, the transition metal halide precursors can be, comprise, or consist essentially of, a chromium(III) halide. In one non-limiting aspect, the transition metal precursor can be, comprise, or consist essentially of, $CrCl_3$. Other general and specific transition metal precursors having the formula $(M^B)_{y1}X_x$ and/or the formula $M^B X_x$ can be described using aspects and embodiments of the present disclosure. These general and specific transition metal precursors are readily apparent and contemplated.

In an aspect, the transition metal precursor utilized in any aspect or any embodiment disclosed herein can be substantially anhydrous; or alternatively, anhydrous. In some embodiments the transition metal precursor can have a water content of less than or equal to 100 ppm; alternatively, less than or equal to 90 ppm; alternatively, less than or equal to 80 ppm; alternatively, less than or equal to 70 ppm; alternatively, less than or equal to 60 ppm; alternatively, less than or equal to 50 ppm; alternatively, less than or equal to 40 ppm; alternatively, less than or equal to 30 ppm; alternatively, less than or equal to 20 ppm; alternatively, less than or equal to 10 ppm; alternatively, less than or equal to 9 ppm; alternatively, less than or equal to 8 ppm; alternatively, less than or equal to 7 ppm; alternatively, less than or equal to 6 ppm; alternatively, less than or equal to 5 ppm; alternatively, less than or equal to 4 ppm; alternatively, less than or equal to 3 ppm; alternatively, less than or equal to 2 ppm; or alternatively, less than or equal to 1 ppm. Generally, the water content of the transition metal precursor can be based on the ppm (by weight) of water in the transition metal precursor. It should be noted that the water present in the transition metal precursor can be in the form of transition metal precursor impurities and/or interstitial water in the transition metal precursor.

In an aspect, the transition metal precursor utilized in any aspect or any embodiment disclosed herein can be substantially acid-free. In some embodiments, the transition metal precursor can have an acid content of less than or equal to 1000 ppm; alternatively, less than or equal to 750 ppm; alternatively, less than or equal to 500 ppm; or alternatively, less than or equal to 250 ppm. In other embodiments, the transition metal precursor can have an acid content of less than or equal to 100 ppm; alternatively, less than or equal to 90 ppm; alternatively, less than or equal to 80 ppm; alternatively, less than or equal to 70 ppm; alternatively, less than or equal to 60 ppm; alternatively, less than or equal to 50 ppm; alternatively, less than or equal to 40 ppm; alternatively, less than or equal to 30 ppm; alternatively, less than or equal to 20 ppm; alternatively, less than or equal to 10 ppm; alternatively, less than or equal to 9 ppm; alternatively, less than or equal to 8 ppm; alternatively, less than or equal to 7 ppm; alternatively, less than or equal to 6 ppm; alternatively, less than or equal to 5 ppm; alternatively, less than or equal to 4 ppm; alternatively, less than or equal to 3 ppm; alternatively, less than or equal to 2 ppm; or alternatively, less than or equal to 1 ppm. Generally, the acid content of the transition metal precursor can be based on the ppm (by weight) of acid in the transition metal precursor. It should be noted that the acid present in the transition metal precursor can be in the form of transition metal precursor impurities and/or interstitial acid in the transition metal precursor.

In accordance with an aspect of this disclosure, the method for making a transition metal carboxylate composition can utilize a Group 1 or Group 2 metal carboxylate; alternatively, a Group 1 metal carboxylate; or alternatively a Group 2 metal carboxylate. Generally, the carboxylate moiety of the Group 1 or Group 2 metal carboxylate can be, comprise, or consist essentially of, a polycarboxylate or a monocarboxylate; alternatively, a polycarboxylate; or alternatively, a monocarboxylate.

In an aspect, the Group 1 or Group 2 metal carboxylate can have the formula $(M^A)_p[(O_2C)_rR^{1c}]_s$. In the Group 1 or Group 2 metal carboxylate having the formula $(M^A)_p[(O_2C)_rR^{1c}]_s$, $M^A$ represents the Group 1 or Group 2 metal, p represents the number of metal atoms in the Group 1 or Group 2 metal carboxylate, $(O_2C)_rR^{1c}$ (which can also be shown with having a −1 charge on the carboxylate moiety i.e. $(^-O_2C)_rR^{1c}$) represents the carboxylate group of the Group 1 or Group 2 metal carboxylate, and s represents the number of carboxylate groups in the Group 1 or Group 2 metal carboxylate. Within the carboxylate group $(^-O_2C)_rR^1$, r represents the number of carboxylate moieties in the carboxylate group and $R^1$ represents the group which links the carboxylate moieties. Generally, the Group 1 or Group 2 metal ($M^A$), the number of Group 1 or Group 2 metal atoms (p), the carboxylate group (($^-O_2C)_rR^{1c}$), the number of carboxylate groups (s), the number of carboxylate moieties in the carboxylate group (r), and the group linking the carboxylate moieties ($R^{1c}$) are independent elements of the Group 1 or Group 2 metal carboxylate having formula $(M^A)_p[(O_2C)_rR^{1c}]_s$, are independently described herein. These independent descriptions can be utilized in any combination to describe the Group 1 or Group 2 metal carboxylate having formula $(M^A)_p[(O_2C)_rR^{1c}]_s$.

In an aspect, the Group 1 or Group 2 metal carboxylate can have the formula $M^A(O_2CR^{2c})_s$. In the Group 1 or Group 2 metal carboxylate having the formula $M^A(O_2CR^{2c})_s$, $M^A$ represents the Group 1 or Group 2 metal, $O_2CR^{2c}$ (which can also be shown with having a −1 charge on the carboxylate moiety—i.e. $^-O_2CR^{2c}$) represents a monocarboxylate group, and s represents the oxidation number of the Group 1 or Group 2 metal. Generally, the Group 1 or Group 2 metal ($M^A$), the monocarboxylate group ($^-O_2CR^{2c}$), the number of monocarboxylate group(s), and $R^{2c}$ are independent elements of the Group 1 or Group 2 metal carboxylate having formula $M^A(O_2CR^{2c})_s$. These independent descriptions can be utilized in any combination to describe the Group 1 or Group 2 metal carboxylate having formula $M^A(O_2CR^{2c})_s$.

In an aspect, the Group 1 or Group 2 metal can be, comprise, or consist essentially of, of any Group 1 or Group 2 metal carboxylate described herein can be, comprise, or consist essentially of, a Group 1 metal; or alternatively, a Group 2 metal. In an embodiment, the Group 1 metal of any Group 1 metal carboxylate described herein can be, comprise, or consist essentially of, Li, Na, or K; alternatively, Na or K; alternatively, Li; alternatively, Na; or alternatively, K. In an embodiment, the Group 2 metal of any Group 2 metal carboxylate described herein can be, comprise, or consist essentially of, Be, Mg, Ca, Sr, or Ba; alternatively, Ca or Mg; alternatively, Be; alternatively, Mg; alternatively, Ca; alternatively, Sr; or alternatively Ba. Generally, the oxidation state of the Group 1 metal is 1 while the oxidation state of the Group 2 metal is 2.

In an aspect, the carboxylate group can be, comprise, or consist essentially of, a $C_2$ to $C_{25}$ carboxylate; alternatively, $C_3$ to $C_{25}$ carboxylate; alternatively, a $C_4$ to $C_{20}$ carboxylate; or alternatively, a $C_5$ to $C_{12}$ carboxylate. In an embodiment, the carboxylate group can have from one to four carboxylate moieties; alternatively, two to four carboxylate moieties; alternatively two to three carboxylate moieties. In some embodiments, the carboxylate group can have only one carboxylate moiety; alternatively, only two carboxylate moieties; alternatively, only three carboxylate moieties; or alternatively, only four carboxylate moieties.

In an aspect, the carboxylate group can have the general formula $(^-O_2C)_rR^{1c}$. Generally, r and $R^{1c}$ are independently described herein and the carboxylate group having the formula $(^-O_2C)_rR^{1c}$ can be described using any combination of r and $R^{1c}$ described herein.

In an aspect, r of the carboxylate group having the formula $(^-O_2C)_rR^{1c}$ can be an integer from 1 to 4; alternatively, from 2 to 4; or alternatively, from 2 to 3. In some embodiments, r of the carboxylate group having the formula $(^-O_2C)_rR^{1c}$ can be 1; alternatively, 2; alternatively, 3; or alternatively, 4. When r is, 1 the carboxylate group having the formula $(^-O_2C)_rR^{1c}$ is equivalent to the monocarboxylate group having the formula $^-O_2CR^{2c}$ and the aspects and embodiments of $R^{2c}$ for the monocarboxylate group having the formula $^-O_2CR^{2c}$ can be utilized as aspects and embodiments of $R^{1c}$ for the carboxylate group having the formula $(^-O_2C)_rR^{1c}$ when r is 1.

In an embodiment where r is 1, $R^{1c}$ can be a $C_1$ to $C_{24}$ organyl group; alternatively, a $C_2$ to $C_{24}$ organyl group; alternatively, a $C_3$ to $C_{19}$ organyl group; or alternatively, a $C_4$ to $C_{11}$ organyl group. In an embodiment where r is 2, $R^{1c}$ can be a bond or a $C_1$ to $C_{23}$ organylene group; alternatively, a bond; alternatively, a $C_1$ to $C_{23}$ organylene group; alternatively, a $C_3$ to $C_{18}$ organylene group; or alternatively, a $C_4$ to $C_{10}$ organylene group. In an embodiment where r is 3, $R^{1c}$ can be a $C_1$ to $C_{22}$ organic group; alternatively, $C_2$ to $C_{22}$ organic group; alternatively, a $C_3$ to $C_{17}$ organic group; or alternatively, a $C_4$ to $C_9$ organic group. In an embodiment where r is 4, $R^{1c}$ can be a $C_2$ to $C_{21}$ organic group; alternatively, a $C_3$ to $C_{16}$ organic group; or alternatively, a $C_4$ to $C_8$ organic group.

In an embodiment where r is 1, $R^{1c}$ can be a $C_1$ to $C_{24}$ organyl group consisting of inert functional groups; alternatively, $C_2$ to $C_{24}$ organyl group consisting of inert functional groups; alternatively, a $C_3$ to $C_{19}$ organyl group consisting of inert functional groups; or alternatively, a $C_4$ to $C_{11}$ organyl group consisting of inert functional groups. In an embodiment where r is 2, $R^{1c}$ can be a bond or $C_1$ to $C_{23}$ organylene group consisting of inert functional groups; alternatively, a bond; alternatively, a $C_1$ to $C_{23}$ organylene group consisting of inert functional groups; alternatively, a $C_3$ to $C_{is}$ organylene group consisting of inert functional groups; or alternatively, a $C_4$ to $C_{10}$ organylene group consisting of inert functional groups. In an embodiment where r is 3, $R^{1c}$ can be a $C_1$ to $C_{22}$ organic group consisting of inert functional groups; alternatively, $C_2$ to $C_{22}$ organic group consisting of inert functional groups; alternatively, a $C_3$ to $C_{17}$ organic group consisting of inert functional groups; or alternatively, a $C_4$ to $C_9$ organic group consisting of inert functional groups. In an embodiment where r is 4, $R^{1c}$ can be a $C_2$ to $C_{21}$ organic group consisting of inert functional groups; alternatively, a $C_3$ to $C_{16}$ organic group consisting of inert functional groups; or alternatively, a $C_4$ to $C_8$ organic group consisting of inert functional groups.

In an embodiment where r is 1, $R^{1c}$ can be a hydrocarbyl group or a substituted hydrocarbyl group; alternatively, a hydrocarbyl group; or alternatively, a substituted hydrocarbyl group. Generally, the hydrocarbyl group and/or substituted hydrocarbyl group which can be utilized as $R^{1c}$ can have the same number of carbon atoms as any organyl group which can be utilized as $R^{1c}$. In an embodiment where r is 2, $R^{1c}$ can be a bond, hydrocarbylene group, or a substituted hydrocarbylene group; alternatively, a bond or a hydrocarbylene group; alternatively, a bond or a substituted hydrocarbylene group; alternatively, a bond; alternatively, a hydrocarbylene group; or alternatively, a substituted hydrocarbylene group. Generally, the hydrocarbylene group and/or substituted hydrocarbylene group which can be utilized as $R^{1c}$ can have the same number of carbon atoms as any organylene group which can be utilized as $R^{1c}$. In an embodiment where r is 3, $R^{1c}$ can be a hydrocarbon group or a substituted hydrocarbon group; alternatively, a hydrocarbon group; or alternatively, a substituted hydrocarbon group. Generally, the hydrocarbon group and/or substituted hydrocarbon group which can be utilized as $R^{1c}$ can have the same number of carbon atoms as any organic group which can be utilized as $R^{1c}$. In an embodiment where r is 4, $R^{1c}$ can be a hydrocarbon group or a substituted hydrocarbon group; alternatively, a hydrocarbon group; or alternatively, a substituted hydrocarbon group. Generally, the hydrocarbon group and/or substituted hydrocarbon group which can be utilized as $R^{1c}$ can have the same number of carbon atoms as any organic group which can be utilized as $R^{1c}$. In an embodiment, each substituent of a substituted hydrocarbyl group, substituted hydrocarbylene group, and/or substituted hydrocarbon group independently can be a halide, a hydrocarbyl group, or a hydrocarboxy group; alternatively, a halide or a hydrocarbyl group; alternatively, a halide or a hydrocarboxy group; alternatively, a hydrocarbyl group or a hydrocarboxy group; alternatively, a halide; alternatively, a hydrocarbyl group; or alternatively, a hydrocarboxy group. Halide, hydrocarbyl group, and hydrocarboxy group substituents (also referred to as non-hydrogen substituents or non-hydrogen substituent groups) are independently disclosed herein. These substituent groups can be utilized without limitation to further describe any substituted hydrocarbyl group, substituted hydrocarbylene group, and/or substituted hydrocarbon group that can be utilized as $R^{1c}$.

In an embodiment where r of the carboxylate group having the formula $(^-O_2C)_rR^{1c}$ is 3 and/or 4, $R^{1c}$ can be an alkane group, a substituted alkane group, an alkene group, a substituted alkene group, a cycloalkane group, a substituted cycloalkane group, a cycloalkene group, a substituted cycloalkene group, an arene group, a substituted arene group, an aralkane group, or a substituted aralkane group; or alternatively, an alkane group, an alkene group, a cycloalkane group, a cycloalkene group, an arene group, or an aralkane group. In some embodiments, $R^{1c}$ of the carboxylate group having the formula $(^-O_2C)_rR^{1c}$ can be an alkane group or a substituted alkane group; alternatively, an alkene group or a substituted alkene group; alternatively, a cycloalkane group or a substituted cycloalkane group; alternatively, a cycloalkene group or a substituted cycloalkene group; alternatively, an arene group or a substituted arene group; or alternatively, an aralkane group or a substituted aralkane group. In other embodiments, $R^{1c}$ of the carboxylate group having the formula $(^-O_2C)_rR^{1c}$ can be an alkane group; alternatively, a substituted alkane group; alternatively, an alkene group; alternatively, a substituted alkene group; alternatively, a cycloalkane group; alternatively, a substituted cycloalkane group; alternatively, a cycloalkene group; alternatively, a substituted cycloalkene group; alternatively, an arene group; alternatively, a substituted arene group; alternatively, an aralkane group; or alternatively, a substituted aralkane group. Generally, the alkane group, substituted alkane group, alkene group, substituted alkene group, cycloalkane group, substituted cycloalkane group, cycloalkene group, substituted cycloalkene group, arene group, substituted arene group, aralkane group, or substituted aralkane group can have the same number of carbon atoms as described for the organic and hydrocarbon groups which can be utilized as $R^{1c}$ of the carboxylate group having the formula $(^-O_2C)_rR^{1c}$ where r is 3 and/or 4.

In an aspect where r of the carboxylate group having the formula $(^-O_2C)_rR^{1c}$ is 3, r can be a $C_1$ to $C_{22}$ alkane group (substituted and/or unsubstituted); alternatively, $C_2$ to $C_{22}$ alkane group (substituted or unsubstituted); alternatively, a $C_3$ to $C_{17}$ alkane group (substituted and/or unsubstituted); or alternatively, a $C_4$ to $C_9$ alkane group (substituted and/or unsubstituted). In an aspect where r of the carboxylate group having the formula $(^-O_2C)_rR^{1c}$ is 4, $R^{1c}$ can be a $C_2$ to $C_{21}$ alkane group (substituted and/or unsubstituted); alternatively, a $C_3$ to $C_{16}$ alkane group (substituted and/or unsubstituted); or alternatively, a $C_4$ to $C_8$ alkane group (substituted and/or unsubstituted). In some embodiments, where r of the carboxylate group having the formula $(^-O_2C)_rR^{1c}$ is 3 and/or 4, $R^{1c}$ can be an ethane group, a propane group, a butane group, a pentane group, a hexane group, a heptane group, an octane group, a nonane group, a decane group, a undecane group, a dodecane group, a tridecane group, a tetradecane group, a pentadecane group, a hexadecane group, a heptadecane group, an octadecane group, or a nonadecane group. In other embodiments where r of the carboxylate group having the formula $(^-O_2C)_rR^{1c}$ is 3 and/or 4, $R^{1c}$ can be a butane group, a pentane group, a hexane group, a heptane group, an octane group, a nonane group, a decane group, or undecane group. In other embodiments where r of the carboxylate group having the formula $(^-O_2C)_rR^{1c}$ is 3 and/or 4, $R^{1c}$ can be a butane group, a pentane group, a hexane group, a heptane group, or an octane group. In an embodiment, any of the alkane groups (general or specific) which can be utilized $R^{1c}$ of the carboxylate having the formula $^-O_2CR^2$ can be substituted. In an embodiment, each substituent of a substituted alkane group (general or specific) which can be utilized as $R^{1c}$ independently can be a halide or hydrocarboxy group; alternatively, a halide; or alternatively a hydrocarboxy group. Halide substituents and hydrocarboxy substituent groups are independently disclosed herein and can be utilized without limitation to further describe a substituted alkane group (general or specific) which can be utilized as $R^{1c}$.

In an aspect where r of the carboxylate group having the formula $(^-O_2C)_rR^{1c}$ is 3, r can be a $C_1$ to $C_{22}$ alkene group (substituted or unsubstituted); alternatively, $C_2$ to $C_{22}$ alkene group (substituted or unsubstituted); alternatively, a $C_3$ to $C_{17}$ alkene group (substituted or unsubstituted); or alternatively, a $C_4$ to $C_9$ alkene group (substituted or unsubstituted). In an aspect where r of the carboxylate group having the formula $(^-O_2C)_rR^{1c}$ is 4, $R^{1c}$ can be a $C_2$ to $C_{21}$ alkene group (substituted or unsubstituted); alternatively, a $C_3$ to $C_{16}$ alkene group (substituted or unsubstituted); or alternatively, a $C_4$ to $C_8$ alkane group (substituted or unsubstituted). In other embodiments where r of the carboxylate group having the formula $(^-O_2C)_rR^{1c}$ is 3 and/or 4, $R^{1c}$ can be a butene group, a pentene group, a hexene group, a heptene group, an octene group, a nonene group, a decene group, or undecene group. In other embodiments where r of the carboxylate group having the formula $(^-O_2C)_rR^{1c}$ can be 3 and/or 4, $R^{1c}$ is a butene group, a pentene group, a hexene group, a heptene group, or an octene group. In an embodiment, each substituent of a substituted alkene group which can be utilized as $R^{1c}$ independently can be a halide or hydrocarboxy group; alternatively, a halide; or alternatively a hydrocarboxy group. Halide substituent and hydrocarboxy substituent groups are independently disclosed herein and can be utilized without limitation to further describe a substituted alkene group which can be utilized as $R^{1c}$.

In an aspect where r of the carboxylate group having the formula $(^-O_2C)_rR^{1c}$ is 3 and/or 4, $R^{1c}$ can be a $C_3$-$C_{21}$ cycloalkane group (substituted or unsubstituted); alternatively, a $C_5$-$C_{16}$ cycloalkane group (substituted or unsubstituted); or alternatively, a $C_5$-$C_{10}$ cycloalkane group (substituted or unsubstituted). In an embodiment where r of the carboxylate group having the formula $(^-O_2C)_rR^{1c}$ is 3 and/or 4, $R^{1c}$ can be a cyclopentane group, a substituted cyclopentane group, a cyclohexane group, a substituted cyclohexane group, a cycloheptane group, or a substituted cycloheptane group; alternatively, a cyclopentane group, a substituted cyclopentane group, a cyclohexane group, or a substituted cyclohexane group; alternatively, cyclopentane group or a substituted cyclopentane group; or alternatively, a cyclohexane group or a substituted cyclohexane group. In some embodiments where r of the carboxylate group having the formula $(^-O_2C)_rR^{1c}$ is 3 and/or 4, $R^{1c}$ can be a cyclopentane group, or a cyclohexane group. In yet other embodiments where r of the carboxylate group having the formula $(^-O_2C)_rR^{1c}$ is 3 and/or 4, $R^{1c}$ can be a cyclopentane group; alternatively, a substituted cyclopentane group; alternatively, a cyclohexane group; or alternatively, a substituted cyclohexane group. In an embodiment, each substituent of a substituted cycloalkane group (general or specific) which can be utilized as $R^{1c}$ independently can be a halide, a hydrocarbyl group, or a hydrocarboxy group; alternatively, a halide or a hydrocarbyl group; alternatively, a halide or a hydrocarboxy group; alternatively, a hydrocarbyl group or a hydrocarboxy group; alternatively, a halide; alternatively, a hydrocarbyl group; or alternatively, a hydrocarboxy group.

In an aspect where r of the carboxylate group having the formula $(^-O_2C)_rR^{1c}$ is 3 and/or 4, $R^{1c}$ can be a $C_3$-$C_{21}$ cycloalkene group (substituted or unsubstituted); alternatively, a $C_5$-$C_{16}$ cycloalkene group (substituted or unsubstituted); or alternatively, a $C_5$-$C_{10}$ cycloalkene group (substituted or unsubstituted). In an embodiment where r of the carboxylate group having the formula $(^-O_2C)_rR^{1c}$ is 3 and/or 4, $R^{1c}$ can be a cyclopentene group, a substituted cyclopentene group, a cyclohexene group, a substituted cyclohexene group, a cycloheptene group, or a substituted cycloheptene group; alternatively, a cyclopentene group, a substituted cyclopentene group, a cyclohexene group, or a substituted cyclohexene group; alternatively, cyclopentene group or a substituted cyclopentene group; or alternatively, a cyclohexene group or a substituted cyclohexene group. In some embodiments where r of the carboxylate group having the formula $(^-O_2C)_rR^{1c}$ is 3 and/or 4, $R^{1c}$ can be a cyclopentene group, or a cyclohexene group. In yet other embodiments where r of the carboxylate group having the formula $(^-O_2C)_rR^{1c}$ is 3 and/or 4, $R^{1c}$ can be a cyclopentene group; alternatively, a substituted cyclopentene group; alternatively, a cyclohexene group; or alternatively, a substituted cyclohexene group. In an embodiment, each substituent of a substituted cycloalkene group (general or specific) which can be utilized as $R^{1c}$ independently can be a halide, a hydrocarbyl group, or a hydrocarboxy group; alternatively, a halide or a hydrocarbyl group; alternatively, a halide or a hydrocarboxy group; alternatively, a hydrocarbyl group or a hydrocarboxy group; alternatively, a halide; alternatively, a hydrocarbyl group; or alternatively, a hydrocarboxy group.

In an aspect where r of the carboxylate group having the formula $(^-O_2C)_rR^{1c}$ is 3 and/or 4, $R^{1c}$ can be a $C_6$-$C_{21}$ benzene group (substituted or unsubstituted), or a $C_{10}$-$C_{21}$ naphthalene group (substituted or unsubstituted); alternatively, a $C_6$-$C_{21}$ benzene group (substituted or unsubstituted); or alternatively, a $C_{10}$-$C_{21}$ naphthalene group (substituted or unsubstituted). In another aspect r of the carboxylate group having the formula $(^-O_2C)_rR^{1c}$ is 3 and/or 4, $R^{1c}$ can be a $C_6$-$C_{16}$ benzene group (substituted or unsubstituted), or a $C_{10}$-$C_{16}$ naphthalene group (substituted or unsubstituted); alternatively, a $C_6$-$C_{16}$ benzene group (substituted or unsubstituted); or alternatively, a $C_{10}$-$C_{16}$ naphthalene group (substituted or unsubstituted). In another aspect r of the carboxylate group having the formula $(^-O_2C)_rR^{1c}$ is 3 and/or 4, $R^{1c}$ can be a $C_6$-$C_{10}$ benzene group (substituted or unsubstituted). In an embodiment, each substituent of a substituted benzene group (general or specific) or substituted naphthalene which can be utilized as $R^{1c}$ independently can be a halide, a hydrocarbyl group, or a hydrocarboxy group; alternatively, a halide or a hydrocarbyl group; alternatively, a halide or a hydrocarboxy group; alternatively, a hydrocarbyl group or a hydrocarboxy group; alternatively, a halide; alternatively, a hydrocarbyl group; or alternatively, a hydrocarboxy group.

In an aspect where r of the carboxylate group having the formula $(^-O_2C)_rR^{1c}$ is 3 and/or 4, $R^{1c}$ can be a $C_7$-$C_{21}$ phenylmethane group (substituted or unsubstituted); alternatively, $C_7$-$C_{16}$ phenylmethane group (substituted or unsubstituted); alternatively, a $C_7$-$C_{10}$ phenylmethane group (substituted or unsubstituted). In an embodiment, each substituent of a substituted phenylmethane group (general or specific) which can be utilized as $R^{1c}$ independently can be a halide, a hydrocarbyl group, or a hydrocarboxy group; alternatively, a halide or a hydrocarbyl group; alternatively, a halide or a hydrocarboxy group; alternatively, a hydrocarbyl group or a hydrocarboxy group; alternatively, a halide; alternatively, a hydrocarbyl group; or alternatively, a hydrocarboxy group.

Halides, hydrocarbyl group substituents, and hydrocarboxy group substituents (also referred to as non-hydrogen substituents or non-hydrogen substituent groups) are independently disclosed herein. These substituent groups can be utilized without limitation to further describe any substituted hydrocarbon group (general or specific), substituted alkane group (general or specific), substituted alkene group (general or specific), substituted cycloalkane group (general or specific), substituted cycloalkene group (general or specific), substituted arene group (general or specific), substituted aralkane group (general or specific) which can be utilized as $R^{1c}$ of the carboxylate group having the formula $(^-O_2C)_rR^{1c}$ described herein.

In an aspect where r of the carboxylate group having the formula $(^-O_2C)_rR^{1c}$ is 2, $R^{1c}$ of the carboxylate group having the formula $(^-O_2C)_rR^{1c}$ any general or specific organic group, organic group consisting of inert functional groups, hydrocarbon group, alkane group, substituted alkane group, alkene group, substituted alkene group, cycloalkane group, substituted cycloalkane group, cycloalkene group, substituted cycloalkene group, arene group, substituted arene group, aralkane group, or substituted aralkane group can be referred to by replacing -ic of organic, -on of hydrocarbon, -ane of general or specific alkane (including aralkane), -e of a general or specific alkene (including cycloalkene), or -ene of a general or specific arene by the suffix -ylene. For example, when r is 2, the general organic group and hydrocarbon group would become an organylene group and hydrocarbylene group (respectively), the general alkane and cycloalkane groups would become alkylene and cycloalkylene (respectively), the specific methane group and ethane groups would become a methylene group and ethylene group (respectively), the general alkene group would become an alkenylene group, the specific ethene group would become an ethenylene group, the general arene group would become an arylene group, and the general aralkane group would become a aralkylene group. Similarly, in an aspect where r of the carboxylate group having the formula $(^-O_2C)_rR^{1c}$ is 1, $R^{1c}$ of the carboxylate group having the formula $(^-O_2C)_rR^{1c}$ any general or specific organic group, organic group consisting of inert functional groups, hydrocarbon group, alkane group, substituted alkane group, alkene group, substituted alkene group, cycloalkane group, substituted cycloalkane group, cycloalkene group, substituted cycloalkene group, arene group, substituted arene group, aralkane group, or substituted aralkane group can be referred to by replacing -ic of organic, -on of hydrocarbon, -ane of general or specific alkane (including aralkane), -e of a general or specific alkene (including cycloalkene), or -ene of a general or specific arene by the suffix -yl. For example, when r is 1, the general organic group and hydrocarbon group would become an organylene group and hydrocarbylene group (respectively), the general alkane and cycloalkane groups would become alkyl and cycloalkyl (respectively), the specific methane group and ethane groups would become a methyl group and ethyl group (respectively), the general alkene group would become an alkenyl group, the specific ethene group would become an ethenyl group, the general arene group would become an aryl group, and the general aralkane group would become an aralkyl group. Extension of these naming conventions to other general or specific groups, along with common name change between general to specific groups (e.g. benzene group to phenylene group or phenyl group, among others) are readily apparent.

In a non-limiting embodiment where the carboxylate group has more than one carboxylate moiety, each carboxylate group can be, comprise, or consist essentially of, oxalate, malonate (1,3-propanedioate), succinate (1,4-butanedioate), glutarate (1,5-pentanedioate), adipate (1,6-hexanedioate), pimelate (1,7-heptanedioate), suberate (1,8-octanedioate), maleate, fumarate, acetylenedicarboxylate, phthalate (1,2-benzene dicarboxylate), isophthalate (1,3-benzene dicarboxylate), terephthalate (1,4-benzene dicarboxylate), phenylene diacetate; citrate, or any combination thereof; alternatively, malonate (1,3-propanedioate), succinate (1,4-butanedioate), glutarate (1,5-pentanedioate), adipate (1,6-hexanedioate), pimelate (1,7-heptanedioate), suberate (1,8-octanedioate), maleate, fumarate, acetylenedicarboxylate, phthalate (1,2-benzene dicarboxylate), isophthalate (1,3-benzene dicarboxylate), terephthalate (1,4-benzene dicarboxylate), phenylene diacetate, or any combination thereof; alternatively, malonate (1,3-propanedioate), succinate (1,4-butanedioate), glutarate (1,5-pentanedioate), adipate (1,6-hexanedioate), pimelate (1,7-heptanedioate), suberate (1,8-octanedioate), or any combination thereof; alternatively, maleate, fumarate, or any combination thereof; alternatively, acetylenedicarboxylate; alternatively, phthalate (1,2-benzene dicarboxylate), isophthalate (1,3-benzene dicarboxylate), terephthalate (1,4-benzene dicarboxylate), or any combination thereof; or alternatively, phenylene diacetate. In other non-limiting embodiments where the carboxylate group has more than one carboxylate moiety, each carboxylate group can be, comprise, or consist essentially of, oxalate; alternatively, malonate (1,3-propanedioate); alternatively, succinate (1,4-butanedioate); alternatively, glutarate (1,5-pentanedioate); alternatively, adipate (1,6-hexanedioate); alternatively, pimelate (1,7-heptanedioate); alternatively, suberate (1,8-octanedioate); alternatively, maleate; alternatively, fumarate; alternatively, acetylenedicarboxylate; alternatively, phthalate (1,2-benzene dicarboxylate); alternatively, isophthalate (1,3-benzene dicarboxylate); alternatively, terephthalate (1,4-benzene dicarboxylate); alternatively, phenylene diacetate; or alternatively citrate.

In an aspect and in any embodiment, the carboxylate group can be, comprise, or consist essentially of, a monocarboxylate having the formula $^-O_2CR^{2c}$. In an embodiment of a carboxylate having the formula $^-O_2CR^{2c}$, $R^{2c}$ can be a organyl group; alternatively, organyl consisting of inert functional groups; alternatively, hydrocarbyl group, or substituted hydrocarbyl group; alternatively, a hydrocarbyl group; or alternatively, a substituted hydrocarbyl group.

Generally, $R^{2c}$ (whether organyl, organyl consisting of inert functional groups, hydrocarbyl, and/or substitute hydrocarbyl) can be a $C_1$ to $C_{24}$ group; alternatively, a $C_2$ to $C_{24}$ group; alternatively, a $C_3$ to $C_{19}$ group; or alternatively, a $C_4$ to $C_{11}$ group.

In an embodiment, $R^{2c}$ of the carboxylate having the formula $^-O_2CR^{2c}$ can be an alkyl group, a substituted alkyl group, an alkenyl group, a substituted alkenyl group, a cycloalkyl group, a substituted cycloalkyl group, a cycloalkenyl group, a substituted cycloalkenyl group, an aryl group, a substituted aryl group, an aralkyl group, or a substituted aralkyl group; or alternatively, an alkyl group, an alkenyl group, a cycloalkyl group, an cycloalkenyl group, an aryl group, or an aralkyl group. In some embodiments, $R^{2c}$ of the carboxylate having the formula $^-O_2CR^{2c}$ can be an alkyl group or a substituted alkyl group; alternatively, a alkenyl group or a substituted alkenyl group; alternatively, a cycloalkyl group or a substituted cycloalkyl group; alternatively, a cycloalkenyl group or a substituted cycloalkenyl group; alternatively, an aryl group or a substituted aryl group; or alternatively, an aralkyl group or a substituted aralkyl. In other embodiments, $R^{2c}$ of the carboxylate having the formula $^-O_2CR^{2c}$ can be an alkyl group; alternatively, a substituted alkyl group; alternatively, alkenyl group; alternatively, a substituted alkenyl group; alternatively, alternatively, a cycloalkyl group; alternatively, a substituted cycloalkyl group; alternatively, a cycloalkenyl group; alternatively, a substituted cycloalkenyl group; alternatively, an aryl group; alternatively, a substituted aryl group; alternatively, an aralkyl group; or alternatively, a substituted aralkyl group. Generally, the alkyl group, substituted alkyl group, alkenyl group, substituted alkenyl group, cycloalkyl group, substituted cycloalkyl group, cycloalkenyl group, substituted cycloalkenyl group, aryl group, substituted aryl group, aralkyl group, or substituted aralkyl group can have the same number of carbon atoms as described for the organic groups, organic groups consisting of inert functional groups, and hydrocarbon groups (substituted or unsubstituted) which can be utilized as $R^{2c}$ within the carboxylate having the formula $^-O_2CR^2$.

In an embodiment, the alkyl group (substituted or unsubstituted) which can be utilized as $R^{2c}$ of the carboxylate having the formula $^-O_2CR^{2c}$ can be a $C_1$-$C_{24}$ alkyl group (substituted or unsubstituted); alternatively, a $C_2$-$C_{24}$ alkyl group (substituted or unsubstituted); alternatively, a $C_3$-$C_{19}$ alkyl group (substituted or unsubstituted); or alternatively, a $C_4$-$C_{11}$ alkyl group (substituted or unsubstituted). In an embodiment, $R^{2c}$ of the carboxylate having the formula $^-O_2CR^{2c}$ can be a butyl group, an pentyl group, a hexyl group, a heptyl group, an octyl group, a nonyl group, a decyl group, or undecyl group. In some embodiments, $R^{2c}$ of the carboxylate having the formula $^-O_2CR^{2c}$ can be a butyl group; alternatively, a pentyl group; alternatively, a hexyl group; alternatively, a heptyl group; alternatively, an octyl group; alternatively, a nonyl group; alternatively, a decyl group; or alternatively, a undecyl group. In an embodiment, any of the alkyl groups (general or specific) which can be utilized as $R^{2c}$ of the carboxylate having the formula $^-O_2CR^{2c}$ can be substituted. In an embodiment, each substituent of a substituted alkyl group (general or specific) which can be utilized as $R^{2c}$ independently can be a halide or hydrocarboxy group; alternatively, a halide; or alternatively a hydrocarboxy group. Halide substituents and hydrocarboxy substituent groups are independently disclosed herein and can be utilized without limitation to further describe a substituted alkyl group (general or specific) which can be utilized as $R^{2c}$.

In an embodiment, $R^{2c}$ of the carboxylate having the formula $^-O_2CR^{2c}$ can be an n-butyl group, a sec-butyl group, a iso-butyl group, a t-butyl group, a n-pentyl group, a pent-3-yl group, an iso-amyl group, a neo-pentyl group, an n-hexyl group, a hexan-2-yl group, a hexan-3-yl group, a 2-methylpentan-1-yl group, 2-ethylbutan-1-yl group, a 2-methylpentan-2-yl group, a 2,3-dimethylbutan-1-yl group, a 2,3-dimethylbutan-2-yl group, an n-heptyl group, a heptan-2-yl group, a heptan-3-yl group, a heptan-4-yl group, a 2-methylhexan-1-yl group, a 2-ethylpentan-1-yl group, a 2-methylhexan-2-yl group, a 2,3-dimethylpentan-1-yl group, a 2,3-dimethylpentan-2-yl group, a 2,3,3-trimethylpentan-1-yl group, a 2,3,3-trimethylpentan-2-yl group, a n-octyl group, an octan-2-yl group, an octan-3-yl group, an octan-4-yl group, a 2-methylheptan-1-yl group, a 2-ethylhexan-1-yl group, a 2-methylheptan-2-yl group, a n-nonyl group, a nonan-2-yl group, a nonan-3-yl group, a nonan-4-yl group, a nonan-5-yl group, a n-decyl group, a decan-2-yl group, a decan-3-yl group, a decan-4-yl group, a decan-5-yl group, or an n-undecyl group. In other embodiments, $R^{2c}$ of the carboxylate having the formula $^-O_2CR^{2c}$ can be an n-propyl group; alternatively, an isopropyl group; alternatively, an n-butyl group; alternatively, a sec-butyl group; alternatively, a iso-butyl group; alternatively, a t-butyl group; alternatively, a n-pentyl group; alternatively, a pent-3-yl group; alternatively, an iso-amyl group; alternatively, a neo-pentyl group; alternatively, an n-hexyl group; alternatively, a hexan-2-yl group; alternatively, a hexan-3-yl group; alternatively, a 2-methylpentan-1-yl group; alternatively, 2-ethylbutan-1-yl group; alternatively, a 2-methylpentan-2-yl group; alternatively, a 2,3-dimethylbutan-1-yl group; alternatively, a 2,3-dimethylbutan-2-yl group; alternatively, an n-heptyl group; alternatively, a heptan-2-yl group; alternatively, a heptan-3-yl group; alternatively, a heptan-4-yl group; alternatively, a 2-methylhexan-1-yl group; alternatively, a 2-ethylpentan-1-yl group; alternatively, a 2-methylhexan-2-yl group; alternatively, a 2,3-dimethylpentan-1-yl group; alternatively, a 2,3-dimethylpentan-2-yl group; alternatively, a 2,3,3-trimethylpentan-1-yl group; alternatively, a 2,3,3-trimethylpentan-2-yl group; alternatively, a n-octyl group; alternatively, an octan-2-yl group; alternatively, an octan-3-yl group; alternatively, an octan-4-yl group; alternatively, a 2-methylheptan-1-yl group; alternatively, a 2-ethylhexan-1-yl group; alternatively, a 2-methylheptan-2-yl group; alternatively, a n-nonyl group; alternatively, a nonan-2-yl group; alternatively, a nonan-3-yl group; alternatively, a nonan-4-yl group; alternatively, a nonan-5-yl group; alternatively, a n-decyl group; alternatively, a decan-2-yl group; alternatively, a decan-3-yl group; alternatively, a decan-4-yl group; or alternatively, a decan-5-yl group. In an embodiment, any of the alkyl groups which can be utilized $R^{2c}$ of the carboxylate having the formula $^-O_2CR^{2c}$ can be substituted. In an embodiment, each substituent of a substituted alkyl group (general or specific) which can be utilized as $R^{2c}$ independently can be a halide or hydrocarboxy group; alternatively, a halide; or alternatively a hydrocarboxy group. Halide substituents and hydrocarboxy substituent groups are independently disclosed herein and can be utilized without limitation to further describe a substituted alkyl group (general or specific) which can be utilized as $R^{2c}$.

In an embodiment, the alkenyl group (substituted or unsubstituted) which can be utilized as $R^{2c}$ of the carboxylate having the formula $^-O_2CR^{2c}$ can be a $C_2$-$C_{24}$ alkenyl group (substituted or unsubstituted); alternatively, a $C_3$-$C_{19}$ alkenyl group (substituted or unsubstituted); or alternatively, a $C_4$-$C_{11}$ alkenyl group (substituted or unsubstituted). In an embodiment, $R^{2c}$ of the carboxylate having the formula $^-O_2CR^{2c}$ can be a propenyl group, a butenyl group, a pentenyl group, a hexenyl group, a heptenyl group, an octenyl group, a nonenyl group, a decenyl group, an undecenyl group, a dodecenyl group, a tridecenyl group, a tetradecenyl group, a pentadecenyl group, a hexadecenyl group, a heptadecenyl group, an octadecenyl group, or a nonadecenyl group; alternatively, a butenyl group, an pentenyl group, a hexenyl group, a heptenyl group, an octenyl group, a nonenyl group, a decenyl group, or undecenyl group. In some embodiments, $R^{2c}$ of the carboxylate having the formula $^-O_2CR^{2c}$ can be an ethenyl group; alternatively, a propenyl group; alternatively, a butenyl group; alternatively, a pentenyl group; alternatively, a hexenyl group; alternatively, a heptenyl group; alternatively, an octenyl group; alternatively, a nonenyl group; alternatively, a decenyl group; or alternatively, a undecenyl group. In an embodiment, any of the alkenyl groups (general or specific) which can be utilized as $R^{2c}$ of the carboxylate having the formula $^-O_2CR^{2c}$ can be substituted. In an embodiment, each substituent of a substituted alkenyl group (general or specific) which can be utilized as $R^{2c}$ independently can be a halide or hydrocarboxy group; alternatively, a halide; or alternatively a hydrocarboxy group. Halide substituents and hydrocarboxy substituent groups are independently disclosed herein and can be utilized without limitation to further describe a substituted alkenyl group (general or specific) which can be utilized as $R^{2c}$.

In an embodiment, the cycloalkyl group (substituted or unsubstituted) which can be utilized as $R^{2c}$ of the carboxylate having the formula $^-O_2CR^{2c}$ can be a $C_3$-$C_{24}$ cycloalkyl group (substituted or unsubstituted); alternatively, a $C_3$-$C_{19}$ cycloalkyl group (substituted or unsubstituted); or alternatively, a $C_4$-$C_{11}$ cycloalkyl group (substituted or unsubstituted). In an embodiment, $R^{2c}$ of the carboxylate having the formula $^-O_2CR^{2c}$ can be a cyclopentyl group, a substituted cyclopentyl group, a cyclohexyl group, or a substituted cyclohexyl group. In some embodiments, $R^{2c}$ of the carboxylate having the formula $^-O_2CR^{2c}$ can be a cyclopentyl group or a substituted cyclopentyl group; or alternatively, a cyclohexyl group or a substituted cyclohexyl group. In some embodiments, $R^{2c}$ of the carboxylate having the formula $^-O_2CR^{2c}$ can be a cyclopentyl group or a cyclohexyl group. In other embodiments, $R^{2c}$ of the carboxylate having the formula $^-O_2CR^{2c}$ can be a cyclopentyl group; alternatively, a substituted cyclopentyl group; alternatively, a cyclohexyl group; or alternatively, a substituted cyclohexyl group. In an embodiment, each substituent of a substituted cycloalkyl group (general or specific) which can be utilized as $R^{2c}$ independently can be a halide, a hydrocarbyl group, or a hydrocarboxy group; alternatively, a halide or a hydrocarbyl group; alternatively, a halide or a hydrocarboxy group; alternatively, a hydrocarbyl group or a hydrocarboxy group; alternatively, a halide; alternatively, a hydrocarbyl group; or alternatively, a hydrocarboxy group.

In an aspect, the aryl group (substituted or unsubstituted) which can be utilized as $R^{2c}$ of the carboxylate having the formula $^-O_2CR^{2c}$ can be a $C_6$-$C_{24}$ aryl group (substituted or unsubstituted); alternatively, a $C_6$-$C_{19}$ aryl group (substituted or unsubstituted); or alternatively, a $C_6$-$C_{11}$ aryl group (substituted or unsubstituted). In an embodiment, $R^{2c}$ of the carboxylate having the formula $^-O_2CR^{2c}$ can be a phenyl group, a substituted phenyl group, a naphthyl group, or a substituted naphthyl group; or alternatively, a phenyl group or a substituted phenyl group; alternatively, a naphthyl group or a substituted naphthyl group. In some embodiments, $R^{2c}$ of the carboxylate having the formula $^-O_2CR^{2c}$ can be a phenyl group or a naphthyl group. In other embodiments, $R^{2c}$ of the carboxylate having the formula $^-O_2CR^{2c}$ can be a phenyl group; alternatively, a substituted phenyl group; alternatively, a naphthyl group; or alternatively, a substituted naphthyl group. In an embodiment, the $R^{2c}$ substituted phenyl group can be a 2-substituted phenyl group, a 3-substituted phenyl group, a 4-substituted phenyl group, a 2,4-disubstituted phenyl group, a 2,6-disubstituted phenyl group, 3,5-disubstituted phenyl group, or a 2,4,6-trisubstituted phenyl group. In other embodiments, the $R^{2c}$ substituted phenyl group can be a 2-substituted phenyl group, a 4-substituted phenyl group, a 2,4-disubstituted phenyl group, or a 2,6-disubstituted phenyl group; alternatively, a 3-substituted phenyl group or a 3,5-disubstituted phenyl group; alternatively, a 2-substituted phenyl group or a 4-substituted phenyl group; alternatively, a 2,4-disubstituted phenyl group or a 2,6-disubstituted phenyl group; alternatively, a 2-substituted phenyl group; alternatively, a 3-substituted phenyl group; alternatively, a 4-substituted phenyl group; alternatively, a 2,4-disubstituted phenyl group; alternatively, a 2,6-disubstituted phenyl group; alternatively, 3,5-disubstituted phenyl group; or alternatively, a 2,4,6-trisubstituted phenyl group. In an embodiment, each substituent of an aryl group (general or specific), substituted phenyl group (general or specific), or substituted naphthyl group (general or specific) which can be utilized as $R^{2c}$ independently can be a halide, a hydrocarbyl group, or a hydrocarboxy group; alternatively, a halide or a hydrocarbyl group; alternatively, a halide or a hydrocarboxy group; alternatively, a hydrocarbyl group or a hydrocarboxy group; alternatively, a halide; alternatively, a hydrocarbyl group; or alternatively, a hydrocarboxy group.

In an aspect, the aralkyl group (substituted or unsubstituted) which can be utilized as $R^{2c}$ of the carboxylate having the formula $^-O_2CR^{2c}$ can be a $C_7$-$C_{24}$ aralkyl group (substituted or unsubstituted); alternatively, a $C_7$-$C_{19}$ aralkyl group (substituted or unsubstituted); or alternatively, a $C_7$-$C_{11}$ aralkyl group (substituted or unsubstituted). In an embodiment, $R^{2c}$ of the carboxylate having the formula $^-O_2CR^{2c}$ can be a benzyl group or a substituted benzyl group. In an embodiment, $R^{2c}$ of the carboxylate having the formula $^-O_2CR^{2c}$ can be a benzyl group; or alternatively, a substituted benzyl group. In an embodiment, each substituent of an aralkyl group (general or specific) which can be utilized as $R^{2c}$ independently can be a halide, a hydrocarbyl group, or a hydrocarboxy group; alternatively, a halide or a hydrocarbyl group; alternatively, a halide or a hydrocarboxy group; alternatively, a hydrocarbyl group or a hydrocarboxy group; alternatively, a halide; alternatively, a hydrocarbyl group; or alternatively, a hydrocarboxy group.

Halides, hydrocarbyl group substituents, and hydrocarboxy group substituents (also referred to as non-hydrogen substituents or non-hydrogen substituent groups) are independently disclosed herein. These substituent groups can be utilized without limitation to further describe any substituted hydrocarbyl group (general or specific), substituted alkyl group (general or specific), substituted alkenyl group (general or specific), substituted cycloalkyl group (general or specific), substituted cycloalkenyl group (general or specific), substituted aryl group (general or specific), substituted aralkyl group (general or specific) described herein.

In an embodiment, the substituted $R^{2c}$ phenyl group can be a tolyl group, a xylyl group, or a trimethylphenyl group; alternatively, a tolyl group; alternatively, a xylene group; or alternatively, a trimethylphenyl group. In some embodiments, the $R^{2c}$ tolyl group can be an ortho-tolyl group, a meta-tolyl group, or a para-tolyl group; alternatively, an ortho-tolyl group; alternatively, a meta-tolyl group; or alternatively, a para-tolyl group. In an embodiment, the $R^{2c}$ xylyl group can be a 2,3-dimethylphenyl group, a 2,4-dimethylphenyl group, a 2,5-dimethylphenyl group, a 2,6-dimethylphenyl group, a 3,4-dimethylphenyl group, or a 3,5-dimethylphenyl group; alternatively, a 2,4-dimethylphenyl group or a 2,6-dimethylphenyl group; alternatively, a 2,3-dimethylphenyl group; alternatively, a 2,4-dimethylphenyl group; alternatively, a 2,5-dimethylphenyl group; alternatively, a 2,6-dimethylphenyl group; alternatively, a 3,4-dimethylphenyl group; or alternatively, a 3,5-dimethyl group.

In an aspect, each monocarboxylate group independently can be, comprise, or consist essentially of, acetate, a propionate, a butyrate, a pentanoate, a hexanoate, a heptanoate, an octanoate, a nonanoate, a decanoate, an undecanoate, a dodecanoate, a tridecanoate, a tetradecanoate, a pentadecanoate, a hexadecanoate, a heptadecanoate, an octadecanoate, or any combination thereof; alternatively, a propionate, a butyrate, a pentanoate, a hexanoate, a heptanoate, an octanoate, a nonanoate, a decanoate, an undecanoate, a dodecanoate, a tridecanoate, a tetradecanoate, a pentadecanoate, a hexadecanoate, a heptadecanoate, an octadecanoate, or any combination thereof; or alternatively, a pentanoate, a hexanoate, a heptanoate, an octanoate, a nonanoate, a decanoate, an undecanoate, a dodecanoate, or any combination thereof. In some embodiments, each monocarboxylate group independently can be, comprise, or consist essentially of, acetate, propionate, n-butyrate, isobutyrate, valerate (n-pentanoate), neo-pentanoate, capronate (n-hexanoate), n-heptanoate, caprylate (n-octanoate), 2-ethylhexanoate, n-nonanoate, caprate (n-decanoate), n-undecanoate, laurate (n-dodecanoate), stearate (n-octadecanoate), or any combination thereof; alternatively, propionate, n-butyrate, isobutyrate, valerate (n-pentanoate), neo-pentanoate, capronate (n-hexanoate), n-heptanoate, caprylate (n-octanoate), 2-ethylhexanoate, n-nonanoate, caprate (n-decanoate), n-undecanoate, laurate (n-dodecanoate), stearate (n-octadecanoate), or any combination thereof; alternatively, valerate (n-pentanoate), neo-pentanoate, capronate (n-hexanoate), n-heptanoate, caprylate (n-octanoate), 2-ethylhexanoate, n-nonanoate, caprate (n-decanoate), n-undecanoate, laurate (n-dodecanoate), or any combination thereof; or alternatively, valerate (n-pentanoate), caprylate (n-octanoate), or 2-ethylhexanoate. In some embodiments, each monocarboxylate group independently can be, comprise, or consist essentially of, acetate; alternatively, a propionate; alternatively, a butyrate; alternatively, n-butyrate; alternatively, isobutyrate; alternatively, a pentanoate; alternatively, valerate (n-pentanoate); alternatively, neo-pentanoate; alternatively, a hexanoate; alternatively, capronate (n-hexanoate); alternatively, a heptanoate; alternatively, an octanoate; alternatively, caprylate (n-octanoate); alternatively, 2-ethylhexanoate; alternatively, a nonanoate; alternatively, a decanoate; alternatively, caprate (n-decanoate); alternatively, an undecanoate; alternatively, a dodecanoate; alternatively, laurate (n-dodecanoate); alternatively, a tridecanoate; alternatively, a tetradecanoate; alternatively, a pentadecanoate; alternatively, a hexadecanoate; alternatively, a heptadecanoate; alternatively, an octadecanoate; or alternatively, stearate(n-octadecanoate).

In an aspect, each monocarboxylate group independently can be, comprise, or consist essentially of, benzoate, a substituted benzoate, a naphthoate, or a substituted naphthoate. In some embodiments, each monocarboxylate group independently can be, comprise, or consist essentially of, benzoate or a substituted benzoate; alternatively, a naphthoate or a substituted naphthoate. In other embodiments, the monocarboxylate group can be, comprise, or consist essentially of, benzoate or naphthoate. In yet other embodiments, monocarboxylate group independently can be, comprise, or consist essentially of, benzoate; alternatively, a substituted benzoate; alternatively, naphthoate; or alternatively, a substituted naphthoate. In some embodiments, each monocarboxylate independently can be, comprise, or consist essentially of, a methyl benzoate, a dimethyl benzoate, a trimethylbenzoate, or any combination thereof; alternatively, a methyl benzoate; alternatively, a dimethyl benzoate; or alternatively, a trimethylbenzoate. In an embodiment, the methylbenzoate can be, comprise, or consist essentially of, 2-methylbenzoate, 3-methylbenzoate, 4-methylbenzoate or any combination thereof; alternatively, 2-methylbenzoate, 4-methylbenzoate, or any combination thereof; alternatively, 2-methylbenzoate; alternatively, 3-methylbenzoate; or alternatively, 4-methylbenzoate. In an embodiment, the dimethylbenzoate can be, comprise, or consist essentially of, 2,3-dimethylbenzoate, 2,4-dimethylbenzoate, 2,5-dimethylbenzoate, 2,6-dimethylbenzoate, 3,4-dimethylbenzoate, 3,5-dimethylbenzoate, or any combination thereof; alternatively, 2,4-dimethylbenzoate 2,6-dimethylbenzoate, or any combination thereof; alternatively, 2,3-dimethylbenzoate; alternatively, 2,4-dimethylbenzoate; alternatively, 2,5-dimethylbenzoate; alternatively, 2,6-dimethylbenzoate; alternatively, 3,4-dimethylbenzoate; or alternatively, 3,5-dimethylbenzoate. In an embodiment, the trimethylbenzoate can be, comprise, or consist essentially of, 2,4,6-trimethylbenzoate. In an embodiment, each monocarboxylic acid can be, comprise, or consist essentially of, phenylacetic acid, a substituted phenylacetic acid, or any combination thereof; alternatively, phenylacetic acid; or alternatively, a substituted phenyl acetic acid.

As disclosed herein, a wide range carboxylates for the Group 1 or Group 2 metal carboxylates can be utilized in the methods disclosed herein. The Group 1 or Group 2 metal and the carboxylates of the Group 1 or Group 2 metal carboxylate are independently described herein and can be utilized in any combination to describe a general or specific metal carboxylates which can utilized in the methods described herein.

In a non-limiting embodiment, the Group 1 or Group 2 metal carboxylate can be, comprise, or consist essentially of, a sodium or potassium carboxylate; alternatively, a sodium carboxylate; or alternatively a potassium carboxylate. In some non-limiting embodiments, the Group 1 or Group 2 metal carboxylate can be, comprise, or consist essentially of, sodium or potassium oxalate, sodium or potassium maleate, sodium or potassium succinate, sodium or potassium glutarate, sodium or potassium adipate, sodium or potassium phthalate, sodium or potassium isophthalate, sodium or potassium terephthalate, sodium or potassium citrate, or any combination thereof; alternatively, sodium or potassium maleate, sodium or potassium succinate, sodium or potassium glutarate, sodium or potassium adipate, sodium or potassium phthalate, sodium or potassium isophthalate, sodium or potassium terephthalate, or any combination thereof; alternatively, sodium oxalate, sodium maleate, sodium succinate, sodium glutarate, sodium adipate, sodium phthalate, sodium isophthalate, sodium terephthalate, sodium citrate, or any combination thereof; alternatively, sodium maleate, sodium succinate, sodium glutarate, sodium adipate, sodium phthalate, sodium isophthalate, sodium terephthalate, or any combination thereof; alternatively, potassium oxalate, potassium maleate, potassium succinate, potassium glutarate, potassium adipate, potassium phthalate, potassium isophthalate, potassium terephthalate, potassium citrate, or any combination thereof or alternatively, potassium maleate, potassium succinate, potassium glutarate, potassium adipate, potassium phthalate, potassium isophthalate, potassium terephthalate, or any combination thereof. In other non-limiting embodiments, the Group 1 or Group 2 metal carboxylate can be, comprise, or consist essentially of, sodium or potassium oxalate; alternatively, sodium or potassium maleate; alternatively, sodium or potassium succinate; alternatively, sodium or potassium glutarate; alternatively, sodium or potassium adipate; alternatively, sodium or potassium phthalate; alternatively, sodium or potassium isophthalate; alternatively, sodium or potassium terephthalate, sodium or potassium citrate; alternatively, sodium oxalate; alternatively, sodium maleate; alternatively, sodium succinate; alternatively, sodium glutarate; alternatively, sodium adipate; alternatively, sodium phthalate; alternatively, sodium isophthalate; alternatively, sodium terephthalate; alternatively, sodium citrate; alternatively, potassium oxalate; alternatively, potassium maleate; alternatively, potassium succinate; alternatively, potassium glutarate; alternatively, potassium adipate; alternatively, potassium phthalate; alternatively, potassium isophthalate; alternatively, potassium terephthalate; or alternatively, potassium citrate.

In a non-limiting embodiment, the Group 1 or Group 2 metal carboxylate can be, comprise, or consist essentially of, sodium or potassium acetate, sodium or potassium propionate, a sodium or potassium butyrate, a sodium or potassium pentanoate, a sodium or potassium hexanoate, a sodium or potassium heptanoate, a sodium or potassium octanoate, a sodium or potassium nonanoate, a sodium or potassium decanoate, a sodium or potassium undecanoate, a sodium or potassium dodecanoate, a sodium or potassium tridecanoate, a sodium or potassium tetradecanoate, a sodium or potassium pentadecanoate, a sodium or potassium hexadecanoate, a sodium or potassium heptadecanoate, a sodium or potassium octadecanoate, a sodium or potassium icosanoate, a sodium or potassium docosanoate, a sodium or potassium tetracosanoate, sodium or potassium benzoate, a substituted sodium or potassium benzoate, or any combination thereof; alternatively, sodium or potassium propionate, a sodium or potassium butyrate, a sodium or potassium pentanoate, a sodium or potassium hexanoate, a sodium or potassium heptanoate, a sodium or potassium octanoate, a sodium or potassium nonanoate, a sodium or potassium decanoate, a sodium or potassium undecanoate, a sodium or potassium dodecanoate, a sodium or potassium tridecanoate, a sodium or potassium tetradecanoate, a sodium or potassium pentadecanoate, a sodium or potassium hexadecanoate, a sodium or potassium heptadecanoate, a sodium or potassium octadecanoate, a sodium or potassium icosanoate, a sodium or potassium docosanoate, a sodium or potassium tetracosanoate, a sodium or potassium benzoate, a substituted sodium or potassium benzoate, or any combination thereof alternatively, a sodium or potassium pentanoate, a sodium or potassium hexanoate, a sodium or potassium heptanoate, a sodium or potassium octanoate, a sodium or potassium nonanoate, a sodium or potassium decanoate, a sodium or potassium undecanoate, a sodium or potassium dodecanoate, or any combination thereof. In a non-limiting embodiment, the Group 1 or Group 2 metal carboxylate can be, comprise, or consist essentially of, sodium acetate, sodium propionate, a sodium butyrate, a sodium pentanoate, a sodium hexanoate, a sodium heptanoate, a sodium octanoate, a sodium nonanoate, a sodium decanoate, a sodium undecanoate, a sodium dodecanoate, a sodium tridecanoate, a sodium tetradecanoate, a sodium pentadecanoate, a sodium hexadecanoate, a sodium heptadecanoate, a sodium octadecanoate, a sodium icosanoate, a sodium docosanoate, a sodium tetracosanoate, sodium benzoate, a substituted sodium benzoate, or any combination thereof alternatively, sodium propionate, a sodium butyrate, a sodium pentanoate, a sodium hexanoate, a sodium heptanoate, a sodium octanoate, a sodium nonanoate, a sodium decanoate, a sodium undecanoate, a sodium dodecanoate, a sodium tridecanoate, a sodium tetradecanoate, a sodium pentadecanoate, a sodium hexadecanoate, a sodium heptadecanoate, a sodium octadecanoate, a sodium icosanoate, a sodium docosanoate, a sodium tetracosanoate, a sodium benzoate, a substituted sodium benzoate, or any combination thereof alternatively, a sodium pentanoate, a sodium hexanoate, a sodium heptanoate, a sodium octanoate, a sodium nonanoate, a sodium decanoate, a sodium undecanoate, sodium dodecanoate, or any combination thereof. In other non-limiting embodiments, the Group 1 or Group 2 metal carboxylate can be, comprise, or consist essentially of, potassium acetate, potassium propionate, a potassium butyrate, a potassium pentanoate, a potassium hexanoate, a potassium heptanoate, a potassium octanoate, a potassium nonanoate, a potassium decanoate, a potassium undecanoate, a potassium dodecanoate, a potassium tridecanoate, a potassium tetradecanoate, a potassium pentadecanoate, a potassium hexadecanoate, a potassium heptadecanoate, a potassium octadecanoate, a potassium icosanoate, a potassium docosanoate, a potassium tetracosanoate, potassium benzoate, a substituted potassium benzoate, or any combination thereof alternatively, potassium propionate, a potassium butyrate, a potassium pentanoate, a potassium hexanoate, a potassium heptanoate, a potassium octanoate, a potassium nonanoate, a potassium decanoate, a potassium undecanoate, a potassium dodecanoate, a potassium tridecanoate, a potassium tetradecanoate, a potassium pentadecanoate, a potassium hexadecanoate, a potassium heptadecanoate, a potassium octadecanoate, a potassium icosanoate, a potassium docosanoate, a potassium tetracosanoate, a potassium benzoate, a substituted potassium benzoate, or any combination thereof; alternatively, a potassium pentanoate, a potassium hexanoate, a potassium heptanoate, a potassium octanoate, a potassium nonanoate, a potassium decanoate, a potassium undecanoate, a potassium dodecanoate, or any combination thereof.

In a non-limiting embodiment, the Group 1 or Group 2 metal carboxylate can be, comprise, or consist essentially of, sodium or potassium acetate, sodium or potassium propionate, sodium or potassium n-butyrate, sodium or potassium isobutyrate, sodium or potassium valerate (n-pentanoate), sodium or potassium neo-pentanoate, sodium or potassium capronate (n-hexanoate), sodium or potassium n-heptanoate, sodium or potassium caprylate (n-octanoate), sodium or potassium 2-ethylhexanoate, sodium or potassium n-nonanoate, sodium or potassium caprate (n-decanoate), sodium or potassium n-undecanoate, sodium or potassium laurate (n-dodecanoate), sodium or potassium stearate (n-octadecanoate), sodium or potassium benzoate, or any combination thereof; alternatively, sodium or potassium propionate, sodium or potassium n-butyrate, sodium or potassium isobutyrate, sodium or potassium valerate (n-pentanoate), sodium or potassium neo-pentanoate, sodium or potassium capronate (n-hexanoate), sodium or potassium n-heptanoate, sodium or potassium caprylate (n-octanoate), sodium or potassium 2-ethylhexanoate, sodium or potassium n-nonanoate, sodium or potassium caprate (n-decanoate), sodium or potassium n-undecanoate, sodium or potassium laurate (n-dodecanoate), sodium or potassium stearate (n-octadecanoate), sodium or potassium benzoate, or any combination thereof; alternatively, sodium or potassium valerate (n-pentanoate), sodium or potassium neo-pentanoate, sodium or potassium capronate (n-hexanoate), sodium or potassium n-heptanoate, sodium or potassium caprylate (n-octanoate), sodium or potassium 2-ethylhexanoate, sodium or potassium n-nonanoate, sodium or potassium caprate (n-decanoate), sodium or potassium n-undecanoate, sodium or potassium laurate (n-dodecanoate), or any combination thereof. In some non-limiting embodiments, the Group 1 or Group 2 metal carboxylate can be, comprise, or consist essentially of, sodium acetate, sodium propionate, sodium n-butyrate, sodium isobutyrate, sodium valerate (n-pentanoate), sodium neo-pentanoate, sodium capronate (n-hexanoate), sodium n-heptanoate, sodium caprylate (n-octanoate), sodium 2-ethylhexanoate, sodium n-nonanoate, sodium caprate (n-decanoate), sodium n-undecanoate, sodium laurate (n-dodecanoate), sodium stearate (n-octadecanoate), sodium benzoate, or any combination thereof alternatively, sodium propionate, sodium n-butyrate, sodium isobutyrate, sodium valerate (n-pentanoate), sodium neo-pentanoate, sodium capronate (n-hexanoate), sodium n-heptanoate, sodium caprylate (n-octanoate), sodium 2-ethylhexanoate, sodium n-nonanoate, sodium caprate (n-decanoate), sodium n-undecanoate, sodium laurate (n-dodecanoate), sodium stearate (n-octadecanoate), sodium benzoate, or any combination thereof; alternatively, sodium valerate (n-pentanoate), sodium neo-pentanoate, sodium capronate (n-hexanoate), sodium n-heptanoate, sodium caprylate (n-octanoate), sodium 2-ethylhexanoate, sodium n-nonanoate, sodium caprate (n-decanoate), sodium n-undecanoate, sodium laurate (n-dodecanoate), or any combination thereof. In other non-limiting embodiments, the Group 1 or Group 2 metal carboxylate can be, comprise, or consist essentially of, potassium acetate, potassium propionate, potassium n-butyrate, potassium isobutyrate, potassium valerate (n-pentanoate), potassium neo-pentanoate, potassium capronate (n-hexanoate), potassium n-heptanoate, potassium caprylate (n-octanoate), potassium 2-ethylhexanoate, potassium n-nonanoate, potassium caprate (n-decanoate), potassium n-undecanoate, potassium laurate (n-dodecanoate), potassium stearate (n-octadecanoate), potassium benzoate, or any combination thereof; alternatively, potassium propionate, potassium n-butyrate, potassium isobutyrate, potassium valerate (n-pentanoate), potassium neo-pentanoate, potassium capronate (n-hexanoate), potassium n-heptanoate, potassium caprylate (n-octanoate), potassium 2-ethylhexanoate, potassium n-nonanoate, potassium caprate (n-decanoate), potassium n-undecanoate, potassium laurate (n-dodecanoate), potassium stearate (n-octadecanoate), potassium benzoate, or any combination thereof; or alternatively, potassium valerate (n-pentanoate), potassium neo-pentanoate, potassium capronate (n-hexanoate), potassium n-heptanoate, potassium caprylate (n-octanoate), potassium 2-ethylhexanoate, potassium n-nonanoate, potassium caprate (n-decanoate), potassium n-undecanoate, potassium laurate (n-dodecanoate), or any combination thereof. In yet other non-limiting embodiments, the Group 1 or Group 2 metal carboxylate can be, comprise, or consist essentially of, sodium acetate; alternatively, sodium propionate; alternatively, sodium n-butyrate; alternatively, sodium isobutyrate; alternatively, sodium valerate (n-pentanoate); alternatively, sodium neo-pentanoate; alternatively, sodium capronate (n-hexanoate); alternatively, sodium n-heptanoate; alternatively, sodium caprylate (n-octanoate); alternatively, sodium 2-ethylhexanoate; alternatively, sodium n-nonanoate; alternatively, sodium caprate (n-decanoate); alternatively, sodium n-undecanoate; alternatively, sodium laurate (n-dodecanoate); alternatively, sodium stearate (n-octadecanoate); alternatively, sodium benzoate; alternatively, potassium acetate; alternatively, potassium propionate; alternatively, potassium n-butyrate; alternatively, potassium isobutyrate; alternatively, potassium valerate (n-pentanoate); alternatively, potassium neo-pentanoate; alternatively, potassium capronate (n-hexanoate); alternatively, potassium n-heptanoate; alternatively, potassium caprylate (n-octanoate); alternatively, potassium 2-ethylhexanoate; alternatively, potassium n-nonanoate; alternatively, potassium caprate (n-decanoate); alternatively, potassium n-undecanoate; alternatively, potassium laurate (n-dodecanoate); alternatively, potassium stearate (n-octadecanoate); or alternatively, potassium benzoate.

In a non-limiting embodiment, the Group 1 or Group 2 metal carboxylate can be, comprise, or consist essentially of, sodium or potassium benzoate, a sodium or potassium methylbenzoate, a sodium or potassium di-methylbenzoate, sodium or potassium naphthenate, or any combination thereof. In some non-limiting embodiments, the Group 1 or Group 2 metal carboxylate can be, comprise, or consist essentially of, sodium benzoate, a sodium methylbenzoate, sodium di-methylbenzoate, sodium naphthenate, or any combination thereof; alternatively, potassium benzoate, a potassium methylbenzoate, a potassium dimethylbenzoate, potassium naphthenate, or any combination thereof. In other non-limiting embodiments, the Group 1 or Group 2 metal carboxylate can be, comprise, or consist essentially of, sodium benzoate; alternatively, a sodium methylbenzoate; alternatively, sodium dimethylbenzoate; alternatively, sodium naphthenate; alternatively, potassium benzoate; alternatively, a potassium methylbenzoate; alternatively, a potassium dimethylbenzoate; or alternatively, potassium naphthenate.

In an aspect, the Group 1 or Group 2 metal carboxylate utilized in any aspect or any embodiment disclosed herein can be substantially anhydrous; or alternatively, anhydrous. In some embodiments the Group 1 or Group 2 metal carboxylate can have a water content of less than or equal to 100 ppm; alternatively, less than or equal to 90 ppm; alternatively, less than or equal to 80 ppm; alternatively, less than or equal to 70 ppm; alternatively, less than or equal to 60 ppm; alternatively, less than or equal to 50 ppm; alternatively, less than or equal to 40 ppm; alternatively, less than or equal to 30 ppm; alternatively, less than or equal to 20 ppm; alternatively, less than or equal to 10 ppm; alternatively, less than or equal to 9 ppm; alternatively, less than or equal to 8 ppm; alternatively, less than or equal to 7 ppm; alternatively, less than or equal to 6 ppm; alternatively, less than or equal to 5 ppm; alternatively, less than or equal to 4 ppm; alternatively, less than or equal to 3 ppm; alternatively, less than or equal to 2 ppm; or alternatively, less than or equal to 1 ppm. Generally, the water content of the Group 1 or Group 2 metal carboxylate can be based on the ppm (by weight) of water in the Group 1 or Group 2 metal carboxylate. It should be noted that the water present in the Group 1 or Group 2 metal carboxylate can be in the form of Group 1 or Group 2 metal carboxylate impurities and/or interstitial water in the Group 1 or Group 2 metal carboxylate.

In an aspect, the Group 1 or Group 2 metal carboxylate utilized in any aspect or any embodiment disclosed herein can be substantially acid-free. In some embodiments, the Group 1 or Group 2 metal carboxylate can have an acid content of less than or equal to 1000 ppm; alternatively, less than or equal to 750 ppm; alternatively, less than or equal to 500 ppm; or alternatively, less than or equal to 250 ppm. In other embodiments, the Group 1 or Group 2 metal carboxylate can have an acid content of less than or equal to 100 ppm; alternatively, less than or equal to 90 ppm; alternatively, less than or equal to 80 ppm; alternatively, less than or equal to 70 ppm; alternatively, less than or equal to 60 ppm; alternatively, less than or equal to 50 ppm; alternatively, less than or equal to 40 ppm; alternatively, less than or equal to 30 ppm; alternatively, less than or equal to 20 ppm; alternatively, less than or equal to 10 ppm; alternatively, less than or equal to 9 ppm; alternatively, less than or equal to 8 ppm; alternatively, less than or equal to 7 ppm; alternatively, less than or equal to 6 ppm; alternatively, less than or equal to 5 ppm; alternatively, less than or equal to 4 ppm; alternatively, less than or equal to 3 ppm; alternatively, less than or equal to 2 ppm; or alternatively, less than or equal to 1 ppm. Generally, the acid content of the Group 1 or Group 2 metal carboxylate can be based on the ppm (by weight) of acid in the Group 1 or Group 2 metal carboxylate. It should be noted that the acid present in the Group 1 or Group 2 metal carboxylate can be in the form of Group 1 or Group 2 metal carboxylate impurities and/or interstitial acid in the Group 1 or Group 2 metal carboxylate.

In an aspect, the solvent that can be utilized in the step of contacting a transition metal precursor, a Group 1 or Group 2 metal carboxylate, and a solvent can be any solvent suitable for the process. In an embodiment, the solvent that can be utilized in the step of contacting a transition metal precursor, a Group 1 or Group 2 metal carboxylate, and a solvent can be, comprise, or consist essentially of, aprotic solvent. In some embodiments, the solvent that can be utilized in the step of contacting a transition metal precursor, a Group 1 or Group 2 metal carboxylate, and a solvent can be, comprise, or consist essentially of, a non-polar solvent, an aprotic polar solvent, or any combination thereof; alternatively, a combination of a non-polar solvent and an aprotic polar solvent; alternatively, a non-polar solvent; or alternatively, an aprotic polar solvent. Solvents (aprotic, non-polar, and/or aprotic polar) are independently described herein and can be utilized without limitation to further describe the solvent that can be utilized in the step of contacting a transition metal precursor, a Group 1 or Group 2 metal carboxylate, and a solvent.

In an embodiment, the non-polar solvent can be, comprise, or consist essentially of, a hydrocarbon, a halogenated hydrocarbon, or any combination thereof; alternatively, a hydrocarbon; or alternatively, a halogenated hydrocarbon. Hydrocarbon solvents and halogenated hydrocarbon solvents are independently described herein and can be utilized without limitation as the solvent in the step of contacting a transition metal precursor, a Group 1 or Group 2 metal carboxylate, and a solvent.

In an embodiment, the aprotic polar solvent can be, comprise, or consist essentially of, any compound which can be utilized as the neutral ligand described herein. In some embodiments, the aprotic polar solvent can be, comprise, or consist essentially of, the same compound which is utilized as the neutral ligand of the utilized transition metal precursor. In other embodiments, the aprotic polar solvent can be, comprise, or consist essentially of, a different compound than that which is utilized as the neutral ligand of the utilized transition metal precursor. In aspects and embodiments, where the transition metal precursor does not have a neutral ligand, the aprotic polar solvent can be, comprise, or consist essentially of, any compound(s) described herein which could be utilized as a neutral ligand for the transition metal precursor. Compounds which can be utilized as the neutral ligand are independently described herein and can be utilized without limitation as the solvent in the step of contacting a transition metal precursor, a Group 1 or Group 2 metal carboxylate, and a solvent.

In an aspect, the solvent utilized in the any aspect or any embodiment disclosed herein can be substantially anhydrous; or alternatively, anhydrous. In some embodiments the solvent can have a water content of less than or equal to 100 ppm; alternatively, less than or equal to 90 ppm; alternatively, less than or equal to 80 ppm; alternatively, less than or equal to 70 ppm; alternatively, less than or equal to 60 ppm; alternatively, less than or equal to 50 ppm; alternatively, less than or equal to 40 ppm; alternatively, less than or equal to 30 ppm; alternatively, less than or equal to 20 ppm; or alternatively, less than or equal to 10 ppm; alternatively, less than or equal to 9 ppm; alternatively, less than or equal to 8 ppm; alternatively, less than or equal to 7 ppm; alternatively, less than or equal to 6 ppm; alternatively, less than or equal to 5 ppm; alternatively, less than or equal to 4 ppm; alternatively, less than or equal to 3 ppm; alternatively, less than or equal to 2 ppm; or alternatively, less than or equal to 1 ppm. Generally, the water content of the solvent can be based on the ppm (by weight) of water in the solvent.

In an aspect, the solvent utilized in any aspect or any embodiment disclosed herein can be substantially acid-free. In some embodiments, the solvent can have an acid content of less than or equal to 1000 ppm; alternatively, less than or equal to 750 ppm; alternatively, less than or equal to 500 ppm; or alternatively, less than or equal to 250 ppm. In other embodiments, the solvent can have an acid content of less than or equal to 100 ppm; alternatively, less than or equal to 90 ppm; alternatively, less than or equal to 80 ppm; alternatively, less than or equal to 70 ppm; alternatively, less than or equal to 60 ppm; alternatively, less than or equal to 50 ppm; alternatively, less than or equal to 40 ppm; alternatively, less than or equal to 30 ppm; alternatively, less than or equal to 20 ppm; alternatively, less than or equal to 10 ppm; alternatively, less than or equal to 9 ppm; alternatively, less than or equal to 8 ppm; alternatively, less than or equal to 7 ppm; alternatively, less than or equal to 6 ppm; alternatively, less than or equal to 5 ppm; alternatively, less than or equal to 4 ppm; alternatively, less than or equal to 3 ppm; alternatively, less than or equal to 2 ppm; or alternatively, less than or equal to 1 ppm. Generally, the acid content of the solvent can be based on the ppm (by weight) of acid in the solvent.

In an aspect, the present disclosure describes a process for preparing a transition metal carboxylate composition comprising: contacting 1) a transition metal precursor, 2) a Group 1 or Group 2 metal carboxylate, and 3) a solvent to form a transition metal carboxylate. In another aspect, the present disclosure describes a process for preparing a transition metal carboxylate composition can comprise: contacting 1) a transition metal precursor, 2) a Group 1 or Group 2 metal carboxylate, and 3) a solvent to form a solution comprising the transition metal carboxylate. In an embodiment, the process for preparing a transition metal carboxylate composition can comprise: a) contacting 1) a transition metal precursor, 2) a Group 1 or Group 2 metal $C_3$-$C_{25}$ carboxylate, and 3) a solvent to form a transition metal $C_3$-$C_{25}$ carboxylate. In some embodiments, the process for preparing a transition metal carboxylate composition can comprise: a) contacting 1) a transition metal precursor, 2) a Group 1 or Group 2 metal $C_3$-$C_{25}$ carboxylate, and 3) a solvent to form a solution comprising the transition metal $C_3$-$C_{25}$ carboxylate. The transition metal precursor (e.g. a chromium(III) precursor, among others disclosed herein), the Group 1 or Group 2 metal carboxylate (e.g. a Group 1 or Group 2 metal $C_3$-$C_{25}$ carboxylate, among others disclosed herein), and the solvent are independent elements of the process of preparing a transition metal carboxylate composition. The process for preparing a transition metal carboxylate can be described using any combination of any aspect or any embodiment of the transition metal precursor, Group 1 or Group 2 metal carboxylate described herein, or solvent described herein.

In an aspect, the transition metal precursor (general or specific) utilized in the process for producing the transition metal carboxylate can be a substantially anhydrous transition metal precursor, alternatively, a substantially acid-free transition metal precursor; or alternatively, a substantially anhydrous and substantially acid-free transition metal precursor. In an embodiment, the transition metal precursor (general or specific) utilized in the process for producing the transition metal carboxylate can have any transition metal precursor water content disclosed herein. In an embodiment, the transition metal precursor (general or specific) utilized in the process for producing the transition metal carboxylate can have any transition metal precursor acid content disclosed herein.

In an aspect, the Group 1 or Group 2 metal carboxylate (general or specific) utilized in the process for producing the transition metal carboxylate can be a substantially anhydrous Group 1 or Group 2 metal carboxylate; alternatively, a substantially acid-free Group 1 or Group 2 metal carboxylate; or alternatively, a substantially anhydrous and substantially acid-free Group 1 or Group 2 metal carboxylate. In an embodiment, the Group 1 or Group 2 metal carboxylate (general or specific) utilized in the process for producing the transition metal carboxylate can have any Group 1 or Group 2 metal carboxylate water content disclosed herein. In an embodiment, the Group 1 or Group 2 metal carboxylate (general or specific) utilized in the process for producing the transition metal carboxylate can have any Group 1 or Group 2 metal carboxylate acid content disclosed herein.

In an aspect, the solvent utilized in the step of contacting the transition metal precursor, the Group 1 or Group 2 metal carboxylate, and the solvent can be a substantially anhydrous; alternatively, a substantially acid-free; or alternatively, a substantially anhydrous and substantially acid-free. In an embodiment, the solvent utilized in the process for producing the transition metal carboxylate can have any solvent water content disclosed herein. In an embodiment, the solvent utilized in the process for producing the transition metal carboxylate can have any solvent acid content disclosed herein.

In an aspect, the transition metal precursor, the Group 1 or Group 2 metal carboxylate, and solvent can be contacted under substantially anhydrous conditions; or alternatively, under anhydrous conditions. In another aspect, the transition metal carboxylate can be formed under substantially anhydrous conditions; or alternatively, under anhydrous conditions. In an aspect, the transition metal precursor, the Group 1 or Group 2 metal carboxylate, and solvent can be contacted under substantially acid-free conditions; or alternatively, under acid-under conditions. In another aspect, the transition metal carboxylate can be formed under substantially acid-free conditions; or alternatively, under acid-free conditions. In an embodiment, the each of the transition metal precursors, the Group 1 or Group 2 metal carboxylate, and the solvent can independently have any water content disclosed herein for the transition metal precursor, the Group 1 or Group 2 metal carboxylate, and the solvent. In an aspect, the transition metal precursor, the Group 1 or Group 2 metal carboxylate, and solvent can be contacted under substantially anhydrous and substantially acid-free conditions; or alternatively, under anhydrous and acid-free conditions. In another aspect, the transition metal carboxylate can be formed under substantially anhydrous and substantially acid-free conditions; or alternatively, under anhydrous and acid-free conditions. In an aspect, the transition metal precursor, the Group 1 or Group 2 metal carboxylate, and solvent can be contacted under substantially acid-free conditions; or alternatively, under acid-under conditions.

In an aspect, the transition metal precursor, the Group 1 or Group 2 metal carboxylate, and the solvent can be contacted in any combination or order. In an embodiment, the transition metal precursor, the Group 1 or Group 2 metal carboxylate, and the solvent can be contacted simultaneously. In an embodiment, the transition metal precursor and the solvent can be contacted to form a mixture, and the mixture subsequently contacted with the Group 1 or Group 2 metal carboxylate; alternatively, the Group 1 or Group 2 metal carboxylate and the solvent can be contacted to form a mixture and the mixture subsequently contacted with the transition metal precursor; or alternatively, 1) the transition metal precursor and a portion of the solvent can be contacted to form a first mixture, 2) the Group 1 or Group 2 metal carboxylate and a portion of the solvent to form a second mixture, and 3) contacting the first and second mixtures. In some embodiments, the solvent of the first mixture is the same as the solvent of the second mixture. In other embodiments, the solvent of the first mixture and second mixture are different.

In an aspect, the step of contacting the transition metal precursor, the Group 1 or Group 2 metal carboxylate, and the solvent is not limited to a specific type of contacting or formation process, a specific reactor, or any particular engineering requirement. In an embodiment, the formation of the transition metal carboxylate can occur via a batch process or a continuous process; alternatively, a batch process; or alternatively, a continuous process. In some embodiments, the formation of the transition metal carboxylate occur via a batch process in a slurry or mixture comprising, or consisting essentially of, the transition metal precursor, the Group 1 or Group 2 metal carboxylate, and the solvent.

In an embodiment, any combination of the transition metal precursor, Group 1 or Group 2 metal carboxylate, and solvent can be contacted at a temperature ranging from −40° C. to 200° C.; alternatively, −40° C. to 150° C.; alternatively, −40° C. to 100° C.; alternatively, −20° C. to 80° C.; or alternatively, 0° C. to 60° C. In an embodiment, the transition metal precursor (general or specific) can be insoluble in the solvent at the temperature at which the transition metal precursor and solvent are contacted; alternatively, partially soluble in the solvent at the temperature at which the transition metal precursor and the solvent are contacted; or alternatively, soluble at the temperature at which the transition metal precursor and the solvent are contacted. In an embodiment, the Group 1 or Group 2 metal carboxylate (general or specific) can be insoluble in the solvent at the temperature the Group 1 or Group 2 metal carboxylate and solvent are contacted; alternatively, partially soluble in the solvent at the temperature at which the Group 1 or Group 2 metal carboxylate and the solvent are contacted; or alternatively, soluble at the temperature at which the Group 1 or Group 2 metal carboxylate and the solvent are contacted.

In an embodiment, the transition metal precursor and the Group 1 or Group 2 metal carboxylate can be contacted at any suitable transition metal precursor to carboxylate group equivalent ratio.

In an aspect, the transition metal carboxylate can be formed at conditions suitable for forming a transition metal carboxylate. Conditions capable of forming the transition metal carboxylate can include, temperature, time, pressure, transition metal precursor to carboxylate group ratio (molar or equivalent), and/or any combination thereof, among other conditions. These transition metal carboxylate formation conditions are independently described herein and can be utilized in any combination to further describe a process for producing a transition metal carboxylate composition.

In an aspect, the transition metal precursor and the Group 1 or Group 2 metal carboxylate can be contacted at any suitable carboxylate group of the Group 1 or Group 2 metal carboxylate to transition metal of the transition metal precursor equivalent ratio (i.e. carboxylate group to transition metal equivalent ratio). In an embodiment, the carboxylate group to transition metal equivalent ratio can fall within a range of carboxylate group to transition metal equivalent ratios. In an embodiment, the minimum equivalent ratio for any range of a carboxylate group to transition metal equivalent ratio can be 0.95:1; alternatively, 1:1; alternatively, 1.03:1; or alternatively, 1.05:1. In an embodiment, the maximum equivalent ratio for any range of a carboxylate group to transition metal equivalent ratio can be 1.3:1; alternatively, 1:25; alternatively, 1.2:1; or alternatively, 1.15:1. In an embodiment, the carboxylate group to transition metal equivalent ratio can range from any minimum carboxylate group to transition metal equivalent ratio described herein to any maximum transition metal carboxylate group to transition metal equivalent ratio described herein. In some non-limiting embodiments, the carboxylate group to transition metal equivalent ratio can range from 0.95:1 to 1.3:1; alternatively, 1:1 to 1.25:1; alternatively, 1:1 to 1.2:1; alternatively, 1.03:1 to 1.25:1; alternatively, 1.03:1 to 1.2:1; alternatively, 1.05:1 to 1.2:1; or alternatively, 1.05:1 to 1.15:1. Other carboxylate group to transition metal equivalent ratio ranges are readily apparent from the present disclosure. In another non-limiting embodiment, the carboxylate group to transition metal equivalent ratio can be about 1.1:1. Generally, the transition metal in the +x oxidation state contains x equivalents of the transition metal.

In an aspect, the transition metal precursor and the Group 1 or Group 2 metal carboxylate can be contacted at any suitable carboxylate group of the Group 1 or Group 2 metal carboxylate to transition metal of the transition metal precursor molar ratio (i.e. carboxylate group to transition metal molar ratio). In an embodiment, the carboxylate group to transition metal molar ratio can fall within a range of carboxylate group to transition metal molar ratios. Generally, the carboxylate group to transition metal molar ratio and the carboxylate group to transition metal equivalent ratio are related by the oxidation state of the transition metal of the transition metal precursor in that the number of moles of carboxylate group utilized equals the x*the number of carboxylate group equivalents. In an embodiment, the minimum molar ratio for any range of a carboxylate group to transition metal molar ratio can be 0.95*x:1; alternatively, 1*x:1; alternatively, 1.03*x:1; or alternatively, 1.05*x:1. In an embodiment, the maximum molar ratio for any range of a carboxylate group to transition metal molar ratio can be 1.3*x:1; alternatively, 1*x:25; alternatively, 1.2*x:1; or alternatively, 1.15*x:1. In an embodiment, the carboxylate group to transition metal molar ratio can range from any minimum carboxylate group to transition metal molar ratio described herein to any maximum transition metal molar ratio described herein. In some non-limiting embodiments, the carboxylate group to transition metal molar ratio can range from 0.95*x:1 to 1.3*x:1; alternatively, 1*x:1 to 1.25*x:1; alternatively, 1*x:1 to 1.2*x:1; alternatively, 1.03*x:1 to 1.25*x:1; alternatively, 1.03*x:1 to 1.2*x:1; alternatively, 1.05*x:1 to 1.2*x:1; or alternatively, 1.05*x:1 to 1.15*x:1. In another non-limiting embodiment, the carboxylate group to transition metal equivalent ratio can be about 1.1*x:1. Other carboxylate group to transition metal molar ratio ranges are readily apparent from the present disclosure.

In an embodiment, the transition metal carboxylate can be formed at a temperature ranging from ranging from −40° C. to 200° C.; alternatively, −40° C. to 150° C.; alternatively, −40° C. to 100° C.; alternatively, −20° C. to 80° C.; or alternatively, 0° C. to 60° C. In an embodiment, the transition metal precursor (general or specific) can be insoluble in the solvent at the temperature at which the transition metal carboxylate can be formed; alternatively, partially soluble in the solvent at the temperature at which the transition metal carboxylate can be formed; or alternatively, soluble at the temperature at which the transition metal carboxylate can be formed. In an embodiment, the Group 1 or Group 2 metal carboxylate (general or specific) can be insoluble in the solvent at the temperature at which the transition metal carboxylate can be formed; alternatively, partially soluble in the solvent at the temperature at which the transition metal carboxylate can be formed; or alternatively, soluble at the temperature at which the transition metal carboxylate can be formed. The temperature at which any combination of the transition metal precursor, Group 1 or Group 2 metal carboxylate, and solvent can be contact temperature and the transition metal carboxylate formation temperature are independent of each other. In should be noted when the contact temperature and the formation temperature is different, that this does not imply that the formation of the transition metal carboxylate cannot begin at the contact temperature or at a temperature between the contact temperature and the formation temperature. The formation temperature just indicates that at some point the formation of a portion of the transition metal carboxylate occurs at the prescribed formation temperature. It should be also noted that the transition metal precursor, Group 1 or Group 2 metal carboxylate, and solvent can be contacted at one temperature (one at which the formation of the transition metal carboxylate can slowly form) and then the transition metal formed at a second temperature (or alternatively, the mixture comprising, consisting essentially of, or consisting of, the transition metal precursor, the Group 1 or Group 2 metal carboxylate, and the solvent subjected to second temperature for formation of the transition metal carboxylate).

In an aspect, the formation time of the transition metal carboxylate (or alternatively, a contact time for transition metal precursor, Group 1 or Group 2 metal carboxylate, and solvent) can be at least 0.1 hours; alternatively, at least 0.15 hours; alternatively, at least 0.2 hours; alternatively, at least 0.25 hours; alternatively, at least 0.3 hours; alternatively, at least 0.35 hours; alternatively, at least 0.45, hours; or alternatively, at least 0.5 hours. In an embodiment, the maximum formation time of the transition metal carboxylate (or alternatively, a contact time for transition metal precursor, Group 1 or Group 2 metal carboxylate, and solvent) can be 168 hours; alternatively, 144 hours; alternatively, 120 hours; alternatively, 96 hours; alternatively, 72 hours; alternatively, 48 hours; alternatively, 36 hours; alternatively, 24 hours; alternatively, 18 hours; alternatively, 15 hours; alternatively, 12 hours; alternatively, 9 hours; alternatively, 8 hours; or alternatively, 7 hours. In some embodiments, a condition capable of forming the chromium(III) halide complex can include a formation time of the transition metal carboxylate (or alternatively, a contact time for transition metal precursor, Group 1 or Group 2 metal carboxylate, and solvent) that can range from any minimum transition metal carboxylate formation time (or alternatively, transition metal precursor, Group 1 or Group 2 metal carboxylate, and solvent contact time) disclosed herein to any maximum transition metal carboxylate formation time (or alternatively, transition metal precursor, Group 1 or Group 2 metal carboxylate, and solvent contact time) described herein. In some non-limiting embodiments, the transition metal carboxylate formation time (or alternatively, transition metal precursor, Group 1 or Group 2 metal carboxylate, and solvent contact time) can be from 0.1 hours to 168 hours; alternatively, from 0.1 hours to 120 hours; alternatively, from 0.25 hours to 72 hours; alternatively, from 0.4 hours to 36 hours; alternatively, from 0.5 hours to 24 hours; or alternatively, from 0.5 hours to 24 hours. Other transition metal carboxylate formation time (or alternatively, transition metal precursor, Group 1 or Group 2 metal carboxylate, and solvent contact time) ranges are readily apparent from the present disclosure.

In an aspect, the transition metal carboxylate can be formed at any pressure capable of forming the transition metal carboxylate. In an embodiment, the conditions capable of forming the transition metal carboxylate can include atmospheric pressure (i.e. about 14.7 psi or about 101 kPa). In an embodiment, a condition capable of forming the transition metal carboxylate can include subjecting a contact mixture comprising the transition metal precursor, the Group 1 or Group 2 metal carboxylate, and the solvent to a pressure greater than ambient pressure. In some embodiments, a condition capable of forming the transition metal carboxylate can include a pressure of at least atmospheric pressure; alternatively, at least 2 psi (14 kPa) greater than atmospheric pressure; alternatively, least 5 psi (34 kPa) greater than atmospheric pressure; alternatively, least 10 psi (69 kPa) greater than atmospheric pressure; or alternatively, least 15 psi (103 kPa) greater than atmospheric pressure. In some embodiments, a condition capable of forming the transition metal carboxylate can include a pressure capable of maintaining the solvent in the liquid state; alternatively, at least 2 psi (14 kPa) greater than the pressure capable of maintaining the solvent in the liquid state; alternatively, at least 5 psi (34 kPa) greater than the pressure capable of maintaining the solvent in the liquid state; alternatively, at least 10 psi (69 kPa) greater than the pressure capable of maintaining the solvent in the liquid state; or alternatively, least at 15 psi (103 kPa) greater than the pressure capable of maintaining the solvent in the liquid state. In other embodiments, a condition capable of forming the transition metal carboxylate can include a maximum pressure of 500 psi (3.4 mPa); alternatively, of 400 psi (2.8 mPa); alternatively, of 250 psi (1.7 mPa); alternatively, of 200 psi (1.4 mPa); alternatively, of 150 psi (1.0 mPa); alternatively, of 100 psi (689 kPa); or alternatively, of 50 psi (345 kPa). In yet other embodiments, a condition capable of forming the transition metal carboxylate can include a pressure that can range from any minimum transition metal carboxylate formation pressure disclosed herein to any maximum transition metal carboxylate formation pressure described herein. In some non-limiting embodiments, a condition capable of forming the transition metal carboxylate can include a pressure from atmospheric pressure to 500 psi (3.4 mPa); alternatively, at least 2 psi (14 kPa) greater than atmospheric pressure to 500 psi (3.4 mPa); alternatively, at least 5 psi (34 kPa) greater than the pressure capable of maintaining the solvent in the liquid state to 500 psi (3.4 mPa). Other pressure ranges which can be a condition capable of forming the transition metal carboxylate are readily apparent from the present disclosure.

In an embodiment, any combination of the transition metal precursor, Group 1 or Group 2 metal carboxylate, and solvent can be contacted at and/or the transition metal carboxylated can be formed under a substantially dry (or alternatively dry) atmosphere. In an embodiment, the substantially dry (or alternatively dry) atmosphere can comprise nitrogen, argon, helium, oxygen, or any combination thereof or alternatively, nitrogen, argon, helium, or any combination thereof. In some embodiments, the substantially dry atmosphere can be substantially dry nitrogen, substantially dry argon, substantially dry helium, or substantially, dry air; alternatively, substantially dry nitrogen; alternatively, substantially dry argon; alternatively, substantially dry helium; or alternatively, substantially, dry air. In other embodiments, the dry atmosphere can be dry nitrogen, dry argon, dry helium, or dry air; alternatively dry nitrogen; alternatively, dry argon; alternatively, dry helium; or alternatively, dry air. In some embodiments, the chromium precursor, Group 1 or Group 2 metal carboxylate, and solvent can be contacted at and/or the chromium carboxylated can be formed under an atmosphere (any described herein) containing less than or equal to 100 ppm water; alternatively, less than or equal to 90 ppm water; alternatively, less than or equal to 80 ppm water; alternatively, less than or equal to 70 ppm water; alternatively, less than or equal to 60 ppm water; alternatively, less than or equal to 50 ppm water; alternatively, less than or equal to 40 ppm water; alternatively, less than or equal to 30 ppm water; alternatively, less than or equal to 20 ppm water; alternatively, less than or equal to 10 ppm water; alternatively, less than or equal to 9 ppm water; alternatively, less than or equal to 8 ppm water; alternatively, less than or equal to 7 ppm water; alternatively, less than or equal to 6 ppm water; alternatively, less than or equal to 5 ppm water; alternatively, less than or equal to 4 ppm water; alternatively, less than or equal to 3 ppm water; alternatively, less than or equal to 2 ppm water; or alternatively, less than or equal to 1 ppm water. Generally, the amount of water which can be present in the atmosphere is provide on a by weight basis.

In an aspect, the process can further comprise evaporating the solvent to provide the transition metal carboxylate composition. In another aspect, the process can comprise evaporating the solvent from the solution comprising the transition metal carboxylate to provide the transition metal carboxylate composition. In an embodiment, the process can further comprise filtering the solution comprising the transition metal carboxylate to produce a filtrate and then evaporating the solvent from the filtrate. In an embodiment, the process can further comprise decanting the solution comprising the transition metal carboxylate and evaporating the solvent. Generally, filtering and decanting can be utilized to remove at least a portion of any insoluble particulates present in a solution comprising the transition metal carboxylate. Evaporation of the solvent can produce the transition metal carboxylate composition. In some embodiments wherein the transition metal carboxylate composition is purified by any method described herein, this first transition metal carboxylate can be referred to as a crude transition metal carboxylate composition. If multiple purification and or isolation steps are performed, the various transition metal carboxylate compositions can be distinguished by prefacing the term "transition metal carboxylate" with a designation such as first, second, third, and so forth.

In an aspect, a crude transition metal carboxylate composition can be purified. In some embodiments, the crude transition metal carboxylate composition can be purified by dissolving the transition metal carboxylate composition in a solvent, filtering the solution containing the dissolved transition metal carboxylate composition to provide a filtrate, and isolating the transition metal carboxylate composition from the filtrate by evaporating the solvent. In an embodiment, the solvent utilized to dissolve the transition metal carboxylate composition can be, comprise, or consist essentially of, an aprotic solvent; alternatively, an aprotic polar solvent; alternatively, a non-polar solvent; alternatively, a non-coordinating solvent. In another aspect, the transition metal carboxylate composition can be purified by contacting the transition metal carboxylate composition with a solvent in which the transition metal carboxylate composition is substantially insoluble while impurities within the transition metal carboxylate composition are soluble and filtering the solution to recover the transition metal carboxylate composition. In yet other embodiments, the transition metal carboxylate composition can be recrystallized from a solvent. In some embodiments, the solvent utilized in the purification of the transition metal carboxylate composition can be, comprise, or consist essentially of, an aprotic solvent; alternatively, an aprotic polar solvent; alternatively, an aprotic non-polar solvent; or alternatively, a non-coordinating solvent. Generally, the transition metal carboxylate composition can be purified utilizing one or any combination of the transition metal carboxylate composition purification methods described herein.

As utilized in the present specification and claims, the term "substantially insoluble" means that no more than 5 grams of the substance (e.g. transition metal carboxylate composition) dissolves in 200 mL of the solvent at the temperature at which the solvent and the transition metal carboxylate are contacted. As utilized in the present specification and claims, the term "soluble" means that greater than 80 grams of the substance dissolves in 200 mL of the solvent at the temperature at which the solvent and the transition metal carboxylate are contacted. As utilized in the present specification and claims the term "partially soluble" means that from 5 to 80 grams of the substance dissolves in 200 mL of the solvent.

In any embodiment wherein a solvent is evaporated, the evaporation of the solvent can be performed using any method known to one having ordinary skill in the art. In some embodiments, the solvent can be evaporated at ambient temperature (15-35° C. no applied external heat source). In other embodiments, the solvent can be evaporated with gentle heating (e.g. at a temperature ranging from 25° C. to 100° C.). In further embodiments, the solvent can be evaporated at ambient temperature under reduced pressure. In yet other embodiments, the solvent can be evaporated with gentle heating under reduced pressure. In any aspect or any embodiment wherein the solvent can be evaporated under reduced pressure, the evaporation can be conducted at a pressure less than 600 Torr; alternatively, less than 500 Torr; alternatively, less than 400 Torr; alternatively, less than 300 Torr; alternatively, less than 200 Torr; alternatively, less than 150 torr; alternatively, less than 100 Torr; alternatively, less than 75 Torr; alternatively, less than 50 Torr; alternatively, less than 25 Torr; alternatively less than 20 Torr; alternatively, less than 15; alternatively, less than 10 Torr; alternatively, less than 5 Torr; or alternatively, less than 1 Torr. In an embodiment, the evaporation of the solvent (regardless of how it is performed or in what step of the process it is performed) can be utilized to remove at least 50, 60, 70, 75, 80, 85, 90, 95, 96, 97, 98, or 99 weight percent of the solvent.

In an aspect and any embodiment disclosed herein, the process for preparing any transition metal carboxylate composition described herein can include a step for reducing the Group 1 or Group 2 metal content in the transition metal carboxylate composition. In any aspect or any embodiment described herein, the Group 1 or Group 2 metal content of the transition metal carboxylate composition can be reduced by contacting the transition metal carboxylate composition with a hydrocarbylsilyl halide. In some aspects and embodiments, the Group 1 or Group 2 metal content of the transition metal carboxylate composition can be reduced by contacting the transition metal carboxylate composition with an alkylsilyl halide. In some embodiments, the transition metal carboxylate composition and the hydrocarbylsilyl halide (or alkylsilyl halide) can be contacted in a solvent. In an embodiment, the solvent in which the transition metal carboxylate composition and the hydrocarbylsilyl halide can be contacted can be, comprise, or consist essentially of, an aprotic solvent; alternatively, an aprotic polar solvent; alternatively, a non-polar solvent; or alternatively, a non-coordinating solvent. Solvents are described herein and the appropriate classes (or specific solvents) which meet the requirements for the contacting of the transition metal carboxylate composition and hydrocarbylsilyl halide (or alkylsilyl halide) can be utilized without limitation. After contacting the transition metal carboxylate composition and the hydrocarbylsilyl halide (or alkylsilyl halide), the formed solution can be filtered to remove a formed Group 1 or Group 2 metal halide salt. After removing the Group 1 or Group 2 metal salt, the transition metal carboxylate composition can then be isolated and optionally purified. Methods for isolating and/or purifying the transition metal carboxylate composition are described herein. Generally, the method for reducing the Group 1 or Group 2 metal content in the transition metal carboxylate composition can be utilized with any general or specific transition metal carboxylate composition described herein (e.g. a chromium(III) carboxylate composition).

In an embodiment, the hydrocarbylsilyl halide can be, comprise, or consist essentially of, a hydrocarbylsilyl trihalide, a dihydrocarbylsilyl dihalide, a trihydrocarbylsilyl halide, or any combination thereof; alternatively, a hydrocarbylsilyl trihalide; alternatively, a dihydrocarbylsilyl dihalide; or alternatively, a trihydrocarbylsilyl halide. In some embodiments, hydrocarbylsilyl halide can be, comprise, or consist essentially of, an alkylsilyl trihalide, a dialkylsilyl dihalide, a trialkylsilyl halide, or any combination thereof; alternatively, an alkylsilyl trihalide; alternatively, a dialkylsilyl dihalide; or alternatively, a trialkylsilyl halide. Hydrocarbyl groups, alkyl groups, and halides have been described herein as substituent groups for substituted cycloalkyl groups, substituted aromatic groups, substituted aryl group, and substituted aralkyl groups (among other groups). These hydrocarbyl groups, alkyl groups, and halides can be utilized without limitation as the hydrocarbyl groups, alkyl groups, halides for any hydrocarbylsilyl halide or alkylsilyl halide described herein. In a non-limiting embodiment, the hydrocarbylsilyl halide can be, comprise, or consist essentially of, trimethylchlorosilane.

When the process for preparing a transition metal carboxylate composition has multiple steps which can utilize a solvent, the solvent utilized in each particular step can be distinguished from one another by the use of the designations first, second, third, and so forth, prefacing the term (or phrase utilizing the term) "solvent."

Properties of the transition metal carboxylate composition are described herein and can be utilized without limitation to describe the process for preparing the transition metal carboxylate composition and the transition metal carboxylate composition produced by the process.

In a non-limiting aspect, this disclosure provides for a process for preparing a chromium(III) carboxylate composition. The process for preparing the chromium(III) carboxylate composition can comprise: contacting 1) a chromium (III) precursor, 2) a Group 1 or Group 2 metal carboxylate, and 3) a solvent to form a chromium(III) carboxylate. In another embodiment, the process for preparing a chromium (III) carboxylate composition can comprise: contacting 1) a chromium(III) precursor, 2) a Group 1 or Group 2 metal carboxylate, and 3) a solvent to form a solution comprising the chromium(III) carboxylate. In other embodiments, the process for making a chromium(III) carboxylate composition can comprise: a) contacting 1) a chromium(III) precursor, 2) a Group 1 or Group 2 metal $C_3$-$C_{25}$ carboxylate, and solvent to form a chromium(III) $C_3$-$C_{25}$ carboxylate. In some embodiments, the process for making a chromium(III) carboxylate composition can comprise: a) contacting 1) a chromium(III) precursor, 2) a Group 1 or Group 2 metal $C_3$-$C_{25}$ carboxylate, and solvent to form a solution comprising the chromium(III) $C_3$-$C_{25}$ carboxylate. The chromium (III) precursor, Group 1 or Group 2 metal carboxylate (e.g. a Group 1 or Group 2 metal $C_3$-$C_{25}$ carboxylate), and the solvent are independent elements of the process of making a chromium(III) carboxylate composition and the process for making a chromium(III) carboxylate can be described using any Group 1 or Group 2 metal carboxylate described herein, chromium(III) precursor described herein, chromium (III) carboxylate described herein, and/or solvent described herein. The process for preparing a chromium(III) carboxylate composition can be described using any combination of any aspect or any embodiment of the chromium(III) precursor, Group 1 or Group 2 metal carboxylate described herein, and/or solvent described herein. Processes for preparing other transition metal carboxylate compositions are readily apparent, and contemplated, on the basis of the present disclosure.

In an embodiment, the chromium(III) precursor (general or specific) utilized in the process for producing the chromium(III) carboxylate (general or specific) can have any water content disclosed herein for the transition metal precursor (including substantially anhydrous and anhydrous) and/or any acid content disclosed herein for the transition metal precursor (including substantially acid-free, and acid-free). In another embodiment, the Group 1 or Group 2 metal carboxylate (general or specific) utilized in the process for producing the chromium(III) carboxylate (general or specific) can have any water content disclosed herein for the Group 1 or Group 2 metal carboxylate (including substantially anhydrous and anhydrous) and/or any acid content disclosed herein for the Group 1 or Group 2 metal carboxylate (including substantially acid-free, and acid-free). In yet another embodiment, the solvent utilized in the process for producing the chromium(III) carboxylate, can have any water content disclosed herein for the solvent (including substantially anhydrous and anhydrous) and/or any acid content disclosed herein for the solvent (including substantially acid-free, and acid-free). In an embodiment, the combining of the chromium(III) precursor (general or specific) and a Group 1 or Group 2 metal carboxylate (general or specific) can occur under any combination method and/or conditions, form any mixture and/or solution as described herein for the combining of the transition metal precursor, Group 1 or Group 2 metal carboxylate, and solvent. In yet other embodiments, the chromium(III) carboxylate can be formed under any condition described herein for forming a transition metal carboxylate. In a non-limiting embodiment, the chromium(III) precursor and the Group 1 or Group 2 metal carboxylate can be contacted at a carboxylate group to chromium(III) molar ratio ranging from range from 2.85:1 to 3.9:1; alternatively, 3:1 to 3.75:1; alternatively, 3:1 to 3.6:1; alternatively, 3.09:1 to 3.75:1; alternatively, 3.09:1 to 3.6:1; alternatively, 3.15:1 to 3.6:1; or alternatively, 3.15:1 to 3.45:1. Other aspects and embodiments of the process for preparing a transition metal carboxylate can also be applied, without limitation, to the process for preparing a chromium (III) carboxylate composition.

In an aspect, a crude chromium(III) carboxylate composition can be purified. In some embodiments, the crude chromium(III) carboxylate composition can be purified by dissolving the chromium(III) carboxylate in a solvent, filtering the solution containing the dissolved chromium(III) carboxylate to provide a filtrate, and isolating the chromium (III) carboxylate composition from the filtrate by evaporating the solvent. In an embodiment, the solvent utilized to dissolve the chromium(III) carboxylate composition can be, comprise, or consist essentially of, an aprotic solvent; alternatively, an aprotic polar solvent; alternatively, a non-polar solvent; or alternatively, a non-coordinating solvent. In some embodiments, the chromium(III) carboxylate composition can be purified by contacting the chromium(III) carboxylate composition with a solvent in which the chromium(III) metal carboxylate composition is substantially insoluble while impurities within the chromium(III) carboxylate composition are soluble and filtering the solution to recover the chromium(III) carboxylate composition. In yet other embodiments, the chromium(III) carboxylate composition can be recrystallized from a solvent. In some embodiments, the solvent utilized in the purification of the chromium(III) carboxylate composition can be, comprise, or consist essentially of, an aprotic solvent; alternatively, an aprotic polar solvent; alternatively, a non-polar solvent; or alternatively, a non-coordinating solvent. Generally, the chromium(III) carboxylate composition can be purified utilizing one or any combination of the chromium(III) carboxylate composition purification methods described herein.

Transition metal carboxylate compositions can be useful in catalyst systems. In particular, chromium carboxylates can be useful in catalyst systems for the synthesis of 1-hexene from ethylene. One widely employed chromium carboxylate is a chromium(III) carboxylate composition comprising the carboxylate 2-ethylhexanoate. As disclosed in references provided herein, chromium carboxylates (and other transition metal carboxylates) are known to contain one or more structures containing more than one chromium atom. Any of these compounds can impact the catalyst system utilized to produce 1-hexene from ethylene and could have impacts in other fields which utilize chromium carboxylates. In one aspect (and without being limited to theory), the processes according to this disclosure provide chromium carboxylate compositions which contain significant quantities of a mononuclear transition metal carboxylate (e.g. tris(carboxylate) chromium(III)). In some non-limiting examples, the chromium carboxylate compositions can be, comprise, or consist essentially of, a $C_3$ to $C_{24}$ monocarboxylate having the formula $^-O_2CR^2$. Other carboxylate groups which can be utilized in the chromium carboxylate composition are readily apparent and contemplated from the present disclosure.

In one non-limiting aspect, this disclosure provides chromium carboxylate compositions in which the carboxylate is a $C_3$ to $C_{25}$ monocarboxylate. In other non-limiting aspects, this disclosure provides for chromium carboxylate compositions in which the carboxylate can be, comprise, or consist essentially of, a monocarboxylate having the formula $^-O_2CR^{2c}$, wherein $R^{2c}$ is a $C_2$ to $C_{24}$ organyl group. Other monocarboxylates which can be utilized to describe the chromium carboxylate are readily apparent and contemplated from the present disclosure. In a non-limiting embodiment of the chromium carboxylate compositions in which the carboxylate has the formula $^-O_2CR^{2c}$, $R^{2c}$ can be a $C_4$ to $C_{11}$ hydrocarbyl group or a $C_4$ to $C_{11}$ substituted hydrocarbyl group; alternatively, a $C_4$ to $C_{11}$ hydrocarbyl group; alternatively, a $C_4$ to $C_{11}$ substituted hydrocarbyl group; or alternatively, $C_4$ to $C_{11}$ alkyl group. In some embodiments, the carboxylate of the chromium carboxylate composition can be, comprise, or consist essentially of, propionate, n-butyrate, isobutyrate, valerate (n-pentanoate), neo-pentanoate, capronate (n-hexanoate), n-heptanoate, caprylate (n-octanoate), 2-ethylhexanoate, n-nonanoate, caprate (n-decanoate), n-undecanoate, laurate (n-dodecanoate), stearate (n-octadecanoate), or any combination thereof; alternatively, valerate (n-pentanoate), neo-pentanoate, capronate (n-hexanoate), n-heptanoate, caprylate (n-octanoate), 2-ethylhexanoate, n-nonanoate, caprate (n-decanoate), n-undecanoate, or laurate (n-dodecanoate), or any combination thereof; or alternatively, valerate (n-pentanoate), caprylate (n-octanoate), or 2-ethylhexanoate. In some embodiments, the carboxylate of the chromium carboxylate composition can be, comprise, or consist essentially of, 2-ethylhexanoate.

In another non-limiting aspect, this disclosure provides for chromium carboxylate compositions wherein $R^{2c}$ of the carboxylate having the formula $^-O_2CR^{2c}$ can be a $C_6$ to $C_{24}$ aryl group or a substituted $C_6$ to $C_{24}$ aryl group; alternatively, a $C_6$ to $C_{19}$ aryl group or a substituted $C_6$ to $C_{19}$ aryl group; or alternatively, a $C_6$ to $C_{11}$ aryl group or a substituted $C_6$ to $C_{11}$ aryl group. In some embodiments, the carboxylate of the chromium carboxylate composition can be, comprise, or consist essentially of, benzoate or a substituted benzoate; alternatively, naphthoate or a substituted naphthoate In a further non-limiting aspect, the chromium carboxylate compositions according to this disclosure can be, comprise, or consist essentially of, a chromium (II) carboxylate composition or a chromium (III) carboxylate composition. In yet a further non-limiting aspect, the chromium carboxylate composition can be, comprise, or consist essentially of, a chromium(III) carboxylate composition.

Other aspects and embodiments for the transition metal carboxylate compositions and/or chromium carboxylate compositions are readily apparent and contemplated from the present disclosure. In an aspect the transition metal carboxylate and/or chromium carboxylate composition can be, comprise, or consist essentially of, a chromium carboxylate composition produced by any process described herein.

Figure 2:
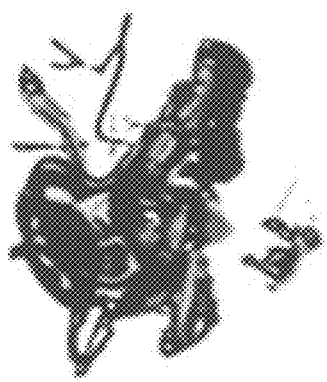
FIG. 2 is a picture of an isolated commercially available transition metal carboxylate (chromium(III) 2-ethylhexanoate).
Figure 3:
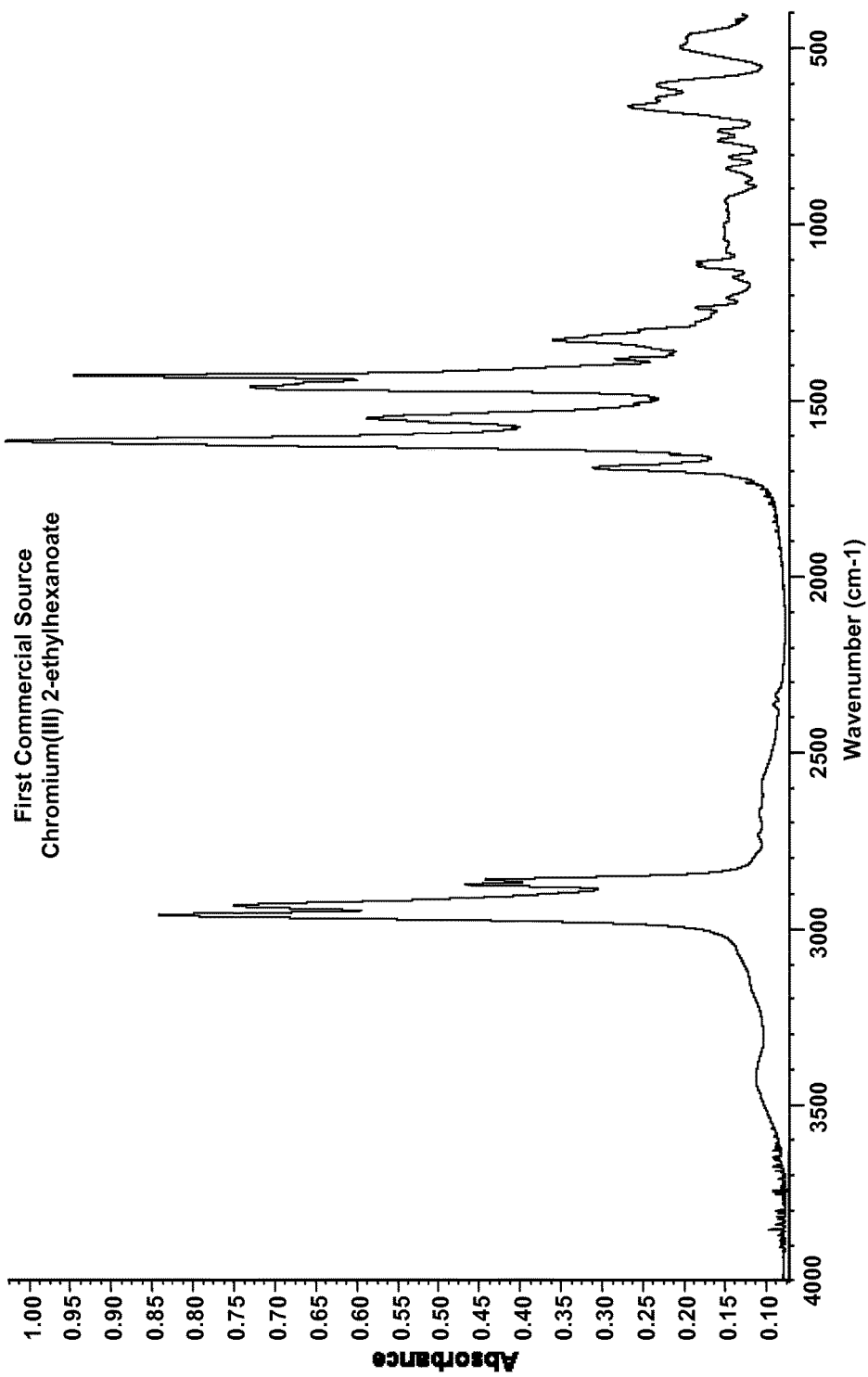
FIG. 3 provides an IR spectrum for a first commercially available chromium(III) 2-ethylhexanoate composition.

It can be observed that the isolated transition metal carboxylate compositions of the present disclosure can appear more crystalline in nature the amorphous mass isolated from commercially available transition metal carboxylate compositions. For example, compare the isolated chromium(III) 2-ethylhexanoate of the present disclosure using a sodium 2-ethylhexanoate to $CrCl_3(THF)_3$ molar ratio of approximately 3.3 (FIG. 1) to an isolated commercially available chromium(III) 2-ethylhexanoate (FIG. 2). However, even after attempting several different crystallization methods, the transition metal carboxylate of the present invention does not form crystals which will allow the elucidation of their structure by traditional X-ray crystallography methods. Consequently, the transition metal carboxylate compositions of the present disclosure need to be distinguished from the present commercially available transition metal carboxylate compositions utilizing one or a combination of more than one other analytical technique.

One technique that can be utilized to distinguish the transition metal carboxylate of the present disclosure from other transition metal carboxylate compositions can be infrared spectroscopy. Another technique which can be utilized to distinguish the transition metal carboxylate of the present disclosure from other transition metal carboxylate compositions can be high energy X-ray diffraction. Particular features associated with infrared spectroscopy and high energy X-ray diffraction are independently described herein and any one or more of these features can be used either individually or in any combination to describe the transition metal carboxylates of the present disclosure.

Spectroscopic analysis of the transitional metal carboxylate composition, particularly infrared (IR) absorption spectroscopy, can provide useful characterization information related to the composition. Aspects of the IR spectra of carboxylate compositions are provided in K. Nakamoto, *Infrared and Raman Spectra of Inorganic and Coordination Compounds*, 4$^{th}$ Ed., J. Wiley & Sons, New York, c. 1986, pp. 231-233. Additionally, Cannon and White (Cannon, R. D and White R. P, *Progress in Inorganic Chemistry*; Volume 36, 1988, pp. 195-298) and Deacon and Phillips (G. B. Deacon and R. J. Phillips, *Coordination Chemistry Reviews*, 33 (1980), pp. 227-250) provide further information regarding the coordination of the carboxylate anion with transition metal and the IR spectra of transition metal carboxylates. Vlachos et al. (A. Vlachos, Psycharis, C. P. Raptopoula, N. Lalioti, Y. Sanakis, G. Diamantopoulos, M. Fardis, M. Karayanni, G. Papavassiliou, and A. Terzis, *Inorganic Chimica Acta*, 357 (2004), pp. 3162-3172), herein referred to as Vlachos, provides IR information about trinuclear chromium(III) oxo carboxylates. The entirety of Cannon and White, Deacon and Phillips, and Vlachosare each incorporated herein by reference for all purposes.

These articles indicate, without being limited to theory, that the $\upsilon_{asym}$ ($CO_2$) IR peak locations for transition metal compounds in which the oxygen atoms of the carboxylate group bridge two transition metal atoms differ from those wherein the oxygen atoms of the carboxylate group are both bound to the same transition metal atom. Additionally, without being limited to theory, the separation between the $\upsilon_{asym}$ ($CO_2$) IR peak(s) and the $\upsilon_{sym}$ ($CO_2$) IR peak of transition metal carboxylate compounds in which the oxygen atoms of the carboxylate group bridge two transition metal atoms and those wherein the oxygen atoms of the carboxylate group are both bound to the same transition metal atom varies in a discernable manner. In particular, the $\upsilon_{asym}$ ($CO_2$) IR peak location for transition metal compounds in which the oxygen atoms of the carboxylate group bond to the same transition metal atom occurs at lower wavenumber than the $\upsilon_{asym}$ ($CO_2$) IR peak locations for transition metal compounds in which the oxygen atoms of the carboxylate group bond bridge to two transition metal atoms. Additionally, the separation between the $\upsilon_{asym}$ ($CO_2$) IR peak(s) and the $\upsilon_{sym}$ ($CO_2$) IR peak of the transition metal compounds in which the oxygen atoms of the carboxylate group bond to the same transition metal atom occurs is smaller than that of the transition metal compounds in which the oxygen atoms of the carboxylate group bond bridge to two transition metal atoms.

These articles also point out that transition metal carboxylate compositions contain species wherein multiple transition metals are bound to a single oxygen atoms. One such species which can be present, without being limited to theory, is the triangular bridged metal complexes having a $MO_3$ unit described in Cannon and White and that the $MO_3$ unit (where M is the transition metal) has a $\upsilon_{asym}$ ($MO_3$) IR peak in the range of 750 cm$^{-1}$ to 500 cm$^{-1}$. For chromium triangular bridged complexes, the $\upsilon_{sym}$ ($CrO_3$) IR peak appears around 750 cm$^{-1}$ to 650 cm$^{-1}$.

Figure 4:
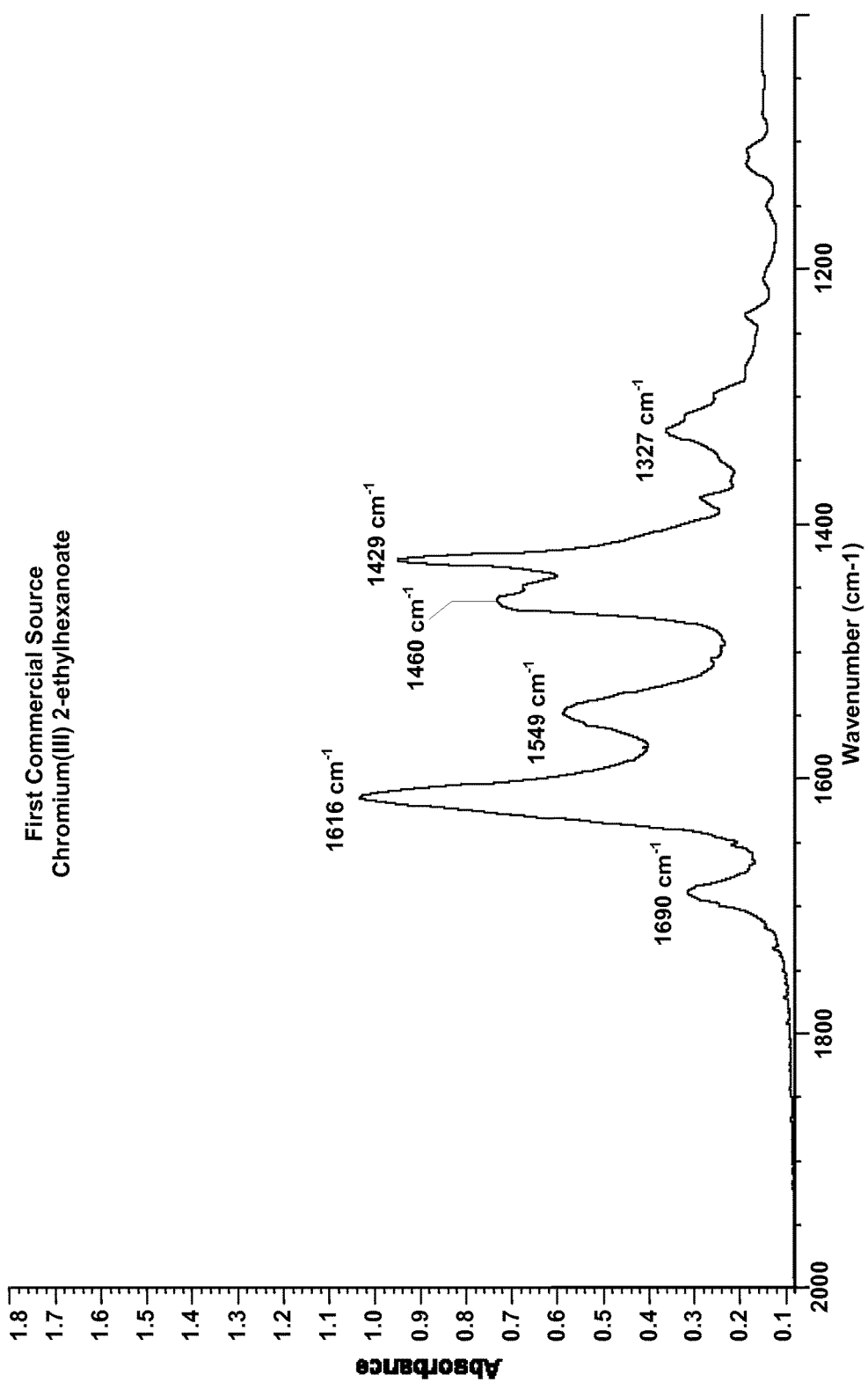
FIG. 4 provides an expanded section, 2000 $cm^{-1}$ to 1000 $cm^{-1}$, of the IR spectrum for the first commercially available chromium(III) 2-ethylhexanoate composition.
Figure 5:
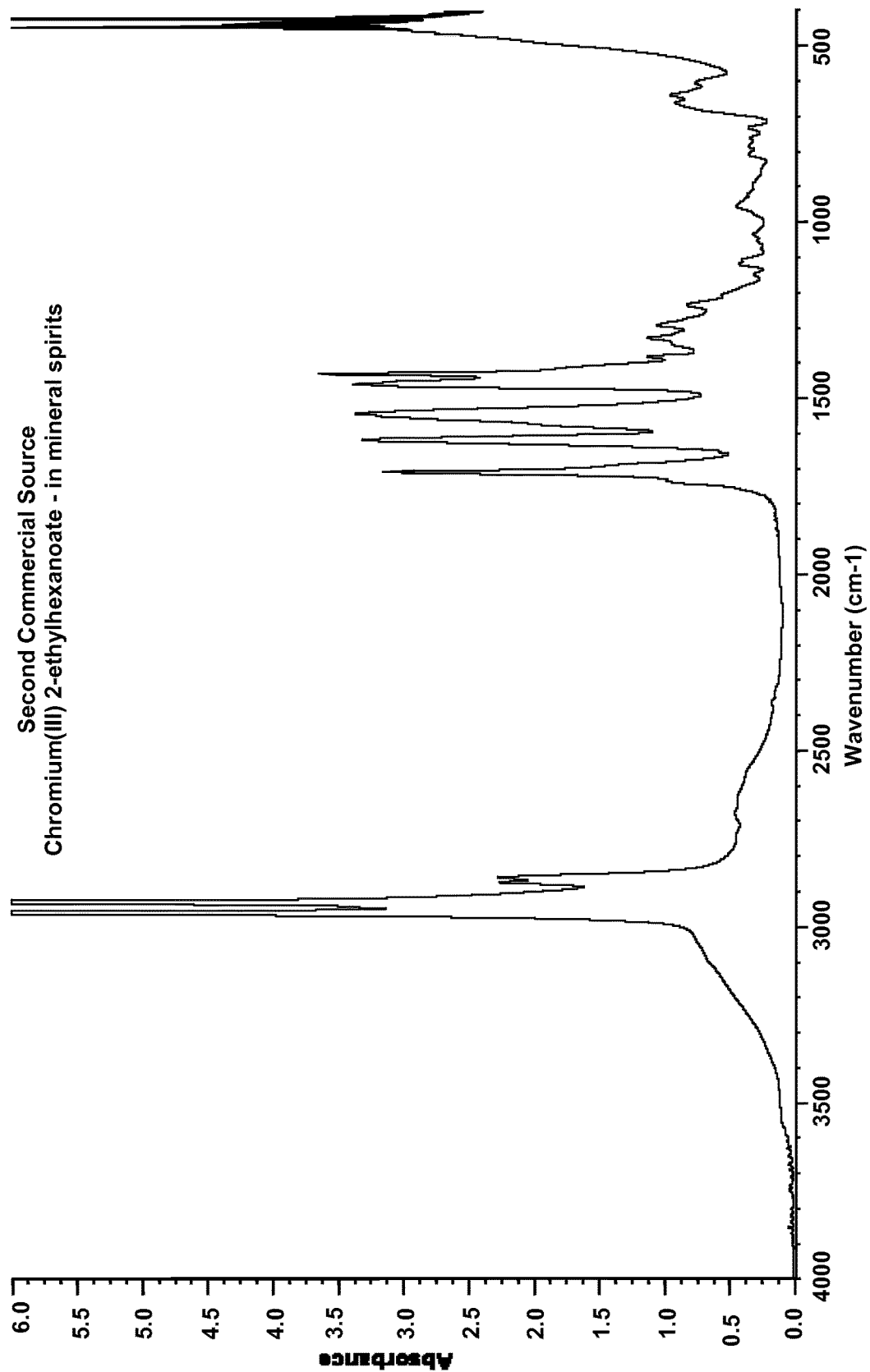
FIG. 5 provides an IR spectrum for a second commercially available chromium(III) 2-ethylhexanoate composition.
Figure 6:
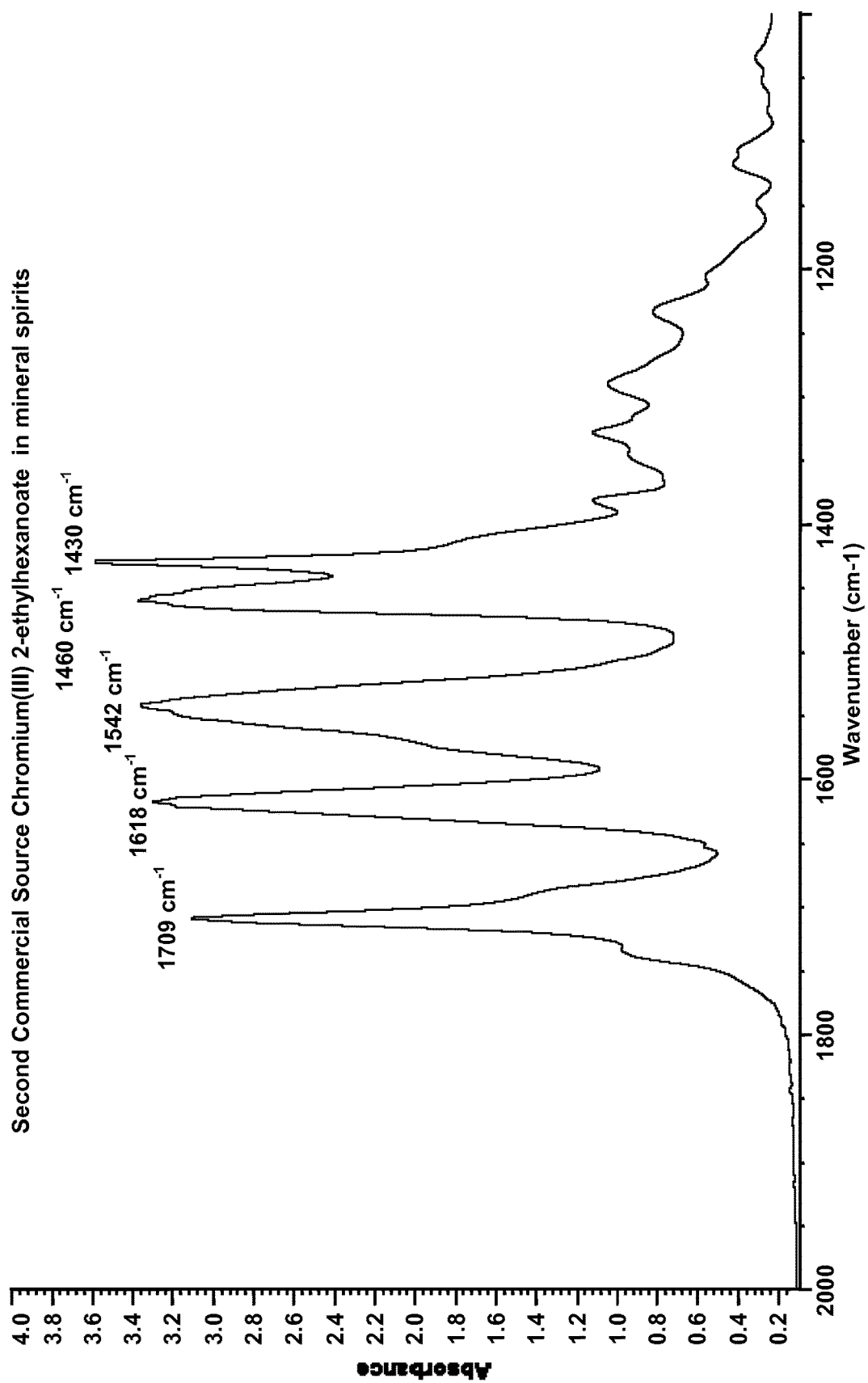
FIG. 6 provides an expanded section, 2000 $cm^{-1}$ to 1000 $cm^{-1}$, of the IR spectrum for the second commercially available chromium(III) 2-ethylhexanoate composition.

FIG. 4 and FIG. 6 provide the 2000 cm$^{-1}$ to 1000 cm$^{-1}$ portion of the IR spectrum for two commercially available chromium(III) 2-ethylhexanoate compositions. Each of these IR spectra show $\upsilon_{asym}$ ($CO_2$) IR peaks at 1616±20 cm$^{-1}$ and 1549±15 cm$^{-1}$ respectively and a $\upsilon_{sym}$ ($CO_2$) IR peak 1429±15 cm$^{-1}$. FIG. 8, FIG. 10, FIG. 12, and FIG. 14 provide the 2000 cm$^{-1}$ to 1000 cm$^{-1}$ portion of the IR spectrum for four chromium(III) 2-ethylhexanoate compositions of the present disclosure. Each of these IR spectra show the presence of a $\upsilon_{asym}$ ($CO_2$) IR peaks at 1516±15 cm$^{-1}$, a $\upsilon_{sym}$ ($CO_2$) IR peak 1429±15 cm$^{-1}$, and significantly diminished $\upsilon_{asym}$ ($CO_2$) IR peaks (if the peaks are even present) at 1616±20 cm$^{-1}$ and 1549±15 cm$^{-1}$. These IR spectra show that the transition metal carboxylate compositions of the present disclosure are significantly different from the transition metal carboxylate compositions which are presently commercially available.

In an aspect, any transition metal carboxylate composition (general or specific) described herein or any transition metal carboxylate composition (general or specific) prepared by any process(es) described herein can have a $\upsilon_{asym}$ ($CO_2$) IR peak within 110 cm$^{-1}$ of the $\upsilon_{sym}$ ($CO_2$) IR peak; alternatively, can have a $\upsilon_{asym}$ ($CO_2$) IR peak within 105 cm$^{-1}$ of the $\upsilon_{sym}$ ($CO_2$) IR peak; alternatively, can have a $\upsilon_{asym}$ ($CO_2$) IR peak within 100 cm$^{-1}$ of the $\upsilon_{sym}$ ($CO_2$) IR peak; alternatively, can have a $\upsilon_{asym}$ ($CO_2$) IR peak within 95 cm$^{-1}$ of the $\upsilon_{sym}$ ($CO_2$) IR peak; or alternatively, can have a $\upsilon_{asym}$ ($CO_2$) IR peak within 90 cm$^{-1}$ of the $\upsilon_{sym}$ ($CO_2$) IR peak. In another aspect, the $\upsilon_{sym}$ ($CO_2$) IR peak within 110 cm$^{-1}$ of the $\upsilon_{sym}$ ($CO_2$) IR peak (or within any other range disclosed herein) can have the largest absorbance peak height of all $\upsilon_{asym}$ ($CO_2$) peaks of the transition metal carboxylate composition.

In other aspect, transition metal carboxylate compositions (general or specific) described herein or any transition metal carboxylate composition (general or specific) prepared by any process(es) described herein can have an IR absorbance peak height ratio of $\upsilon_{asym}$ ($CO_2$) IR peak within 110 cm$^{-1}$ of the $\upsilon_{sym}$ ($CO_2$) IR peak (or within any other range disclosed herein) to $\upsilon_{sym}$ ($CO_2$) IR peak of greater than or equal to 0.5:1; alternatively, greater than or equal to 0.75:1; alternatively, greater than or equal to 1:1; alternatively, greater than or equal to 1.25:1; alternatively, greater than or equal to 1.5:1; or alternatively, greater than or equal to 1.75:1. In another aspect, the transition metal carboxylate composition (general or specific) described herein or any transition metal carboxylate composition (general or specific) prepared by any process(es) described herein can have an IR absorbance peak height ratio of $\upsilon_{asym}$ ($CO_2$) IR peak within 110 cm$^{-1}$ of the $\upsilon_{sym}$ ($CO_2$) IR peak (or within any other range disclosed herein) to $\upsilon_{sym}$ ($CO_2$) IR peak ranging from 0.5:1 to 100:1; alternatively, greater than or equal to 0.75:1 to 80:1; alternatively, greater than or equal to 1:1 to 60:1; alternatively, greater than or equal to 1.25:1 to 40:1; alternatively, greater than or equal to 1.5:1 to 3:1; or alternatively, greater than or equal to 1.75:1 to 20:1.

In a non-limiting embodiment, any transition metal carboxylate composition (general or specific) described herein or any transition metal carboxylate composition (general or specific) prepared by any process(es) described herein can have an IR absorbance peak height ratio of the $\upsilon_{asym}$ ($CO_2$) IR peak within 110 cm$^{-1}$ of the $\upsilon_{sym}$ ($CO_2$) IR peak (or within any other range disclosed herein) to a non-transition metal bound carboxylate ($CO_2$) IR peak greater than or equal to 5:1; alternatively, greater than or equal to 6:1; alternatively, greater than or equal to 7:1; alternatively, greater than or equal to 8:1; alternatively, greater than or equal to 9:1; or alternatively, greater than or equal to 10:1. In other non-limiting embodiments, any transition metal carboxylate composition described herein (general or specific) described herein or any transition metal carboxylate composition (general or specific) prepared by any process(es) described herein can have an IR absorbance peak height ratio of the $\upsilon_{asym}$ ($CO_2$) IR peak within 110 cm$^{-1}$ of the $\upsilon_{sym}$ ($CO_2$) IR peak (or within any other range disclosed herein) to a non-transition metal bound carboxylate ($CO_2$) IR peak ranging from 5:1 to 100:1; alternatively, ranging from 6:1 to 90:1; alternatively, ranging from 7:1 to 80:1; alternatively, ranging from 8:1 to 60:1; alternatively, ranging from 9:1 to 50:1; or alternatively, ranging from 10:1 to 40:1.

In a non-limiting embodiment, any transition metal carboxylate composition described herein (general or specific), can have an IR absorbance peak height ratio of the $\upsilon_{sym}$ ($CO_2$) IR peak to a non-transition metal bound carboxylate ($CO_2$) IR peak greater than or equal to 3.5:1; alternatively, greater than or equal to 3.75:1; alternatively, greater than or equal to 4; alternatively, greater than or equal to 4.25:1; alternatively, greater than or equal to 4.5:1; or alternatively, greater than or equal to 4.75:1. In other non-limiting embodiments, Alternatively, any transition metal carboxylate composition (general or specific) described herein or any transition metal carboxylate composition (general or specific) prepared by any process(es) described herein can have an IR absorbance peak height ratio of the $\upsilon_{sym}$ ($CO_2$) IR peak (or within any other range disclosed herein) to a non-transition metal bound carboxylate ($CO_2$) IR peak ranging from 3.5:1 to 100:1; alternatively, ranging from 3.75:1 to 90:1; alternatively, ranging from 4:1 to 80:1; alternatively, ranging from 4.25:1 to 60:1; alternatively, ranging from 4.5:1 to 50:1; or alternatively, ranging from 4.75:1 to 40:1.

In a non-limiting embodiment, any transition metal carboxylate composition (general or specific) described herein or any transition metal carboxylate composition (general or specific) prepared by any process(es) described herein can have can have an IR absorbance peak height ratio of the $\upsilon_{sym}$ ($CO_2$) IR peak located outside of 150 cm$^{-1}$ of the $\upsilon_{sym}$ ($CO_2$) IR peak to the IR absorbance peak height of the $\upsilon_{asym}$ ($CO_2$) IR peak located within 110 cm$^{-1}$ of the $\upsilon_{sym}$ ($CO_2$) IR peak (or within any other range disclosed herein) can less than or equal to 0.9:1; alternatively, greater than or equal to 0.85:1; alternatively, greater than or equal to 0.8:1; alternatively, greater than or equal to 0.75:1; alternatively, greater than or equal to 0.7:1; or alternatively, greater than or equal to 0.65:1.

In a non-limiting embodiment, any transition metal carboxylate composition (general or specific) described herein or any transition metal carboxylate composition (general or specific) prepared by any process(es) described herein can have an IR absorbance peak height ratio of the $\upsilon_{asym}$ ($CO_2$) IR peak within 110 cm$^{-1}$ of the $\upsilon_{sym}$ ($CO_2$) IR peak (or within any other range disclosed herein) to a $\upsilon_{asym}$ ($MO_3$) IR peak greater than or equal to 1.5:1; alternatively, greater than or equal to 3:1; alternatively, greater than or equal to 5:1; alternatively, greater than or equal to 6:1; or alternatively, greater than or equal to 7:1. In other non-limiting embodiments, any transition metal carboxylate composition (general or specific) described herein or any transition metal carboxylate composition (general or specific) prepared by any process(es) described herein can have an IR absorbance peak height ratio of the $\upsilon_{asym}$ ($CO_2$) IR peak within 110 $cm^{-1}$ of the $\upsilon_{sym}$ ($CO_2$) IR peak (or within any other range disclosed herein) to a $\upsilon_{asym}$ ($MO_3$) IR peak ranging from 1.5:1 to 100:1; alternatively, ranging from 3:1 to 90:1; alternatively, ranging from 5:1 to 80:1; alternatively, ranging from 6:1 to 60:1; or alternatively, ranging from 7:1 to 50:1.

In some non-limiting embodiments, the transition metal carboxylate can be, comprise, or consist essentially of, a chromium carboxylate composition (general or specific); alternatively, a chromium(III) carboxylate composition (general or specific); or alternatively, any chromium(III) carboxylate composition (general or specific) described herein or any chromium(III) carboxylate composition (general or specific) prepared by any process(es) described herein wherein the carboxylate is any monocarboxylate disclosed herein. In an embodiment, any chromium carboxylate composition (general or specific) described herein or any chromium(III) carboxylate composition (general or specific) prepared by any process(es) described herein can have a $\upsilon_{asym}$ ($CO_2$) IR peak within 110 $cm^{-1}$ of the $\upsilon_{sym}$ ($CO_2$) IR peak (or within any other range disclosed herein for the transition metal carboxylate composition). In some embodiments, any chromium carboxylate composition (general or specific) described herein or any chromium(III) carboxylate composition (general or specific) prepared by any process(es) described herein can have a $\upsilon_{asym}$ ($CO_2$) IR peak at 1516±15 $cm^{-1}$. In any chromium carboxylate composition (general or specific) described herein or any chromium(III) carboxylate composition (general or specific) prepared by any process(es) described herein aspect or embodiment, the largest absorbance IR peak height attributable to the chromium(III) carboxylate can be the $\upsilon_{asym}$ ($CO_2$) IR peak at 1516±15 $cm^{-1}$. In some embodiments, any chromium carboxylate composition (general or specific) described herein or any chromium(III) carboxylate composition (general or specific) prepared by any process(es) described herein can have an IR absorbance peak height ratio of the IR peak at 1516±15 $cm^{-1}$ to the IR peak at 1429±15 $cm^{-1}$ of greater than or equal to 0.5:1; alternatively, greater than or equal to 0.75:1; alternatively, greater than or equal to 1:1; alternatively, greater than or equal to 1.25:1; alternatively, greater than or equal to 1.5:1; alternatively, greater than or equal to 1.55:1; alternatively, greater than or equal to 1.6:1; alternatively, greater than or equal to 1.65:1; alternatively, greater than or equal to 1.7:1; or alternatively, greater than or equal to 1.75:1. In other embodiments, any chromium carboxylate composition (general or specific) described herein or any chromium(III) carboxylate composition (general or specific) prepared by any process(es) described herein can have an IR absorbance peak height ratio of the IR peak at 1516±15 $cm^{-1}$ to the IR peak at 1429±15 $cm^{-1}$ ranging from 0.5:1 to 100:1; alternatively, greater than or equal to 0.75:1 to 80:1; alternatively, greater than or equal to 1:1 to 60:1; alternatively, greater than or equal to 1.25:1 to 40:1; alternatively, greater than or equal to 1.5:1 to 3:1; or alternatively, greater than or equal to 1.75:1 to 20:1.

In a non-limiting embodiment, any chromium carboxylate composition (general or specific) described herein or any chromium(III) carboxylate composition (general or specific) prepared by any process(es) described herein can have a IR peak height ratio of the $\upsilon_{asym}$ ($CO_2$) IR peak located at 1516±15 $cm^{-1}$ to the $\upsilon_{sym}$ ($CO_2$) IR peak located at 1616±20 $cm^{-1}$ greater than or equal to 1:1; alternatively, greater than or equal to 1.5:1; alternatively, greater than or equal to 2:1; alternatively, greater than or equal to 2.5:1; or alternatively, greater than or equal to 3:1. In some non-limiting embodiments, any chromium carboxylate composition (general or specific) described herein or any chromium(III) carboxylate composition (general or specific) prepared by any process(es) described herein can have a IR peak height ratio of the $\upsilon_{asym}$ ($CO_2$) IR peak located at 1516±15 $cm^{-1}$ to the $\upsilon_{sym}$ ($CO_2$) IR peak located at 1616±20 $cm^{-1}$ ranging from 1:1 to 100:1; alternatively, ranging from 1.5:1 to 80:1; alternatively, ranging from 2:1 to 60:1; alternatively, ranging from 2.5:1 to 50:1; or alternatively, ranging from 3:1 to 40:1.

In a non-limiting embodiment, any chromium carboxylate composition (general or specific) described herein or any chromium(III) carboxylate composition (general or specific) prepared by any process(es) described herein can have an IR peak height ratio of the $\upsilon_{sym}$ ($CO_2$) IR peak located at 1516±15 $cm^{-1}$ to the non-chromium ($CO_2$) bound IR peak located at 1685±20 $cm^{-1}$ greater than or equal to 5:1; alternatively, greater than or equal to 6:1; alternatively, greater than or equal to 7:1; alternatively, greater than or equal to 8:1; alternatively, greater than or equal to 9:1; or alternatively, greater than or equal to 10:1. In other non-limiting embodiments, any chromium carboxylate composition (general or specific) described herein or any chromium(III) carboxylate composition (general or specific) prepared by any process(es) described herein can have an IR peak height ratio of the $\upsilon_{asym}$ ($CO_2$) IR peak located at 1516±15 $cm^{-1}$ to the non-chromium ($CO_2$) bound IR peak located at 1685±20 $cm^{-1}$ ranging from 5:1 to 100:1; alternatively, ranging from 6:1 to 90:1; alternatively, ranging from 7:1 to 80:1; alternatively, ranging from 8:1 to 60:1; alternatively, ranging from 9:1 to 50:1; or alternatively, ranging from 10:1 to 40:1.

In a non-limiting embodiment, any chromium carboxylate composition (general or specific) described herein or any chromium(III) carboxylate composition (general or specific) prepared by any process(es) described herein can have an IR peak height ratio of the $\upsilon_{sym}$ ($CO_2$) IR peak located at 1429±15 $cm^{-1}$ to the non-chromium ($CO_2$) bound IR peak located at 1685±20 $cm^{-1}$ greater than or equal to 3.5:1; alternatively, greater than or equal to 3.75:1; alternatively, greater than or equal to 4:1; alternatively, greater than or equal to 4.25:1; alternatively, greater than or equal to 4.5:1; or alternatively, greater than or equal to 4.75:1. In other non-limiting embodiments, any chromium carboxylate composition (general or specific) described herein or any chromium(III) carboxylate composition (general or specific) prepared by any process(es) described herein can have an IR peak height ratio of the $\upsilon_{sym}$ ($CO_2$) IR peak located at 1429±15 $cm^{-1}$ to the non-chromium ($CO_2$) bound IR peak located at 1685±20 $cm^{-1}$ ranging from 3.5:1 to 100:1; alternatively, ranging from 3.75:1 to 90:1; alternatively, ranging from 4:1 to 80:1; alternatively, ranging from 4.25:1 to 60:1; alternatively, ranging from 4.5:1 to 50:1; or alternatively, ranging from 4.75:1 to 40:1.

In a non-limiting embodiment, any chromium carboxylate composition (general or specific) described herein or any chromium(III) carboxylate composition (general or specific) prepared by any process(es) described herein can have an IR absorbance peak height ratio of the $\upsilon_{sym}$ ($CO_2$) IR peak located at 1616±20 $cm^{-1}$ to the IR absorbance peak height of the $\upsilon_{asym}$ ($CO_2$) IR peak located at 1429±15 $cm^{-1}$ can be less than or equal to 0.9:1; alternatively, greater than or equal to 0.85:1; alternatively, less than or equal to 0.8:1; alternatively, less than or equal to 0.75:1; alternatively, less than or equal to 0.7:1; or alternatively, less than or equal to 0.65:1.

In a non-limiting embodiment, any chromium carboxylate composition (general or specific) described herein or any chromium(III) carboxylate composition (general or specific) prepared by any process(es) described herein can have an IR absorbance peak height ratio of an IR peak located at 695±20 cm$^{-1}$ to the IR absorbance peak height of the $\upsilon_{asym}$ ($CO_2$) IR peak located at 1429±15 cm$^{-1}$ can be less than or equal to 1:1; alternatively, less than or equal to 0.8:1; alternatively, less than or equal to 0.6:1; alternatively, less than or equal to 0.4:1; alternatively, less than or equal to 0.3:1; alternatively, less than or equal to 0.25:1; alternatively, less than or equal to 0.2:1; alternatively, less than or equal to 0.18:1; or alternatively, less than or equal to 0.16:1.

In a non-limiting embodiment, any chromium carboxylate composition (general or specific) described herein or any chromium(III) carboxylate composition (general or specific) prepared by any process(es) described herein can have an IR absorbance peak height ratio of an IR peak located at 695±20 cm$^{-1}$ to the IR absorbance peak height of the $\upsilon_{asym}$ ($CO_2$) IR peak located at 1429±15 cm$^{-1}$ can be less than or equal to 1:1; alternatively, less than or equal to 0.8:1; alternatively, less than or equal to 0.6:1; alternatively, less than or equal to 0.4:1; alternatively, less than or equal to 0.3:1; alternatively, less than or equal to 0.25:1; alternatively, less than or equal to 0.2:1; alternatively, less than or equal to 0.18:1; or alternatively, less than or equal to 0.16:1.

In a non-limiting embodiment, any chromium carboxylate composition (general or specific) described herein or any chromium(III) carboxylate composition (general or specific) prepared by any process(es) described herein can have an IR peak height ratio of the $\upsilon_{asym}$ ($CO_2$) IR peak at 1516±15 cm$^{-1}$ to IR peak located at 700±50 cm$^{-1}$ greater than or equal to 1.5:1; alternatively, greater than or equal to 3:1; alternatively, greater than or equal to 5:1; alternatively, greater than or equal to 6:1; or alternatively, greater than or equal to 7:1. In other non-limiting embodiments, any chromium carboxylate composition (general or specific) described herein or any chromium(III) carboxylate composition (general or specific) prepared by any process(es) described herein can have an IR peak height ratio of the $\upsilon_{sym}$ ($CO_2$) IR peak located at 1429±15 cm$^{-1}$ to the non-chromium ($CO_2$) bound IR peak located at 700±50 cm$^{-1}$ ranging from 1.5:1 to 100:1; alternatively, ranging from 3:1 to 90:1; alternatively, ranging from 5:1 to 80:1; alternatively, ranging from 6:1 to 60:1; or alternatively, ranging from 7:1 to 50:1

In an embodiment, these IR peak related features can be determined by subjecting the chromium(III) carboxylate composition (or any other transition metal carboxylate composition described herein) contained in KBr (KBr pellet) to infrared analysis. Alternatively, if the chromium(III) carboxylate composition (or any other transition metal carboxylate composition described herein) is not suitable for analysis in a KBr pellet, the IR analysis can be performed by placing the transition metal carboxylate composition in a solvent or a dispersing agent that is IR transparent in the necessary IR peak regions (e.g. a mineral oil such as Nujol, among others). Additionally, the IR peak height ratio features can be based upon the raw peak heights or baseline corrected peak heights.

Generally, X-ray crystallography can be utilized to characterize the materials which form well defined crystals. However, in some instances, materials which one having ordinary skill in the art would believe to form well defined crystals do not form crystals which are suitable for traditional X-ray crystallography. For example, commercially available chromium(III) 2-ethylhexanoate forms an amorphous mass which is not suitable for traditional X-ray crystallography (see FIG. 2). Similarly, the chromium(III) 2-ethylhexanoate prepared using the methods described herein can form an amorphous mass (see FIG. 1); the produced chromium(III) 2-ethylhexanoate was a green tacky solid, showed no evidence of crystallinity, and was not suitable for traditional X-ray crystallography. In some of these instances, high energy X-ray diffraction can be utilized to provide structural information about the material. The high energy X-ray diffraction data for these materials can be compared to high energy X-ray diffraction data of other materials or to calculated high energy diffraction data of theoretical models of materials to determine the material's structure and/or whether or not the material is similar to other known materials.

In some embodiments, any transition metal carboxylate composition (general or specific) described herein or any transition metal carboxylate composition prepared by any process(es) described herein can be analyzed by high energy X-ray diffraction to determine the structure or structures of the transition metal carboxylate molecule(s) present in the transition metal carboxylate composition and/or compared to calculated high energy diffraction data of theoretical models of materials believed to be present in the transition metal carboxylate composition. For example, "Synthesis and structural studies of metal (Cr, Zn and Bi) carboxylate liquids" R. T. Hart Jr., N. A. Eckert, J. K. Ngala, A. F. Polley, C. J. Benmore, A. Clark, S. Macha, Presentation CATL 20, The 237th ACS National Meeting, Salt Lake City, Utah, Mar. 23, 2009, compared high energy X-ray diffraction g(r) data points of an aqueous metathesis process and displacement process produced chromium(III) carboxylate to the theoretical high energy X-ray diffraction g(r) data points of models of $Cr_3O(O_2CCH_3)_6$, $Cr_8(OH)_8(O_2CCH_3)_{12}$, and $Cr_{12}O(O_2CCH_3)_6$, constructed from data presented in M. Eshel, et al., *Inorg. Chem.*, 2000, 39, pp 1376, and M. Eshel, et al., *Inorg Chim. Acta*, 2002, 329, pp 45. The entirety of Hart Jr. et al. and M. Eshel et al. are incorporated herein by reference.

Without being limited to theory, it is believed that the transition metal carboxylate composition(s) described herein or prepared according to any process(es) disclosed herein can contain substantial quantities of mononuclear transition metal carboxylate. To test this hypothesis, one can compare the high energy X-ray diffraction g(r) data points for any transition metal carboxylate composition described herein or any transition metal carboxylate composition prepared according to any process(es) disclosed herein to the high energy X-ray diffraction g(r) data points for the authentic mononuclear transition metal carboxylate. In many instances pure and/or authentic samples of mononuclear transition metal carboxylates are not available. In these instances, the high energy X-ray diffraction g(r) data points for any transition metal carboxylate composition described herein or any transition metal carboxylate composition prepared according to any process(es) disclosed herein can be compared to a calculated high energy X-ray diffraction g(r) data points of a theoretical model of the mononuclear transition metal carboxylate. The model of the mononuclear transition metal carboxylate can be produced utilizing any number of methods available to those skilled in the art. In one example, the model of a mononuclear chromium(III) carboxylate can be obtained by using Spartan 08 with optimizations that assume a high spin Cr(III) center with quartet ground spin state by obtaining initial geometries via PM3 geometry optimizations with conformational searching and further geometry optimization utilized DFT B3LYP with the LACVP basis set with an effective core potential on Cr and 6-31 g** on H, C, O. In another example, the model of the mononuclear transition metal carboxylate can be obtained using a heuristic method similar to the one described herein for chromium(III) carboxylates. The high energy X-ray diffraction g(r) data points calculated for the mononuclear transition metal carboxylate model can be calculated using methods and/or programs available to those skilled in the art (e.g. the PDFFit library of functions and routines as implemented in PDFgui—version 1.0—C. L. Farrow, P. Juhás, J. W. Liu, D. Božin, E. S. Bolin, J. Bloch, Th. Proffen and S. J. L. Billinge, PDFfit2 and PDFgui: computer programs for studying nanostructure in crystals, *J. Phys.: Condens. Matter* 19, 335219 (2007)) and can be utilized to calculate the high energy X-ray diffraction d(r) data points for a mononuclear chromium carboxylate model which can then be converted to high energy X-ray diffraction g(r) data points.

The comparison of the high energy X-ray diffraction g(r) data points for transition metal carboxylate compositions described herein or prepared according to the process(es) disclosed herein to the high energy X-ray diffraction g(r) data points for the authentic mononuclear transition metal carboxylate or a calculated high energy X-ray diffraction g(r) data points of a theoretical model of the mononuclear transition metal carboxylate can be made using techniques known and used by those skilled in the art. One method for comparing the high energy X-ray diffraction g(r) data points for transition metal carboxylate compositions described herein or prepared according to the process(es) disclosed herein to the high energy X-ray diffraction g(r) data points for the authentic mononuclear transition metal carboxylate or a calculated high energy X-ray diffraction g(r) data points of a theoretical model(s) of the mononuclear transition metal carboxylate can be to perform a goodness of fit test. The closer the goodness of fit test test value, $R^2$, is to 1, the more likely the transition metal carboxylate composition contains a significant quantity of mononuclear transition metal carboxylate.

It should be noted that when the comparison is made using a calculated high energy X-ray diffraction g(r) data points of a theoretical model of the mononuclear transition metal carboxylate, one does not necessarily expect a goodness of fit $R^2$ test value very close to 1 because the comparison is made to a theoretical model of the mononuclear transition metal carboxylate and as such is not the actual structure for the mononuclear transition metal carboxylate. While not wishing to be bound by theory, it is believed that even if any of the herein described transition metal carboxylate compositions or any of the transition metal carboxylate compositions produced by any process(es) described herein is a pure mononuclear transition metal carboxylate, the goodness of fit $R^2$ test value would unlikely be 1 because there could likely be differences between the structure of the theoretical model of the mononuclear transition metal carboxylate and the actual pure mononuclear transition carboxylate. The difference between these structures could result in differences in the measured high energy X-ray diffraction g(r) data points and the calculated high energy X-ray diffraction g(r) data points. Consequently, the goodness of fit test value, $R^2$, would not be expected to be 1. However, the goodness of fit test value, $R^2$, still has value since the high energy X-ray diffraction g(r) data points for transition metal carboxylate compositions having significant quantities of mononuclear transition metal carboxylate will have a goodness of fit test value, $R^2$, closer to 1 than a transition metal carboxylate composition which has significant quantities of dinuclear, trinuclear, or higher polynuclear transition metal carboxylate species.

Depending upon the number of carbon atoms in the carboxylate of the transition metal carboxylate, it can be impractical or difficult to prepare a theoretical model of the mononuclear transition metal carboxylate. Reviewing theoretical structures of mononuclear transition metal carboxylates, it can be apparent that the transition metal atom, the two oxygen atoms of the carboxylate group chelated with the transition metal, the carboxylate group carbon and oxygen atoms, and the carbon atom attached to the carboxylate group can be relatively fixed in space because they do not have free rotation about any bond that could change its distance from the other atoms. Consequently, one could expect that there could not be large variations in the respective bond distances and bond angles between these atoms as a function of the carboxylate of the transition metal carboxylate. Without any further substituents, these atoms could form a transition metal acetate. Consequently, in an embodiment, any transition metal carboxylate composition described herein or any transition metal carboxylate composition produced by any process described herein can be compared to a mononuclear transition metal acetate. If any transition metal carboxylate composition described herein or any transition metal carboxylate composition produced by any process(es) described herein contains significant quantities of mononuclear transition metal carboxylate, one could expect that the high energy X-ray diffraction g(r) data points of a mononuclear transition metal carboxylate composition can be compared to the high energy X-ray diffraction g(r) data points of an authentic transition metal acetate or the calculated high energy X-ray diffraction g(r) data points of a theoretical model of the mononuclear transition metal transition metal acetate. Without being limited to theory, the comparison between any transition metal carboxylate composition described herein or any transition metal carboxylate composition produced by any process(es) described herein could be expected to be fairly similar to the high energy X-ray diffraction g(r) data points of an authentic transition metal acetate or a calculated high energy X-ray diffraction g(r) data points of a theoretical model of the mononuclear transition metal transition metal acetate. In particular, the comparison could be expected to be reasonable up to and including r values of 4 Å where the contributions from intermolecular interactions and contributions of the non-hydrogen atoms of the carboxylate group beyond the carbon atom attached to the carboxylate (C=O) carbon atom could be expected to be small.

Regarding the goodness of fit test value, $R^2$, the goodness of fit test value can be calculated using the equation $R^2=1-(SS_{err}/SS_{tot})$. Within the equation $R^2=1-(SS_{err}/SS_{tot})$, $SS_{err}$ is the summation of the squares of the residual between the high energy X-ray diffraction g(r) data points of the transition metal carboxylate composition and either a) the high energy X-ray diffraction g(r) data points for the actual mononuclear transition metal carboxylate or b) the calculated high energy X-ray diffraction g(r) data points for a theoretical model of the mononuclear transition metal carboxylate. Within the equation $R^2=1-(SS_{err}/SS_{tot})$, $SS_{tot}$ is the summation of the squares of the differences between the high energy X-ray diffraction g(r) data points of the transition metal carboxylate composition and the mean of the high energy X-ray diffraction g(r) data points of the transition metal carboxylate composition. In order for the goodness of fit test value to have reasonable meaning, the test should be performed using a reasonable number of high energy X-ray diffraction g(r) data points. Herein, the goodness of fit test value can be calculated using high energy X-ray diffraction g(r) data points separated by 0.01 Angstroms over the r value range to which the goodness of fit test value is to be calculated. Typically, the high energy X-ray diffraction g(r) data points can be at exact hundredths of an Angstrom r values. However, the high energy X-ray diffraction g(r) data points can be based upon any set of g(r) data points separated by r values of 0.01 Angstroms. Additionally, to provide the best basis for the goodness of fit test value (and to avoid interpolation of the g(r) data points), the high energy X-ray diffraction g(r) data points of the transition metal carboxylate composition and the high energy X-ray diffraction g(r) data points for the actual mononuclear transition metal carboxylate or the calculated high energy X-ray diffraction g(r) data for a theoretical model of the mononuclear transition metal carboxylate should located at the same r values.

In an embodiment, the goodness of fit test value can be based on the application of the goodness of fit test over a range of r values of the high energy X-ray diffraction g(r) data points of the transition metal carboxylate composition and the high energy X-ray diffraction g(r) data points for the actual mononuclear transition metal carboxylate or the calculated high energy X-ray diffraction g(r) data points for a theoretical model of the mononuclear transition metal carboxylate. In some embodiments, the minimum r value for the range of values for the goodness of fit test value for the comparison of the high energy X-ray diffraction g(r) data points of the transition metal carboxylate composition and the high energy X-ray diffraction g(r) data points for the actual mononuclear transition metal carboxylate or the calculated high energy X-ray diffraction g(r) data points for a theoretical model of the mononuclear transition metal carboxylate can be 1.2 angstroms; alternatively, 1.25 angstroms; alternatively, 1.3 angstroms; alternatively, 1.35 angstroms; or alternatively, 1.4 angstroms. In some embodiments, the maximum r value for the range of values for the goodness of fit test value for the comparison of the high energy X-ray diffraction g(r) data points of the transition metal carboxylate composition and the high energy X-ray diffraction g(r) data points for the actual mononuclear transition metal carboxylate or the calculated high energy X-ray diffraction g(r) data points for a theoretical model of the mononuclear transition metal carboxylate can be 4 angstroms; alternatively, 3.9 angstroms; alternatively, 3.8 angstroms; alternatively, 3.7 angstroms; or alternatively, 3.6 angstroms; alternatively, 3.5 angstroms; alternatively, 3.4 angstroms; alternatively, 3.3 angstroms; alternatively, 3.2 angstroms; alternatively, 3.1 angstroms; or alternatively, 3.0 angstroms. In an embodiment, the goodness of fit test value can be based upon the application of the goodness of fit test for the comparison of the high energy X-ray diffraction g(r) data points of the transition metal carboxylate composition and the high energy X-ray diffraction g(r) data points for the actual mononuclear transition metal carboxylate or the calculated high energy X-ray diffraction g(r) data points for a theoretical model of the mononuclear transition metal carboxylate over an r value range that ranges from any minimum r value described herein to any maximum r value described herein. In some non-limiting embodiments, the goodness of fit test value can based upon the application of the goodness of fit test for the comparison of the high energy X-ray diffraction g(r) data points of the transition metal carboxylate composition and the high energy X-ray diffraction g(r) data points for the actual mononuclear transition metal carboxylate or the calculated high energy X-ray diffraction g(r) data points for a theoretical model of the mononuclear transition metal carboxylate over a r value range of 1.3 Angstroms to 4 Angstroms; or alternatively, the goodness of fit test value is based upon the application of the goodness of fit test over a r value range of 1.3 Angstroms to 3.2 Angstroms; alternatively, 1.3 Angstroms to 3.3 Angstroms; alternatively, 1.3 Angstroms to 3.4 Angstroms; alternatively, 1.3 Angstroms to 3.5 Angstroms; alternatively, 1.3 Angstroms to 3.6 Angstroms; alternatively, 1.3 Angstroms to 3.7 Angstroms; alternatively, 1.3 Angstroms to 3.8 Angstroms; alternatively, 1.3 Angstroms to 3.9 Angstroms; alternatively, 1.3 Angstroms to 4.0 Angstroms.

The r values of these ranges can seem arbitrary. However, the selection of the maximum r value of the ranges can be based upon supposition, without being limited to theory, that intermolecular contributions and effects of bond rotation beyond the carbon atom attached to the carboxylate (C=O) carbon atom cannot be accurately accounted for when using a calculated high energy X-ray diffraction of transition metal carboxylate theoretical model. Thus the longer r value can be selected to exclude these difficult to model characteristics. The lower limit of the r value of these ranges can be based upon the supposition, without being limited to theory, that the more important and/or more meaningful atom to atom distances can have an average atom to atom distance of at least 1.2 to 1.3 angstroms. Additionally, the only bond distances shorter than 1.2 Angstroms are then carbon-hydrogen bonds which contribute less than 1 percent to the scattering intensity and are not generally considered in the data handling and modeling. Thus, the lower limit of the shorter r value can be selected to include the contributions from the shortest important and/or meaningful atom to atom distances.

In an embodiment, the goodness of fit test can be performed between the high energy X-ray diffraction g(r) data points for any transition metal carboxylate composition described herein and/or any transition metal carboxylate composition prepared according to any process(es) disclosed herein, and the high energy X-ray diffraction g(r) data points for an authentic mononuclear transition metal carboxylate. In another embodiment, the goodness of fit test can be performed between the high energy X-ray diffraction g(r) data points for any transition metal carboxylate composition described herein and/or any transition metal carboxylate composition prepared according to any process(es) disclosed herein, and the high energy X-ray diffraction g(r) data points for a theoretical model of the mononuclear transition metal carboxylate. In an embodiment, the goodness of fit test value, $R^2$, can be based upon the high energy X-ray diffraction g(r) data points over any range of r disclosed herein. In an embodiment, $R^2$ for the goodness of fit test (over any range of r disclosed herein) between the high energy X-ray diffraction g(r) data points for any transition metal carboxylate composition described herein and/or any transition metal carboxylate composition prepared according to any process(es) disclosed herein, and the high energy X-ray diffraction g(r) data points for an authentic mononuclear transition metal carboxylate or a calculated high energy X-ray diffraction g(r) of a theoretical model of the mononuclear transition metal carboxylate can be at least 0.55; alternatively, at least 0.60; alternatively, at least 0.625; alternatively, at least 0.65; alternatively, at least 0.675; alternatively, at least 0.70; alternatively, at least 0.725; alternatively, at least 0.75; alternatively, at least 0.775; alternatively, at least 0.80; alternatively, at least 0.825; alternatively, at least 0.85; alternatively, at least 0.875; or alternatively, at least 0.90. In another embodiment, $R^2$ for the goodness of fit test (over any range of r disclosed herein) between the high energy X-ray diffraction g(r) data points for any transition metal carboxylate composition described herein and/or any transition metal carboxylate composition prepared according to any process(es) disclosed herein, and the high energy X-ray diffraction g(r) data points for an authentic mononuclear transition metal carboxylate or a calculated high energy X-ray diffraction g(r) of a theoretical model of the mononuclear transition metal carboxylate can range from 0.55 to 1; alternatively, range from 0.60 to 1; alternatively, range from 0.625 to 1; alternatively, range from 0.65 to 1; alternatively, range from 0.675 to 1; alternatively, range from 0.70 to 1; alternatively, range from 0.725 to 1; alternatively, range from 0.75 to 1; alternatively, range from 0.775 to 1; alternatively, range from 0.80 to 1; alternatively, range from 0.825 to 1; alternatively, range from 0.85 to 1; alternatively, range from 0.875 to 1; or alternatively, range from 0.90 to 1.

In an embodiment, a goodness of fit test can be performed between the high energy X-ray diffraction g(r) data points for any transition metal carboxylate composition described herein and/or any transition metal carboxylate composition prepared according to any process(es) disclosed herein, and the high energy X-ray diffraction g(r) data points for the authentic mononuclear transition metal acetate. In another embodiment, the goodness of fit test can be performed between the high energy X-ray diffraction g(r) data points for any transition metal carboxylate composition described herein and/or any transition metal carboxylate composition prepared according to any process(es) disclosed herein, and the calculated high energy X-ray diffraction g(r) data points of a theoretical model of the mononuclear transition metal acetate. In an embodiment, the goodness of fit test value, $R^2$, can be based upon the high energy X-ray diffraction g(r) data points over any range of r disclosed herein. In an embodiment, $R^2$ for the goodness of fit test (over any range of r disclosed herein) between the high energy X-ray diffraction g(r) data points for any transition metal carboxylate composition described herein and/or any transition metal carboxylate composition prepared according to any process(es) disclosed herein and the high energy X-ray diffraction g(r) data points for a high energy X-ray diffraction g(r) data points for an authentic mononuclear transition metal acetate or a calculated high energy X-ray diffraction g(r) of a theoretical model of the mononuclear transition metal acetate can be at least 0.55; alternatively, at least 0.60; alternatively, at least 0.625; alternatively, at least 0.65; alternatively, at least 0.675; alternatively, at least 0.70; alternatively, at least 0.725; alternatively, at least 0.75; alternatively, at least 0.775; alternatively, at least 0.80; alternatively, at least 0.825; alternatively, at least 0.85; alternatively, at least 0.875; or alternatively, at least 0.90. In an embodiment, $R^2$ for the goodness of fit test (over any range of r disclosed herein) between the high energy X-ray diffraction g(r) data points for any transition metal carboxylate composition described herein and/or any transition metal carboxylate composition prepared according to any process(es) disclosed herein and the high energy X-ray diffraction g(r) data points for a high energy X-ray diffraction g(r) data points for an authentic mononuclear transition metal acetate or a calculated high energy X-ray diffraction g(r) of a theoretical model of the mononuclear transition metal acetate can range from 0.55 to 1; alternatively, range from 0.60 to 1; alternatively, range from 0.625 to 1; alternatively, range from 0.65 to 1; alternatively, range from 0.675 to 1; alternatively, range from 0.70 to 1; alternatively, range from 0.725 to 1; alternatively, range from 0.75 to 1; alternatively, range from 0.775 to 1; alternatively, range from 0.80 to 1; alternatively, range from 0.825 to 1; alternatively, range from 0.85 to 1; alternatively, range from 0.875 to 1; or alternatively, range from 0.90 to 1.

In a non-limiting embodiment, the high energy X-ray diffraction g(r) data points for any chromium(III) carboxylate composition described herein or any chromium(III) carboxylate composition prepared according to any process described herein can be compared to the high energy X-ray diffraction g(r) data points of an authentic mononuclear chromium(III) carboxylate using the goodness of fit test. In another non-limiting embodiment, the high energy X-ray diffraction g(r) data points for any chromium(III) carboxylate composition described herein or any chromium(III) carboxylate composition prepared according to any process described herein can be compared to a calculated high energy X-ray diffraction g(r) data points of a theoretical model of the mononuclear chromium(III) carboxylate using the goodness of fit test. In other non-limiting embodiments, the high energy X-ray diffraction g(r) data points for any chromium(III) carboxylate composition described herein or any chromium(III) carboxylate composition prepared according to any process described herein can be compared to the high energy X-ray diffraction g(r) data points of authentic mononuclear chromium(III) acetate using the goodness of fit test. In another non-limiting embodiment, the high energy X-ray diffraction g(r) data points for any chromium(III) carboxylate composition described herein or any chromium(III) carboxylate composition prepared according to any process described herein can be compared to a calculated high energy X-ray diffraction g(r) data points of a theoretical model of mononuclear chromium(III) acetate using the goodness of fit test. In any embodiment or aspect described herein, the goodness of fit test value, $R^2$, for the goodness of fit test (over any range of r disclosed herein) between the high energy X-ray diffraction g(r) data points of any chromium(III) carboxylate composition described herein and/or any chromium(III) carboxylate composition prepared according to any process(es) disclosed herein and the high energy X-ray diffraction g(r) data points for an authentic mononuclear chromium(III) carboxylate, the high energy X-ray diffraction g(r) data points for an authentic mononuclear chromium(III) acetate, a calculated high energy X-ray diffraction g(r) of a theoretical model of the mononuclear chromium(III) carboxylate, or a calculated high energy X-ray diffraction g(r) of a theoretical model of the mononuclear chromium(III) acetate can be at least 0.55; alternatively, at least 0.60; alternatively, at least 0.625; alternatively, at least 0.65; alternatively, at least 0.675; alternatively, at least 0.70; alternatively, at least 0.725; alternatively, at least 0.75; alternatively, at least 0.775; alternatively, at least 0.80; alternatively, at least 0.825; alternatively, at least 0.85; alternatively, at least 0.875; or alternatively, at least 0.90. In any embodiment or aspect described herein, the goodness of fit test value, $R^2$, for the goodness of fit test (over any range of r disclosed herein) between the high energy X-ray diffraction g(r) data points of any chromium(III) carboxylate composition described herein and/or any chromium(III) carboxylate composition prepared according to any process(es) disclosed herein and the high energy X-ray diffraction g(r) data points for an authentic mononuclear chromium(III) carboxylate, the high energy X-ray diffraction g(r) data points for an authentic mononuclear chromium(III) acetate, a calculated high energy X-ray diffraction g(r) of a theoretical model of the mononuclear chromium(III) carboxylate, or a calculated high energy X-ray diffraction g(r) of a theoretical model of the mononuclear chromium(III) acetate can range from 0.55 to 1; alternatively, range from 0.60 to 1; alternatively, range from 0.625 to 1; alternatively, range from 0.65 to 1; alternatively, range from 0.675 to 1; alternatively, range from 0.70 to 1; alternatively, range from 0.725 to 1; alternatively, range from 0.75 to 1; alternatively, range from 0.775 to 1; alternatively, range from 0.80 to 1; alternatively, range from 0.825 to 1; alternatively, range from 0.85 to 1; alternatively, range from 0.875 to 1; or alternatively, range from 0.90 to 1.

In some non-limiting embodiments, any chromium(III) carboxylate composition described herein or any chromium (III) carboxylate composition produced by any process(es) described herein, can be characterized using singly, or in any combination, any characterizing embodiment described herein; for example the presence or absence of an infrared peak disclosed herein, any infrared peak height feature disclosed herein, any infrared peak wavelength separation described herein, any infrared peak height ratio disclosed herein, the presence or absence of any high energy X-ray diffraction peak described herein, and/or any goodness of fit $R^2$ test value disclosed herein, among other. Each of these characterizing elements is disclosed herein and can be utilized without limitation to describe the chromium(III) carboxylate composition(s) of the present disclosure.

Various aspect and embodiments described herein refer to non-hydrogen substituents such as halogen (or halo, halide), hydrocarbyl, hydrocarboxy, alkyl, and/or alkoxy substituents, among others. The non-hydrogen substituents of any aspect or any embodiment calling for a substituent can be a halide, a $C_1$ to $C_{10}$ hydrocarbyl group, or a $C_1$ to $C_{10}$ hydrocarboxy group; alternatively, a halide or a $C_1$ to $C_{10}$ hydrocarbyl group; alternatively, a halide or a $C_1$ to $C_{10}$ hydrocarboxy group; alternatively, a $C_1$ to $C_{10}$ hydrocarbyl group or a $C_1$ to $C_{10}$ hydrocarboxy group; alternatively, a halide; alternatively, a $C_1$ to $C_{10}$ hydrocarbyl group; or alternatively, a $C_1$ to $C_{10}$ hydrocarboxy group. In other embodiments, the non-hydrogen substituents of any aspect or any embodiment calling for a substituent can be a halide, a $C_1$ to $C_5$ hydrocarbyl group, or a $C_1$ to $C_5$ hydrocarboxy group; alternatively, a halide or a $C_1$ to $C_5$ hydrocarbyl group; alternatively, a halide or a $C_1$ to $C_5$ hydrocarboxy group; alternatively, a $C_1$ to $C_5$ hydrocarbyl group or a $C_1$ to $C_5$ hydrocarboxy group; alternatively, a halide; alternatively, a $C_1$ to $C_5$ hydrocarbyl group; or alternatively, a $C_1$ to $C_5$ hydrocarboxy group.

In an embodiment, any halide substituent of any aspect or any embodiment calling for a substituent can be a fluoride, chloride, bromide, or iodide; alternatively, a fluoride or chloride. In some embodiments, any halide substituent of any aspect or any embodiment calling for a substituent can be a fluoride; alternatively, a chloride; alternatively, a bromide; or alternatively, an iodide.

In an embodiment, any hydrocarbyl substituent can be an alkyl group, an aryl group, or an aralkyl group; alternatively, an alkyl group; alternatively, an aryl group; or alternatively, an aralkyl group. Generally, the alkyl substituent group(s), the aryl substituent group(s), and/or an aralkyl substituent group(s) can have the same number of carbon atoms of the hydrocarbyl substituent group disclosed herein. In an embodiment, any alkyl substituent of any aspect or any embodiment calling for a substituent can be a methyl group, an ethyl group, an n-propyl group, an isopropyl group, an n-butyl group, a sec-butyl group, an isobutyl group, a tert-butyl group, an n-pentyl group, a 2-pentyl group, a 3-pentyl group, a 2-methyl-1-butyl group, a tert-pentyl group, a 3-methyl-1-butyl group, a 3-methyl-2-butyl group, or a neo-pentyl group; alternatively, a methyl group, an ethyl group, an isopropyl group, a tert-butyl group, or a neo-pentyl group; alternatively, a methyl group; alternatively, an ethyl group; alternatively, an isopropyl group; alternatively, a tert-butyl group; or alternatively, a neo-pentyl group. In an embodiment, any aryl substituent of any aspect or any embodiment calling for a substituent can be phenyl group, a tolyl group, a xylyl group, or a 2,4,6-trimethylphenyl group; alternatively, a phenyl group; alternatively, a tolyl group; alternatively, a xylyl group; or alternatively, a 2,4,6-trimethylphenyl group. In an embodiment, any aralkyl substituent of any aspect or any embodiment calling for a substituent can be benzyl group or an ethylphenyl group (2-phenyleth-1-yl or 1-phenyleth-1-yl); alternatively, a benzyl group; alternatively, an ethylphenyl group; alternatively, a 2-phenyleth-1-yl group; or alternatively, a 1-phenyleth-1-yl group.

In an embodiment, any hydrocarboxy substituent of any aspect or any embodiment calling for a substituent can be an alkoxy group, an aryloxy group, or an aralkoxy group; alternatively, an alkoxy group; alternatively, an aryloxy group, or an aralkoxy group. Generally, the alkoxy substituent group(s), the aroxy substituent group(s), and/or an aralkoxy substituent group(s) can have the same number of carbon atoms of the hydrocarboxy substituent group disclosed herein. In an embodiment, any alkoxy substituent of any aspect or any embodiment calling for a substituent can be a methoxy group, an ethoxy group, an n-propoxy group, an isopropoxy group, an n-butoxy group, a sec-butoxy group, an isobutoxy group, a tert-butoxy group, an n-pentoxy group, a 2-pentoxy group, a 3-pentoxy group, a 2-methyl-1-butoxy group, a tert-pentoxy group, a 3-methyl-1-butoxy group, a 3-methyl-2-butoxy group, or a neo-pentoxy group; alternatively, a methoxy group, an ethoxy group, an isopropoxy group, a tert-butoxy group, or a neo-pentoxy group; alternatively, a methoxy group; alternatively, an ethoxy group; alternatively, an isopropoxy group; alternatively, a tert-butoxy group; or alternatively, a neo-pentoxy group. In an embodiment, any aryloxy substituent of any aspect or any embodiment calling for a substituent can be phenoxy group, a toloxy group, a xyloxy group, or a 2,4,6-trimethylphenoxy group; alternatively, a phenoxy group; alternatively, a toloxy group; alternatively, a xyloxy group; or alternatively, a 2,4,6-trimethylphenoxy group. In an embodiment, any aralkoxy substituent of any aspect or any embodiment calling for a substituent can be benzoxy group.

The methods described herein can utilize one or more solvents. Non-limiting examples of solvents which can be utilized in aspects and/or embodiments of the present disclosure include without limitation hydrocarbons, halogenated hydrocarbons, ethers, thioethers, nitriles, amines, phosphines, phosphites, carbonates, esters, ketones, aldehydes, alcohols, or any combination thereof; alternatively, hydrocarbons, halogenated hydrocarbons, ethers, thioethers, nitriles, amines, phosphines, phosphites, or any combination thereof. In some aspects and/or embodiments, a method can call for a polar solvent; or alternatively, a non-polar solvent. Polar solvents which can be utilized include without limitation ethers, thioethers, nitriles, amines, phosphines, phosphites, carbonates, esters, ketones, aldehydes, alcohols, or any combination thereof; alternatively, ethers, thioethers, nitriles, amines, phosphines, phosphites, or any combination thereof alternatively, ethers; alternatively, thioethers; alternatively, nitriles; alternatively, amines; alternatively, phosphines; or alternatively, and phosphites. In some aspects and embodiments, a method can call for a non-polar solvent.

Non-polar solvents include without limitation hydrocarbons, halogenated hydrocarbons, or any combination thereof; alternatively, a hydrocarbon; or alternatively, a halogenated hydrocarbon. In other aspects and/or embodiments, the various process steps, isolation steps, and/or purification steps in the process of making the transition metal carboxylate composition can utilize an aprotic solvent. Aprotic solvents which can be utilized in various aspects and/or embodiments of the present disclosure can include hydrocarbons, halogenated hydrocarbons, ethers, thioethers, esters, ketones, aldehydes, nitriles, and any combination thereof; alternatively, hydrocarbons, halogenated hydrocarbons, ethers, thioethers, nitriles, and any combination thereof; alternatively, hydrocarbons, halogenated hydrocarbons, any combination thereof; alternatively, ethers, esters, ketones, aldehydes, nitriles, and any combination thereof; alternatively, ethers, nitriles, and thereof; alternatively, hydrocarbons; alternatively, halogenated hydrocarbons; alternatively, ethers; alternatively, esters; alternatively, thioethers, alternatively, ketones; alternatively, aldehydes; or alternatively, nitriles. In some aspects and/or embodiments, the various process steps, isolation steps, and/or purification steps in the process of making the transition metal carboxylate composition can utilize an aprotic polar solvent. Aprotic polar solvents which can be utilized include ethers, thioethers, esters, ketones, aldehydes, nitriles, and any combination thereof; alternatively, ethers, thioethers, nitriles and any combination thereof; alternatively, esters, ketones, aldehydes and mixtures thereof; alternatively, ethers; alternatively, thioethers, alternatively, esters; alternatively, ketones; alternatively, aldehydes; or alternatively, nitriles. In some aspects, the aprotic polar solvent can be, comprise, or consist essentially of, any neutral ligand (or combination of neutral ligands) disclosed herein. In some aspects and/or embodiments, the various process steps, isolation steps, and/or purification steps in the process of making the transition metal carboxylate composition can utilize a non-polar solvent. Non-polar solvents which can be utilized in various aspects and/or embodiments of the present disclosure can include hydrocarbons, halogenated hydrocarbons, or any combination thereof; alternatively, hydrocarbons; or alternatively, a halogenated hydrocarbons. In other aspects and/or embodiments, the various process steps, isolation steps, and/or purification steps in the process of making the transition metal carboxylate composition can utilize a coordinating solvent. Coordinating solvents which can be utilized in various aspects and/or embodiments of the present disclosure can include ethers, esters, ketones, aldehydes, nitriles, or mixtures thereof; alternatively, ethers, nitriles, or mixtures thereof; alternatively, ethers; alternatively, esters; alternatively, ketones; alternatively, aldehydes; or alternatively, nitriles. In some aspects, the coordinating solvent can be comprise, or consist essentially of, any neutral ligand (or combination of neutral ligands) disclosed herein. In other aspects and/or embodiments, the various process steps, isolation steps, and/or purification steps in the process of making the transition metal carboxylate composition can utilize a non-coordinating solvent. Non-coordinating solvents which can be utilized in various aspects and/or embodiments of the present disclosure can include hydrocarbons, halogenated hydrocarbons, or mixture thereof; alternatively, hydrocarbons; alternatively, halogenated hydrocarbons.

Ethers, thioethers, nitriles, amines, phosphines, and phosphites are described herein. These ethers, nitriles, amines, phosphines, and phosphites can be utilized without limitation as a member of a particular solvent class described herein.

Hydrocarbons and halogenated hydrocarbons which can include aliphatic hydrocarbons, aromatic hydrocarbons, petroleum distillates, halogenated aliphatic hydrocarbons, halogenated aromatic hydrocarbons, or combinations thereof; or alternatively aliphatic hydrocarbons, aromatic hydrocarbons, halogenated aliphatic hydrocarbons, halogenated aromatic hydrocarbons, and combinations thereof. In some embodiments, hydrocarbons and halogenated hydrocarbons can include aliphatic hydrocarbons; alternatively, aromatic hydrocarbons; alternatively, halogenated aliphatic hydrocarbons; or alternatively, halogenated aromatic hydrocarbons.

Aliphatic hydrocarbons which can be useful as a general solvent, a non-polar solvent, and/or a non-coordinating solvent include $C_4$ to $C_{20}$ aliphatic hydrocarbons; alternatively $C_4$ to $C_{15}$ aliphatic hydrocarbons; or alternatively, $C_5$ to $C_{10}$ aliphatic hydrocarbons. Aliphatic hydrocarbons can be cyclic or acyclic and/or can be linear or branched, unless otherwise specified. Non-limiting examples of suitable acyclic aliphatic hydrocarbon solvents which can be utilized as a general solvent, a non-polar solvent, and/or a non-coordinating solvent include iso-butane, n-butane, butane (n-butane or a mixture of linear and branched $C_4$ acyclic aliphatic hydrocarbons), pentane (n-pentane or a mixture of linear and branched $C_5$ acyclic aliphatic hydrocarbons), hexane (n-hexane or mixture of linear and branched $C_6$ acyclic aliphatic hydrocarbons), heptane (n-heptane or mixture of linear and branched $C_7$ acyclic aliphatic hydrocarbons), octane (n-octane or a mixture of linear and branched $C_8$ acyclic aliphatic hydrocarbons), and any combination thereof; alternatively, iso-butane, n-butane, butane (n-butane or a mixture of linear and branched $C_4$ acyclic aliphatic hydrocarbons), pentane (n-pentane or a mixture of linear and branched $C_5$ acyclic aliphatic hydrocarbons), hexane (n-hexane or mixture of linear and branched $C_6$ acyclic aliphatic hydrocarbons), heptane (n-heptane or mixture of linear and branched $C_7$ acyclic aliphatic hydrocarbons), octane (n-octane or a mixture of linear and branched $C_8$ acyclic aliphatic hydrocarbons), and any combination thereof; alternatively, iso-butane, n-butane, butane (n-butane or a mixture of linear and branched $C_4$ acyclic aliphatic hydrocarbons), pentane (n-pentane or a mixture of linear and branched $C_5$ acyclic aliphatic hydrocarbons), heptane (n-heptane or mixture of linear and branched $C_7$ acyclic aliphatic hydrocarbons), octane (n-octane or a mixture of linear and branched $C_8$ acyclic aliphatic hydrocarbons), and any combination thereof; alternatively, iso-butane; alternatively, n-butane; alternatively, butane (n-butane or a mixture of linear and branched $C_4$ acyclic aliphatic hydrocarbons); alternatively, pentane (n-pentane or a mixture of linear and branched $C_5$ acyclic aliphatic hydrocarbons); alternatively, hexane (n-hexane or mixture of linear and branched $C_6$ acyclic aliphatic hydrocarbons); alternatively, heptane (n-heptane or mixture of linear and branched $C_7$ acyclic aliphatic hydrocarbons); or alternatively, octane (n-octane or a mixture of linear and branched $C_8$ acyclic aliphatic hydrocarbons). Non-limiting examples, of suitable cyclic aliphatic hydrocarbon solvents which can be utilized as the non-coordinating solvent, include cyclohexane, methyl cyclohexane, and any combination thereof; alternatively cyclohexane; or alternatively, methylcyclohexane.

Aromatic hydrocarbons which can be useful as a general solvent, a non-polar solvent, and/or a non-coordinating solvent include $C_6$ to $C_{20}$ aromatic hydrocarbons; or alternatively, $C_6$ to $C_{10}$ aromatic hydrocarbons. Non-limiting examples of suitable aromatic hydrocarbons which can be utilized as a general solvent, a non-polar solvent, and/or a non-coordinating solvent include benzene, toluene, xylene (including ortho-xylene, meta-xylene, para-xylene, or mixtures thereof), and ethylbenzene, or any combination thereof; alternatively, benzene; alternatively, toluene; alternatively, xylene (including ortho-xylene, meta-xylene, para-xylene or mixtures thereof); or alternatively, ethylbenzene.

Halogenated aliphatic hydrocarbons which can be utilized as a general solvent, a non-polar solvent, and/or a non-coordinating solvent can include $C_1$ to $C_{15}$ halogenated aliphatic hydrocarbons; alternatively, $C_1$ to $C_{10}$ halogenated aliphatic hydrocarbons; or alternatively, $C_1$ to $C_5$ halogenated aliphatic hydrocarbons. The halogenated aliphatic hydrocarbons can be cyclic or acyclic and/or can be linear or branched, unless otherwise specified. Non-limiting examples of suitable halogenated aliphatic hydrocarbons which can be utilized as a general solvent, a non-polar solvent, and/or a non-coordinating solvent can include methylene chloride, chloroform, carbon tetrachloride, dichloroethane, trichloroethane, or any combination thereof; alternatively, methylene chloride, chloroform, dichloroethane, trichloroethane, or any combinations thereof; alternatively, methylene chloride; alternatively, chloroform; alternatively, carbon tetrachloride; alternatively, dichloroethane; or alternatively, trichloroethane. Halogenated aromatic hydrocarbons which can be utilized as a general solvent, a non-polar solvent, and/or a non-coordinating solvent can include $C_6$ to $C_{20}$ halogenated aromatic hydrocarbons; or alternatively, $C_6$ to $C_{10}$ halogenated aromatic hydrocarbons. Non-limiting examples of suitable halogenated aromatic hydrocarbons which can be utilized as a general solvent, a non-polar solvent, and/or a non-coordinating solvent can include chlorobenzene, dichlorobenzene, or any combination thereof; alternatively chlorobenzene; or alternatively, dichlorobenzene.

Ethers, thioethers, carbonates, esters, ketones, aldehydes, or alcohols which can be useful as a solvent can be, comprise, or consist essentially or, $C_2$ to $C_{20}$ ethers, $C_2$ to $C_{20}$ thioethers, $C_2$ to $C_{20}$ carbonates, $C_2$ to $C_{20}$ esters, $C_2$ to $C_{20}$ ketones, $C_2$ to $C_{20}$ aldehydes, or $C_2$ to $C_{20}$ alcohols; alternatively, $C_2$ to $C_{20}$ ethers, $C_2$ to $C_{20}$ thioethers or $C_2$ to $C_{20}$ carbonates; alternatively, $C_2$ to $C_{20}$ ethers; alternatively, $C_2$ to $C_{20}$ thioethers; alternatively, $C_2$ to $C_{20}$ carbonates; alternatively, $C_2$ to $C_{20}$ esters; alternatively, $C_2$ to $C_{20}$ ketones; alternatively, $C_2$ to $C_{20}$ aldehydes; or alternatively, $C_2$ to $C_{20}$ alcohols. In some embodiments, a useful solvent can be, comprise, or consist essentially of, $C_2$ to $C_{10}$ ethers, $C_2$ to $C_{10}$ thioethers, $C_2$ to $C_{10}$ carbonates, $C_2$ to $C_{10}$ esters, $C_2$ to $C_{10}$ ketones, $C_2$ to $C_{10}$ aldehydes, or $C_2$ to $C_{10}$ alcohols; alternatively, $C_2$ to $C_{10}$ ethers, $C_2$ to $C_{10}$ thioethers, or $C_2$ to $C_{10}$ carbonates; alternatively, $C_2$ to $C_{20}$ ethers; alternatively, $C_2$ to $C_{10}$ thioethers; alternatively, $C_2$ to $C_{20}$ carbonates; alternatively, $C_2$ to $C_{20}$ esters; alternatively, $C_2$ to $C_{20}$ ketones; alternatively, $C_2$ to $C_{20}$ aldehydes; or alternatively, $C_2$ to $C_{20}$ alcohols. Suitable ether solvents can be cyclic or acyclic. Non-limiting examples of suitable ethers which can be useful as a solvent include dimethyl ether, diethyl ether, methyl ethyl ether, monoethers or diethers of glycols (e.g., dimethyl glycol ether), furan, substituted furans, dihydrofuran, substituted dihydrofurans, tetrahydrofuran (THF), substituted tetrahydrofurans, tetrahydropyran, substituted tetrahydropyrans, 1,3-dioxane, substituted 1,3-dioxanes, 1,4-dioxane, substituted 1,4-dioxanes, or mixtures thereof; alternatively, dimethyl ether, diethyl ether, methyl ethyl ether, monoethers or diethers of glycols (e.g., dimethyl glycol ether), or mixtures thereof; alternatively, furan, substituted furans, dihydrofuran, substituted dihydrofurans, tetrahydrofuran (THF), substituted tetrahydrofurans, tetrahydropyran, substituted tetrahydropyrans, 1,3-dioxane, substituted 1,3-dioxanes, 1,4-dioxane, substituted 1,4-dioxanes, or mixtures thereof; alternatively, dimethyl ether, diethyl ether, methyl ethyl ether, or mixtures thereof; alternatively, monoethers or diethers of glycols (e.g., dimethyl glycol ether); alternatively, tetrahydrofuran (THF), substituted tetrahydrofurans, tetrahydropyran, substituted tetrahydropyrans, 1,3-dioxane, substituted 1,3-dioxanes, 1,4-dioxane, substituted 1,4-dioxanes, or mixtures thereof; alternatively, tetrahydrofuran (THF), tetrahydropyran, 1,3-dioxane, 1,4-dioxane, or mixtures thereof; or alternatively, tetrahydrofuran. In an embodiment, each substituent of a substituted furan, substituted dihydrofuran, substituted tetrahydrofuran, substituted tetrahydropyran, substituted 1,3-dioxane, or substituted 1,4-dioxane, can be a $C_1$ to $C_5$ alkyl group. $C_1$ to $C_5$ alkyl substituent groups are disclosed herein and can be utilized without limitation of further describe the substituted tetrahydrofurans, substituted dihydrofurans, substituted furans, substituted 1,3-dioxanes, or substituted 1,4 dioxanes which can be utilized as the polar aprotic solvent. Non-limiting examples of suitable carbonates which can be utilized as a solvent include ethylene carbonate, propylene carbonate, diethyl carbonate, diethyl carbonate, glycerol carbonate, and combinations thereof. Non-limiting examples of suitable esters which can be utilized as a solvent include ethyl acetate, propyl acetate, butyl acetate, isobutyl isobutyrate, and combinations thereof. Non-limiting examples of suitable ketones which can be utilized as a solvent include acetone, ethyl methyl ketone, methyl isobutyl ketone, and combinations thereof. Non-limiting examples of suitable alcohols which can be utilized as a solvent include methanol, ethanol, propanol, isopropanol, n-butanol, isobutanol, pentanol, hexanol, heptanol, octanol, benzyl alcohol, phenol, cyclohexanol, and the like, or combinations thereof.

Nitriles which can be utilized as a solvent include $C_2$ to $C_{12}$ nitriles; alternatively, $C_2$ to $C_{10}$ nitriles; or alternatively, $C_2$ to $C_8$ nitriles. Generally, the nitriles which can be utilized as a solvent can be cyclic or acyclic, linear or branched, and/or aliphatic or aromatic. Non-limiting examples of nitriles which can be utilized as a solvent include, but are not limited to, acetonitrile, propionitrile, butyronitrile, benzonitrile, or any combination thereof; alternatively, acetonitrile, propionitrile, butyronitrile, or any combination thereof. In some embodiments, the solvent can be, comprise, or consist essentially of, acetonitrile.

In an aspect, the solvent in which the transition metal precursor and the Group 1 or Group 2 carboxylate are contacted, if utilized, can be, comprise, or consist essentially of, any neutral ligand described herein. In some embodiments wherein the transition metal precursor contains a neutral ligand, the solvent in which the transition metal precursor and the Group 1 or Group 2 carboxylate are contacted, if utilized, can be, comprise, or consist essentially of, any neutral ligand present in the transition metal precursor. In other embodiments, wherein the transition metal precursor contains a neutral ligand, the solvent in which the transition metal precursor and the Group 1 or Group 2 carboxylate are contacted, if utilized, can be different than any neutral ligand present in the transition metal precursor. Neutral ligands are described herein and these neutral ligands can be utilized without limitation as the solvent, if utilized, for contacting the transition metal precursor and the Group 1 or Group 2 carboxylate.

In a non-limiting embodiment, the polar aprotic solvent can be, comprise, or consist essentially of, monoethers or diethers of glycols (e.g., dimethyl glycol ether), furan, substituted furans, dihydrofuran, substituted dihydrofurans, tetrahydrofuran (THF), substituted tetrahydrofurans, tetrahydropyran, substituted tetrahydropyrans, 1,3-dioxane, substituted 1,3-dioxanes, 1,4-dioxane, substituted 1,4-dioxanes, or mixtures thereof. In an embodiment, each substituent of a substituted furan, substituted dihydrofuran, substituted tetrahydrofuran, substituted tetrahydropyran, substituted 1,3-dioxane, or substituted 1,4-dioxane, can be a $C_1$ to $C_5$ alkyl group. $C_1$ to $C_5$ alkyl substituent groups are disclosed herein and can be utilized without limitation of further describe the substituted tetrahydrofurans, substituted dihydrofurans, substituted furans, substituted 1,3-dioxanes, or substituted 1,4 dioxanes which can be utilized as the polar aprotic solvent. In an embodiment, the polar aprotic solvent can be, comprise, or consist essentially of, tetrahydrofuran (THF), furan, 2-methyltetrahydrofuran, 3-methyltetrahydrofuran, dihydrofuran, pyran, tetrahydropyran, 2,3-dihydropyran, 1,3-dioxane, 1,4-dioxane, morpholine, N-methylmorpholine, dimethyl ether, diethyl ether, methyl ethyl ether, methyl phenyl ether, methyl t-butyl ether, diisopropyl ether, di-n-butyl ether, 1,2-dimethoxyethane, bis(2-methoxyethyl) ether, or any combination thereof. In some embodiments, the polar aprotic solvent can be, comprise, or consist essentially of, tetrahydrofuran (THF), furan, 2-methyltetrahydrofuran, 3-methyltetrahydrofuran, dihydrofuran, pyran, tetrahydropyran, 2,3-dihydropyran, 1,3-dioxane, 1,4-dioxane, dimethyl ether, diethyl ether, methyl ethyl ether, methyl phenyl ether, methyl t-butyl ether, diisopropyl ether, di-n-butyl ether, 1,2-dimethoxyethane, bis(2-methoxyethyl) ether, or any combination thereof; alternatively, tetrahydrofuran (THF), furan, 2-methyltetrahydrofuran, 3-methyltetrahydrofuran, dihydrofuran, pyran, tetrahydropyran, 2,3-dihydropyran, 1,3-dioxane, 1,4-dioxane, or any combination thereof; alternatively, dimethyl ether, diethyl ether, methyl ethyl ether, methyl phenyl ether, methyl t-butyl ether, diisopropyl ether, di-n-butyl ether, 1,2-dimethoxyethane, bis(2-methoxyethyl) ether, or any combination thereof. In other embodiments, the polar aprotic solvent can be, comprise, or consist essentially of, tetrahydrofuran (THF), 2-methyltetrahydrofuran, 3-methyltetrahydrofuran, tetrahydropyran, 1,3-dioxane, 1,4-dioxane, or any combination thereof. In other embodiments, the polar aprotic solvent can be, comprise, or consist essentially of, tetrahydrofuran (THF).

Similarly, examples of suitable nitriles that can be utilized as the polar aprotic solvent include, but are not limited to, a $C_2$ to $C_{20}$ alkyl nitrile, or a $C_7$ to $C_{20}$ aryl nitrile or any combination thereof. Further in this aspect and in any embodiment, suitable nitriles which can be utilized as the coordinating first solvent include $C_2$ to $C_{12}$ nitriles; alternatively, $C_2$ to $C_{10}$ nitriles; or alternatively, $C_2$ to $C_8$ nitriles. Suitable nitrile solvents which can be utilized as the coordinating first solvent can be cyclic or acyclic, linear or branched, aliphatic or aromatic. Non-limiting examples of suitable nitriles which can be useful as a polar aprotic first solvent include, but are not limited to, acetonitrile, propionitrile, butyronitrile, benzonitrile, or any combination thereof; alternatively, acetonitrile, propionitrile, butyronitrile, or any combination thereof. In some embodiments, the solvent can be, comprise, or consist essentially of, acetonitrile.

In a further aspect, thioethers that can be utilized as a solvent can be, comprise, or consist essentially of, a $C_2$ to $C_{20}$ dialkyl thioether, a $C_2$ to $C_{20}$ dialkyl thioether, a $C_4$ to $C_5$ cyclic thioether, or any combination thereof. In some embodiments, a thioether which can be utilized as a can be, comprise, or consist essentially of, thiophene, 2-methylthiophene, 3-methylthiophene, tetrahydrothiophene, or any combination thereof.

For the purpose of any U.S. national stage filing from this application, all publications and patents mentioned in this disclosure are incorporated herein by reference in their entireties, for the purpose of describing and disclosing the constructs and methodologies described in those publications, which might be used in connection with the methods of this disclosure. Any publications and patents discussed above and throughout the text are provided solely for their disclosure prior to the filing date of the present application. Nothing herein is to be construed as an admission that the inventors are not entitled to antedate such disclosure by virtue of prior invention.

Unless indicated otherwise, when a range of any type is disclosed or claimed, for example a range of molar ratios, temperatures, and the like, it is intended to disclose or claim individually each possible number that such a range could reasonably encompass, including any sub-ranges encompassed therein. When describing a range of measurements such as molar ratios, every possible number that such a range could reasonably encompass can, for example, refer to values within the range with one significant digit more than is present in the end points of a range. In this example, a molar ratio between 1.03:1 and 1.12:1 includes individually molar ratios of 1.03:1, 1.04:1, 1.05:1, 1.06:1, 1.07:1, 1.08:1, 1.09:1, 1.10:1, 1.11:1, and 1.12:1. Applicants' intent is that these two methods of describing the range are interchangeable. Moreover, when a range of values is disclosed or claimed, which Applicants intend to reflect individually each possible number that such a range could reasonably encompass, Applicants also intend for the disclosure of a range to reflect, and be interchangeable with, disclosing any and all sub-ranges and combinations of sub-ranges encompassed therein. When describing a range in which the end points of the range have different numbers of significant digits, for example, a molar ratio from 1:1 to 1.2:1, every possible number that such a range could reasonably encompass can, for example, refer to values within the range with one significant digit more than is present in the end point of a range having the greatest number of significant digits, in this case 1.2:1. In this example, a molar ratio from 1:1 to 1.2:1 includes individually molar ratios of 1.01, 1.02, 1.03, 1.04, 1.05, 1.06, 1.07, 1.08, 1.09, 1.10, 1.11, 1.12, 1.13, 1.14, 1.15, 1.16, 1.17, 1.18, 1.19, and 1.20, all relative to 1, and any and all sub-ranges and combinations of sub-ranges encompassed therein. Accordingly, Applicants reserve the right to proviso out or exclude any individual members of any such group, including any sub-ranges or combinations of sub-ranges within the group, if for any reason Applicants choose to claim less than the full measure of the disclosure, for example, to account for a reference that Applicants are unaware of at the time of the filing of the application.

In any application before the United States Patent and Trademark Office, the Abstract of this application is provided for the purpose of satisfying the requirements of 37 C.F.R. §1.72 and the purpose stated in 37 C.F.R. §1.72(b) "to enable the United States Patent and Trademark Office and the public generally to determine quickly from a cursory inspection the nature and gist of the technical disclosure." Therefore, the Abstract of this application is not intended to be used to construe the scope of the claims or to limit the scope of the subject matter that is disclosed herein. Moreover, any headings that can be employed herein are also not intended to be used to construe the scope of the claims or to limit the scope of the subject matter that is disclosed herein. Any use of the past tense to describe an example otherwise indicated as constructive or prophetic is not intended to reflect that the constructive or prophetic example has actually been carried out.

For any particular compound disclosed herein, the general structure presented is also intended to encompass all conformational isomers and stereoisomers that can arise from a particular set of substituents, unless indicated otherwise. Thus, the general structure encompasses all structural isomer (e.g. a reference to a propyl group includes n-propyl and iso-propyl, or e.g. a reference to diazole include 1,2-diazole and 1,3-diazole), enantiomers, diastereomers, and other optical isomers whether in enantiomeric or racemic forms, as well as mixtures of stereoisomers, as the context permits or requires, unless specifically indicated otherwise. For any particular formula that is presented, any general formula presented also encompasses all conformational isomers, regioisomers, and stereoisomers that can arise from a particular set of substituents. Moreover and unless otherwise specified, the disclosure of a general compound or structure that can encompass more than one regioisomer is intended to encompass all possible regioisomers within such a general disclosure. For example, by the disclosure of L can be, comprise, or consist essentially of, diazepine, a diazepine, or diazepines, it is intended to reflect that L can be, comprise, or consist essentially of, 1,2-diazepine, 1,3-diazepine, or 1,4-diazepine.

The present disclosure is further illustrated by the following examples, which are not to be construed in any way as imposing limitations upon the scope thereof. On the contrary, it is to be clearly understood that resort can be had to various other aspects, embodiments, modifications, and equivalents thereof which, after reading the description herein, can suggest themselves to one of ordinary skill in the art without departing from the spirit of the present invention or the scope of the appended claims.

The data and descriptions provided in the following examples are given to show particular aspects and embodiments of the compounds, catalyst systems, and olefin oligomerization and/or olefin polymerization methods disclosed, and to demonstrate a number of the practices and advantages thereof. The examples are given as a more detailed demonstration of some of the aspects and embodiments described herein and are not intended to limit the disclosure or claims in any manner.

EXAMPLES

General Experimental Procedures and Starting Materials

Unless specified otherwise, all reactions were performed under an inert and at least substantially dry atmosphere. All glassware was dried in an oven at 100° C. for 4 hr and brought into an inert and at least substantially dry atmosphere glovebox (drybox) while warm.

The starting material $CrCl_3(THF)_3$ was purchased from Aldrich Chemical Company and dried further as described below. The 2-ethylhexanoic acid was purchased from Aldrich and used without further purification. All solvents were purchased from Aldrich as anhydrous grade and were stored over freshly activated 5 Å molecular sieves.

Example 1

A round bottom flask (250 mL) was charged with a stir bar, sodium hydroxide (13.87 g, 0.347 mol) and methanol (200 mL) under ambient conditions. 2-Ethylhexanoic acid (50.00 g, 0.347 mol) was added dropwise to the stirred solution over 30 min. The solvent was then removed by rotary evaporation producing a white, tacky solid. This white solid was then heated at 185° C. and a pressure less that 25 torr for 18 hr, yielding anhydrous sodium 2-ethylhexanoate as a hard, white solid (97% isolated yield). Anhydrous sodium 2-ethylhexanoate is very hygroscopic and was handled under an inert and substantially dry atmosphere.

Example 2

Commercially available $CrCl_3(THF)_3$ obtained from Aldrich contained significant amounts of water; therefore, further drying was used to provide anhydrous $CrCl_3(THF)_3$ as follows. A round bottom flask (50 mL) was charged with a stir bar, $CrCl_3(THF)_3$ (8 g) and THF (25 mL). Trimethylsilylchloride (8 mL) was added dropwise to the vigorously stirring solution. The mixture was allowed to stir overnight. The purple solid was collected by filtration, washed once with pentane (50 mL) and dried under dynamic vacuum to afford the product (93% yield). The anhydrous $CrCl_3(THF)_3$ was a fine, pink-purple powder, while the damp material is a darker purple, clumpy solid.

Example 3

Figure 7:
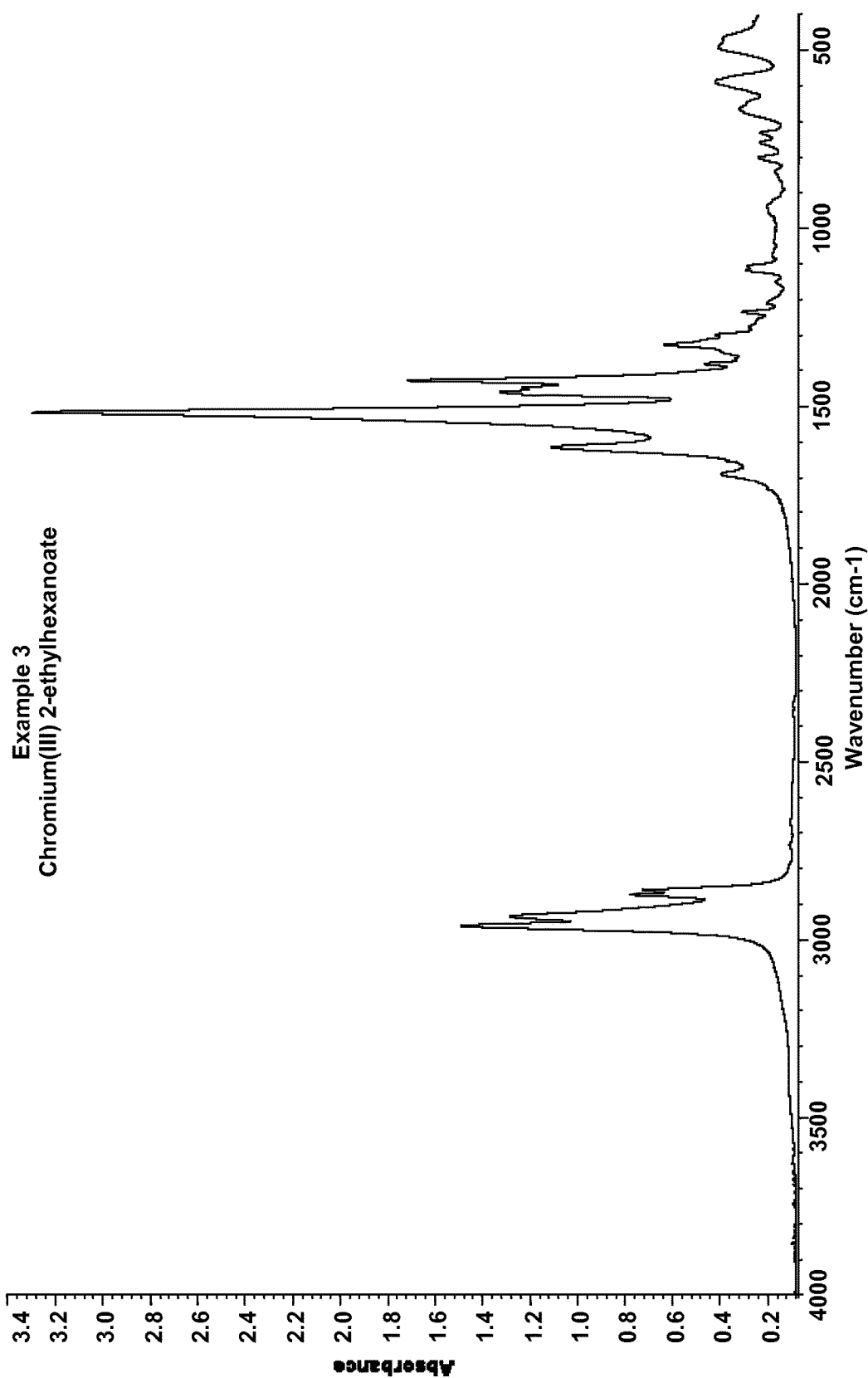
FIG. 7 provides an IR spectrum for a chromium(III) 2-ethylhexanoate produced according to the methods disclosed herein wherein the sodium 2-ethylhexanoate to $CrCl_3(THF)_3$ molar ratio was approximately 3:1.
Figure 8:
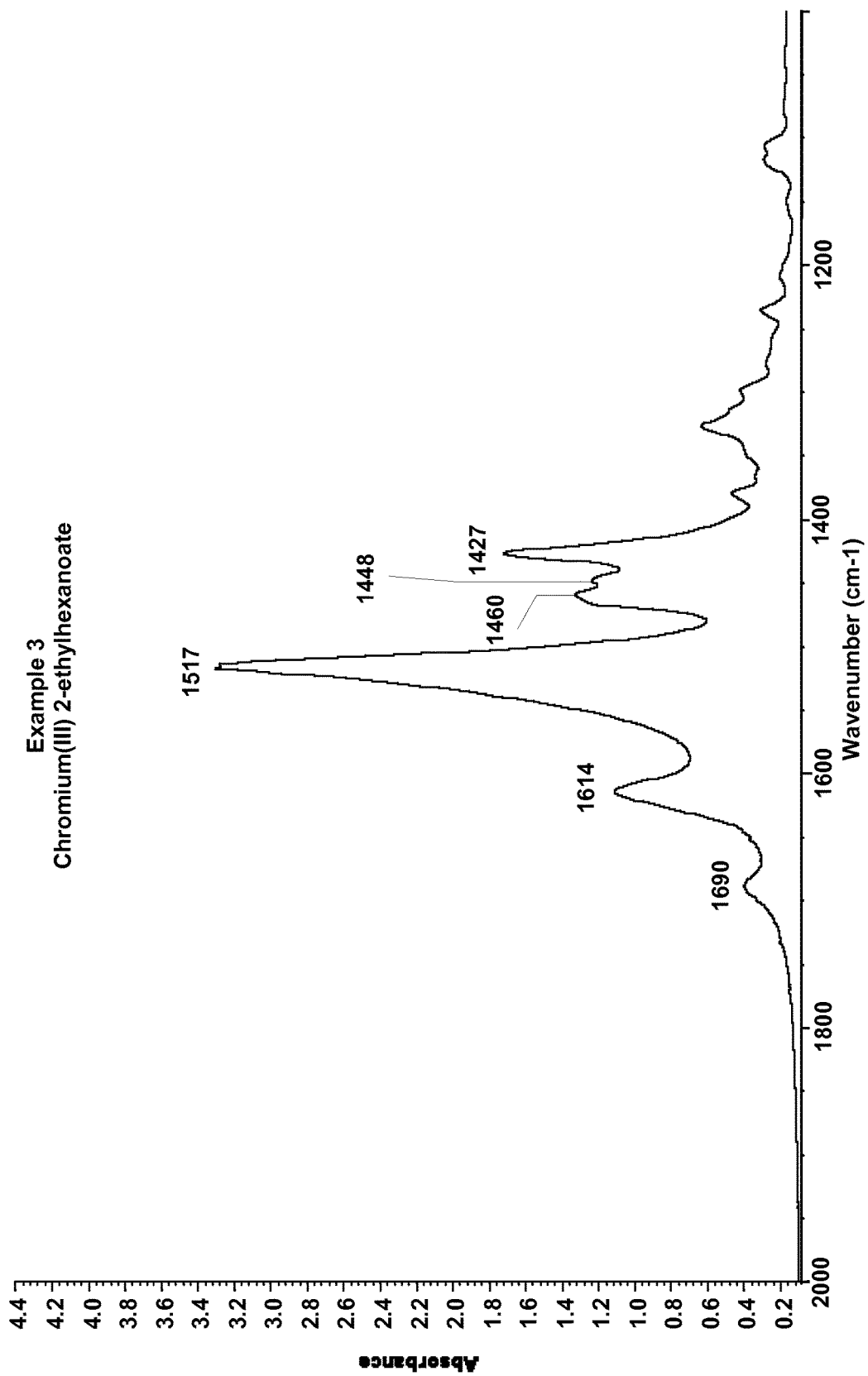
FIG. 8 provides an expanded section, 2000 $cm^{-1}$ to 1000 $cm^{-1}$, of the IR spectrum for a chromium(III) 2-ethylhexanoate produced according to the methods disclosed herein wherein the sodium 2-ethylhexanoate to $CrCl_3(THF)_3$ molar ratio was approximately 3.

A round bottom flask (1 L) was charged with $CrCl_3(THF)_3$ (21.01 g, 0.0561 mol), anhydrous sodium 2-ethylhexanoate (27.99 g, 0.168 mol) and THF (250 mL). The reaction was allowed to stir at 23° C. for 96 hr, and the solvent was removed to yield a green tar-like material. The solid was heated at 30° C. under vacuum for 2 hr then extracted into pentane (600 mL) and filtered through Celite® filter aid. The solution was very viscous making it difficult to filter. A large amount of green solid remained undissolved after filtration. The solvent was removed producing a green film (5.1 g). FIG. 7 provides an IR spectrum for the chromium(III) 2-ethylhexanoate produced using a sodium 2-ethyl hexanoate to $CrCl_3(THF)_3$ molar ratio of approximately 3. FIG. 8 provides an expanded section, 2000 $cm^{-1}$ to 1000 $cm^{-1}$, of the IR spectrum for the chromium(III) 2-ethylhexanoate produced using the sodium 2-ethyl hexanoate to $CrCl_3(THF)_3$ molar ratio of approximately 3. The infrared peak height and various infrared peak height ratios are provide in Table 1.

Example 4

Figure 9:
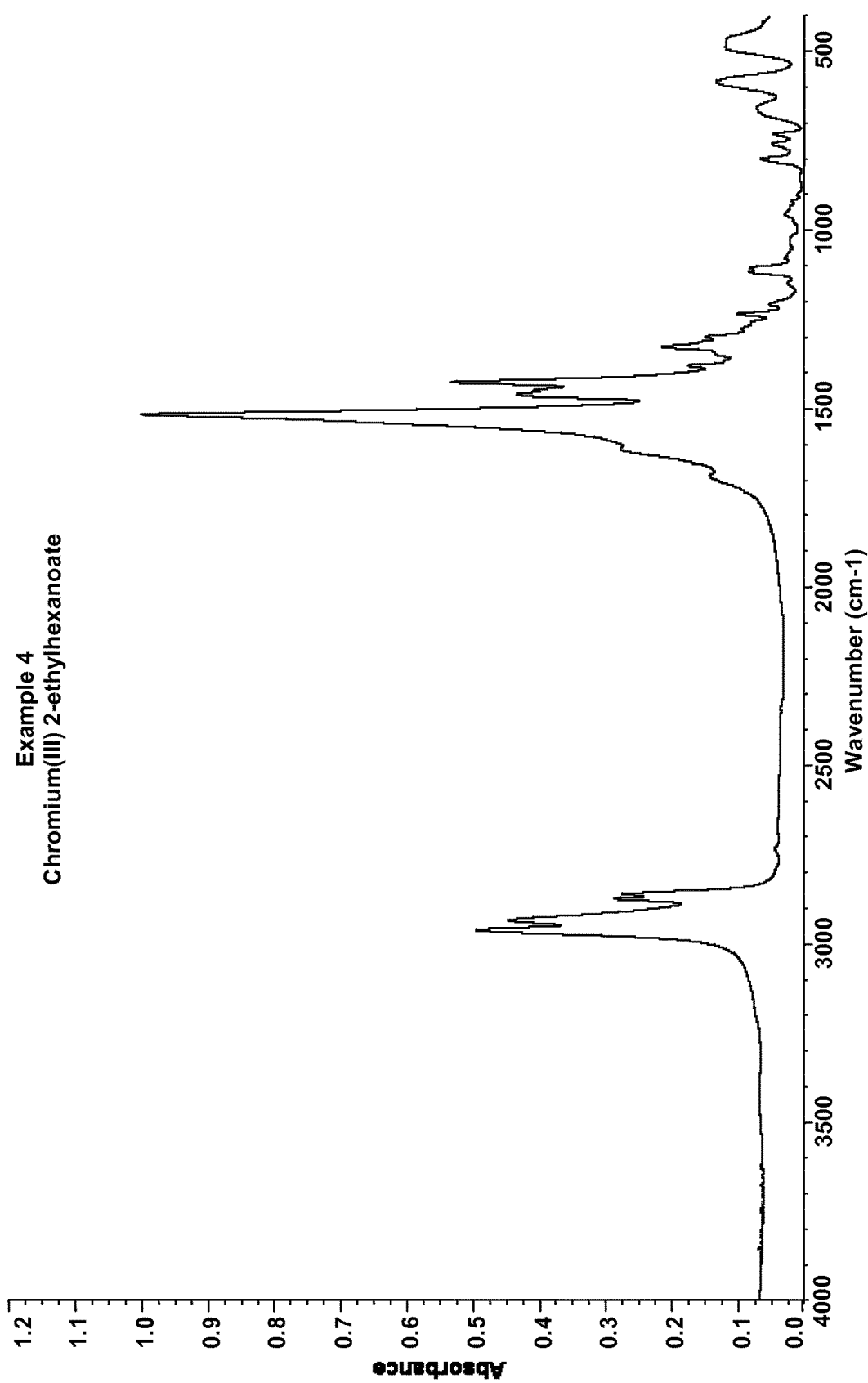
FIG. 9 provides an IR spectrum for a chromium(III) 2-ethylhexanoate produced according to the methods disclosed herein wherein the sodium 2-ethylhexanoate to $CrCl_3(THF)_3$ molar ratio was approximately 3.1:1.
Figure 10:
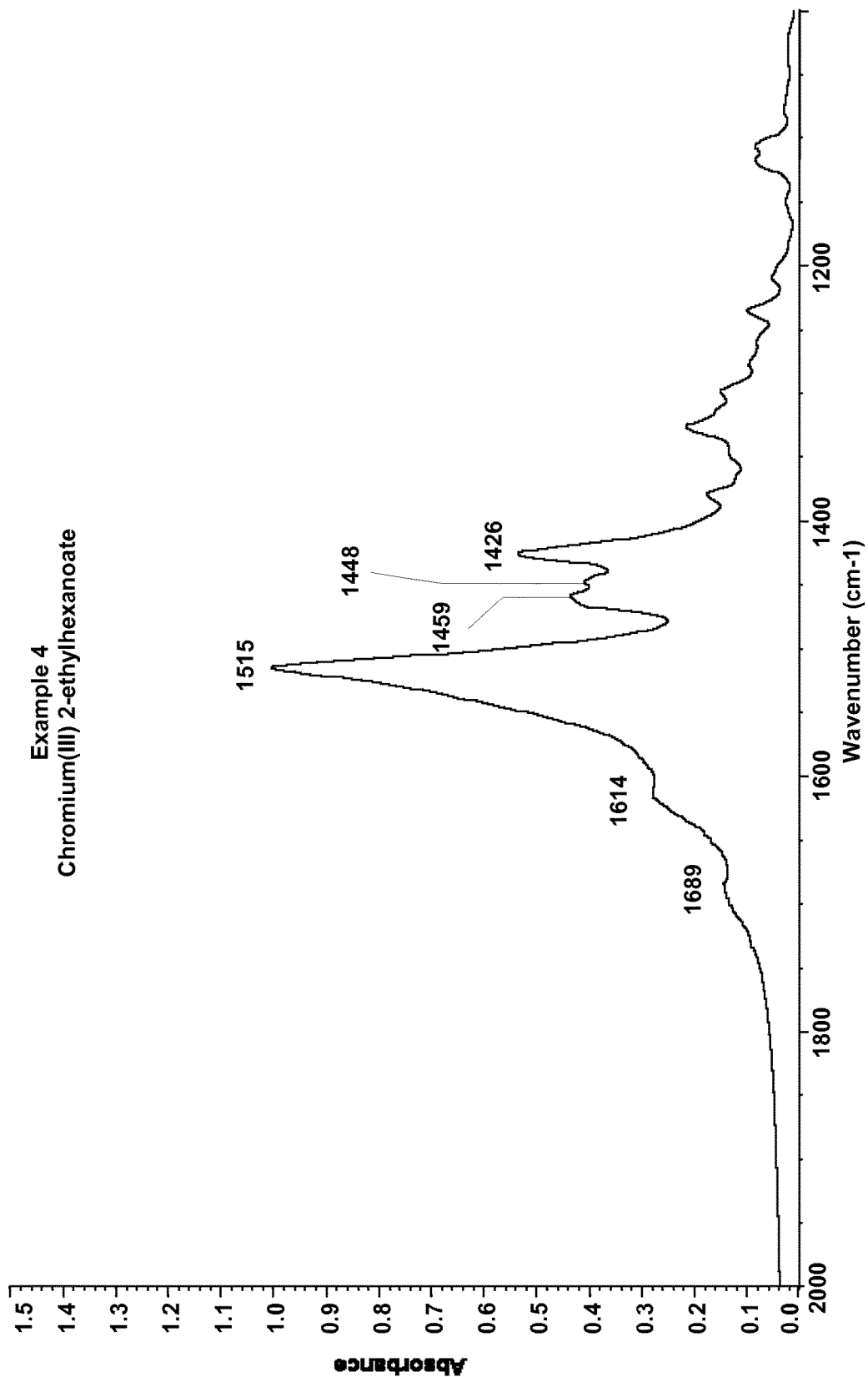
FIG. 10 provides an expanded section, 2000 $cm^{-1}$ to 1000 $cm^{-1}$, of the IR spectrum for a chromium(III) 2-ethylhexanoate produced according to the methods disclosed herein wherein the sodium 2-ethylhexanoate to $CrCl_3(THF)_3$ molar ratio was approximately 3.1:1.

A round bottom flask (500 mL) was charged with $CrCl_3(THF)_3$ (7.27 g, 0.0194 mol) and THF (100 mL). A solution of anhydrous sodium 2-ethylhexanoate (10.00 g, 0.0602 mol) in THF (60 mL) was added to the heterogeneous $CrCl_3(THF)_3$ solution while stirring. The reaction mixture was allowed to stir at 25° C. for 24 hr, after which time the solvent was removed to yield a green tacky solid. This green solid was then heated at 35° C. under vacuum for 2 hr, after which the product was extracted into cyclohexane (400 mL) and filtered through Celite® filter aid. The solvent was removed from the filtrate under vacuum producing a green tacky solid (7.1 g). FIG. 9 provides an IR spectrum for the chromium(III) 2-ethylhexanoate produced using the sodium 2-ethyl hexanoate to $CrCl_3(THF)_3$ molar ratio of approximately 3.1. FIG. 10 provides an expanded section, 2000 $cm^{-1}$ to 1000 $cm^{-1}$, of the IR spectrum for the chromium(III) 2-ethylhexanoate produced using the sodium 2-ethyl hexanoate to CrCl₃(THF)₃ molar ratio of approximately 3.1. The infrared peak height and various infrared peak height ratios are provide in Table 1.

Example 5

Figure 11:
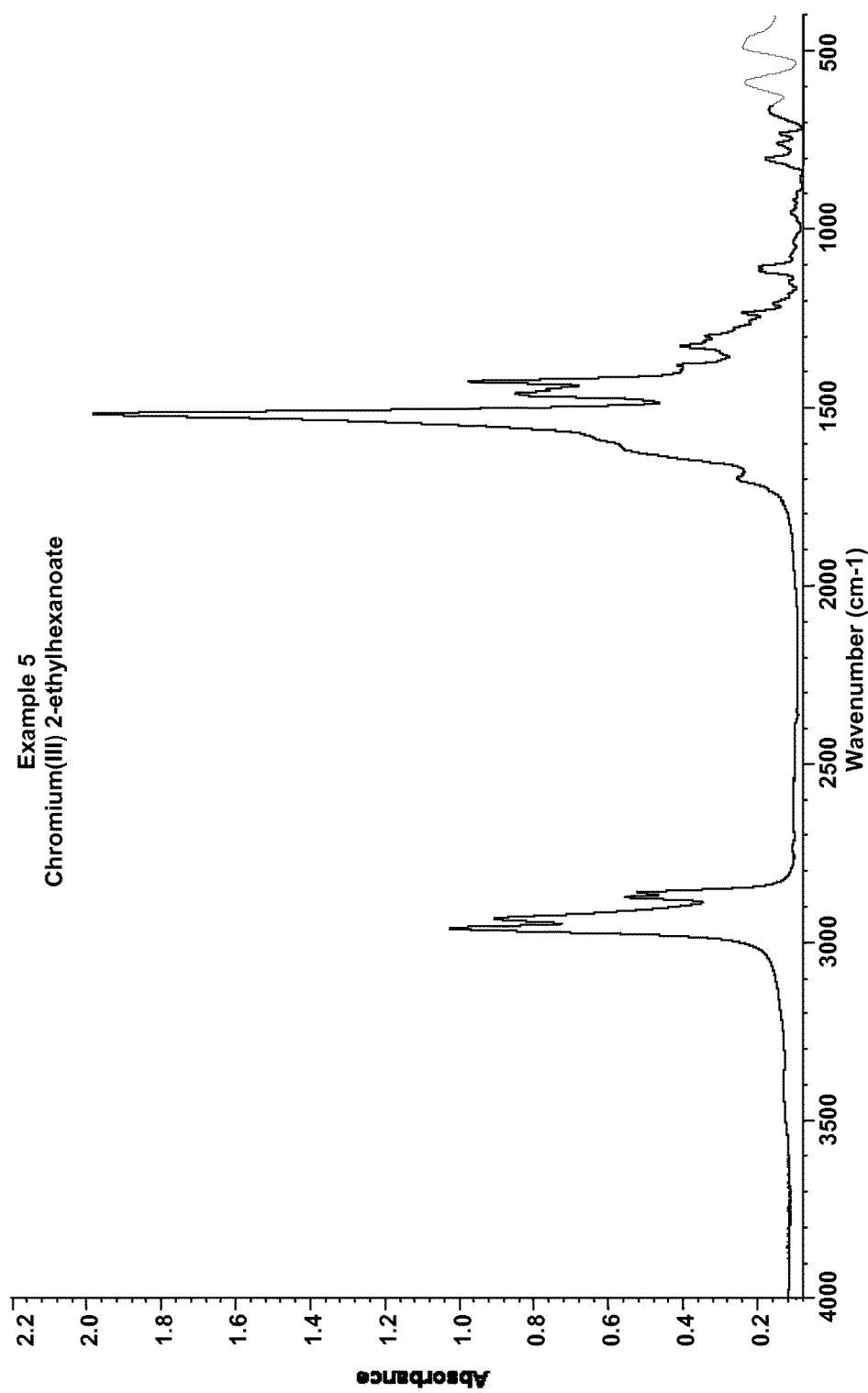
FIG. 11 provides an IR spectrum for chromium(III) 2-ethylhexanoate produced according to the methods disclosed herein wherein the sodium 2-ethylhexanoate to $CrCl_3(THF)_3$ molar ratio was approximately 3.3:1.
Figure 12:
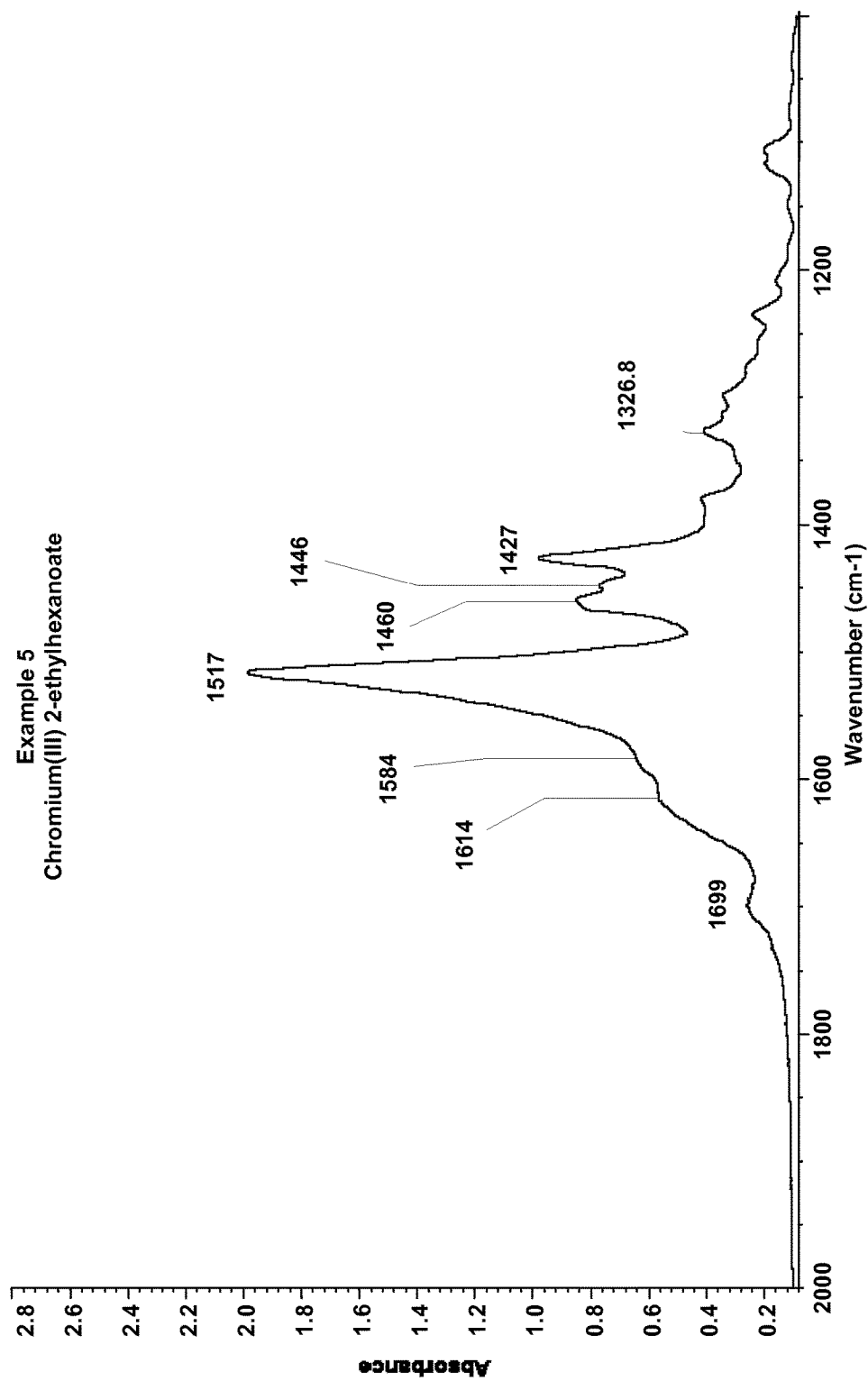
FIG. 12 provides an expanded section, 2000 $cm^{-1}$ to 1000 $cm^{-1}$, of the IR spectrum for a chromium(III) 2-ethylhexanoate produced according to the methods disclosed herein wherein the sodium 2-ethylhexanoate to $CrCl_3(THF)_3$ molar ratio was approximately 3.3:1.

A round bottom flask (500 mL) was charged with CrCl₃(THF)₃ (20.10 g, 0.0537 mol). A solution of anhydrous sodium 2-ethylhexanoate (29.42 g, 0.177 mol) in THF (250 mL) was added to the solid CrCl₃(THF)₃ while stirring. The reaction mixture was allowed to stir at 23° C. for 72 hr, after which time the solvent was removed to yield a green tacky solid. This green solid was than heated at 30° C. under vacuum for 2 hr, after which the product was extracted into pentane (500 mL) and filtered through Celite®. The solvent was removed from the filtrate under vacuum producing a green tacky solid (24.5 g). FIG. 11 provides an IR spectrum for the chromium(III) 2-ethylhexanoate produced using a sodium 2-ethylhexanoate to CrCl₃(THF)₃ molar ratio of approximately 3.3. FIG. 12 provides an expanded section, 2000 cm$^{-1}$ to 1000 cm$^{-1}$, of the IR spectrum for the chromium(III) 2-ethylhexanoate produced using the sodium 2-ethylhexanoate to CrCl₃(THF)₃ molar ratio of approximately 3.3. The infrared peak height and various infrared peak height ratios are provide in Table 1.

Example 6

Sodium Removal

Method A—
Me₃SiCl method. A 20 mL vial was charged with the product of EXAMPLE 5 (0.373 g, approximately 0.68 mmol) and 10 mL of cyclohexane. The vial was then shaken vigorously to dissolve the chromium complex, resulting in a viscous solution. Me₃SiCl (0.030 g, 0.28 mmol) was then added to the solution and a white precipitate formed immediately. The reaction mixture was allowed to stand overnight, over which time a green gel had formed that settled out, leaving behind a very light green solution.

Method B)—
2-Ethylhexanoic acid method. A 20 mL vial was charged with CrCl₃(THF)₃ (1.00 g, 2.67 mmol), sodium 2-ethylhexanoate (1.340 g, 8.06 mmol), 2-ethylhexanoic acid (0.116 g, 0.80 mmol) and THF (15 mL). The mixture was stirred for 3 days, over which time a red-violet solution and a white solid formed. The solvent was removed under vacuum and the product was extracted with cyclohexane, filtered through Celite® filter aid, and dried under vacuum to produce a blue-green oil. ICP-OES: Cr, 11.85 wt. %; Na, 0.02 wt. %.

Figure 13:
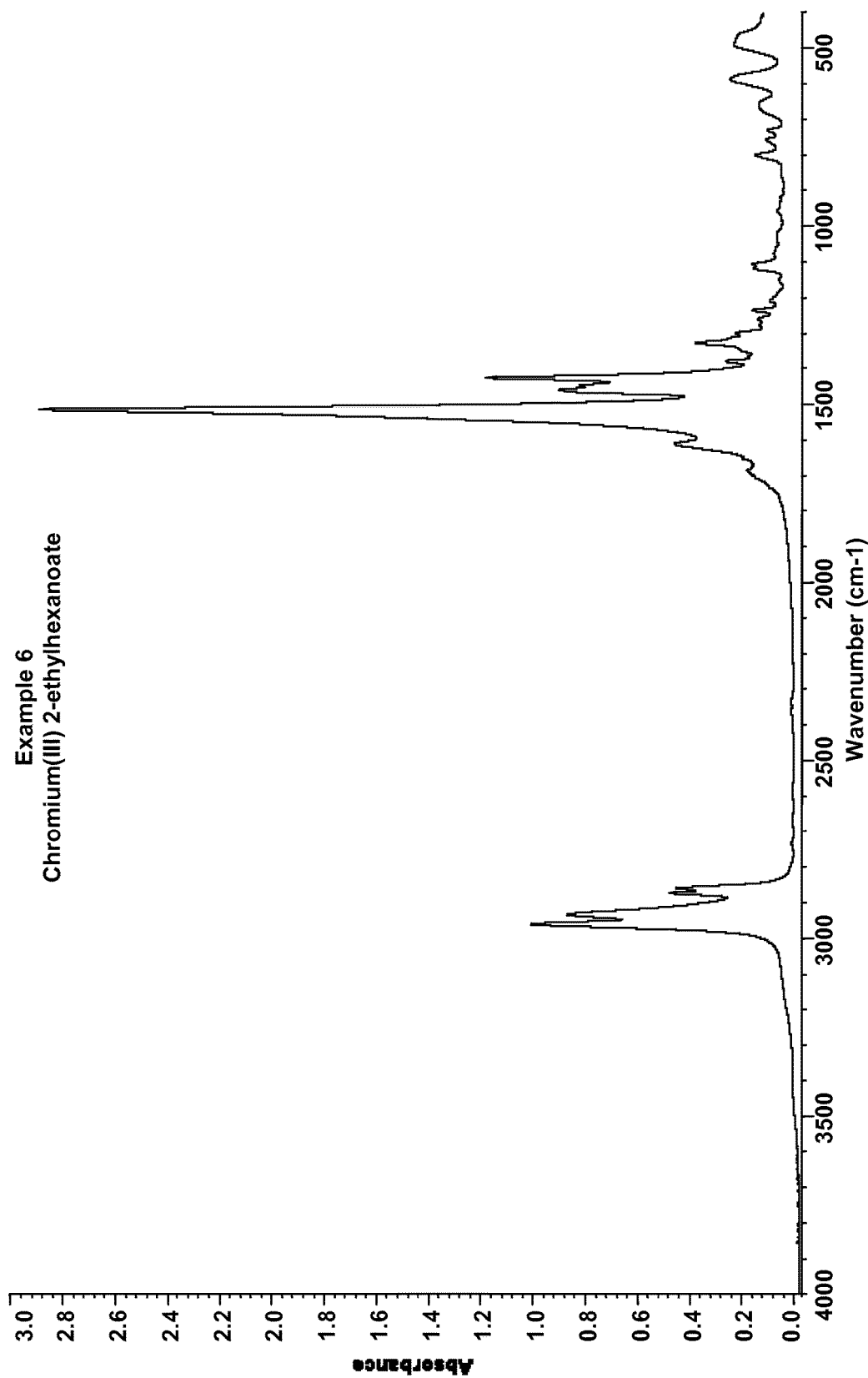
FIG. 13 provides an IR spectrum for the sodium free chromium(III) 2-ethylhexanoate produced according to the methods disclosed herein wherein the sodium 2-ethylhexanoate to $CrCl_3(THF)_3$ molar ratio was approximately 3.3:1.
Figure 14:
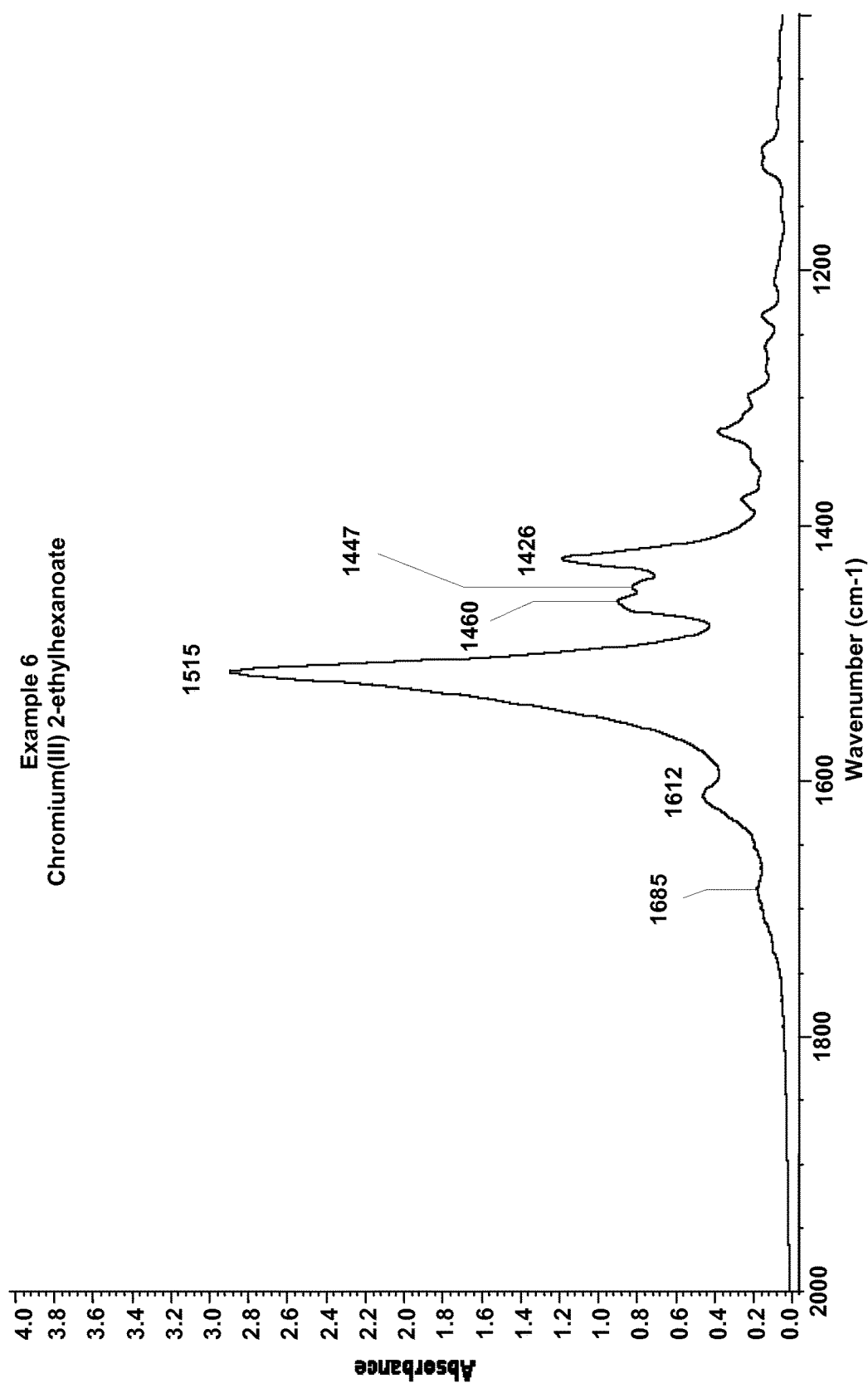
FIG. 14 provides an expanded section, 2000 $cm^{-1}$ to 1000 $cm^{-1}$, of the IR spectrum for the sodium free chromium(III) 2-ethylhexanoate produced according to the methods disclosed herein wherein the sodium 2-ethylhexanoate to $CrCl_3(THF)_3$ molar ratio was approximately 3.3:1.

FIG. 13 provides an IR spectrum for the sodium-free chromium(III) 2-ethylhexanoate produced using Method A on the chromium(III) 2-ethylhexanoate produced using the sodium 2-ethylhexanoate to CrCl₃(THF)₃ molar ratio of approximately 3.3 (EXAMPLE 5). FIG. 14 provides an expanded section, 2000 cm$^{-1}$ to 1000 cm$^{-1}$, of the IR spectrum for the sodium free chromium(III) 2-ethylhexanoate produced using the sodium 2-ethylhexanoate to CrCl₃(THF)₃ molar ratio of approximately 3.3 (EXAMPLE 5). The infrared peak height and various infrared peak height ratios are provide in Table 1.

Example 7

Figure 15:
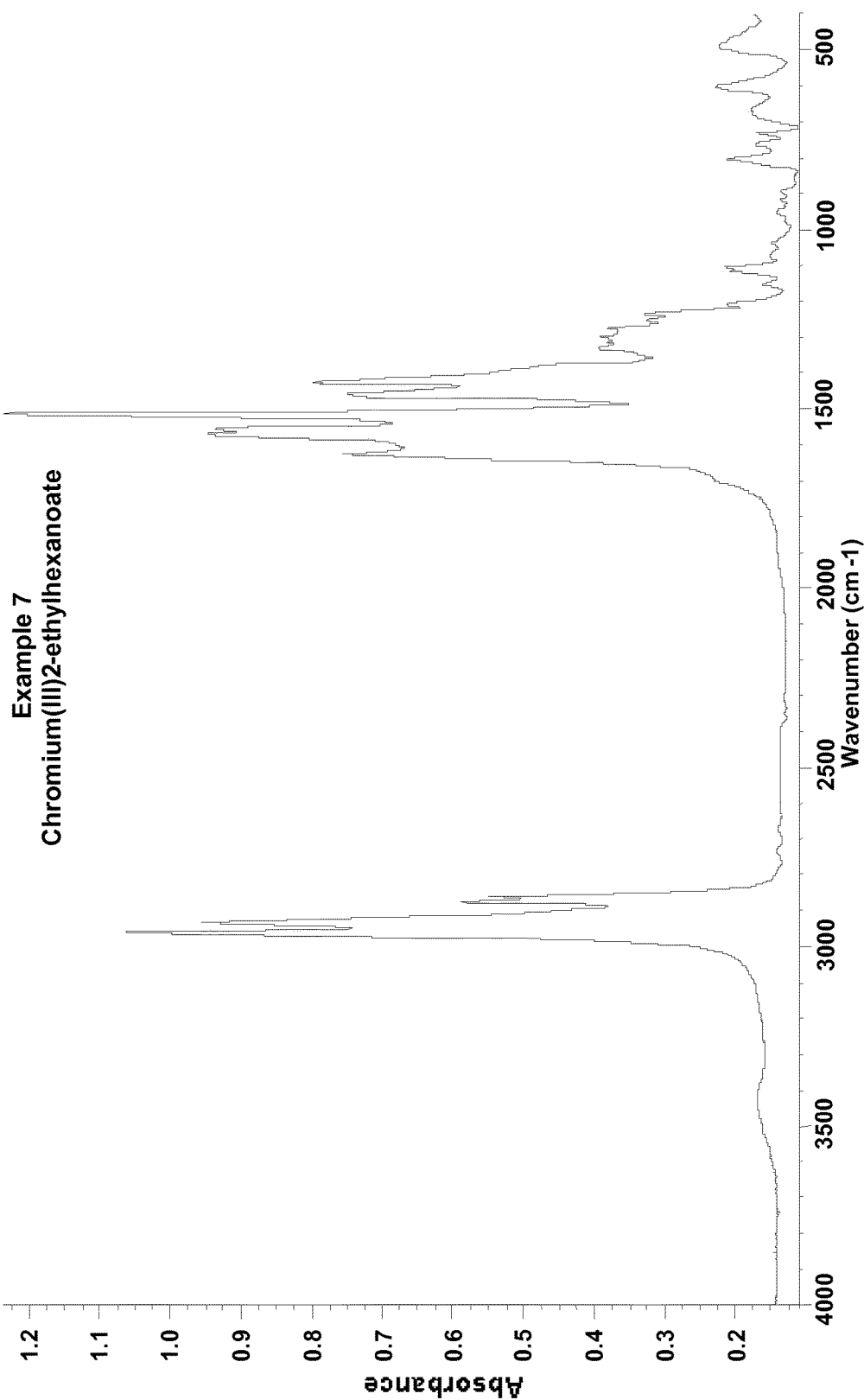
FIG. 15 provides an IR spectrum for the chromium(III) 2-ethylhexanoate produced according to the methods disclosed herein wherein the sodium 2-ethylhexanoate to $CrCl_3(THF)_3$ molar ratio was approximately 4:1.
Figure 16:
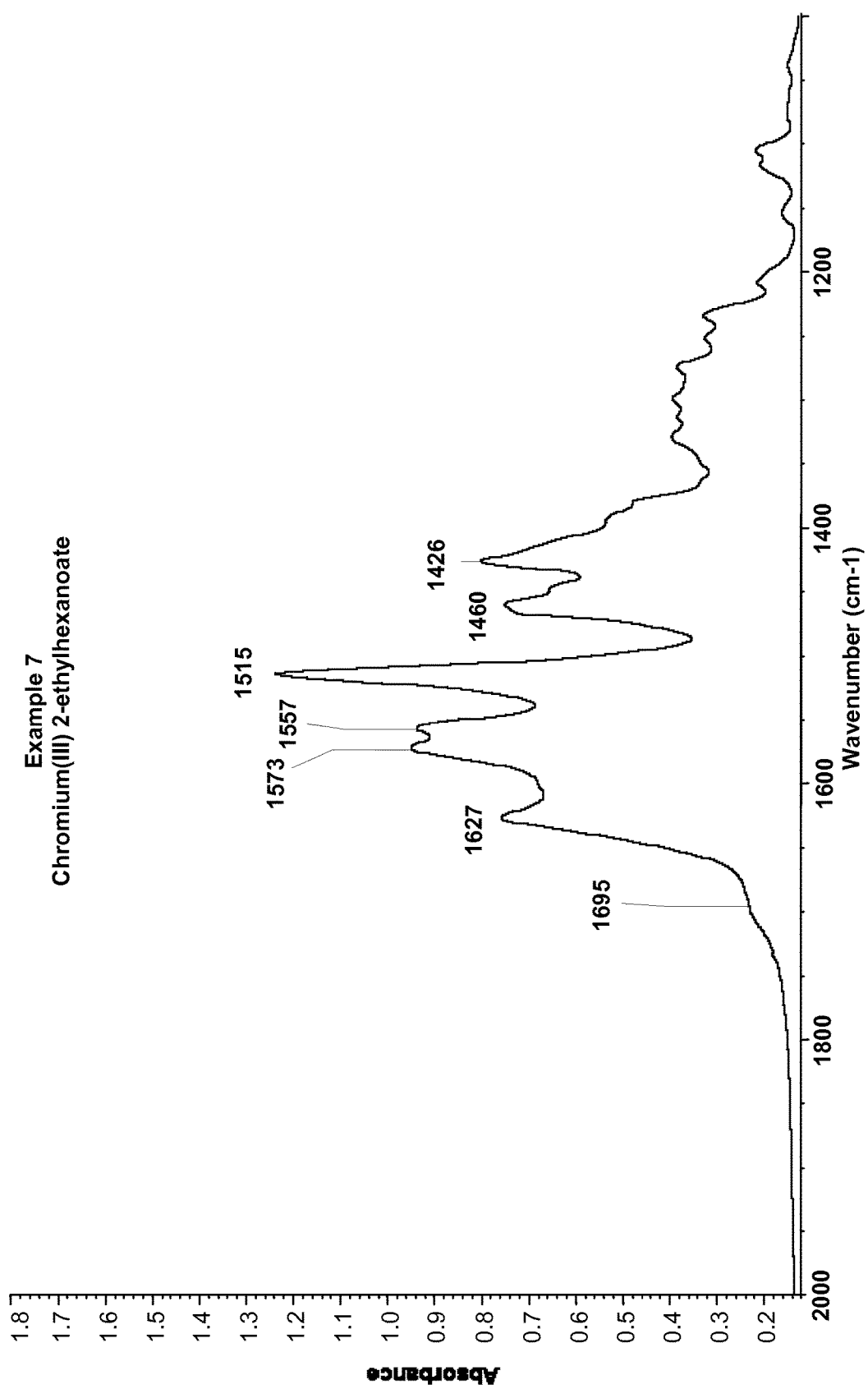
FIG. 16 provides an expanded section, 2000 $cm^{-1}$ to 1000 $cm^{-1}$, of the IR spectrum for the chromium(III) 2-ethylhexanoate produced according to the methods disclosed herein wherein the sodium 2-ethylhexanoate to $CrCl_3(THF)_3$ molar ratio was approximately 4:1.

A round bottom flask (500 mL) was charged with CrCl₃(THF)₃ (19.00 g, 0.0507 mol). A solution of anhydrous sodium 2-ethylhexanoate (34.00 g, 0.205 mol) in THF (200 mL) was added to the solid CrCl₃(THF)₃ while stirring. This reaction mixture was allowed to stir at 23° C. for 60 hr, after which time the solvent was removed to yield a green foamy solid. This solid was heated at 30° C. under vacuum for 2 hr, then extracted into pentane (200 mL) and filtered through Celite® filter aid twice. The solvent was removed from the filtrate under vacuum to provide a green film (27.9 g). FIG. 15 provides an IR spectrum for this chromium(III) 2-ethylhexanoate produced using the sodium 2-ethylhexanoate to CrCl₃(THF)₃ molar ratio of approximately 4. FIG. 16 provides an expanded section, 2000 cm$^{-1}$ to 1000 cm$^{-1}$, of the IR spectrum for this chromium(III) 2-ethylhexanoate produced using the sodium 2-ethylhexanoate to CrCl₃(THF)₃ molar ratio of approximately 4. The infrared peak height and various infrared peak height ratios are provide in Table 1.

Infrared Analysis

Two commercially available chromium(III) 2-ethylhexanoate samples and the four chromium(III) 2-ethylhexanoate samples produced in Example 3-7 were analyzed using infrared analysis. The first commercially available chromium(III) 2-ethylhexanoate sample and the four chromium(III) 2-ethylhexanoate samples were prepared for IR analysis using the following procedure. In a drybox, 5 mg of the sample and 500 mg of anhydrous KBr were extensively ground together by mortar and pestle. A 10-mm KBr sample pellet was then formed by placing 100 mg of the extensively ground sample in a Spectra-Tech Econo-Press Kit. The sample was then transferred to the IR via an airtight receptacle. The IR spectrum was then acquired under a nitrogen purge. Background spectra using pure KBr pellets were collected prior to collecting the desired spectra.

The second commercially available chromium(III) 2-ethylhexanoate sample was manufactured using mineral spirits as the diluent. A couple of drops of the second commercially available chromium(III) 2-ethylhexanoate sample were then placed between two salt KBr plates and transferred to the IR via an airtight receptacle. The IR spectrum was then acquired under a nitrogen purge.

The IR spectra were obtained using a Nicolet® Magna-IR 560 Fourier Transform Infrared spectrometer with a Class 2, 1 mW HeNe laser source, KBr beamsplitter and DTGS detector. A typical experiment encompassed 64 scans (1-4 cm$^{-1}$ resolution) with the background scans collected after the sample scans. The spectra were analyzed using OMNIC® 7.4 software from Thermo Fisher Scientific Inc.

TABLE 1

| | Raw infrared baseline peak heights. | | | | | | | |
|---|---|---|---|---|---|---|---|---|
| Material | 1685 ± 20 cm$^{-1}$ | 1616 ± 20 cm$^{-1}$ | 1579 ± 15 cm$^{-1}$ | 1549 ± 15 cm$^{-1}$ | 1516 ± 15 cm$^{-1}$ | 1460 ± 10 cm$^{-1}$ | 1447 ± 10 cm$^{-1}$ | 1429 ± 15 cm$^{-1}$ |
| First Commercial Source Chromium(III) 2-ethylhexanoate | 0.31 | 1.03 | — | 0.58 | — | 0.73 | — | 0.95 |

TABLE 1-continued

Raw infrared baseline peak heights.

| Material | 1685 ± 20 cm$^{-1}$ | 1616 ± 20 cm$^{-1}$ | 1579 ± 15 cm$^{-1}$ | 1549 ± 15 cm$^{-1}$ | 1516 ± 15 cm$^{-1}$ | 1460 ± 10 cm$^{-1}$ | 1447 ± 10 cm$^{-1}$ | 1429 ± 15 cm$^{-1}$ |
|---|---|---|---|---|---|---|---|---|
| Second Commercial Source Chromium(III) 2-ethylhexanoate | 3.14 | 3.31 | — | 3.36 | — | 3.38 | — | 3.64 |
| Chromium(III) 2-ethylhexanoate of Example 3 | 0.39 | 1.10 | — | — | 3.22 | 1.19 | 1.23 | 1.71 |
| Chromium(III) 2-ethylhexanoate of Example 4 | 0.14 | 0.27 | — | — | 1.00 | 0.43 | 0.41 | 0.53 |
| Chromium(III) 2-ethylhexanoate of Example 5 | 0.25 | 0.56 | 0.63 | — | 1.97 | 0.84 | 0.76 | 0.97 |
| Chromium(III) 2-ethylhexanoate of Example 6 | 0.17 | 0.45 | — | — | 2.89 | 0.86 | 0.81 | 1.17 |
| Chromium(III) 2-ethylhexanoate of Example 7 | 0.23 | 0.75 | 0.94 | 0.93 | 1.24 | 0.75 | — | 0.80 |

TABLE 2

Infrared peak ratios using raw infrared baseline peak heights at the indicated average wavelengths.

| Material | 1516 ± 15 cm$^{-1}$/ 1429 ± 15 cm$^{-1}$ | 1516 ± 15 cm$^{-1}$/ 1616 ± 20 cm$^{-1}$ | 1516 ± 15 cm$^{-1}$/ 1685 ± 20 cm$^{-1}$ | 1429 ± 15 cm$^{-1}$/ 1685 ± 20 cm$^{-1}$ | 1616 ± 20 cm$^{-1}$/ 1429 ± 15 cm$^{-1}$ |
|---|---|---|---|---|---|
| First Commercial Source Chromium(III) 2-ethylhexanoate | 0:1 | 0:1 | 0:1 | 3.1:1 | 1.09:1 |
| Second Commercial Source Chromium(III) 2-ethylhexanoate | 0:1 | 0:1 | 0:1 | 1.15:1 | 0.91:1 |
| Chromium(III) 2-ethylhexanoate of Example 3 | 1.8:1 | 2.9:1 | 8.3:1 | 4.4:1 | 0.64:1 |
| Chromium(III) 2-ethylhexanoate of Example 4 | 1.8:1 | 3.7:1 | 7.2:1 | 3.8:1 | 0.51:1 |
| Chromium(III) 2-ethylhexanoate of Example 5 | 2.0:1 | 3.6:1 | 7.9:1 | 3.9:1 | 0.57:1 |
| Chromium(III) 2-ethylhexanoate of Example 6 | 2.5:1 | 6.5:1 | 17.2:1 | 6.9:1 | 0.38:1 |
| Chromium(III) 2-ethylhexanoate of Example 7 | 1.5:1 | 1.6:1 | 5.4:1 | 3.4:1 | 0.95:1 |

TABLE 3

Drawn infrared baseline (1850 cm$^{-1}$ to 1170 cm$^{-1}$) peak heights.

| Material | 1685 ± 20 cm$^{-1}$ | 1616 ± 20 cm$^{-1}$ | 1579 ± 15 cm$^{-1}$ | 1549 ± 15 cm$^{-1}$ | 1516 ± 15 cm$^{-1}$ | 1460 ± 10 cm$^{-1}$ | 1447 ± 10 cm$^{-1}$ | 1429 ± 15 cm$^{-1}$ |
|---|---|---|---|---|---|---|---|---|
| First Commercial Source Chromium(III) 2-ethylhexanoate | 0.22 | 0.93 | — | 0.49 | — | 0.63 | — | 0.84 |
| Second Commercial Source Chromium(III) 2-ethylhexanoate | 3.01 | 3.12 | — | 3.19 | — | 3.20 | — | 3.46 |
| Chromium(III) 2-ethylhexanoate of Example 3 | 0.28 | 0.99 | — | — | 3.11 | 1.19 | 1.11 | 1.59 |
| Chromium(III) 2-ethylhexanoate of Example 4 | 0.10 | 0.24 | — | — | 0.97 | 0.41 | 0.38 | 0.51 |
| Chromium(III) 2-ethylhexanoate of Example 5 | 0.15 | 0.46 | 0.54 | — | 1.88 | 0.75 | 0.67 | 0.88 |
| Chromium(III) 2-ethylhexanoate of Example 6 | 0.15 | 0.42 | — | — | 2.86 | 0.86 | 0.79 | 1.14 |
| Chromium(III) 2-ethylhexanoate of Example 7 | 0.09 | 0.62 | 0.81 | 0.80 | 1.10 | 0.61 | — | 0.66 |

TABLE 4

Infrared peak ratios using drawn infrared baseline peak heights at the indicated average wavelengths.

| Material | $1516 \pm 15$ cm$^{-1}$/ $1429 \pm 15$ cm$^{-1}$ | $1516 \pm 15$ cm$^{-1}$/ $1616 \pm 20$ cm$^{-1}$ | $1516 \pm 15$ cm$^{-1}$/ $1685 \pm 20$ cm$^{-1}$ | $1429 \pm 15$ cm$^{-1}$/ $1685 \pm 20$ cm$^{-1}$ | $1616 \pm 20$ cm$^{-1}$/ $1429 \pm 15$ cm$^{-1}$ |
|---|---|---|---|---|---|
| First Commercial Source Chromium(III) 2-ethylhexanoate | 0:1 | 0:1 | 0:1 | 3.9:1 | 1.11:1 |
| Second Commercial Source Chromium(III) 2-ethylhexanoate | 0:1 | 0:1 | 0:1 | 1.15:1 | 0.90:1 |
| Chromium(III) 2-ethylhexanoate of Example 3 | 2.0:1 | 3.2:1 | 11.3:1 | 5.8:1 | 0.62:1 |
| Chromium(III) 2-ethylhexanoate of Example 4 | 1.9:1 | 4.0:1 | 9.6:1 | 5.0:1 | 0.47:1 |
| Chromium(III) 2-ethylhexanoate of Example 5 | 2.1:1 | 4.1:1 | 12.4:1 | 5.8:1 | 0.52:1 |
| Chromium(III) 2-ethylhexanoate of Example 6 | 2.5:1 | 1.8:1 | 12.1:1 | 7.8:1 | 0.37:1 |
| Chromium(III) 2-ethylhexanoate of Example 7 | 1.6:1 | 0.56:1 | | 7.3:1 | 0.93:1 |

High Energy X-Ray Diffraction Analysis

The first commercially available chromium(III) 2-ethylhexanoate composition, the chromium(III) 2-ethylhexanoate composition produced using the procedure of Example 5, and the chromium(III) 2-ethylhexanoate composition as produced according to R. T. Hart Jr., N. A. Eckert, J. K. Ngala, A. F. Polley, C. J. Benmore, A. Clark, S. Macha, Presentation CATL 20, The 237th ACS National Meeting, Salt Lake City, Utah, Mar. 23, 2009, (hereafter "the Hart chromium(III) 2-ethylhexanoate composition") was analyzed using high energy X-ray diffraction. The high energy X-ray diffraction data was collected at station 11-ID-C of the Advanced Photon Source at Argonne National Laboratory using a monochromatic X-ray beam of 115 keV having an oval beam profile with a major axis of 15 μm and a minor axis of 1.5 of μm was used to illuminate a 3 mm thick sample approximately 1130 mm from the detector. In this particular instance, a sufficient amount of sample (0.1 mg to 100 mg) to provide a 3 mm path length was placed in a 5 mm 0 D Pyrex® tube having 1 mm thick walls. Once the sample was placed in the Pyrex® tube, the Pyrex® tube was then evacuated, backfilled with $N_2$, and then flame sealed. The high energy X-ray diffraction pattern for the sample contained in the Pyrex® tube was then obtained by impinging the monochromatic X-ray beam of 115 keV (having an oval beam profile with a major axis of 15 μm and a minor axis of 1.5 of μm) upon the sample at a temperature of 298° K. The resulting diffraction pattern was collected on a MAR345 image plate (a 345 mm diameter image plate) at approximately 1130 millimeters from the sample. The angle between the X-ray beam source and the image plate was 180 degrees and a beamstop lined up with the center of the image plate between the sample and the image plate. Typically, the image plate is exposed for 0.5 seconds. Generally, the exposure time can be adjusted to obtain a balance between signal to noise ratio (longer exposure time provide improved signal to noise ratios) and image plate saturation (shorter exposure times reduced image plate detector saturation). Sample to detector distance, beam energy and detector orientation were determined using an external reference scan of $CeO_2$ powder. Background diffractions of an identical empty Pyrex® tube and air were also collected on MAR345 image plates to provide environment and background corrections, respectively, for the sample analysis. High energy X-ray diffraction image manipulations and data analysis was performed using FIT2D (Hammersley, A. P.; Svensson, S. O.; Hanfland, M.; Fitch, A. N.; Häusermann, D. High Pressure Res. 1996, 14, 235-248) version 12.077 (Apr. 5, 2005—Internal Report (1998), ESRF98HA01T, FIT2D V9. 129 Reference Manual V3. 1; A. P. Hammersley) and PDFgetX2 (Qiu, X.; Thompson, J. W.; Billinge, S. J. L. J. Appl. Crystallogr. 2004, 37, 678).

The raw sample image (sample contained in a Pyrex® tube), environment image (empty Pyrex® tube), and background image (air) were corrected for alignment, orientation and sample to detector distance using Fit2D and were then converted to momentum space intensity histograms, I(Q), by radially summing the corrected data images (using standard corrections for multiple scattering, and X-ray polarization using PDFgetX2 (version 1) as shown in B Tomberli, C J Benmore, P A Egelstaff, J Neuefeind and V Honkimäki. 2000 J. Phys.: Condens. Matter, 12, 2597). The environment and the background momentum space intensity histograms were then subtracted from the raw sample momentum space intensity histogram within PDFgetX2 to provide a pure sample momentum space intensity histogram. The pure sample momentum space intensity histogram, I(Q), was then converted to a Structure function, S(Q) which was then converted to the pair distribution function, G(r), by the Fourier transformation of the Structure function, $$G(r) = 4\pi r[\rho(r) - \rho_0] = \left(\frac{2}{\pi}\right)\int_{Q=0}^{Q_{max}} Q[S(Q) - 1]\sin(Qr)\,dQ$$

(where $Q = 4\pi \sin(\theta)/\lambda$, $\rho(r)$ is the local density, and $\rho_0$ is the average density) up to $Q_{max} = 25$ Å$^{-1}$ within PDFgetX2. The pair distribution function, G(r) was then normalized to provide the reduced pair distribution function, g(r) where $g(r) = G(r)\rho_0$. The data points (r,g(r)) are referred to herein as the high energy X-Ray diffraction g(r) data points. Table 5 provides the high energy X-ray diffraction g(r) data points (from 1 angstrom to 6 angstroms) for a chromium(III)

Figure 17:
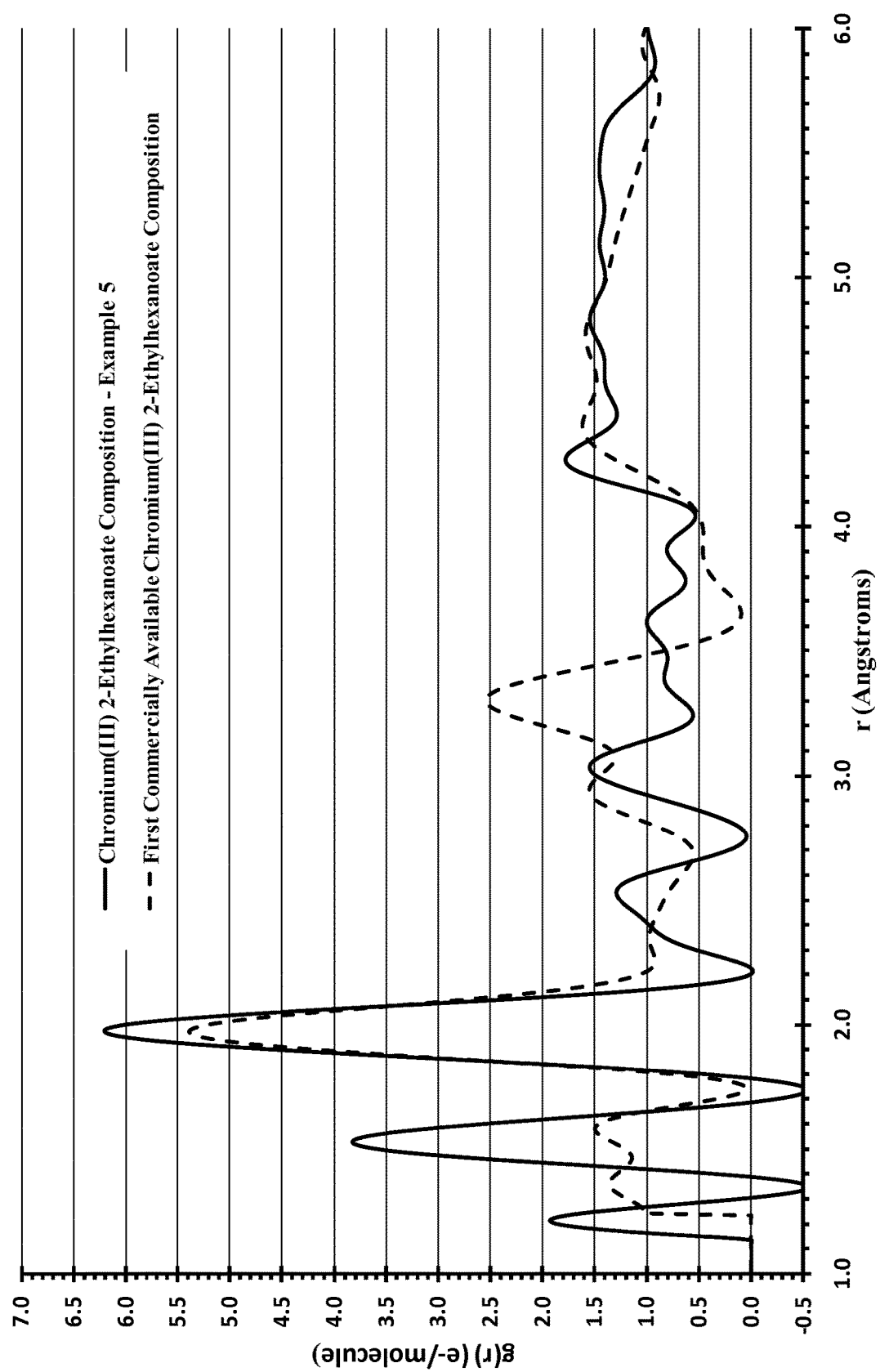
FIG. 17 provides a comparison between the high energy X-ray diffraction g(r) data points of a chromium(III) 2-ethyl hexanoate composition prepared according to the procedures described herein and the high energy X-ray diffraction g(r) data points of a first commercially available chromium (III) 2-ethyl hexanoate composition.
Figure 18:
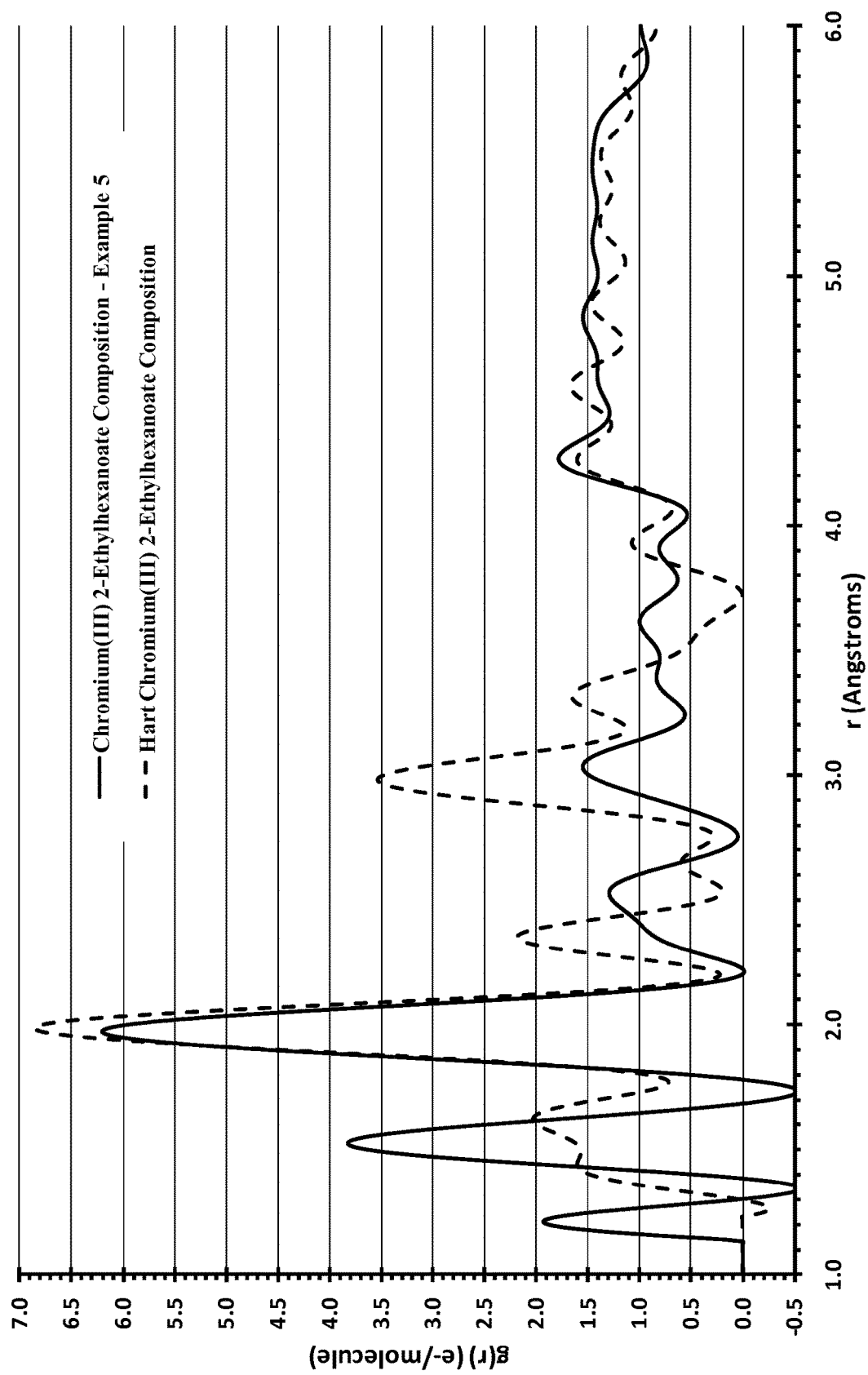
FIG. 18 provides a comparison between the high energy X-ray diffraction g(r) data points of a chromium(III) 2-ethyl hexanoate composition prepared according to the procedures described herein and the high energy X-ray diffraction g(r) data points of a literature reported chromium(III) 2-ethyl hexanoate composition.

2-ethylhexanoate composition prepared according to the procedure of Example 5, the Hart chromium(III) 2-ethylhexanoate composition, and the first commercially available chromium(III) 2-ethylhexanoate composition. FIG. 17 provides a plot of g(r) versus r (from 1 angstrom to 6 angstroms) for the chromium(III) 2-ethylhexanoate composition prepared according to the procedure of Example 5 and the first commercially available chromium(III) 2-ethylhexanoate composition. FIG. 18 provides a plot of g(r) versus r (from 1 angstrom to 6 angstroms) for the chromium(III) 2-ethylhexanoate composition prepared according to the procedure of Example 5 and the Hart chromium(III) 2-ethylhexanoate composition. It can be clearly seen that the chromium(III) 2-ethylhexanoate composition prepared according to the procedure of Example 5 is significantly different from the first commercially available chromium(III) 2-ethylhexanoate composition and the Hart chromium(III) 2-ethylhexanoate composition.

TABLE 5

Chromium(III) 2-ethylhexanoate g(r) data points

| r (Å) | g(r) Exam. 5 Sample | g(r) Hart | g(r) 1st comm. Sample |
|---|---|---|---|
| 1.00 | 0.0000 | 0.0000 | 0.0000 |
| 1.01 | 0.0000 | 0.0000 | 0.0000 |
| 1.02 | 0.0000 | 0.0000 | 0.0000 |
| 1.03 | 0.0000 | 0.0000 | 0.0000 |
| 1.04 | 0.0000 | 0.0000 | 0.0000 |
| 1.05 | 0.0000 | 0.0000 | 0.0000 |
| 1.06 | 0.0000 | 0.0000 | 0.0000 |
| 1.07 | 0.0000 | 0.0000 | 0.0000 |
| 1.08 | 0.0000 | 0.0000 | 0.0000 |
| 1.09 | 0.0000 | 0.0000 | 0.0000 |
| 1.10 | 0.0000 | 0.0000 | 0.0000 |
| 1.11 | 0.0000 | 0.0000 | 0.0000 |
| 1.12 | 0.0000 | 0.0000 | 0.0000 |
| 1.13 | 0.0000 | 0.0000 | 0.0000 |
| 1.14 | 0.2350 | 0.0000 | 0.0000 |
| 1.15 | 0.6456 | 0.0000 | 0.0000 |
| 1.16 | 1.0192 | 0.0000 | 0.0000 |
| 1.17 | 1.3413 | 0.0000 | 0.0000 |
| 1.18 | 1.6002 | 0.0000 | 0.0000 |
| 1.19 | 1.7877 | 0.0000 | 0.0000 |
| 1.20 | 1.8988 | 0.0000 | 0.0000 |
| 1.21 | 1.9323 | 0.0000 | 0.0000 |
| 1.22 | 1.8907 | 0.0000 | 0.0000 |
| 1.23 | 1.7796 | 0.0000 | 0.0000 |
| 1.24 | 1.6077 | −0.1367 | 1.0345 |
| 1.25 | 1.3862 | −0.2256 | 1.0295 |
| 1.26 | 1.1282 | −0.2610 | 1.0428 |
| 1.27 | 0.8482 | −0.2467 | 1.0705 |
| 1.28 | 0.5613 | −0.1877 | 1.1088 |
| 1.29 | 0.2825 | −0.0903 | 1.1534 |
| 1.30 | 0.0260 | 0.0382 | 1.2004 |
| 1.31 | −0.1949 | 0.1901 | 1.2460 |
| 1.32 | −0.3690 | 0.3574 | 1.2867 |
| 1.33 | −0.4872 | 0.5324 | 1.3200 |
| 1.34 | −0.5431 | 0.7077 | 1.3438 |
| 1.35 | −0.5326 | 0.8769 | 1.3570 |
| 1.36 | −0.4549 | 1.0343 | 1.3593 |
| 1.37 | −0.3115 | 1.1755 | 1.3510 |
| 1.38 | −0.1067 | 1.2974 | 1.3336 |
| 1.39 | 0.1530 | 1.3980 | 1.3087 |
| 1.40 | 0.4590 | 1.4768 | 1.2786 |
| 1.41 | 0.8012 | 1.5342 | 1.2461 |
| 1.42 | 1.1684 | 1.5720 | 1.2140 |
| 1.43 | 1.5487 | 1.5928 | 1.1850 |
| 1.44 | 1.9300 | 1.5997 | 1.1617 |
| 1.45 | 2.3005 | 1.5967 | 1.1462 |
| 1.46 | 2.6491 | 1.5876 | 1.1402 |
| 1.47 | 2.9657 | 1.5764 | 1.1448 |
| 1.48 | 3.2415 | 1.5668 | 1.1602 |
| 1.49 | 3.4694 | 1.5621 | 1.1860 |
| 1.50 | 3.6440 | 1.5650 | 1.2208 |
| 1.51 | 3.7615 | 1.5773 | 1.2629 |
| 1.52 | 3.8202 | 1.6000 | 1.3095 |
| 1.53 | 3.8201 | 1.6330 | 1.3576 |
| 1.54 | 3.7628 | 1.6756 | 1.4039 |
| 1.55 | 3.6514 | 1.7259 | 1.4445 |
| 1.56 | 3.4903 | 1.7815 | 1.4760 |
| 1.57 | 3.2850 | 1.8391 | 1.4948 |
| 1.58 | 3.0418 | 1.8951 | 1.4980 |
| 1.59 | 2.7675 | 1.9456 | 1.4831 |
| 1.60 | 2.4696 | 1.9866 | 1.4484 |
| 1.61 | 2.1553 | 2.0144 | 1.3930 |
| 1.62 | 1.8323 | 2.0256 | 1.3170 |
| 1.63 | 1.5077 | 2.0175 | 1.2215 |
| 1.64 | 1.1884 | 1.9881 | 1.1087 |
| 1.65 | 0.8812 | 1.9367 | 0.9817 |
| 1.66 | 0.5920 | 1.8633 | 0.8445 |
| 1.67 | 0.3264 | 1.7692 | 0.7021 |
| 1.68 | 0.0895 | 1.6570 | 0.5598 |
| 1.69 | −0.1141 | 1.5304 | 0.4237 |
| 1.70 | −0.2807 | 1.3942 | 0.2998 |
| 1.71 | −0.4068 | 1.2539 | 0.1944 |
| 1.72 | −0.4895 | 1.1161 | 0.1135 |
| 1.73 | −0.5267 | 0.9878 | 0.0625 |
| 1.74 | −0.5166 | 0.8762 | 0.0464 |
| 1.75 | −0.4583 | 0.7886 | 0.0691 |
| 1.76 | −0.3513 | 0.7321 | 0.1335 |
| 1.77 | −0.1959 | 0.7131 | 0.2415 |
| 1.78 | 0.0069 | 0.7373 | 0.3935 |
| 1.79 | 0.2553 | 0.8093 | 0.5888 |
| 1.80 | 0.5467 | 0.9321 | 0.8254 |
| 1.81 | 0.8775 | 1.1077 | 1.0997 |
| 1.82 | 1.2436 | 1.3360 | 1.4072 |
| 1.83 | 1.6396 | 1.6155 | 1.7425 |
| 1.84 | 2.0596 | 1.9428 | 2.0988 |
| 1.85 | 2.4967 | 2.3128 | 2.4691 |
| 1.86 | 2.9436 | 2.7190 | 2.8457 |
| 1.87 | 3.3923 | 3.1533 | 3.2206 |
| 1.88 | 3.8343 | 3.6063 | 3.5858 |
| 1.89 | 4.2612 | 4.0677 | 3.9337 |
| 1.90 | 4.6644 | 4.5268 | 4.2569 |
| 1.91 | 5.0354 | 4.9721 | 4.5488 |
| 1.92 | 5.3665 | 5.3925 | 4.8036 |
| 1.93 | 5.6504 | 5.7769 | 5.0164 |
| 1.94 | 5.8807 | 6.1153 | 5.1834 |
| 1.95 | 6.0524 | 6.3983 | 5.3022 |
| 1.96 | 6.1615 | 6.6181 | 5.3714 |
| 1.97 | 6.2055 | 6.7685 | 5.3907 |
| 1.98 | 6.1833 | 6.8448 | 5.3614 |
| 1.99 | 6.0957 | 6.8445 | 5.2855 |
| 2.00 | 5.9447 | 6.7671 | 5.1661 |
| 2.01 | 5.7341 | 6.6140 | 5.0074 |
| 2.02 | 5.4688 | 6.3888 | 4.8141 |
| 2.03 | 5.1554 | 6.0969 | 4.5915 |
| 2.04 | 4.8012 | 5.7455 | 4.3452 |
| 2.05 | 4.4146 | 5.3432 | 4.0813 |
| 2.06 | 4.0043 | 4.9000 | 3.8056 |
| 2.07 | 3.5797 | 4.4270 | 3.5240 |
| 2.08 | 3.1500 | 3.9355 | 3.2419 |
| 2.09 | 2.7241 | 3.4375 | 2.9644 |
| 2.10 | 2.3107 | 2.9447 | 2.6962 |
| 2.11 | 1.9174 | 2.4684 | 2.4413 |
| 2.12 | 1.5511 | 2.0191 | 2.2028 |
| 2.13 | 1.2175 | 1.6064 | 1.9834 |
| 2.14 | 0.9210 | 1.2384 | 1.7849 |
| 2.15 | 0.6648 | 0.9217 | 1.6085 |
| 2.16 | 0.4507 | 0.6612 | 1.4547 |
| 2.17 | 0.2791 | 0.4600 | 1.3234 |
| 2.18 | 0.1492 | 0.3193 | 1.2137 |
| 2.19 | 0.0592 | 0.2385 | 1.1246 |
| 2.20 | 0.0062 | 0.2151 | 1.0545 |
| 2.21 | −0.0136 | 0.2452 | 1.0015 |

TABLE 5-continued

Chromium(III) 2-ethylhexanoate g(r) data points

| r (Å) | g(r) Exam. 5 Sample | g(r) Hart | g(r) 1st comm. Sample |
|---|---|---|---|
| 2.22 | −0.0044 | 0.3233 | 0.9636 |
| 2.23 | 0.0291 | 0.4426 | 0.9385 |
| 2.24 | 0.0819 | 0.5954 | 0.9241 |
| 2.25 | 0.1492 | 0.7734 | 0.9182 |
| 2.26 | 0.2262 | 0.9678 | 0.9187 |
| 2.27 | 0.3087 | 1.1697 | 0.9237 |
| 2.28 | 0.3928 | 1.3705 | 0.9315 |
| 2.29 | 0.4753 | 1.5621 | 0.9407 |
| 2.30 | 0.5537 | 1.7370 | 0.9500 |
| 2.31 | 0.6260 | 1.8889 | 0.9584 |
| 2.32 | 0.6911 | 2.0123 | 0.9653 |
| 2.33 | 0.7485 | 2.1034 | 0.9702 |
| 2.34 | 0.7982 | 2.1594 | 0.9727 |
| 2.35 | 0.8409 | 2.1792 | 0.9728 |
| 2.36 | 0.8773 | 2.1628 | 0.9706 |
| 2.37 | 0.9088 | 2.1118 | 0.9662 |
| 2.38 | 0.9368 | 2.0287 | 0.9599 |
| 2.39 | 0.9625 | 1.9172 | 0.9520 |
| 2.40 | 0.9873 | 1.7820 | 0.9428 |
| 2.41 | 1.0123 | 1.6282 | 0.9326 |
| 2.42 | 1.0383 | 1.4615 | 0.9219 |
| 2.43 | 1.0658 | 1.2879 | 0.9107 |
| 2.44 | 1.0949 | 1.1130 | 0.8993 |
| 2.45 | 1.1254 | 0.9425 | 0.8879 |
| 2.46 | 1.1566 | 0.7815 | 0.8764 |
| 2.47 | 1.1878 | 0.6345 | 0.8648 |
| 2.48 | 1.2176 | 0.5053 | 0.8532 |
| 2.49 | 1.2447 | 0.3965 | 0.8413 |
| 2.50 | 1.2676 | 0.3101 | 0.8290 |
| 2.51 | 1.2848 | 0.2470 | 0.8162 |
| 2.52 | 1.2947 | 0.2069 | 0.8027 |
| 2.53 | 1.2962 | 0.1889 | 0.7883 |
| 2.54 | 1.2880 | 0.1909 | 0.7730 |
| 2.55 | 1.2695 | 0.2105 | 0.7566 |
| 2.56 | 1.2401 | 0.2442 | 0.7391 |
| 2.57 | 1.1998 | 0.2886 | 0.7207 |
| 2.58 | 1.1488 | 0.3396 | 0.7015 |
| 2.59 | 1.0878 | 0.3934 | 0.6816 |
| 2.60 | 1.0180 | 0.4462 | 0.6615 |
| 2.61 | 0.9406 | 0.4943 | 0.6415 |
| 2.62 | 0.8572 | 0.5349 | 0.6221 |
| 2.63 | 0.7698 | 0.5654 | 0.6039 |
| 2.64 | 0.6802 | 0.5841 | 0.5873 |
| 2.65 | 0.5905 | 0.5900 | 0.5732 |
| 2.66 | 0.5026 | 0.5831 | 0.5620 |
| 2.67 | 0.4186 | 0.5640 | 0.5544 |
| 2.68 | 0.3402 | 0.5342 | 0.5511 |
| 2.69 | 0.2690 | 0.4959 | 0.5526 |
| 2.70 | 0.2063 | 0.4521 | 0.5594 |
| 2.71 | 0.1532 | 0.4062 | 0.5719 |
| 2.72 | 0.1105 | 0.3620 | 0.5904 |
| 2.73 | 0.0787 | 0.3234 | 0.6151 |
| 2.74 | 0.0581 | 0.2945 | 0.6460 |
| 2.75 | 0.0486 | 0.2793 | 0.6830 |
| 2.76 | 0.0500 | 0.2815 | 0.7259 |
| 2.77 | 0.0619 | 0.3041 | 0.7741 |
| 2.78 | 0.0836 | 0.3497 | 0.8272 |
| 2.79 | 0.1145 | 0.4203 | 0.8843 |
| 2.80 | 0.1538 | 0.5168 | 0.9448 |
| 2.81 | 0.2007 | 0.6394 | 1.0075 |
| 2.82 | 0.2544 | 0.7874 | 1.0714 |
| 2.83 | 0.3141 | 0.9589 | 1.1354 |
| 2.84 | 0.3790 | 1.1515 | 1.1983 |
| 2.85 | 0.4483 | 1.3618 | 1.2590 |
| 2.86 | 0.5214 | 1.5857 | 1.3163 |
| 2.87 | 0.5974 | 1.8185 | 1.3692 |
| 2.88 | 0.6758 | 2.0551 | 1.4167 |
| 2.89 | 0.7558 | 2.2902 | 1.4578 |
| 2.90 | 0.8367 | 2.5182 | 1.4921 |
| 2.91 | 0.9178 | 2.7337 | 1.5188 |
| 2.92 | 0.9982 | 2.9316 | 1.5378 |
| 2.93 | 1.0769 | 3.1073 | 1.5489 |
| 2.94 | 1.1532 | 3.2564 | 1.5523 |
| 2.95 | 1.2259 | 3.3757 | 1.5483 |
| 2.96 | 1.2940 | 3.4625 | 1.5377 |
| 2.97 | 1.3563 | 3.5151 | 1.5211 |
| 2.98 | 1.4119 | 3.5327 | 1.4995 |
| 2.99 | 1.4595 | 3.5156 | 1.4743 |
| 3.00 | 1.4982 | 3.4649 | 1.4466 |
| 3.01 | 1.5271 | 3.3827 | 1.4179 |
| 3.02 | 1.5454 | 3.2719 | 1.3897 |
| 3.03 | 1.5526 | 3.1362 | 1.3635 |
| 3.04 | 1.5484 | 2.9797 | 1.3407 |
| 3.05 | 1.5326 | 2.8072 | 1.3228 |
| 3.06 | 1.5056 | 2.6237 | 1.3111 |
| 3.07 | 1.4679 | 2.4343 | 1.3067 |
| 3.08 | 1.4201 | 2.2442 | 1.3106 |
| 3.09 | 1.3636 | 2.0581 | 1.3234 |
| 3.10 | 1.2995 | 1.8808 | 1.3457 |
| 3.11 | 1.2296 | 1.7163 | 1.3778 |
| 3.12 | 1.1555 | 1.5681 | 1.4194 |
| 3.13 | 1.0791 | 1.4391 | 1.4704 |
| 3.14 | 1.0024 | 1.3314 | 1.5301 |
| 3.15 | 0.9273 | 1.2463 | 1.5977 |
| 3.16 | 0.8556 | 1.1842 | 1.6720 |
| 3.17 | 0.7892 | 1.1449 | 1.7517 |
| 3.18 | 0.7294 | 1.1274 | 1.8354 |
| 3.19 | 0.6775 | 1.1299 | 1.9214 |
| 3.20 | 0.6346 | 1.1501 | 2.0079 |
| 3.21 | 0.6011 | 1.1853 | 2.0933 |
| 3.22 | 0.5775 | 1.2324 | 2.1757 |
| 3.23 | 0.5637 | 1.2879 | 2.2534 |
| 3.24 | 0.5592 | 1.3483 | 2.3247 |
| 3.25 | 0.5632 | 1.4102 | 2.3880 |
| 3.26 | 0.5750 | 1.4703 | 2.4419 |
| 3.27 | 0.5931 | 1.5254 | 2.4852 |
| 3.28 | 0.6163 | 1.5729 | 2.5170 |
| 3.29 | 0.6430 | 1.6104 | 2.5363 |
| 3.30 | 0.6717 | 1.6362 | 2.5427 |
| 3.31 | 0.7011 | 1.6489 | 2.5359 |
| 3.32 | 0.7296 | 1.6480 | 2.5158 |
| 3.33 | 0.7561 | 1.6331 | 2.4826 |
| 3.34 | 0.7796 | 1.6047 | 2.4366 |
| 3.35 | 0.7993 | 1.5637 | 2.3786 |
| 3.36 | 0.8148 | 1.5112 | 2.3092 |
| 3.37 | 0.8258 | 1.4489 | 2.2295 |
| 3.38 | 0.8323 | 1.3787 | 2.1406 |
| 3.39 | 0.8348 | 1.3026 | 2.0436 |
| 3.40 | 0.8338 | 1.2228 | 1.9398 |
| 3.41 | 0.8301 | 1.1413 | 1.8306 |
| 3.42 | 0.8245 | 1.0602 | 1.7173 |
| 3.43 | 0.8180 | 0.9813 | 1.6012 |
| 3.44 | 0.8116 | 0.9063 | 1.4837 |
| 3.45 | 0.8063 | 0.8364 | 1.3660 |
| 3.46 | 0.8031 | 0.7726 | 1.2493 |
| 3.47 | 0.8025 | 0.7155 | 1.1347 |
| 3.48 | 0.8052 | 0.6653 | 1.0233 |
| 3.49 | 0.8115 | 0.6220 | 0.9159 |
| 3.50 | 0.8216 | 0.5850 | 0.8135 |
| 3.51 | 0.8351 | 0.5538 | 0.7166 |
| 3.52 | 0.8519 | 0.5274 | 0.6259 |
| 3.53 | 0.8712 | 0.5046 | 0.5418 |
| 3.54 | 0.8922 | 0.4843 | 0.4648 |
| 3.55 | 0.9140 | 0.4653 | 0.3951 |
| 3.56 | 0.9354 | 0.4463 | 0.3328 |
| 3.57 | 0.9555 | 0.4263 | 0.2781 |
| 3.58 | 0.9731 | 0.4044 | 0.2308 |
| 3.59 | 0.9872 | 0.3799 | 0.1910 |
| 3.60 | 0.9968 | 0.3525 | 0.1585 |
| 3.61 | 1.0013 | 0.3218 | 0.1329 |
| 3.62 | 1.0000 | 0.2882 | 0.1140 |
| 3.63 | 0.9928 | 0.2521 | 0.1015 |
| 3.64 | 0.9797 | 0.2143 | 0.0949 |
| 3.65 | 0.9608 | 0.1757 | 0.0938 |
| 3.66 | 0.9368 | 0.1376 | 0.0976 |
| 3.67 | 0.9083 | 0.1014 | 0.1060 |

TABLE 5-continued

Chromium(III) 2-ethylhexanoate g(r) data points

| r (Å) | g(r) Exam. 5 Sample | g(r) Hart | g(r) 1st comm. Sample |
|---|---|---|---|
| 3.68 | 0.8764 | 0.0685 | 0.1182 |
| 3.69 | 0.8422 | 0.0405 | 0.1338 |
| 3.70 | 0.8070 | 0.0188 | 0.1522 |
| 3.71 | 0.7720 | 0.0047 | 0.1728 |
| 3.72 | 0.7386 | −0.0005 | 0.1952 |
| 3.73 | 0.7081 | 0.0041 | 0.2186 |
| 3.74 | 0.6814 | 0.0192 | 0.2427 |
| 3.75 | 0.6597 | 0.0451 | 0.2669 |
| 3.76 | 0.6435 | 0.0818 | 0.2908 |
| 3.77 | 0.6334 | 0.1289 | 0.3139 |
| 3.78 | 0.6296 | 0.1856 | 0.3360 |
| 3.79 | 0.6318 | 0.2510 | 0.3567 |
| 3.80 | 0.6398 | 0.3236 | 0.3757 |
| 3.81 | 0.6528 | 0.4017 | 0.3929 |
| 3.82 | 0.6700 | 0.4834 | 0.4082 |
| 3.83 | 0.6902 | 0.5667 | 0.4213 |
| 3.84 | 0.7121 | 0.6495 | 0.4325 |
| 3.85 | 0.7345 | 0.7295 | 0.4415 |
| 3.86 | 0.7560 | 0.8048 | 0.4487 |
| 3.87 | 0.7752 | 0.8734 | 0.4540 |
| 3.88 | 0.7910 | 0.9336 | 0.4576 |
| 3.89 | 0.8022 | 0.9840 | 0.4598 |
| 3.90 | 0.8081 | 1.0235 | 0.4608 |
| 3.91 | 0.8080 | 1.0514 | 0.4609 |
| 3.92 | 0.8018 | 1.0674 | 0.4602 |
| 3.93 | 0.7895 | 1.0715 | 0.4591 |
| 3.94 | 0.7715 | 1.0643 | 0.4579 |
| 3.95 | 0.7484 | 1.0468 | 0.4568 |
| 3.96 | 0.7213 | 1.0201 | 0.4561 |
| 3.97 | 0.6913 | 0.9859 | 0.4561 |
| 3.98 | 0.6600 | 0.9461 | 0.4570 |
| 3.99 | 0.6290 | 0.9026 | 0.4590 |
| 4.00 | 0.5999 | 0.8578 | 0.4625 |
| 4.01 | 0.5745 | 0.8137 | 0.4675 |
| 4.02 | 0.5545 | 0.7726 | 0.4743 |
| 4.03 | 0.5414 | 0.7365 | 0.4831 |
| 4.04 | 0.5366 | 0.7073 | 0.4939 |
| 4.05 | 0.5413 | 0.6866 | 0.5070 |
| 4.06 | 0.5562 | 0.6757 | 0.5224 |
| 4.07 | 0.5819 | 0.6755 | 0.5402 |
| 4.08 | 0.6186 | 0.6865 | 0.5606 |
| 4.09 | 0.6661 | 0.7090 | 0.5835 |
| 4.10 | 0.7237 | 0.7426 | 0.6090 |
| 4.11 | 0.7906 | 0.7866 | 0.6370 |
| 4.12 | 0.8656 | 0.8401 | 0.6677 |
| 4.13 | 0.9471 | 0.9015 | 0.7008 |
| 4.14 | 1.0334 | 0.9694 | 0.7364 |
| 4.15 | 1.1227 | 1.0418 | 0.7742 |
| 4.16 | 1.2128 | 1.1166 | 0.8142 |
| 4.17 | 1.3018 | 1.1919 | 0.8562 |
| 4.18 | 1.3877 | 1.2655 | 0.8998 |
| 4.19 | 1.4685 | 1.3355 | 0.9450 |
| 4.20 | 1.5426 | 1.3999 | 0.9913 |
| 4.21 | 1.6085 | 1.4572 | 1.0384 |
| 4.22 | 1.6649 | 1.5061 | 1.0860 |
| 4.23 | 1.7110 | 1.5454 | 1.1336 |
| 4.24 | 1.7459 | 1.5745 | 1.1810 |
| 4.25 | 1.7697 | 1.5931 | 1.2277 |
| 4.26 | 1.7822 | 1.6012 | 1.2732 |
| 4.27 | 1.7839 | 1.5993 | 1.3172 |
| 4.28 | 1.7754 | 1.5881 | 1.3593 |
| 4.29 | 1.7578 | 1.5688 | 1.3991 |
| 4.30 | 1.7323 | 1.5427 | 1.4362 |
| 4.31 | 1.7001 | 1.5114 | 1.4704 |
| 4.32 | 1.6628 | 1.4765 | 1.5013 |
| 4.33 | 1.6218 | 1.4399 | 1.5288 |
| 4.34 | 1.5789 | 1.4033 | 1.5527 |
| 4.35 | 1.5353 | 1.3686 | 1.5729 |
| 4.36 | 1.4927 | 1.3372 | 1.5894 |
| 4.37 | 1.4522 | 1.3107 | 1.6021 |
| 4.38 | 1.4149 | 1.2903 | 1.6112 |
| 4.39 | 1.3818 | 1.2769 | 1.6169 |
| 4.40 | 1.3535 | 1.2710 | 1.6192 |
| 4.41 | 1.3304 | 1.2731 | 1.6185 |
| 4.42 | 1.3128 | 1.2829 | 1.6152 |
| 4.43 | 1.3006 | 1.3002 | 1.6094 |
| 4.44 | 1.2937 | 1.3242 | 1.6016 |
| 4.45 | 1.2916 | 1.3541 | 1.5921 |
| 4.46 | 1.2938 | 1.3885 | 1.5815 |
| 4.47 | 1.2997 | 1.4262 | 1.5700 |
| 4.48 | 1.3085 | 1.4655 | 1.5580 |
| 4.49 | 1.3193 | 1.5050 | 1.5460 |
| 4.50 | 1.3316 | 1.5430 | 1.5343 |
| 4.51 | 1.3444 | 1.5779 | 1.5233 |
| 4.52 | 1.3572 | 1.6084 | 1.5131 |
| 4.53 | 1.3692 | 1.6332 | 1.5041 |
| 4.54 | 1.3801 | 1.6513 | 1.4965 |
| 4.55 | 1.3895 | 1.6618 | 1.4905 |
| 4.56 | 1.3972 | 1.6644 | 1.4860 |
| 4.57 | 1.4030 | 1.6587 | 1.4833 |
| 4.58 | 1.4070 | 1.6449 | 1.4824 |
| 4.59 | 1.4094 | 1.6234 | 1.4831 |
| 4.60 | 1.4104 | 1.5948 | 1.4854 |
| 4.61 | 1.4104 | 1.5602 | 1.4892 |
| 4.62 | 1.4097 | 1.5206 | 1.4943 |
| 4.63 | 1.4088 | 1.4775 | 1.5007 |
| 4.64 | 1.4082 | 1.4322 | 1.5080 |
| 4.65 | 1.4081 | 1.3862 | 1.5160 |
| 4.66 | 1.4091 | 1.3411 | 1.5246 |
| 4.67 | 1.4113 | 1.2983 | 1.5334 |
| 4.68 | 1.4151 | 1.2593 | 1.5422 |
| 4.69 | 1.4205 | 1.2251 | 1.5508 |
| 4.70 | 1.4277 | 1.1968 | 1.5590 |
| 4.71 | 1.4364 | 1.1752 | 1.5666 |
| 4.72 | 1.4466 | 1.1609 | 1.5733 |
| 4.73 | 1.4580 | 1.1540 | 1.5789 |
| 4.74 | 1.4702 | 1.1545 | 1.5834 |
| 4.75 | 1.4829 | 1.1622 | 1.5867 |
| 4.76 | 1.4957 | 1.1765 | 1.5886 |
| 4.77 | 1.5080 | 1.1965 | 1.5890 |
| 4.78 | 1.5194 | 1.2213 | 1.5880 |
| 4.79 | 1.5295 | 1.2498 | 1.5855 |
| 4.80 | 1.5379 | 1.2807 | 1.5816 |
| 4.81 | 1.5443 | 1.3126 | 1.5763 |
| 4.82 | 1.5484 | 1.3442 | 1.5698 |
| 4.83 | 1.5500 | 1.3743 | 1.5621 |
| 4.84 | 1.5490 | 1.4015 | 1.5533 |
| 4.85 | 1.5456 | 1.4249 | 1.5437 |
| 4.86 | 1.5397 | 1.4436 | 1.5332 |
| 4.87 | 1.5317 | 1.4567 | 1.5222 |
| 4.88 | 1.5218 | 1.4639 | 1.5107 |
| 4.89 | 1.5105 | 1.4649 | 1.4990 |
| 4.90 | 1.4980 | 1.4596 | 1.4871 |
| 4.91 | 1.4849 | 1.4484 | 1.4753 |
| 4.92 | 1.4716 | 1.4317 | 1.4636 |
| 4.93 | 1.4586 | 1.4101 | 1.4523 |
| 4.94 | 1.4464 | 1.3845 | 1.4413 |
| 4.95 | 1.4352 | 1.3559 | 1.4307 |
| 4.96 | 1.4256 | 1.3253 | 1.4207 |
| 4.97 | 1.4176 | 1.2940 | 1.4113 |
| 4.98 | 1.4116 | 1.2629 | 1.4025 |
| 4.99 | 1.4075 | 1.2333 | 1.3942 |
| 5.00 | 1.4055 | 1.2061 | 1.3866 |
| 5.01 | 1.4054 | 1.1823 | 1.3794 |
| 5.02 | 1.4070 | 1.1627 | 1.3728 |
| 5.03 | 1.4103 | 1.1478 | 1.3666 |
| 5.04 | 1.4148 | 1.1381 | 1.3607 |
| 5.05 | 1.4202 | 1.1338 | 1.3552 |
| 5.06 | 1.4263 | 1.1348 | 1.3498 |
| 5.07 | 1.4325 | 1.1410 | 1.3445 |
| 5.08 | 1.4387 | 1.1519 | 1.3393 |
| 5.09 | 1.4444 | 1.1671 | 1.3341 |
| 5.10 | 1.4494 | 1.1858 | 1.3288 |
| 5.11 | 1.4534 | 1.2071 | 1.3234 |
| 5.12 | 1.4562 | 1.2303 | 1.3178 |
| 5.13 | 1.4578 | 1.2543 | 1.3120 |

TABLE 5-continued

Chromium(III) 2-ethylhexanoate g(r) data points

| r (Å) | g(r) Exam. 5 Sample | g(r) Hart | g(r) 1st comm. Sample |
|---|---|---|---|
| 5.14 | 1.4580 | 1.2783 | 1.3059 |
| 5.15 | 1.4569 | 1.3013 | 1.2997 |
| 5.16 | 1.4547 | 1.3225 | 1.2932 |
| 5.17 | 1.4514 | 1.3412 | 1.2865 |
| 5.18 | 1.4472 | 1.3568 | 1.2796 |
| 5.19 | 1.4424 | 1.3689 | 1.2726 |
| 5.20 | 1.4372 | 1.3771 | 1.2654 |
| 5.21 | 1.4319 | 1.3814 | 1.2580 |
| 5.22 | 1.4268 | 1.3818 | 1.2506 |
| 5.23 | 1.4221 | 1.3786 | 1.2431 |
| 5.24 | 1.4181 | 1.3720 | 1.2355 |
| 5.25 | 1.4149 | 1.3627 | 1.2279 |
| 5.26 | 1.4127 | 1.3511 | 1.2203 |
| 5.27 | 1.4116 | 1.3381 | 1.2126 |
| 5.28 | 1.4115 | 1.3243 | 1.2049 |
| 5.29 | 1.4126 | 1.3104 | 1.1972 |
| 5.30 | 1.4147 | 1.2972 | 1.1895 |
| 5.31 | 1.4176 | 1.2853 | 1.1818 |
| 5.32 | 1.4213 | 1.2754 | 1.1740 |
| 5.33 | 1.4256 | 1.2679 | 1.1662 |
| 5.34 | 1.4303 | 1.2631 | 1.1583 |
| 5.35 | 1.4351 | 1.2613 | 1.1504 |
| 5.36 | 1.4399 | 1.2625 | 1.1424 |
| 5.37 | 1.4445 | 1.2667 | 1.1344 |
| 5.38 | 1.4486 | 1.2736 | 1.1264 |
| 5.39 | 1.4523 | 1.2828 | 1.1184 |
| 5.40 | 1.4552 | 1.2939 | 1.1103 |
| 5.41 | 1.4575 | 1.3063 | 1.1023 |
| 5.42 | 1.4590 | 1.3193 | 1.0943 |
| 5.43 | 1.4598 | 1.3323 | 1.0863 |
| 5.44 | 1.4600 | 1.3444 | 1.0784 |
| 5.45 | 1.4594 | 1.3551 | 1.0706 |
| 5.46 | 1.4583 | 1.3637 | 1.0629 |
| 5.47 | 1.4568 | 1.3695 | 1.0552 |
| 5.48 | 1.4549 | 1.3722 | 1.0476 |
| 5.49 | 1.4527 | 1.3713 | 1.0401 |
| 5.50 | 1.4503 | 1.3667 | 1.0327 |
| 5.51 | 1.4476 | 1.3583 | 1.0252 |
| 5.52 | 1.4448 | 1.3462 | 1.0178 |
| 5.53 | 1.4418 | 1.3305 | 1.0103 |
| 5.54 | 1.4384 | 1.3117 | 1.0027 |
| 5.55 | 1.4346 | 1.2903 | 0.9950 |
| 5.56 | 1.4303 | 1.2668 | 0.9872 |
| 5.57 | 1.4253 | 1.2420 | 0.9792 |
| 5.58 | 1.4193 | 1.2165 | 0.9711 |
| 5.59 | 1.4122 | 1.1911 | 0.9628 |
| 5.60 | 1.4038 | 1.1667 | 0.9543 |
| 5.61 | 1.3938 | 1.1438 | 0.9458 |
| 5.62 | 1.3822 | 1.1233 | 0.9372 |
| 5.63 | 1.3686 | 1.1056 | 0.9287 |
| 5.64 | 1.3532 | 1.0912 | 0.9203 |
| 5.65 | 1.3357 | 1.0805 | 0.9123 |
| 5.66 | 1.3162 | 1.0736 | 0.9046 |
| 5.67 | 1.2948 | 1.0705 | 0.8976 |
| 5.68 | 1.2717 | 1.0712 | 0.8913 |
| 5.69 | 1.2470 | 1.0753 | 0.8859 |
| 5.70 | 1.2210 | 1.0825 | 0.8815 |
| 5.71 | 1.1941 | 1.0922 | 0.8784 |
| 5.72 | 1.1665 | 1.1037 | 0.8767 |
| 5.73 | 1.1387 | 1.1165 | 0.8764 |
| 5.74 | 1.1112 | 1.1296 | 0.8777 |
| 5.75 | 1.0843 | 1.1424 | 0.8806 |
| 5.76 | 1.0584 | 1.1540 | 0.8851 |
| 5.77 | 1.0340 | 1.1638 | 0.8913 |
| 5.78 | 1.0115 | 1.1710 | 0.8989 |
| 5.79 | 0.9911 | 1.1751 | 0.9079 |
| 5.80 | 0.9730 | 1.1756 | 0.9182 |
| 5.81 | 0.9576 | 1.1722 | 0.9295 |
| 5.82 | 0.9449 | 1.1649 | 0.9415 |
| 5.83 | 0.9349 | 1.1534 | 0.9541 |
| 5.84 | 0.9277 | 1.1381 | 0.9668 |
| 5.85 | 0.9231 | 1.1191 | 0.9795 |
| 5.86 | 0.9210 | 1.0970 | 0.9918 |
| 5.87 | 0.9211 | 1.0722 | 1.0033 |
| 5.88 | 0.9232 | 1.0455 | 1.0137 |
| 5.89 | 0.9270 | 1.0176 | 1.0229 |
| 5.90 | 0.9322 | 0.9893 | 1.0306 |
| 5.91 | 0.9384 | 0.9613 | 1.0365 |
| 5.92 | 0.9453 | 0.9346 | 1.0406 |
| 5.93 | 0.9525 | 0.9098 | 1.0428 |
| 5.94 | 0.9599 | 0.8877 | 1.0430 |
| 5.95 | 0.9670 | 0.8689 | 1.0413 |
| 5.96 | 0.9736 | 0.8539 | 1.0378 |
| 5.97 | 0.9796 | 0.8431 | 1.0327 |
| 5.98 | 0.9848 | 0.8368 | 1.0262 |
| 5.99 | 0.9892 | 0.8350 | 1.0186 |
| 6.00 | 0.9925 | 0.8377 | 1.0102 |

A vacuum phase mononuclear chromium(III) acetate model was constructed heuristically based on the strong correlations in the experimental radial distribution function of the chromium(III) 2-ethyl hexanoate produced according to Example 5. The initial mononuclear chromium(III) acetate structure was built using a reasonable chromium-oxygen bond distance obtained from the high-energy X-ray diffraction of the chromium(III) 2-ethylhexanoate sample produced by the method in Example 5 and the carbon-oxygen, carbon-carbon, and carbon-hydrogen bond distances of the acetate anion published in *Nature* 205, 694-695 (13 Feb. 1965). It should be noted that all three high energy X-ray diffraction analyzed chromium(III) 2-ethylhexanoate compositions provide nearly the same chromium-oxygen bond distance (within 0.05 of an Angstrom). Consequently, without being limited to theory, it was believed that this was a good initial starting point for the chromium-oxygen bond distance on which to construct a gas phase mononuclear chromium(III) acetate model. The initial model was then optimized using SemiChemGaussView (version 3.0) by varying the chromium-oxygen bond distance and the oxygen-chromium-oxygen-carbon dihedral angle while imposing $D_{3h}$ symmetry on the 10 central atoms. Table 6 provides the atomic coordinates of the optimized chromium(III) acetate model obtained from SemiChemGaussView.

TABLE 6

Atomic Coordinates for an Optimized Chromium(III) Acetate Model

| Atom | X | Y | Z |
|---|---|---|---|
| Cr | 0 | 0 | 0 |
| C1 | 1.843475 | −0.40852 | −1.43058 |
| O1 | 0.738585 | −1.038881 | −1.567619 |
| O2 | 1.90289 | 0.461636 | −0.494039 |
| C2 | 3.026757 | −0.697968 | −2.303537 |
| H1 | 3.586188 | 0.221029 | −2.49448 |
| H2 | 2.70492 | −1.158746 | −3.239287 |
| H3 | 3.689716 | −1.395002 | −1.777323 |
| O3 | −0.772555 | 1.631901 | −0.909192 |
| O4 | −0.481341 | 1.511899 | 1.249048 |
| C4 | −1.400219 | 3.584765 | 0.389991 |
| C3 | −0.872192 | 2.190556 | 0.236797 |
| H4 | −1.932477 | 3.891686 | −0.511821 |
| H5 | −2.054935 | 3.640368 | 1.263653 |
| H6 | −0.55862 | 4.266381 | 0.559197 |
| O5 | 0.288007 | −1.521043 | 1.29563 |
| O6 | −1.664703 | −1.059059 | 0.43961 |

TABLE 6-continued

Atomic Coordinates for an Optimized Chromium(III) Acetate Model

| Atom | X | Y | Z |
|---|---|---|---|
| C5 | −0.959016 | −1.79628 | 1.210803 |
| C6 | −1.568434 | −2.912588 | 2.003767 |
| H7 | −2.492313 | −3.252317 | 1.531746 |
| H8 | −1.803373 | −2.543365 | 3.009177 |
| H9 | −0.856348 | −3.735188 | 2.102561 |

PDFFit as implemented in PDFgui was then used to then calculate the pair distribution functions of the optimized mononuclear chromium(III) model (Proffen, T.; Billinge, S. J. L. J. Appl. Crystallogr. 1999, 32, 572-575). Table 7 provides the calculated high energy X-ray diffraction d(r) data points for the optimized chromium(III) acetate model. It should be noted that the utilized procedure generates a radial distribution function, d(r), and it is the d(r) data points that are presented in Table 7. To compare the calculated high energy X-ray diffraction d(r) data of the optimized mononuclear chromium(III) acetate model to high energy X-ray diffraction g(r) data of a chromium carboxylate sample, the d(r) data points must to converted to g(r) data. The relationship between high energy X-ray diffraction d(r) data generated by PDFgui and high energy X-ray diffraction g(r) data points is $g(r)=(d(r)/(4\pi*r*\rho_0))+1$.

TABLE 7

Chromium(III) Acetate Model d(r) data points.

| r (Å) | d(r) Cr(OAc)$_3$ |
|---|---|
| 1.00 | 0.5453 |
| 1.01 | 0.5422 |
| 1.02 | 0.5399 |
| 1.03 | 0.5410 |
| 1.04 | 0.5472 |
| 1.05 | 0.5602 |
| 1.06 | 0.5804 |
| 1.07 | 0.6076 |
| 1.08 | 0.6408 |
| 1.09 | 0.6779 |
| 1.10 | 0.7163 |
| 1.11 | 0.7525 |
| 1.12 | 0.7828 |
| 1.13 | 0.8031 |
| 1.14 | 0.8097 |
| 1.15 | 0.7992 |
| 1.16 | 0.7688 |
| 1.17 | 0.7167 |
| 1.18 | 0.6426 |
| 1.19 | 0.5471 |
| 1.20 | 0.4326 |
| 1.21 | 0.3030 |
| 1.22 | 0.1634 |
| 1.23 | 0.0203 |
| 1.24 | −0.1186 |
| 1.25 | −0.2453 |
| 1.26 | −0.3511 |
| 1.27 | −0.4275 |
| 1.28 | −0.4667 |
| 1.29 | −0.4615 |
| 1.30 | −0.4065 |
| 1.31 | −0.2978 |
| 1.32 | −0.1335 |
| 1.33 | 0.0860 |
| 1.34 | 0.3580 |
| 1.35 | 0.6774 |
| 1.36 | 1.0370 |
| 1.37 | 1.4275 |
| 1.38 | 1.8382 |

TABLE 7-continued

Chromium(III) Acetate Model d(r) data points.

| r (Å) | d(r) Cr(OAc)$_3$ |
|---|---|
| 1.39 | 2.2570 |
| 1.40 | 2.6713 |
| 1.41 | 3.0681 |
| 1.42 | 3.4351 |
| 1.43 | 3.7607 |
| 1.44 | 4.0350 |
| 1.45 | 4.2496 |
| 1.46 | 4.3988 |
| 1.47 | 4.4791 |
| 1.48 | 4.4897 |
| 1.49 | 4.4324 |
| 1.50 | 4.3115 |
| 1.51 | 4.1335 |
| 1.52 | 3.9069 |
| 1.53 | 3.6413 |
| 1.54 | 3.3474 |
| 1.55 | 3.0365 |
| 1.56 | 2.7193 |
| 1.57 | 2.4060 |
| 1.58 | 2.1056 |
| 1.59 | 1.8254 |
| 1.60 | 1.5710 |
| 1.61 | 1.3458 |
| 1.62 | 1.1510 |
| 1.63 | 0.9860 |
| 1.64 | 0.8483 |
| 1.65 | 0.7338 |
| 1.66 | 0.6373 |
| 1.67 | 0.5531 |
| 1.68 | 0.4753 |
| 1.69 | 0.3984 |
| 1.70 | 0.3181 |
| 1.71 | 0.2311 |
| 1.72 | 0.1362 |
| 1.73 | 0.0340 |
| 1.74 | −0.0726 |
| 1.75 | −0.1785 |
| 1.76 | −0.2768 |
| 1.77 | −0.3587 |
| 1.78 | −0.4140 |
| 1.79 | −0.4318 |
| 1.80 | −0.4009 |
| 1.81 | −0.3107 |
| 1.82 | −0.1514 |
| 1.83 | 0.0847 |
| 1.84 | 0.4032 |
| 1.85 | 0.8068 |
| 1.86 | 1.2950 |
| 1.87 | 1.8637 |
| 1.88 | 2.5055 |
| 1.89 | 3.2093 |
| 1.90 | 3.9610 |
| 1.91 | 4.7434 |
| 1.92 | 5.5374 |
| 1.93 | 6.3223 |
| 1.94 | 7.0765 |
| 1.95 | 7.7785 |
| 1.96 | 8.4079 |
| 1.97 | 8.9459 |
| 1.98 | 9.3763 |
| 1.99 | 9.6860 |
| 2.00 | 9.8656 |
| 2.01 | 9.9099 |
| 2.02 | 9.8180 |
| 2.03 | 9.5935 |
| 2.04 | 9.2438 |
| 2.05 | 8.7805 |
| 2.06 | 8.2185 |
| 2.07 | 7.5755 |
| 2.08 | 6.8712 |
| 2.09 | 6.1266 |
| 2.10 | 5.3630 |
| 2.11 | 4.6014 |
| 2.12 | 3.8618 |
| 2.13 | 3.1619 |

TABLE 7-continued

Chromium(III) Acetate Model d(r) data points.

| r (Å) | d(r) Cr(OAc)$_3$ |
|---|---|
| 2.14 | 2.5174 |
| 2.15 | 1.9409 |
| 2.16 | 1.4416 |
| 2.17 | 1.0255 |
| 2.18 | 0.6952 |
| 2.19 | 0.4499 |
| 2.20 | 0.2860 |
| 2.21 | 0.1971 |
| 2.22 | 0.1749 |
| 2.23 | 0.2097 |
| 2.24 | 0.2905 |
| 2.25 | 0.4061 |
| 2.26 | 0.5457 |
| 2.27 | 0.6990 |
| 2.28 | 0.8569 |
| 2.29 | 1.0116 |
| 2.30 | 1.1572 |
| 2.31 | 1.2895 |
| 2.32 | 1.4062 |
| 2.33 | 1.5065 |
| 2.34 | 1.5913 |
| 2.35 | 1.6626 |
| 2.36 | 1.7233 |
| 2.37 | 1.7772 |
| 2.38 | 1.8279 |
| 2.39 | 1.8792 |
| 2.40 | 1.9342 |
| 2.41 | 1.9958 |
| 2.42 | 2.0655 |
| 2.43 | 2.1442 |
| 2.44 | 2.2315 |
| 2.45 | 2.3264 |
| 2.46 | 2.4266 |
| 2.47 | 2.5293 |
| 2.48 | 2.6311 |
| 2.49 | 2.7284 |
| 2.50 | 2.8175 |
| 2.51 | 2.8947 |
| 2.52 | 2.9571 |
| 2.53 | 3.0020 |
| 2.54 | 3.0276 |
| 2.55 | 3.0330 |
| 2.56 | 3.0181 |
| 2.57 | 2.9836 |
| 2.58 | 2.9309 |
| 2.59 | 2.8622 |
| 2.60 | 2.7799 |
| 2.61 | 2.6870 |
| 2.62 | 2.5863 |
| 2.63 | 2.4808 |
| 2.64 | 2.3731 |
| 2.65 | 2.2654 |
| 2.66 | 2.1594 |
| 2.67 | 2.0563 |
| 2.68 | 1.9569 |
| 2.69 | 1.8611 |
| 2.70 | 1.7688 |
| 2.71 | 1.6794 |
| 2.72 | 1.5922 |
| 2.73 | 1.5065 |
| 2.74 | 1.4218 |
| 2.75 | 1.3379 |
| 2.76 | 1.2552 |
| 2.77 | 1.1744 |
| 2.78 | 1.0972 |
| 2.79 | 1.0256 |
| 2.80 | 0.9622 |
| 2.81 | 0.9102 |
| 2.82 | 0.8730 |
| 2.83 | 0.8541 |
| 2.84 | 0.8569 |
| 2.85 | 0.8843 |
| 2.86 | 0.9389 |
| 2.87 | 1.0222 |
| 2.88 | 1.1346 |
| 2.89 | 1.2757 |
| 2.90 | 1.4433 |
| 2.91 | 1.6342 |
| 2.92 | 1.8438 |
| 2.93 | 2.0664 |
| 2.94 | 2.2953 |
| 2.95 | 2.5227 |
| 2.96 | 2.7409 |
| 2.97 | 2.9416 |
| 2.98 | 3.1168 |
| 2.99 | 3.2592 |
| 3.00 | 3.3622 |
| 3.01 | 3.4207 |
| 3.02 | 3.4307 |
| 3.03 | 3.3903 |
| 3.04 | 3.2990 |
| 3.05 | 3.1585 |
| 3.06 | 2.9720 |
| 3.07 | 2.7446 |
| 3.08 | 2.4828 |
| 3.09 | 2.1944 |
| 3.10 | 1.8880 |
| 3.11 | 1.5728 |
| 3.12 | 1.2581 |
| 3.13 | 0.9530 |
| 3.14 | 0.6660 |
| 3.15 | 0.4047 |
| 3.16 | 0.1754 |
| 3.17 | −0.0168 |
| 3.18 | −0.1686 |
| 3.19 | −0.2782 |
| 3.20 | −0.3456 |
| 3.21 | −0.3721 |
| 3.22 | −0.3606 |
| 3.23 | −0.3149 |
| 3.24 | −0.2400 |
| 3.25 | −0.1415 |
| 3.26 | −0.0251 |
| 3.27 | 0.1032 |
| 3.28 | 0.2378 |
| 3.29 | 0.3735 |
| 3.30 | 0.5058 |
| 3.31 | 0.6310 |
| 3.32 | 0.7464 |
| 3.33 | 0.8500 |
| 3.34 | 0.9409 |
| 3.35 | 1.0190 |
| 3.36 | 1.0848 |
| 3.37 | 1.1392 |
| 3.38 | 1.1838 |
| 3.39 | 1.2200 |
| 3.40 | 1.2494 |
| 3.41 | 1.2732 |
| 3.42 | 1.2926 |
| 3.43 | 1.3080 |
| 3.44 | 1.3196 |
| 3.45 | 1.3270 |
| 3.46 | 1.3294 |
| 3.47 | 1.3257 |
| 3.48 | 1.3145 |
| 3.49 | 1.2942 |
| 3.50 | 1.2634 |
| 3.51 | 1.2207 |
| 3.52 | 1.1653 |
| 3.53 | 1.0967 |
| 3.54 | 1.0151 |
| 3.55 | 0.9211 |
| 3.56 | 0.8162 |
| 3.57 | 0.7025 |
| 3.58 | 0.5825 |
| 3.59 | 0.4595 |
| 3.60 | 0.3367 |
| 3.61 | 0.2177 |
| 3.62 | 0.1060 |
| 3.63 | 0.0049 |

TABLE 7-continued

Chromium(III) Acetate Model d(r) data points.

| r (Å) | d(r) Cr(OAc)$_3$ |
|---|---|
| 3.64 | −0.0826 |
| 3.65 | −0.1545 |
| 3.66 | −0.2089 |
| 3.67 | −0.2452 |
| 3.68 | −0.2633 |
| 3.69 | −0.2641 |
| 3.70 | −0.2493 |
| 3.71 | −0.2210 |
| 3.72 | −0.1823 |
| 3.73 | −0.1361 |
| 3.74 | −0.0860 |
| 3.75 | −0.0350 |
| 3.76 | 0.0138 |
| 3.77 | 0.0580 |
| 3.78 | 0.0958 |
| 3.79 | 0.1261 |
| 3.80 | 0.1488 |
| 3.81 | 0.1646 |
| 3.82 | 0.1753 |
| 3.83 | 0.1832 |
| 3.84 | 0.1916 |
| 3.85 | 0.2041 |
| 3.86 | 0.2246 |
| 3.87 | 0.2571 |
| 3.88 | 0.3053 |
| 3.89 | 0.3725 |
| 3.90 | 0.4613 |
| 3.91 | 0.5734 |
| 3.92 | 0.7094 |
| 3.93 | 0.8688 |
| 3.94 | 1.0499 |
| 3.95 | 1.2498 |
| 3.96 | 1.4643 |
| 3.97 | 1.6885 |
| 3.98 | 1.9166 |
| 3.99 | 2.1422 |
| 4.00 | 2.3588 |
| 4.01 | 2.5597 |
| 4.02 | 2.7387 |
| 4.03 | 2.8901 |
| 4.04 | 3.0090 |
| 4.05 | 3.0916 |
| 4.06 | 3.1355 |
| 4.07 | 3.1392 |
| 4.08 | 3.1031 |
| 4.09 | 3.0286 |
| 4.10 | 2.9184 |
| 4.11 | 2.7766 |
| 4.12 | 2.6079 |
| 4.13 | 2.4179 |
| 4.14 | 2.2126 |
| 4.15 | 1.9984 |
| 4.16 | 1.7814 |
| 4.17 | 1.5674 |
| 4.18 | 1.3618 |
| 4.19 | 1.1692 |
| 4.20 | 0.9932 |
| 4.21 | 0.8366 |
| 4.22 | 0.7012 |
| 4.23 | 0.5878 |
| 4.24 | 0.4961 |
| 4.25 | 0.4253 |
| 4.26 | 0.3738 |
| 4.27 | 0.3392 |
| 4.28 | 0.3193 |
| 4.29 | 0.3113 |
| 4.30 | 0.3126 |
| 4.31 | 0.3207 |
| 4.32 | 0.3335 |
| 4.33 | 0.3492 |
| 4.34 | 0.3664 |
| 4.35 | 0.3843 |
| 4.36 | 0.4024 |
| 4.37 | 0.4206 |
| 4.38 | 0.4391 |
| 4.39 | 0.4584 |
| 4.40 | 0.4790 |
| 4.41 | 0.5015 |
| 4.42 | 0.5261 |
| 4.43 | 0.5531 |
| 4.44 | 0.5824 |
| 4.45 | 0.6134 |
| 4.46 | 0.6455 |
| 4.47 | 0.6775 |
| 4.48 | 0.7081 |
| 4.49 | 0.7356 |
| 4.50 | 0.7586 |
| 4.51 | 0.7753 |
| 4.52 | 0.7843 |
| 4.53 | 0.7844 |
| 4.54 | 0.7749 |
| 4.55 | 0.7554 |
| 4.56 | 0.7260 |
| 4.57 | 0.6877 |
| 4.58 | 0.6417 |
| 4.59 | 0.5900 |
| 4.60 | 0.5349 |
| 4.61 | 0.4792 |
| 4.62 | 0.4257 |
| 4.63 | 0.3776 |
| 4.64 | 0.3376 |
| 4.65 | 0.3084 |
| 4.66 | 0.2923 |
| 4.67 | 0.2909 |
| 4.68 | 0.3053 |
| 4.69 | 0.3356 |
| 4.70 | 0.3812 |
| 4.71 | 0.4408 |
| 4.72 | 0.5123 |
| 4.73 | 0.5927 |
| 4.74 | 0.6789 |
| 4.75 | 0.7670 |
| 4.76 | 0.8531 |
| 4.77 | 0.9330 |
| 4.78 | 1.0031 |
| 4.79 | 1.0599 |
| 4.80 | 1.1004 |
| 4.81 | 1.1223 |
| 4.82 | 1.1242 |
| 4.83 | 1.1055 |
| 4.84 | 1.0664 |
| 4.85 | 1.0082 |
| 4.86 | 0.9327 |
| 4.87 | 0.8425 |
| 4.88 | 0.7411 |
| 4.89 | 0.6319 |
| 4.90 | 0.5189 |
| 4.91 | 0.4059 |
| 4.92 | 0.2967 |
| 4.93 | 0.1948 |
| 4.94 | 0.1030 |
| 4.95 | 0.0237 |
| 4.96 | −0.0414 |
| 4.97 | −0.0913 |
| 4.98 | −0.1261 |
| 4.99 | −0.1460 |
| 5.00 | −0.1524 |
| 5.01 | −0.1470 |
| 5.02 | −0.1319 |
| 5.03 | −0.1095 |
| 5.04 | −0.0824 |
| 5.05 | −0.0531 |
| 5.06 | −0.0239 |
| 5.07 | 0.0030 |
| 5.08 | 0.0261 |
| 5.09 | 0.0440 |
| 5.10 | 0.0561 |
| 5.11 | 0.0621 |
| 5.12 | 0.0623 |
| 5.13 | 0.0574 |

TABLE 7-continued

Chromium(III) Acetate Model d(r) data points.

| r (Å) | d(r) Cr(OAc)$_3$ |
|---|---|
| 5.14 | 0.0483 |
| 5.15 | 0.0364 |
| 5.16 | 0.0230 |
| 5.17 | 0.0096 |
| 5.18 | −0.0026 |
| 5.19 | −0.0125 |
| 5.20 | −0.0191 |
| 5.21 | −0.0220 |
| 5.22 | −0.0210 |
| 5.23 | −0.0162 |
| 5.24 | −0.0082 |
| 5.25 | 0.0021 |
| 5.26 | 0.0137 |
| 5.27 | 0.0255 |
| 5.28 | 0.0362 |
| 5.29 | 0.0447 |
| 5.30 | 0.0500 |
| 5.31 | 0.0514 |
| 5.32 | 0.0486 |
| 5.33 | 0.0414 |
| 5.34 | 0.0303 |
| 5.35 | 0.0160 |
| 5.36 | −0.0002 |
| 5.37 | −0.0170 |
| 5.38 | −0.0325 |
| 5.39 | −0.0449 |
| 5.40 | −0.0524 |
| 5.41 | −0.0531 |
| 5.42 | −0.0455 |
| 5.43 | −0.0282 |
| 5.44 | −0.0003 |
| 5.45 | 0.0387 |
| 5.46 | 0.0886 |
| 5.47 | 0.1488 |
| 5.48 | 0.2184 |
| 5.49 | 0.2957 |
| 5.5 | 0.3787 |
| 5.51 | 0.4652 |
| 5.52 | 0.5528 |
| 5.53 | 0.6388 |
| 5.54 | 0.7207 |
| 5.55 | 0.7963 |
| 5.56 | 0.8635 |
| 5.57 | 0.9207 |
| 5.58 | 0.9666 |
| 5.59 | 1.0005 |
| 5.60 | 1.0223 |
| 5.61 | 1.0322 |
| 5.62 | 1.0313 |
| 5.63 | 1.0205 |
| 5.64 | 1.0017 |
| 5.65 | 0.9764 |
| 5.66 | 0.9468 |
| 5.67 | 0.9145 |
| 5.68 | 0.8816 |
| 5.69 | 0.8495 |
| 5.70 | 0.8196 |
| 5.71 | 0.7927 |
| 5.72 | 0.7695 |
| 5.73 | 0.7499 |
| 5.74 | 0.7338 |
| 5.75 | 0.7204 |
| 5.76 | 0.7087 |
| 5.77 | 0.6977 |
| 5.78 | 0.6859 |
| 5.79 | 0.6720 |
| 5.80 | 0.6548 |
| 5.81 | 0.6333 |
| 5.82 | 0.6065 |
| 5.83 | 0.5739 |
| 5.84 | 0.5356 |
| 5.85 | 0.4916 |
| 5.86 | 0.4427 |
| 5.87 | 0.3900 |
| 5.88 | 0.3346 |
| 5.89 | 0.2783 |
| 5.9 | 0.2227 |
| 5.91 | 0.1695 |
| 5.92 | 0.1204 |
| 5.93 | 0.0771 |
| 5.94 | 0.0407 |
| 5.95 | 0.0123 |
| 5.96 | −0.0076 |
| 5.97 | −0.0187 |
| 5.98 | −0.0214 |
| 5.99 | −0.0164 |
| 6.00 | −0.0046 |

The high energy X-ray diffraction g(r) data points of the chromium(III) 2-ethylhexanoate composition prepared according to the procedure of Example 5, the Hart chromium (III) 2-ethylhexanoate composition, and the first commercially available chromium(III) 2-ethylhexanoate composition were compared to the calculated high energy X-ray diffraction data points of the mononuclear chromium(III) acetate model to determine how well these chromium(III) 2-ethylhexanoate compositions compared to a mononuclear chromium(III) 2-ethylhexanoate via a model of a mononuclear chromium(III) acetate. The comparisons were performed by separately optimizing the fit between each chromium(III) 2-ethylhexanoate composition and the chromium (III) acetate model over the desired range of r values and calculating the goodness of fit test value, $R^2$, via the equation $R^2=1-(SS_{err}/SS_{tot})$ for the same range of r as described herein.

Each optimization fit was performed by 1) converting the calculated high energy X-ray diffraction d(r) data points for the mononuclear chromium(III) acetate model to calculated high energy X-ray diffraction g(r) data points for the mononuclear chromium(III) acetate model and scaling the calculated high energy X-ray diffraction g(r) data points to the high energy X-ray diffraction data points of the chromium (III) 2-ethylhexanoate composition using the equation $g(r)=((((d(r)/(4\pi*r*\rho_0))+1)*fac)+C)$ and 2) minimizing the sum of the squared differences between the calculated high energy X-ray diffraction g(r) data points for the mononuclear chromium(III) acetate model and the high energy X-ray diffraction g(r) data points of the chromium(III) 2-ethylhexanoate composition using rho, fac, and C as scaling and optimization variables under the constraint that the scaled and optimized calculated high energy X-ray diffraction g(r) data point for the mononuclear chromium(III) acetate model g(r) data point at r=1.79 Angstroms is equal to 0. Within this procedure, $g(r)=(d(r)/(4\pi*r*\rho_0))$ converts the radial distribution d(r) data points of the optimized mononuclear chromium(III) acetate model presented Table 6 to g(r) data points which can be compared to the high energy X-ray diffraction g(r) data points obtained by experiment for the tested chromium(III) 2-ethylhexanoate compositions, and fac and C are scaling factors to allow for an optimum fit between the calculated high energy X-ray diffraction data points of the mononuclear chromium(III) acetate model to the high energy X-ray diffraction data points of the chromium(III) 2-ethylhexanoate compositions. The optimization operations were performed using the Solver function within the Microsoft® Excel spreadsheet program but can be performed using other programs capable of solving for the minimum sum of squared differences using $\rho_0$, fac, and C as variables in the scaling function under a constraint that the mononuclear chromium(III) acetate model g(r) data point (resulting from the scaling operation) at r=1.79 Angstroms equals 0.

The following procedure provides the steps utilized to create the Microsoft® Excel worksheet to optimize the fit between the high energy X-ray diffraction g(r) data points of the chromium(III) 2-ethylhexanoate composition of Example 5 and the calculated high energy X-ray diffraction d(r) data points of the chromium(III) acetate model over an r value range of 1.3 to 4.0. Within a clean Microsoft® Excel worksheet:

1. The values of r from 1.00 to 6.00 separated by the interval of 0.01 were placed into cells A10-A510 in ascending order.
2. The corresponding values of d(r) for each r value of the calculated high energy X-ray diffraction d(r) data points of the chromium(III) acetate model from Table 7 were placed into cells B10-B510.
3. The corresponding values of g(r) for each r value of the high energy X-ray diffraction g(r) data points of the chromium 2-ethylhexanoate sample of Example 5 were placed in cells C10-0510.
4. A non-zero initial guess for $\rho_0$, a non-zero initial guess for the optimization constant fac, and an initial guess for the optimization constant C were placed in cells D4, D5, and D6, respectively.
5. The formula=((($B10/(4*PI( )*$A10*$D$4))+1)*$D$5)+$D$6 was placed into cell D10 and then referentially copied into cells D11-D510 (i.e. when referentially copied, the formula in D510 was =((($B510/(4*PI( )$A510*$D$4))+1)*$D$5)+$D$6).
6. The formula=SUM(E10:E510) was placed into cell E8.
7. The formula=(C40–D40)^2 was placed in cell E40 and referentially copied into cells E41-E310 (i.e., when referentially copied, the formula in E310 was =(C310–D310)^2) and ensuring that cells E10-E39 and E311-E510 were blank.
8. The optimization between the high energy X-ray diffraction g(r) data points of the chromium(III) 2-ethylhexanoate composition of Example 5 and the calculated high energy X-ray diffraction d(r) data points of the chromium(III) acetate model was then performed by:
   a. Opening the Solver routine in Microsoft® Excel;
   b. Inputting E8 the Solver routine box labeled "Set Target Cell";
   c. Selecting the target cell to equal to a minimum value;
   d. Inputting cells D4, D5, and D6 ($D$4:$D$6) into the Solver routine box labeled "By Changing Cells";
   e. Inputting the constraint that cell $D$89=0 into the Solver routine box labeled "Subject to the Constraints";
   f. Clicking the solve box and then clicking the OK button if Solver routine successfully converged to a solution (while ensuring that the keep solution radio button was selected).

It should be noted that these steps created a worksheet that includes data points and utilize general formulas, relational formulas, and procedures that can allow the worksheet to be adapted to optimizing the fit between the high energy X-ray diffraction g(r) data points of the chromium(III) 2-ethylhexanoate composition of Example 5 and the calculated high energy X-ray diffraction d(r) data points of the chromium (III) acetate model over other r values ranges.

When performing the procedure to optimize the fit between the high energy X-ray diffraction g(r) data points of the chromium(III) 2-ethylhexanoate composition of Example 5 and the calculated high energy X-ray diffraction d(r) data points of the chromium(III) acetate model and utilizing initial values of $\rho_0$=0.1, fac=0.1, and C=0, the Solver routine converged to a solution having $\rho_0$=0.0101, fac=0.1410, and C=0.1266 (rounded to four decimal places), and a minimized sum of the squared differences between the calculated high energy X-ray diffraction g(r) data points for the mononuclear chromium(III) acetate model and the high energy X-ray diffraction g(r) data points of the chromium (III) 2-ethylhexanoate composition of Example 5 equal to 136.5487 (rounded to four decimal places). It should be noted that there can be multiple converge solutions for the values of $\rho_0$, fac, and C which can provide the same minimized sum of the squared differences between the calculated high energy X-ray diffraction g(r) data points for the mononuclear chromium(III) acetate model and the high energy X-ray diffraction g(r) data points of the chromium (III) 2-ethylhexanoate composition. Often the difference in the converged values of $\rho_0$, fac, and C can be the selection of the initial values for $\rho_0$, fac, and C. For example, a minimized sum of the squared differences between the calculated high energy X-ray diffraction g(r) data points for the mononuclear chromium(III) acetate model and the high energy X-ray diffraction g(r) data points of the chromium (III) 2-ethylhexanoate composition of Example 5 of 136.5487 (rounded to four decimal places) can be obtained utilizing initial values of $\rho_0$=0.1, fac=0.1, and C=0.1 (which converge to provide values of to a solution having $\rho_0$=0.0203, fac=0.2828, and C=−0152, rounded to four decimal places) or utilizing initial values of $\rho_0$=0.2, fac=0.2, and C=0 (which converge to provide values of to a solution having $\rho_0$=0.0230, fac=0.3207, and C=−0.0531, rounded to four decimal places). Consequently, the initial values of $\rho_0$, fac, and C, and the converged values of $\rho_0$, fac, and C are not particularly important as long as the true minimized sum of the squared differences between the calculated high energy X-ray diffraction g(r) data points for the mononuclear chromium(III) acetate model and the high energy X-ray diffraction g(r) data points of the chromium(III) 2-ethylhexanoate composition is obtained.

The goodness of fit test value was then calculated by applying the equation $R^2=1-(SS_{err}/SS_{tot})$ where $SS_{err}=\Sigma_{r(int)}^{r(fin)}(\text{comp } g(r)-\text{model } g(r))^2$ and $SS_{tot}=\Sigma_{r(int)}^{r(fin)}(\text{comp } g(r)-\text{mean of model } g(r))^2$ where r(int) is the initial r value of g(r) over which the goodness of fit is to be calculates and r(fin) is the final r value of g(r) over which the goodness of fit is to be calculated. Generally, the goodness of fit test can be applied over the same range of r values as the optimization between the chromium(III) carboxylate composition and the chromium(III) acetate model. However, in some instances, it can be desirable to perform the goodness of fit test over a subset of the r values over which optimization between the chromium(III) carboxylate composition and the chromium(III) acetate model was performed.

The following procedure provides the steps utilized to extend the Microsoft® Excel worksheet utilized to optimize the fit between the high energy X-ray diffraction g(r) data points of the chromium(III) 2-ethylhexanoate composition of Example 5 and the calculated high energy X-ray diffraction d(r) data points of the chromium(III) acetate model over an r value range of 1.3 to 4.0 to include the formulas to calculate the goodness of fit test value, $R^2$, between the optimized fit between the high energy X-ray diffraction g(r) data points of the chromium(III) 2-ethylhexanoate composition of Example 5 and the calculated high energy X-ray diffraction d(r) data points of the chromium(III) acetate model over an r value range of 1.3 to 4.0. The procedure builds upon the Microsoft® Excel worksheet utilized to optimize the fit between the high energy X-ray diffraction g(r) data points of the chromium(III) 2-ethylhexanoate composition of Example 5 and the calculated high energy X-ray diffraction d(r) data points of the chromium(III) acetate model over an r value range of 1.3 to 4.0. It should be noted the steps to create the worksheet include data points and utilize general formulas, relational formulas, and procedures to allow the worksheet to be easily adapted to calculate the goodness of fit between the optimized fit between the high energy X-ray diffraction g(r) data points of the chromium (III) 2-ethylhexanoate composition of Example 5 and the calculated high energy X-ray diffraction d(r) data points of the chromium(III) acetate model over other r values ranges.

Within the Microsoft® Excel worksheet that was created to optimize the fit between the high energy X-ray diffraction g(r) data points of the chromium(III) 2-ethylhexanoate composition of Example 5 and the calculated high energy X-ray diffraction d(r) data points of the chromium(III) acetate model over an r value range of 1.3 to 4.0:

1. The formula=SUM(F10:F510) was place into cell F8.
2. The number 1 into cells F40 to F310 (the cells corresponding the r value range over which the goodness of fit is to be calculated all other cells over the range of F10 to F510 are blank).
3. The formula=SUM(G10:G510) was placed into cell G8.
4. The formula=(C40–D40)^2 was placed into cell G40 and was then referentially copied into cells G41-G310 (i.e. when referentially copied, the formula in G310 was =(C310–D310)^2).
5. The formula=SUM(H10:H510) was placed into cell H8.
6. The formula=C130 was placed into cell H40 and was then referentially copied into cells H41-H310 (i.e. when referentially copied, the formula in H310 was =C310).
7. The formula=SUM(I10:I510) was placed into cell I8.
8. The formula=(H40–(H$8/F$8))^2 was placed into cell I40 and was then referentially copied into cells I41-I310 (i.e. when referentially copied, the formula in I310 was =(H310–(H$8/F$8))^2).
9. The formula=1–(G8/I8) was placed into cell I4 and provides the goodness of fit test value.

It should be noted that these steps created a worksheet that includes data points and utilize general formulas, relational formulas, and procedures that would allow the worksheet to be adapted to calculating the goodness of fit test value between the optimized fit between the high energy X-ray diffraction g(r) data points of the chromium(III) 2-ethylhexanoate composition of Example 5 and the calculated high energy X-ray diffraction d(r) data points of the chromium (III) acetate model over other r values ranges by selecting the appropriate cell references and formulas.

Figure 19:
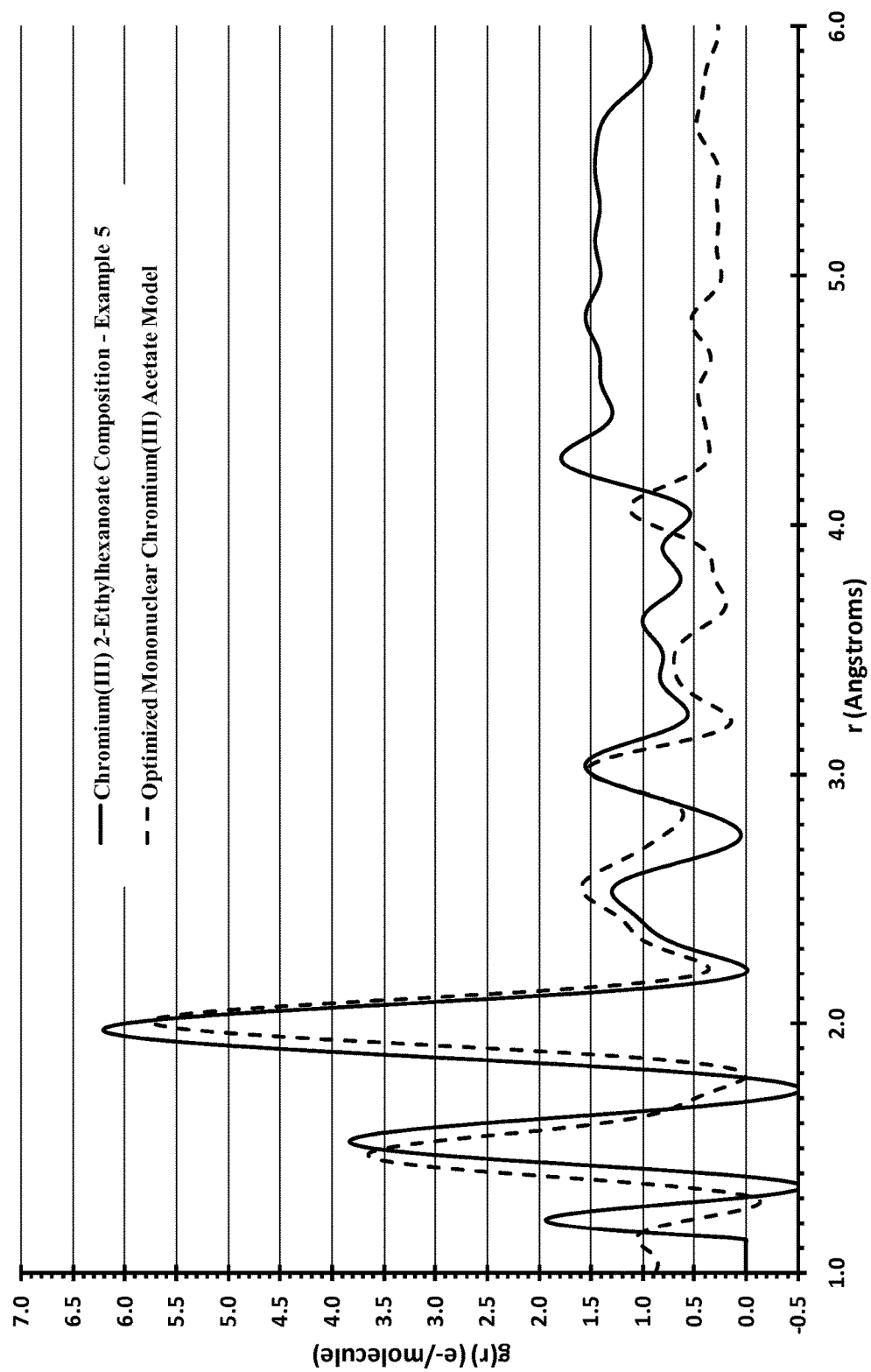
FIG. 19 provides a comparison between the high energy X-ray diffraction g(r) data points of a chromium(III) 2-ethyl hexanoate composition prepared according to the procedures described herein and an optimized calculated high energy X-ray diffraction g(r) data points of a theoretical mononuclear chromium(III) acetate model.
Figure 20:
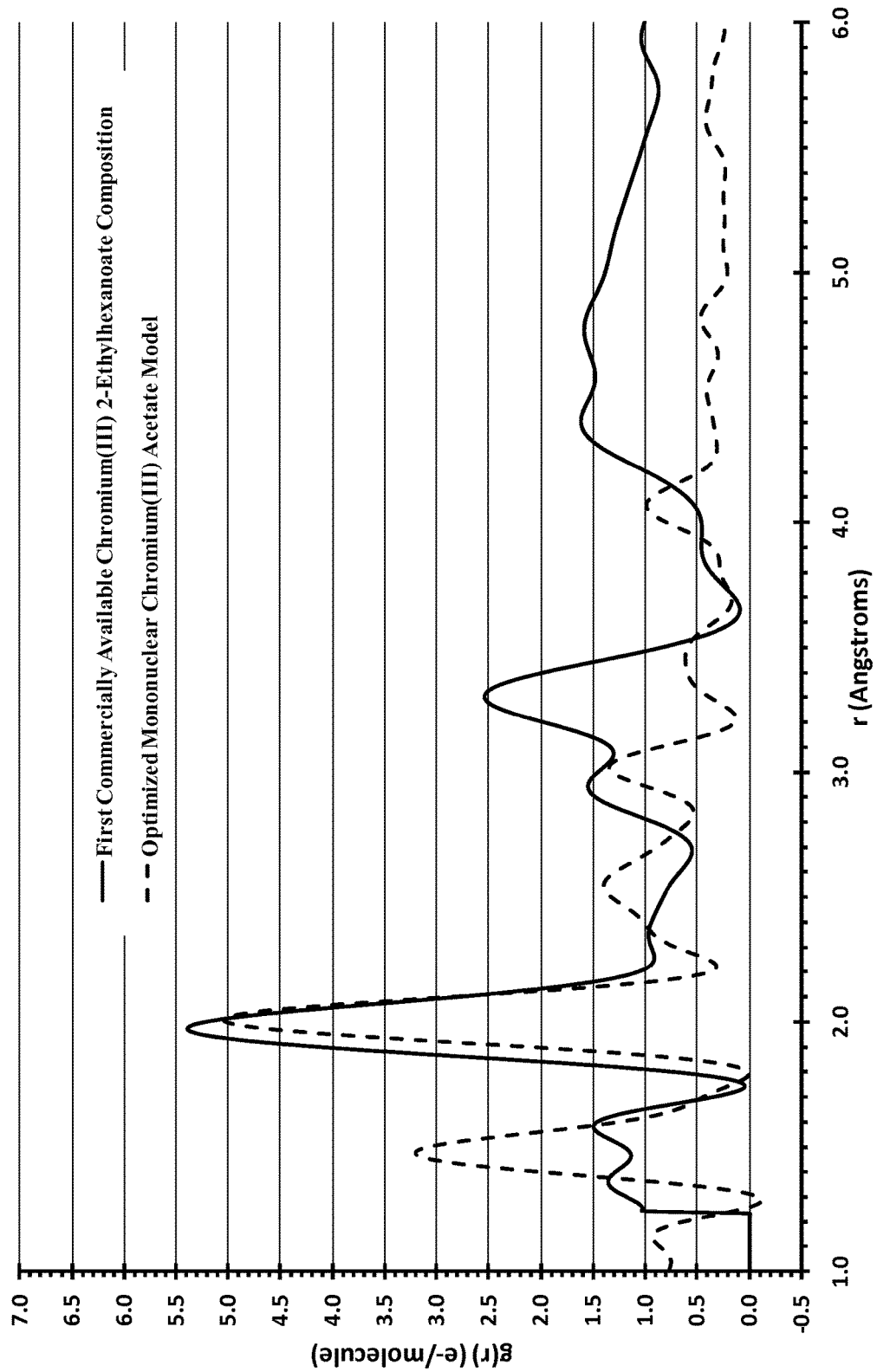
FIG. 20 provides a comparison between the high energy X-ray diffraction g(r) data points of a commercially available chromium(III) 2-ethyl hexanoate composition and an optimized calculated high energy X-ray diffraction g(r) data points of a theoretical mononuclear chromium(III) acetate model.
Figure 21:
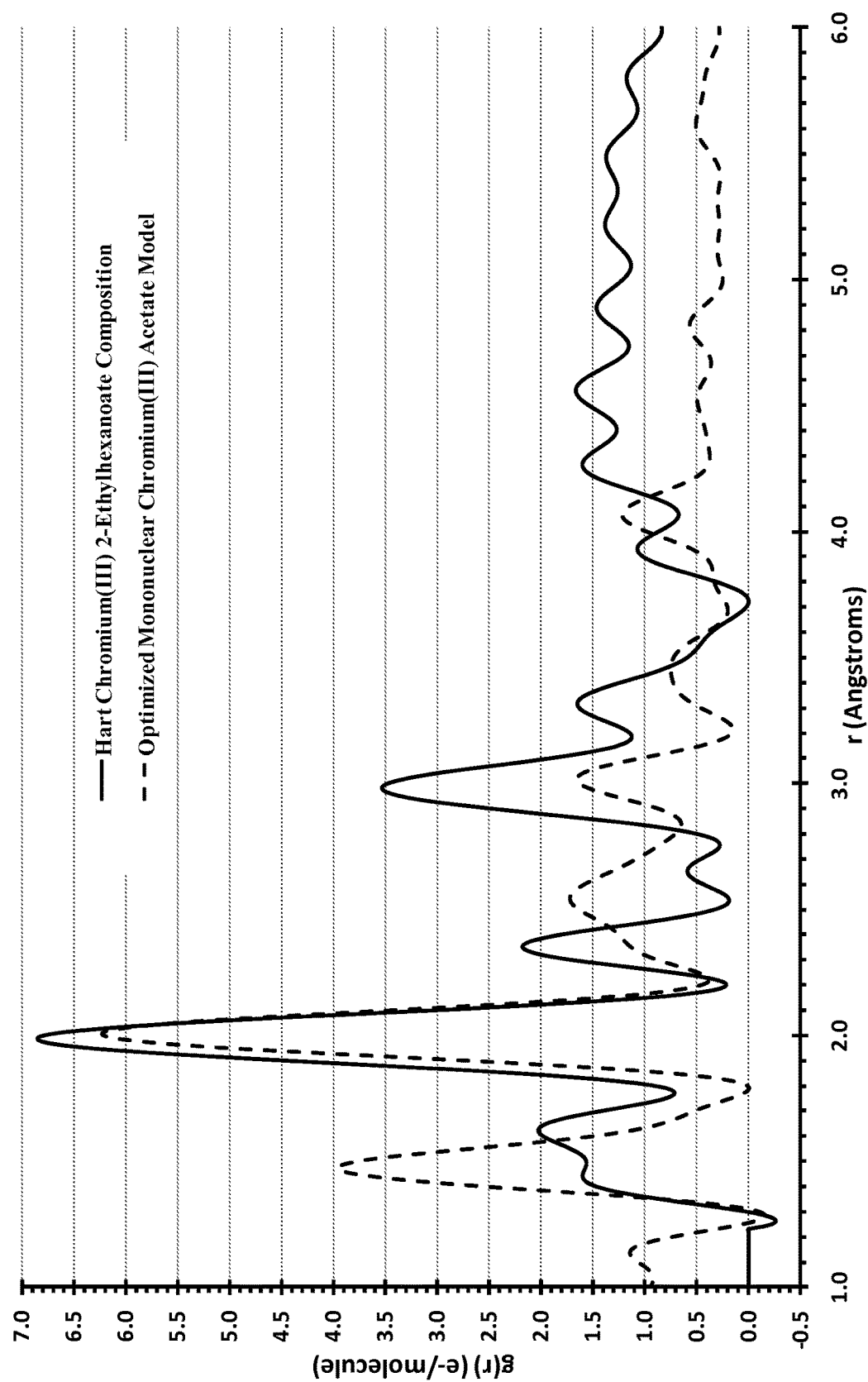
FIG. 21 provides a comparison between the high energy X-ray diffraction g(r) data points of a literature prepared chromium(III) 2-ethylhexanoate composition and an optimized calculated high energy X-ray diffraction g(r) data points of a theoretical mononuclear chromium(III) acetate model.

Table 8 provides the goodness of fit test values for comparing the high energy X-ray diffraction g(r) data points of the chromium(III) 2-ethylhexanoate composition prepared according to the procedure of Example 5, the high energy X-ray diffraction of the first commercially available chromium(III) 2-ethylhexanoate composition, and the Hart chromium(III) 2-ethylhexanoate composition to a calculated high energy X-ray diffraction g(r) points of a mononuclear chromium(III) acetate model for various ranges of r. In each instance, the optimization was performed between the indicated chromium(III) 2-ethylhexanoate and the calculated and high energy X-ray diffraction d(r) points of the mononuclear chromium(III) acetate model in Table 7 over the identical r value range as the r values for the goodness of fit test values. FIGS. 18, 19, and 20, provide plots comparing the high energy X-ray diffraction g(r) data of the chromium (III) 2-ethylhexanoate composition prepare according to the procedure of Example 5, the first commercially available chromium(III) 2-ethylhexanoate composition, and an aqueous metathesis produced sample of chromium(III) acetate to the calculated high energy X-ray diffraction g(r) data of the mononuclear chromium(III) acetate model (optimized over the r value range of 1.3 to 4.0 Angstroms) described herein. The goodness of fit test values and FIGS. 18, 19, and 20 show that the chromium(III) 2-ethylhexanoate composition prepared according to the procedure of Example 5 more closely resembles a mononuclear chromium(III) carboxylate (via comparison to a mononuclear chromium(III) acetate model) than the first commercially available chromium(III) 2-ethylhexanoate composition and the aqueous metathesis produced sample of chromium(III) acetate.

TABLE 8

Goodness of fit test values for comparison of the high energy X-ray diffraction g(r) data points of three the chromium(III) 2-ethylhexanoate compositions to a calculated high energy X-ray diffraction g(r) points of a mononuclear chromium(III) acetate model for various ranges of r.

|  | Chromium(III) 2-Ethyl-hexanoate Composition of Example 5 | 1st Commercially Available Chromium(III) 2-Ethyl-hexanoate Composition | Hart Chromium(III) 2-ethylhexanoate |
|---|---|---|---|
| 1.3 to 3.0 | 0.761 | 0.585 | 0.570 |
| 1.3 to 3.1 | 0.760 | 0.582 | 0.542 |
| 1.3 to 3.2 | 0.757 | 0.517 | 0.531 |
| 1.3 to 3.3 | 0.758 | 0.365 | 0.506 |
| 1.3 to 3.4 | 0.759 | 0.266 | 0.492 |
| 1.3 to 3.5 | 0.760 | 0.250 | 0.501 |
| 1.3 to 3.6 | 0.757 | 0.284 | 0.517 |
| 1.3 to 3.7 | 0.749 | 0.326 | 0.538 |
| 1.3 to 3.8 | 0.747 | 0.354 | 0.556 |
| 1.3 to 3.9 | 0.746 | 0.371 | 0.559 |
| 1.3 to 4.0 | 0.746 | 0.385 | 0.559 |

We claim:

1. A transition metal carboxylate composition produced by the process comprising: contacting under substantially anhydrous and substantially acid-free conditions
   1) a transition metal precursor having the formula $[((M^B)_{y1}X_{x1}L_l)^m]_q[C^c]_{m1}[A^a]_{m2}$ where
      $M^B$ is a transition metal in the +x oxidation state where x is an integer from +1 to +6; each X independently is an anionic ligand having charge y where y is an integer from −3 to −1;
      each L independently is a neutral ligand;
      l is an integer from 0 to 7;
      m is an integer from −4 to 4;
      m=(y*x1)+(x*y1);
      C is a cationic species having a charge c and c is an integer from +1 to +3;
      A is an anionic species having a charge a and a is an integer from −1 to −3;
      when m<0, |m*q|=c*m1 and m2=0;
      when m=0, m1=0 and m=0; and
      when m>0, m*q=|a*m2| and m1=0,
   2) a Group 1 or Group 2 metal $C_3$-$C_{25}$ carboxylate, and
   3) a first solvent
   to form a transition metal carboxylate.

2. The composition of claim 1, wherein the transition metal precursor has the formula $M^B X_x L_l$ where $M^B$ is a transition metal in the x oxidation state and x is an integer from 1 to 6; each X independently is a monoanionic ligand; each L independently is a neutral ligand; and l is an integer from 0 to 7.

3. The composition of claim 1, wherein $M^B$ is Ti, Zr, V, Nb, Cr, Mn, Fe, Co or Cu.

4. The composition of claim 1, wherein each X independently is a halide, nitrate, sulfate, or phosphate and each L independently is a $C_2$-$C_{40}$ ether, a $C_2$-$C_{40}$ thioether, a $C_2$-$C_{20}$ nitrile, a $C_1$-$C_{60}$ amine, a $C_3$-$C_{60}$ phosphine, or any combination thereof.

5. The composition of claim 1, wherein the Group 1 or Group 2 metal carboxylate has the formula $(M^A)_q[(O_2C)_rR^{1c}]_s$ where $M^A$ is a Group 1 or Group 2 metal; $(O_2C)_rR^{1c}$ is a $C_3$-$C_{25}$ carboxylate where r is an integer from 1 to 4 and $R^{1c}$ is a hydrocarbon group or a substituted hydrocarbon group; q is r divided by the greatest common divisor of r and the oxidation state of $M^A$; and s is the oxidation state of $M^A$ divided by the greatest common divisor of r and the oxidation state of $M^A$.

6. The composition of claim 1, wherein the Group 1 or Group 2 metal carboxylate has the formula $M^AO_2CR^{2c}$ where $M^A$ is a Group 1 metal, $O_2CR^{2C}$ is a $C_3$-$C_{25}$ monocarboxylate, and $R^{2c}$ is a hydrocarbyl group or a substituted hydrocarbyl group.

7. The composition of claim 1, wherein the carboxylate of the transition metal carboxylate composition comprises a monocarboxylate having a formula $^-O_2CR^{2c}$ wherein $R^{2c}$ is hydrocarbyl group or a substituted hydrocarbyl group.

8. The composition of claim 1, wherein the transition metal precursor and Group 1 or Group 2 metal carboxylate are contacted at a carboxylate group to transition metal equivalent ratio from 0.95:1 to 1.3:1.

9. The composition of claim 1, wherein the first solvent comprises a $C_2$-$C_{40}$ ether, a $C_2$-$C_{40}$ thioether, a $C_2$-$C_{20}$ nitrile, a $C_1$-$C_{60}$ amine, a $C_3$-$C_{60}$ phosphine, or any combination thereof.

10. The composition of claim 1, wherein the transition metal precursor has a formula $CrX_3L_l$ where
each X independently is a halide,
each L independently is a $C_2$-$C_{10}$ ether, a $C_2$-$C_{10}$ thioether, a $C_2$-$C_5$ nitrile, a $C_1$-$C_{30}$ amine, or a $C_3$-$C_{30}$ phosphine, or any combination thereof, and
l ranges from 0 to 7, and
the Group 1 or Group 2 metal carboxylate is a Group 1 metal $C_3$-$C_{25}$ monocarboxylate.

11. The composition of claim 10, wherein the carboxylate of the Group 1 metal carboxylate comprises a propionate, a butyrate, a pentanoate, a hexanoate, a heptanoate, an octanoate, a nonanoate, a decanoate, an undecanoate, a dodecanoate, a tridecanoate, a tetradecanoate, a pentadecanoate, a hexadecanoate, a heptadecanoate, an octadecanoate, or any combination thereof.

12. The composition of claim 10, wherein the carboxylate of the Group 1 metal carboxylate comprises 2-ethylhexanoate.

13. The composition of claim 10, wherein the transition metal precursor having the formula $CrX_3L_3$ and the Group 1 metal carboxylate are contacted at a Group 1 metal carboxylate to chromium molar ratio from 3:1 to 3.6:1.

14. The composition of claim 10, wherein the first solvent comprises a $C_2$-$C_{40}$ ether, a $C_2$-$C_{40}$ thioether, a $C_2$-$C_{20}$ nitrile, a $C_1$-$C_{60}$ amine, or a $C_3$-$C_{60}$ phosphine, or any combination thereof.

15. The composition of claim 10, further comprising evaporating the first solvent from the mixture to provide the transition metal carboxylate composition.

16. The composition claim 15, further comprising purifying the transition metal carboxylate composition by contacting the first transition metal carboxylate composition with a non-coordinating solvent to form a solution, filtering the solution, and evaporating the non-coordinating solvent to provide a purified transition metal carboxylate composition.

17. The composition of claim 1, having a KBr pellet infrared spectrum with a $\upsilon_{asym}$ ($CO_2$) peak infrared adsorption peak within 110 cm$^{-1}$ of a $\upsilon_{sym}$ ($CO_2$) infrared adsorption peak.

18. The composition of claim 17, having an infrared absorbance peak height ratio of a $\upsilon_{asym}$ ($CO_2$) infrared absorbance peak at 1516±15 cm$^{-1}$ to infrared absorbance peak located at 700±50 cm$^{-1}$ greater than or equal to 3:1.

* * * * *

UNITED STATES PATENT AND TRADEMARK OFFICE
CERTIFICATE OF CORRECTION

PATENT NO. : 9,580,453 B2  
APPLICATION NO. : 14/575803  
DATED : February 28, 2017  
INVENTOR(S) : Orson L. Sydora et al.

Page 1 of 1

It is certified that error appears in the above-identified patent and that said Letters Patent is hereby corrected as shown below:

In the Claims

Claim 1, Column 166, Line 53, replace "when $m = 0$, $m1 = 0$, and $m = 0$; and" with --when $m = 0$, $m1 = 0$, and $m2 = 0$; and--

Signed and Sealed this  
Sixteenth Day of May, 2017

Michelle K. Lee  
*Director of the United States Patent and Trademark Office*